(12) United States Patent　　(10) Patent No.:　US 12,626,779 B2

Califano et al.　　(45) **Date of Patent:　*May 12, 2026**

(54) DETERMINING A TARGETED THERAPY USING VIRTUAL INFERENCE OF PROTEIN ACTIVITY BY REGULON ENRICHMENT ANALYSIS OF AN INDIVIDUAL SUBJECT TISSUE SAMPLE

(71) Applicant: The Trustees of Columbia University in the City of New York, New York, NY (US)

(72) Inventors: Andrea Califano, New York, NY (US); Mariano Javier Alvarez, Cortlandt Manor, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1409 days.

This patent is subject to a terminal disclaimer.

(21) Appl. No.: 17/033,312

(22) Filed: Sep. 25, 2020

(65) Prior Publication Data

US 2021/0327537 A1　　Oct. 21, 2021

Related U.S. Application Data

(63) Continuation of application No. 15/248,975, filed on Aug. 26, 2016, now Pat. No. 10,790,040.

(60) Provisional application No. 62/253,342, filed on Nov. 10, 2015, provisional application No. 62/211,562, filed on Aug. 28, 2015, provisional application No. 62/211,373, filed on Aug. 28, 2015.

(51) Int. Cl.

| *G16B 20/20* | (2019.01) |
| *G16B 5/00* | (2019.01) |
| *G16B 5/20* | (2019.01) |
| *G16B 20/00* | (2019.01) |
| *G16B 25/00* | (2019.01) |
| *G16B 25/10* | (2019.01) |

(52) U.S. Cl.

CPC .............. *G16B 20/20* (2019.02); *G16B 5/20* (2019.02); *G16B 20/00* (2019.02); *G16B 25/00* (2019.02); *G16B 25/10* (2019.02); *G16B 5/00* (2019.02)

(58) Field of Classification Search

None

See application file for complete search history.

(56) References Cited

U.S. PATENT DOCUMENTS

| 9,631,195 B2 | 4/2017 | Palaniappan |
| 2004/0209942 A1 | 10/2004 | Li |
| 2009/0163564 A1 | 6/2009 | Borden |
| 2011/0172929 A1 | 7/2011 | Califano |

| 2011/0275534 A1 | 11/2011 | Cohn |
| 2013/0144887 A1 | 6/2013 | Chen |
| 2013/0156795 A1 | 6/2013 | Tavarone |
| 2014/0199692 A1 | 7/2014 | Jamieson |
| 2015/0213115 A1 | 7/2015 | Mukherjee |
| 2017/0056530 A1 | 3/2017 | Califano |

FOREIGN PATENT DOCUMENTS

| CN | 102292456 A | 12/2011 |
| CN | 103224905 A | 7/2013 |
| WO | 2000/054046 A2 | 9/2000 |
| WO | 2009/092024 A1 | 7/2009 |
| WO | 2015/127101 A1 | 8/2015 |
| WO | 2015/127104 A1 | 8/2015 |

OTHER PUBLICATIONS

Bild, Andrea H., et al. "Oncogenic pathway signatures in human cancers as a guide to targeted therapies." Nature 439.7074 (2006): 353-357.*

Alvarez, M.J., et al., "A Precision Oncology Approach to the Pharmacological Targeting of Mechanistic Dependencies in Neuroendocrine Tumors," Nature Genetics 50(7):979-989, Jul. 2018.

Lee, W.P., and W.S. Tzou, "Computational Methods for Discovering Gene Networks From Expression Data," Briefings in Bioinformatics 10(4):408-423, 2009.

Segal, E., et al., "From Signatures to Models: Understanding Cancer Using Microarrays," Nature Genetics 37(Suppl 6):S38-S45, 2005.

Van Noort, V., et al., "Novel Drug Candidates for the Treatment of Metastatic Colorectal Cancer Through Global Inverse Gene-Expression Profiling," Cancer Research 74(20):5690-5699, 2014.

Chinese Office Action dated Mar. 2, 2021, issued in Chinese Patent Application No. 201680062051.4, filed Aug. 26, 2016, 12 pages.

Chinese Office Action dated Apr. 9, 2021, issued in Chinese Patent Application No. 201680062241.6, filed Aug. 26, 2016, 17 pages.

Affara, M., et al., "Vasohibin-1 is Identified as a Master-Regulator of Endothelial Cell Apoptosis Using Gene Network Analysis," BMC Genomics, BioMed Central 14(1):1-12, Jan. 16, 2013.

Ajani, J., and V. Allgood, "Molecular Mechanisms in Cancer: What Should Clinicians Know?" Seminars in Oncology 32(Supplemental 8):2-4, Dec. 2005.

(Continued)

*Primary Examiner* — G. Steven Vanni

(74) *Attorney, Agent, or Firm* — Barry L. Davison; Davis Wright Tremaine LLP

(57)　　ABSTRACT

Methods for determining regulon enrichment in gene expression signatures are disclosed herein. An example method can include obtaining a set of transcriptional targets of a regulon. The method can include obtaining a gene expression signature by comparing a gene expression profile of a test sample to gene expression profiles of a plurality of samples representing control phenotypes. The method can include calculating a regulon enrichment score for each regulon in the gene expression signature. The method can including determining whether a number of control samples in the control phenotypes is above a predetermined threshold to support evaluation of statistical significance using permutation analysis. The method can include, in response to determining that the number of control samples is above the predetermined threshold, calculating a significance value by comparing each regulon enrichment score to a null model.

25 Claims, 104 Drawing Sheets

(99 of 104 Drawing Sheet(s) Filed in Color)

(56)                    References Cited

OTHER PUBLICATIONS

Alvarez, M.J., et al., "Correlating Measurements Across Samples Improves Accuracy of Large-Scale Expression Profile Experiments," Genome Biol. 10:R143, 2009.

Alvarez, M.J., et al., "Functional Characterization of Somatic Mutations in Cancer Using Network-Based Inference of Protein Activity," Nature Genetics 48(8):838-847, 2016.

Alvarez, M.J., et al., "Using Viper, a Package for Virtual Inference of Protein-Activity by Enriched Regulon Analysis," Bioconductor Website, Oct. 17, 2016, pp. 1-15.

Alvarez, M.J., et al., "Using Viper, a Package for Virtual Inference of Protein-Activity by Enriched Regulon Analysis," <https://static1.squarespace.com/static/5697c2e5e0327ca6778bc453/t/56f40934f8baf3727f8e7e78/1458833718573/Viper.pdf> [retrieved Feb. 8, 2019], Jul. 22, 2013, pp. 1-14.

Alvarez, M.J., et al., "Using Viper, a Package for Virtual Inference of Protein-Activity by Enriched Regulon Analysis," <http://citeseerx.ist.psu.edu/viewdoc/download;jsessionid=A046487756888564E244A5E5AB118F22?doi=10.1.1.671.7432&rep=rep1&type=pdf> [retrieved Feb. 11, 2019], Oct. 13, 2014, pp. 1-14.

Aytes, A., et al., "Cross-Species Regulatory Network Analysis Identifies a Synergistic Interaction Between FOXM1 and CENPF That Drives Prostate Cancer Malignancy," Cancer Cell 25:638-651, 2014.

Baca-López, K., et al., "The Role of Master Regulators in the Metabolic/Transcriptional Coupling in Breast Carcinomas," PLOS One 7(8)(e42678):1-17, Aug. 27, 2012.

Bansal, M., et al., "A Community Computational Challenge to Predict the Activity of Pairs of Compounds," Nat. Biotechnol. 32(12): 1213-1222, 2014.

Bansal N., et al., "Tumor Suppressor Protein p53 Recruits Human Sin3B/HDAC1 Complex for Down-Regulation of Its Target Promoters in Response to Genotoxic Stress," PloS One 6(10):e26156, Oct. 2011, 12 pages.

Borelli, F.F., et al., "Gene Regulatory Networks Inference Using a Multi-GPU Exhaustive Search Algorithm," BMC Bioinformatics 14(Suppl. 18):S5, 2013.

Bozdag, S., et al., "Master Regulators, Regulatory Networks, and Pathways of Glioblastoma Subtypes," Cancer Informatics 13(S3):33-44, 2014.

Bild, A.H., et al., "Oncogenic Pathway Signatures in Human Cancers as a Guide to Targeted Therapies," Nature 439(19):353-357, Jan. 2006.

Califano, A., "National Center: Multiscale Analysis of Genomic and Cellular Networks (Magnet)," NIH Grant #: 5U54CA121852-08, U.S. Dept. of Health and Human Services, NIH Research Portfolio Online Reporting Tools (Accessed on Feb. 8, 2017).

Califano, A., "Systems Biology of Tumor Progression and Drug Resistance," NIH Grant #: 1U01CA168426-01, U.S. Dept. of Health and Human Services, NIH Research Portfolio Online Reporting Tools (Accessed on Feb. 8, 2017).

Carro, M.S., et al., "The Transcriptional Network for Mesenchymal Transformation of Brain Tumours," Nature 463:318-325, 2010.

Chen, J.C., et al., "Identification of Causal Genetic Drivers of Human Disease through Systems-Level Analysis of Regulatory Networks," Cell 159:402-414, 2014.

Della Gatta, G., et al., "Reverse Engineering of TLX Oncogenic Transcriptional Networks Identifies RUNX1 as Tumor Suppressor in T-ALL," Nat. Med. 18(3):436-440, 2012.

Fletcher, M.N.C., et al., "Master Regulators of FGFR2 Signalling and Breast Cancer Risk," Nature Communications 4(1):1-12, Sep. 17, 2013.

Giorgi, F.M., et al., "Inferring Protein Modulation From Gene Expression Data Using Conditional Mutual Information," PLOS One 9(10)(e109569):1-9,, Oct. 14, 2014.

Hajingabo, L.J., et al., "Predicting Interactome Network Perturbations in Human Cancer: Application to Gene Fusions in Acute Lymphoblastic Leukemia," Mol. Biol. Cell 25:3973-3985, Dec. 2014.

Hanahan, D., and R.A. Weinberg, R., "Hallmarks of Cancer: The Next Generation," Cell 144:646-674, 2011.

Hu, H., "An Efficient Algorithm to Identify Coordinately Activated Transcription Factors," Genomics 95(3):143-150, 2010.

Kiz, B., et al., "The Regulatory Machinery of Neurodegeneration in In Vitro Models of Amyotrophic Lateral Sclerosis," Cell Reports 12:335-345, 2015.

Keith, C.T., et al., "Multicomponent Therapeutics for Networked Systems," Nat. Rev. Drug Discov. 4:71-78, 2005.

Lefebvre, C., et al. "A Human B-Cell Interactome Identifies MYB and FOXM1 as Master Regulators of Proliferation in Germinal Centers," Molecular Systems Biology 6:377:1-10, 2010.

Margolin, A.A.., et al., "ARACNE: An Algorithm for the Reconstruction of Gene Regulatory Networks in a Mammalian Cellular Context," BMC Bioinformatics 7(Suppl. 1):S7, Mar. 20, 2006.

Niola, F., et al., "Mesenchymal High-Grade Glioma is Maintained by the ID-RAP1 Axis," The Journal of Clinical Investigation 123(1):405-417, Dec. 17, 2012.

Palomero, T., et al., "NOTCH1 Directly Regulates c-MYC and Activates a Feed-Forward-Loop Transcriptional Network Promoting Leukemic Cell Growth," PNAS 103(48):18261-18266, 2006.

Paull, E., et al., "Master Regulator and Network Diffusion Analysis Reveals Convergent Cancer Driver Programs Across Pan-Cancer Samples," The Cancer Genome Atlas 4th Annual Scientific Symposium May 11-12, 2015, <http://www.capconcorp.com/meeting/2015/TCGASymposium/TCGA-Abstracts_(050815).pdf> [retrieved Feb. 11, 2019], p. 81.

Phillips, H.S., et al., "Molecular Subclasses of High-Grade Glioma Predict Prognosis, Delineate a Pattern of Disease Progression, and Resemble Stages in Neurogenesis," Cancer Cell 9:157-173, 2006.

Piovan, E., et al., "Direct Reversal of Glucocorticoid Resistance by AKT Inhibition in Acute Lymphoblastic Leukemia," Cancer Cell 24:766-776, 2013.

Prat, A., et al. "Phenotypic and Molecular Characterization of the Claudin-Low Intrinsic Subtype of Breast Cancer," Breast Cancer Res. 12:R68, 2010.

Subramanian, A., et al., "Gene Set Enrichment Analysis: A Knowledge-Based Approach for Interpreting Genome-Wide Expression Profiles," Proceedings of the National Academy of Sciences of the United States of America 102(43):15545-15550, Oct. 25, 2005.

Vaske, C.J., et al., "Inference of Patient-Specific Pathway Activities From Multi-Dimensional Cancer Genomics Data Using PARADIGM," Bioinformatics 26(12):1237-i245, 2010.

Weinstein, I. B., "Addiction to Oncogenes-the Achilles Heal of Cancer," Science 297:63-4, 2002.

Woo, J.H., et al., "Elucidating Compound Mechanism of Action by Network Perturbation Analysis," Cell 162(2):441-451, Jul. 1, 2015.

Zhang, L., et al., "Gene Expression Profiles in Normal and Cancer Cells," Science 276(5316):1268-1272, May 23, 1997.

Zhang, P., et al., "DDAH1 Deficiency Attenuates Endothelial Cell Cycle Progression and Angiogenesis," PloS One 8(11):e79444, Nov. 2013, 9 pages.

Zhang, Y., et al., "Network Motif-Based Identification of Transcription Factor-Target Gene Relationships by Integrating Multi-Source Biological Data," BMC Bioinformatics 9:203, 2008.

International Search Report and Written Opinion dated Nov. 23, 2016, in International Application No. PCT/US2016/049070, filed Aug. 26, 2016, 8 pages.

International Search Report and Written Opinion dated Nov. 23, 2016, in International Application No. PCT/US2016/049063, filed Aug. 26, 2016, 11 pages.

Partial European Search Report dated Feb. 15, 2019, issued in European Patent Application No. 16842698.9, filed Aug. 26, 2016, 15 pages.

Extended European Search Report dated Feb. 21, 2019, issued in European Patent Application No. 16842702.9, filed Aug. 26, 2016, 8 pages.

Supplemental European Search Report dated May 14, 2019, issued in European Patent Application No. 16842698.9, filed Aug. 26, 2016, 13 pages.

(56) References Cited

OTHER PUBLICATIONS

Alvarez, M.J., "Unbiased Assessment of H-STS Cells as High-Fidelity Models for Gastro-Enteropancreatic Neuroendocrine Tumor Drug Mechanism of Action Analysis," bioRxiv, Jun. 22, 2019, pp. 1-11.

* cited by examiner

Pleiotropy correction

R1                                          R4

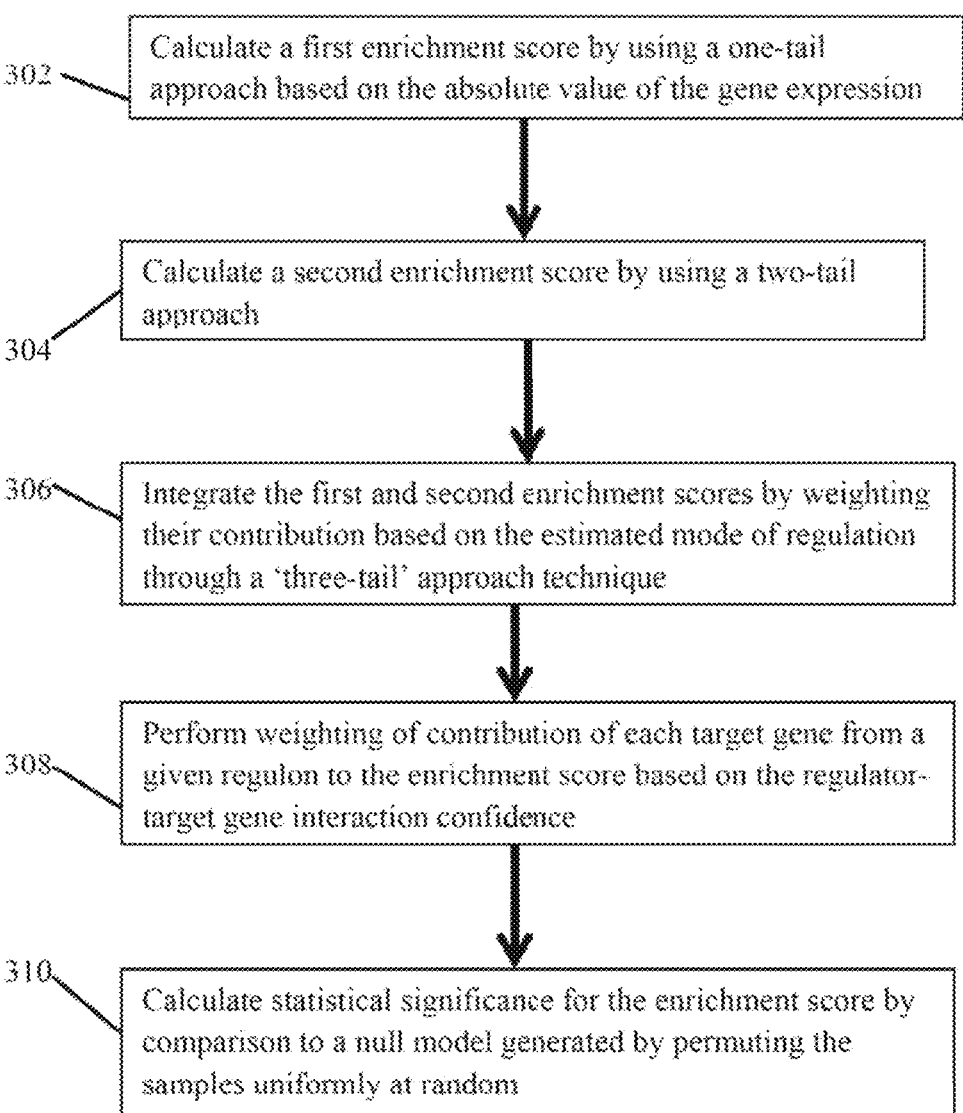

300

302 — Calculate a first enrichment score by using a one-tail approach based on the absolute value of the gene expression 304 — Calculate a second enrichment score by using a two-tail approach 306 — Integrate the first and second enrichment scores by weighting their contribution based on the estimated mode of regulation through a 'three-tail' approach technique 308 — Perform weighting of contribution of each target gene from a given regulon to the enrichment score based on the regulator-target gene interaction confidence 310 — Calculate statistical significance for the enrichment score by comparison to a null model generated by permuting the samples uniformly at random

FIG. 3

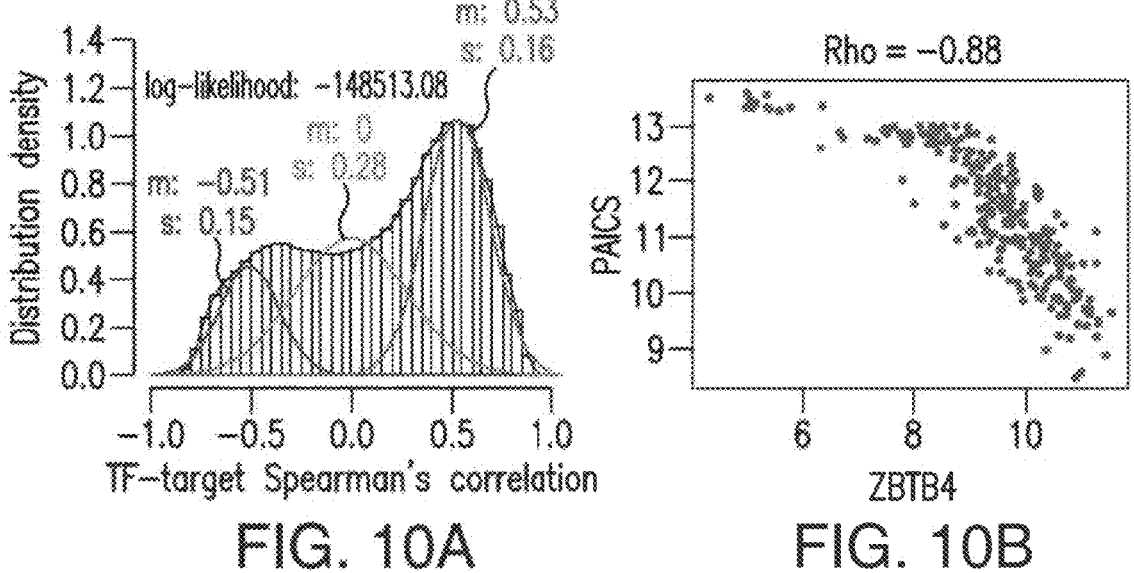
FIG. 10A
FIG. 10B
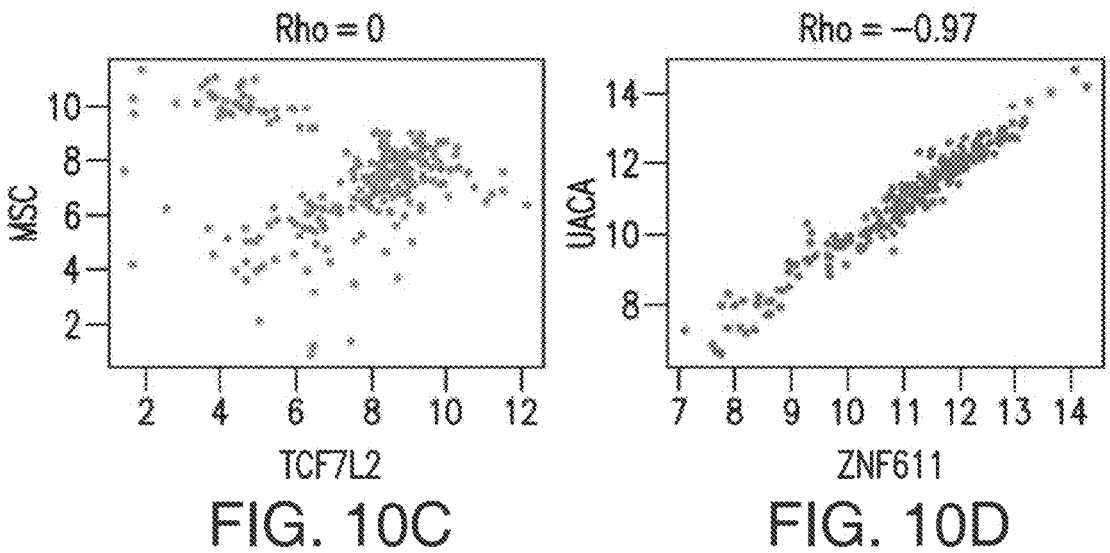
FIG. 10C
FIG. 10D

Germinal Center
S1 = U95A signatures
S2 = U133p2 signatures
N1 = U95A network
N2 = U133p2 network

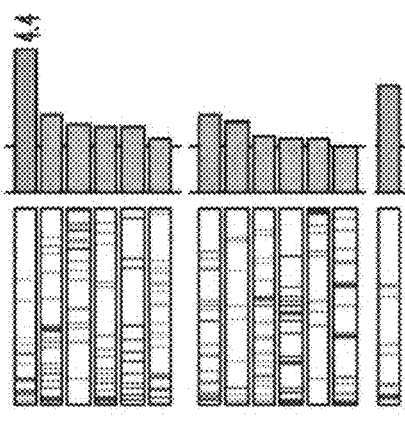
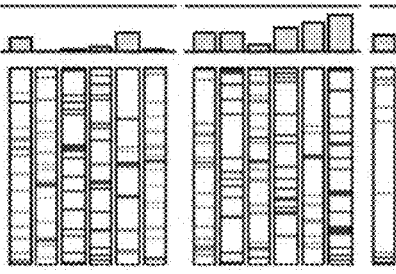
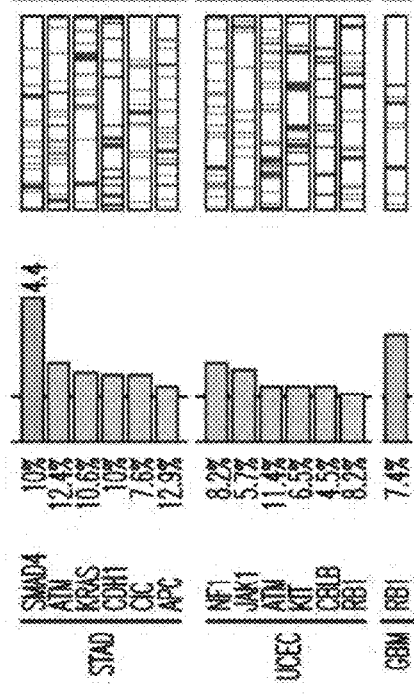
FIG. 20C Continued

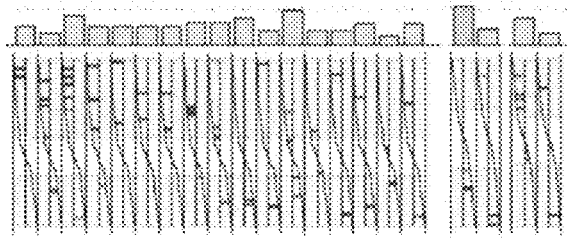
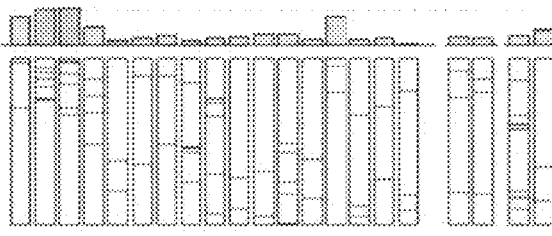
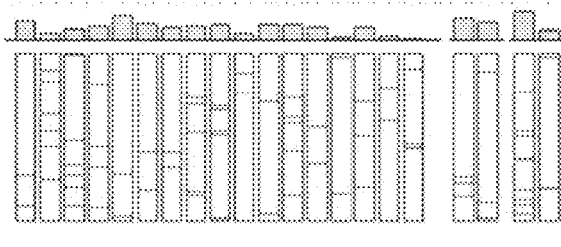
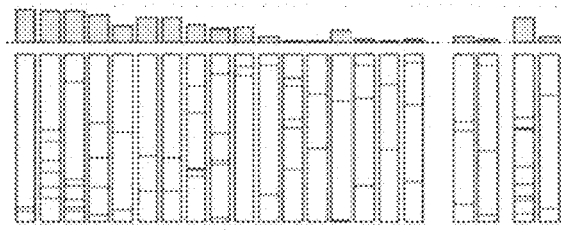
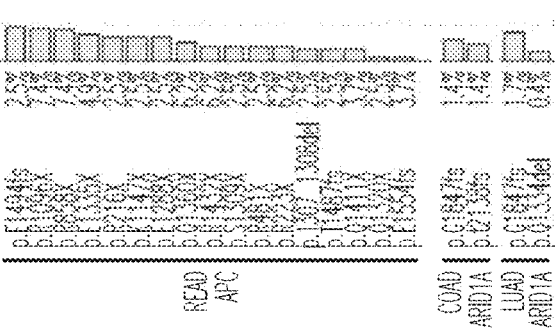
FIG. 22A Continued

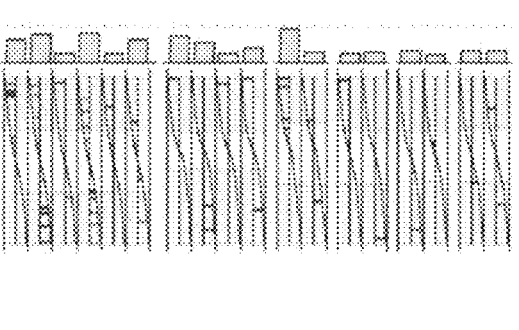
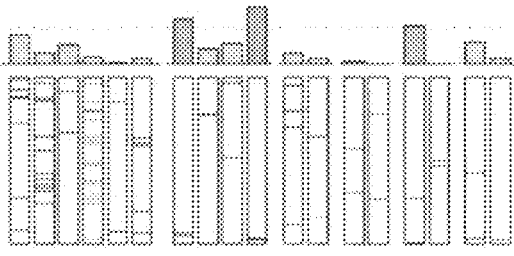
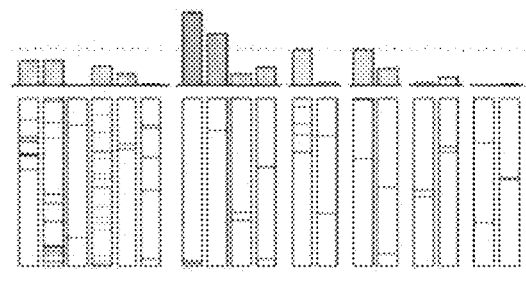
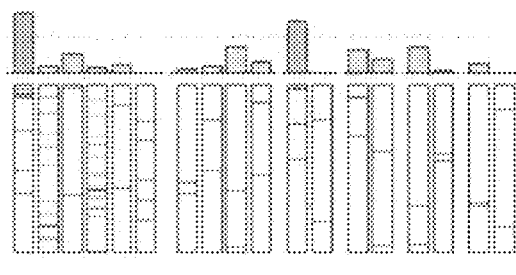
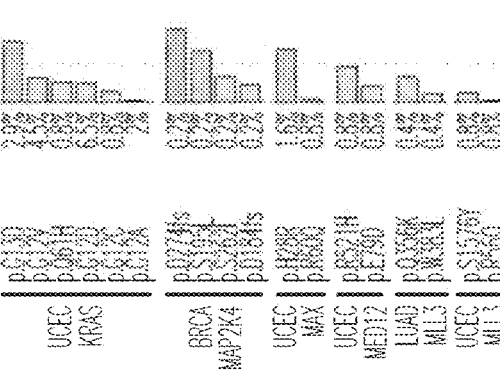
FIG. 22C Continued

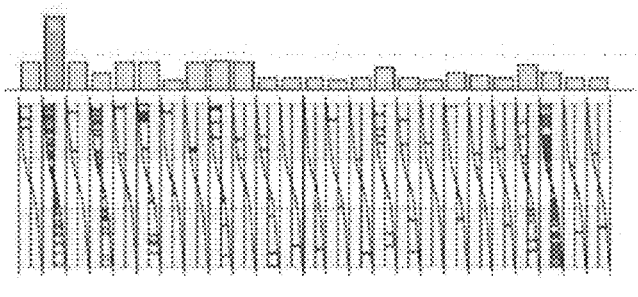
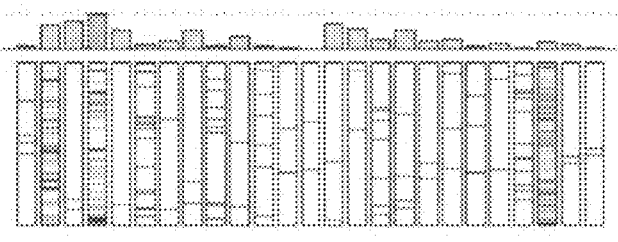
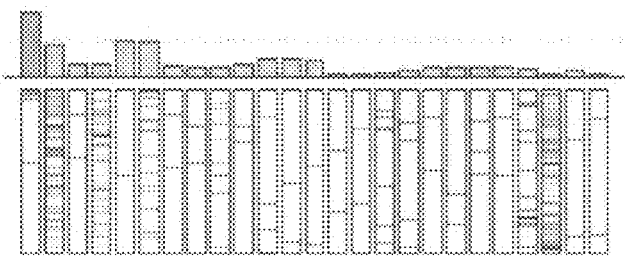
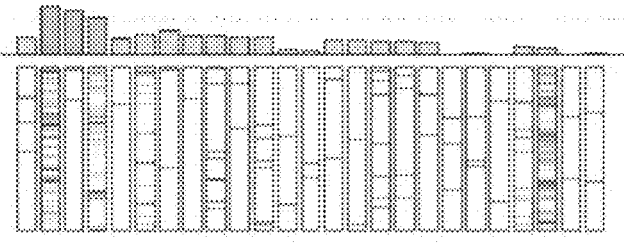
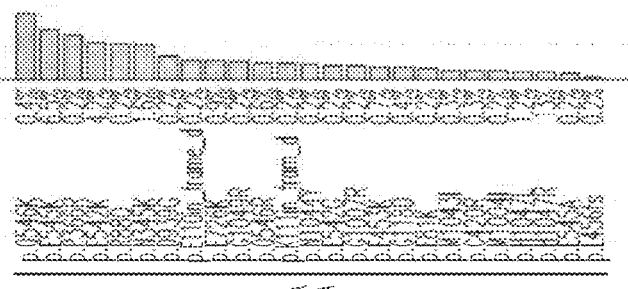
FIG. 22D Continued

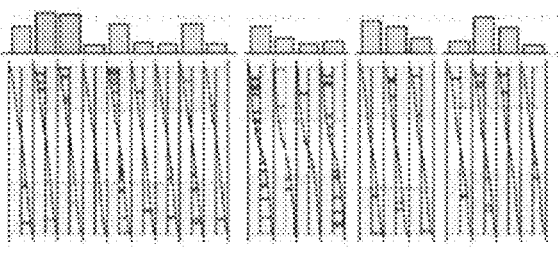
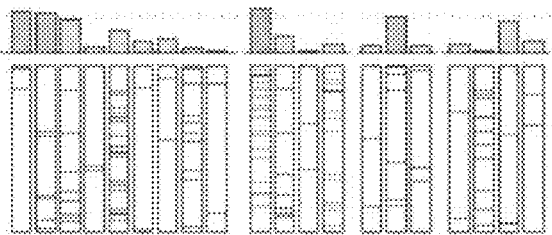
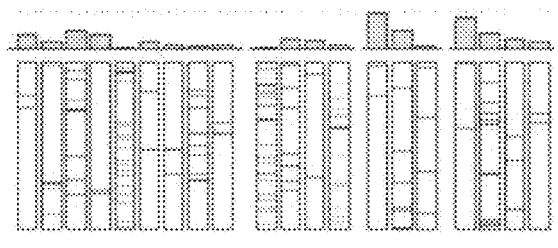
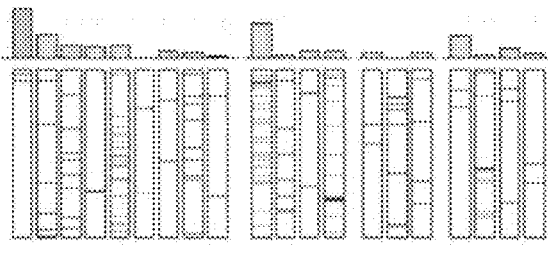
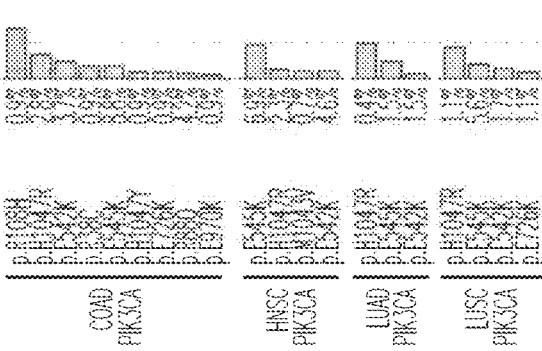
FIG. 22D Continued

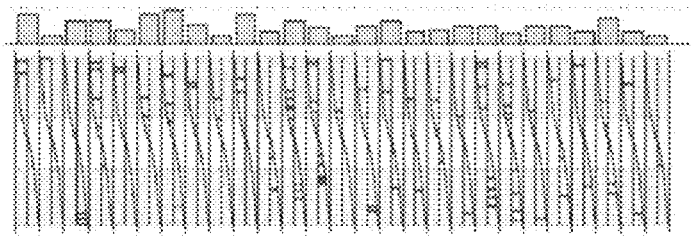
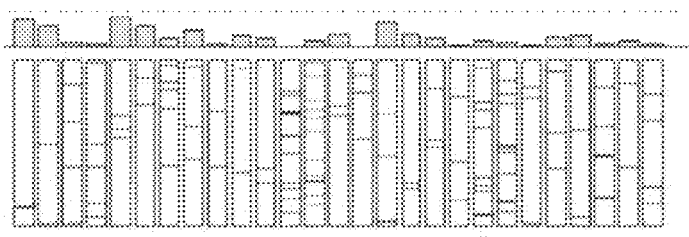
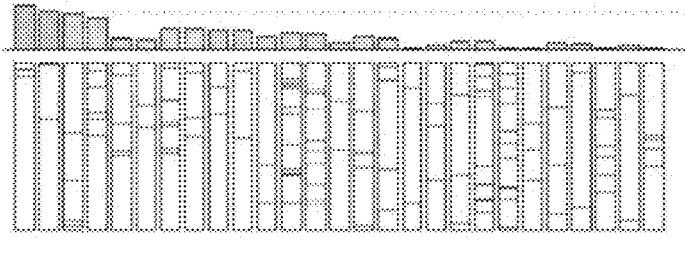
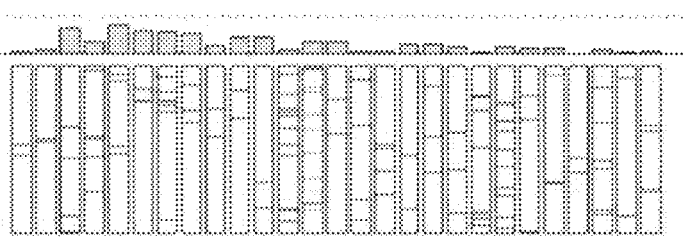
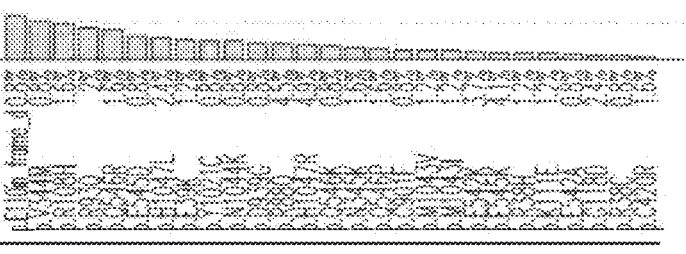
FIG. 22E

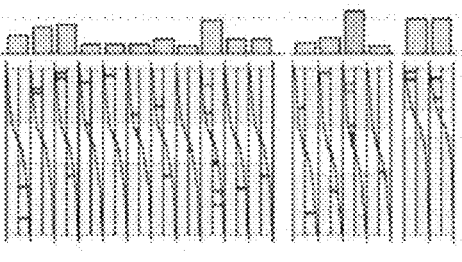
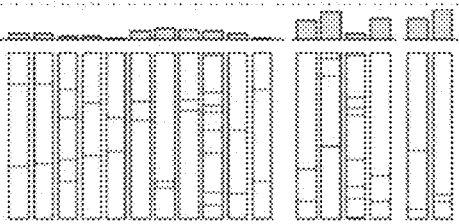
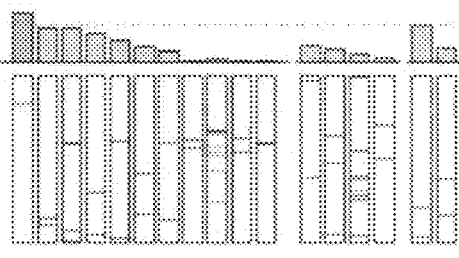
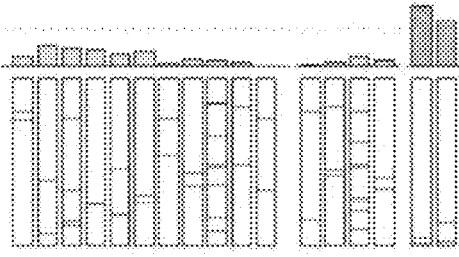
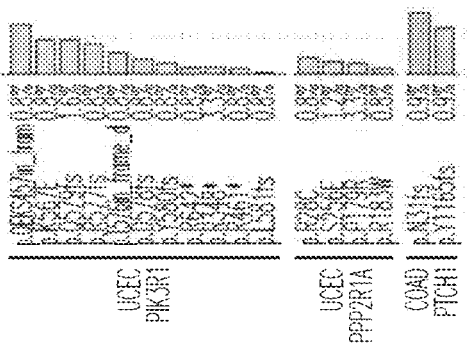
FIG. 22E Continued

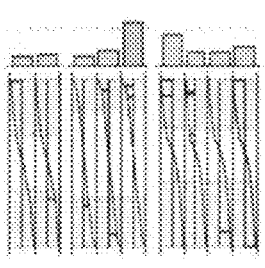
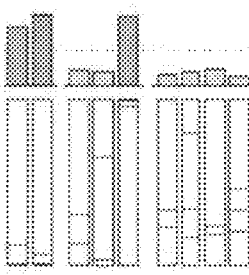
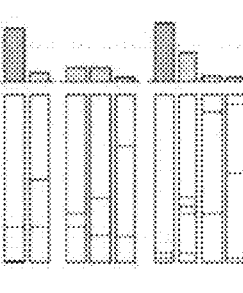
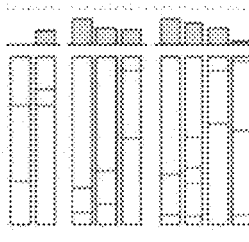
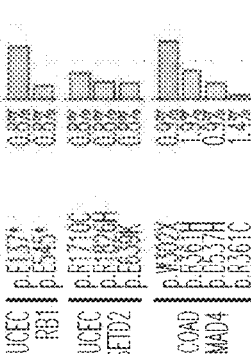
FIG. 22F Continued

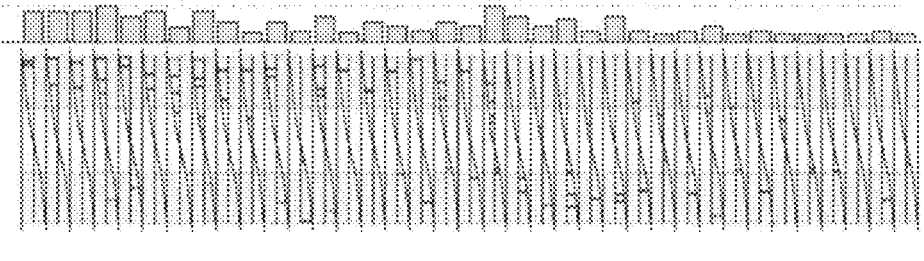
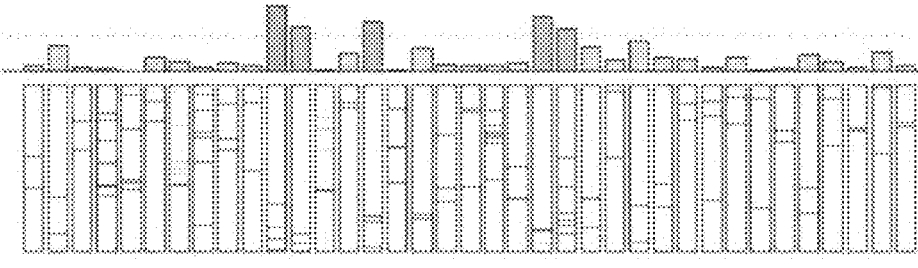
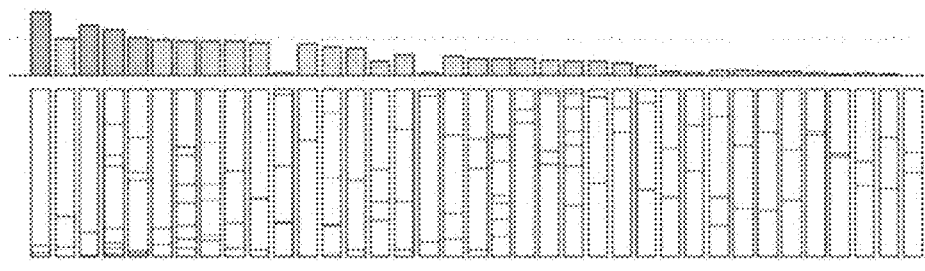
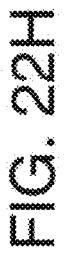
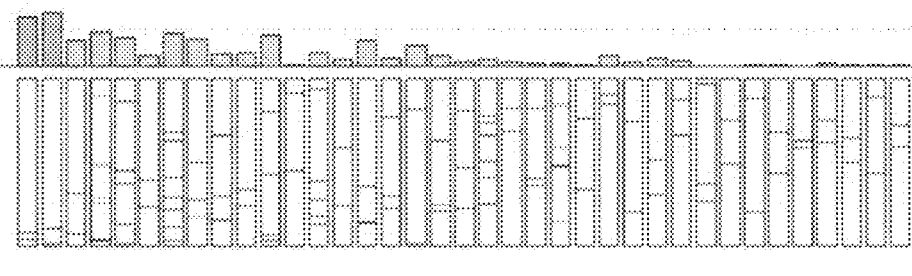
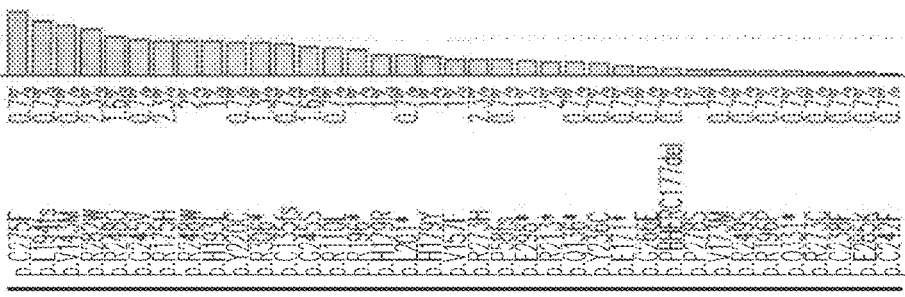
FIG. 22H

| | | |
|---|---|---|
| p.H193L | 0.21% | |
| p.V157F | 0.27% | |
| p.H193R | 0.24% | |
| p.L194R | 0.18% | |
| p.C238Y | 0.12% | |
| p.G266V | 0.12% | |
| p.V143M | 0.06% | |
| p.T211I | 0.06% | |
| p.L194fs | 0.06% | |
| p.A159P | 0.15% | |
| p.R267P | 0.06% | |
| p.P278S | 0.09% | |
| p.G244C | 0.06% | |
| TP53 | p.V272M | 0.06% |

FIG. 28

DETERMINING A TARGETED THERAPY USING VIRTUAL INFERENCE OF PROTEIN ACTIVITY BY REGULON ENRICHMENT ANALYSIS OF AN INDIVIDUAL SUBJECT TISSUE SAMPLE

CROSS-REFERENCE TO RELATED APPLICATIONS

This application is a continuation of U.S. patent application Ser. No. 15/248,975, filed Aug. 26, 2016, now U.S. Pat. No. 10,790,040, which claims the benefit of and priority to U.S. Provisional Patent Application No. 62/211,373, filed on Aug. 28, 2015, U.S. Provisional Patent Application No. 62/211,562, filed on Aug. 28, 2015, and U.S. Provisional Patent Application No. 62/253,342, filed on Nov. 10, 2015, the disclosures of which are incorporated by reference herein in their entirety.

STATEMENT REGARDING FEDERALLY SPONSORED RESEARCH

This invention was made with government support under grants CA121852 and CA168426 awarded by the National Institutes of Health. The Government has certain rights in this invention.

BACKGROUND

Cancer initiation and progression can be driven by aberrant activity of oncoproteins working in concert to regulate critical tumor hallmark programs. Pharmacological inhibition of aberrantly activated oncoproteins can elicit oncogene dependency, which can motivate the development and use of targeted inhibitors in precision cancer medicine. While activating genetic alterations can allow identification of candidate drug targets, activating mutations can represent only one of several techniques to dysregulate the activity of an oncoprotein. Genetic and epigenetic events in cognate binding partners, competitive endogenous RNAs and upstream regulators can contribute to the aberrant activity of oncoproteins. Thus, although cells in which mutations have been activated in a specific oncogene can be generally more sensitive to corresponding targeted inhibitors, cells lacking such mutations can present equivalent sensitivity.

Conversely, an activating mutation cannot be guaranteed to induce aberrant protein activity due to autoregulatory mechanisms and epigenetic allele silencing. Thus, there is a need for a more universal and systematic methodology for the accurate and reproducible assessment of protein activity to complement the ability to identify targeted therapy responders based on mutational analysis, especially because many cancer patients have no actionable oncogene mutations.

In addition, change of protein activity following treatment of a tissue with a perturbagen can be critically relevant to determining whether that perturbagen has therapeutic value in that specific tissue context. Perturbagens can include, without limitation, small molecules, biologics, biophysical perturbations, and antibodies. For example, determining that small molecule A can inhibit protein kinase B, which can be aberrantly activated or mutated in cancer C, can be used as the basis to develop A as a targeted drug for tumor C.

While gene expression data are ubiquitous in cancer research. Certain methods to measure protein abundance based on arrays or mass spectrometry technologies can be labor-intensive, costly, and either cover a small fraction of the proteomic landscape or require large amounts of tissue. More importantly, these methods provide only an indirect measure of protein activity, because the latter is determined by a complex cascade of events, including protein synthesis, degradation, post-translational modification, complex formation and subcellular localization. It is ultimately unclear whether protein activity can be directly and systematically assessed by certain individual assays.

One issue is a dearth of certain experimentally validated methods to accurately assess the activity of arbitrary proteins in individual samples based on the expression of their regulon genes. Reasons for this include a lack of accurate and context-specific protein regulon models, the largely pleiotropic nature of transcriptional regulation, and a lack of methodologies to assess statistical significance from single samples. This can limit the ability to understand the functional effect of mutations on protein activity and to identify candidate responders to targeted inhibitors based on aberrant protein activity rather than mutations.

Accordingly, there is a need to develop an experimentally validated method to accurately assess the activity of arbitrary proteins in individual samples based on the expression of their regulon genes.

SUMMARY

The disclosed subject matter provides systems and methods to infer protein activity from gene expression profile data. This can be used (a) to determine the functional impact of genetic mutations, (b) to identify the key regulator(s) responsible for implementing the transition between two phenotypic states in either physiological (e.g., tissue differentiation or reprogramming) and/or pathological (e.g., transition between normal and disease related state) context, (c) to identify the non-oncogene driver genes in cancer, both for a single patient, and also at the single cell level, and (d) to characterize the cell context-specific mechanism of action of different types of perturbation to the cell, and in particular of those implemented by perturbagens such as small molecule compounds, antibodies, nutrients, and other biologics.

In accordance with an example embodiment, the disclosed subject leverages context specific models of transcriptional regulation to estimate differential protein activity from the differential expression of their regulon genes. Regulons can be defined as the multiplicity of target genes of a specific protein. For example, protein activity of transcription factors, and signal transduction proteins can be estimated by using the transcriptional abundance of their regulon genes as a gene reporter assay. By systematically inferring regulons from tissue-specific gene expression data, regulon models can be generated for certain proteins of interest in certain tissue contexts of interest. In order to estimate differential activity of signaling proteins and other post-translational regulators, high information path targets can be identified, thus allowing for identification of regulons that are predictive of the activity of these proteins.

In some embodiments, the disclosed subject matter can include a systematic framework for testing for regulon enrichment in genes that are differentially expressed in a specific gene expression signatures. The gene expression signature (GES) can be determined by comparing the gene expression profiles (GEP) of two groups of samples representing distinctive phenotypes and/or treatments to assess the statistical significance of the differential expression of each gene in the profiles, for instance using the Student T-test statistics. Additionally or alternatively, a single-sample based gene expression signatures can be determined by comparing the expression levels of each gene in the sample GEP against that of the same gene in a set of GEPs from reference (e.g., control) samples. The enrichment of each regulon in genes differentially expressed in a GES can be determined by using a plurality of different implementations of an analytic rank-based enrichment analysis technique (aREA) and/or other equivalent methods for measuring gene set enrichment analysis. The aREA technique can test for a global shift in the position of each regulon genes when projected on the rank-sorted gene expression signature. The statistical significance (e.g., the p-value and a normalized enrichment score) can be estimated by comparing each regulon enrichment score to a null model generated by randomly and uniformly permuting the samples for a plurality of different iterations. In an alternative embodiment, if it is determined that the number of samples is not sufficient to support permutation, permutation of the genes in the gene expression signature and/or its analytic approximation can be used.

The disclosed subject matter can also assess the activity of regulatory proteins in a sample from the corresponding gene expression profile, thus producing informative protein activity profiles. For example, the disclosed subject matter can infer protein activity based on the abundance of downstream transcriptional targets (e.g., a protein's regulon), which optimally reflects the activity of the regulatory active protein isoform, including the effect of post-translational modifications, proper subcellular localization, and interaction with co-factors.

In some embodiments, the disclosed subject matter can use a rigorous probabilistic framework that accounts for targets directionality, confidence, and/or pleiotropic regulation, resulting in high accuracy, specificity, and reproducibility of activity predictions from both single sample and multiple sample data sets. In addition, by establishing the least indirectly regulated targets and by analyzing their differential expression, activity of signal transduction proteins and of other non-transcriptional regulators can be inferred.

In an exemplary embodiment, the disclosed subject matter can be applied to identify the key regulatory proteins that are necessary to implement and maintain the transcriptional state of a single tumor. For example, the disclosed subject matter can be used to infer the regulators of cell state for 85 individual cells from a single murine glioma tumor.

In some embodiments, the disclosed subject matter can be applied to detect the functional impact of genetic mutations on protein activity, including of coding and non-coding mutations. For example, the disclosed subject matter can be used to prioritize the functional relevance of rare and private non-synonymous mutations as hypomorph, hypermorph, or neutral events. In another exemplary embodiment, the disclosed subject matter can be used to distinguish between transcriptionally and post-translationally mediated mutational effects. In another exemplary embodiment, the disclosed subject matter can be used to elucidate the proteins that mediate the pharmacological activity of a perturbagen, such as a small molecule compound, antibody, nutrient, and other biologics (i.e., its mechanism of action) and that are causally responsible for implementing the transcriptional cell state resulting from treatment of a tissue with that compound or biologic.

The description herein merely illustrates the principles of the disclosed subject matter. Various modifications and alterations to the described embodiments will be apparent to those skilled in the art in view of the teachings herein. Accordingly, the disclosure herein is intended to be illustrative, but not limiting, of the scope of the disclosed subject matter.

BRIEF DESCRIPTION OF THE FIGURES

The patent or application file contains at least one drawing executed in color. Copies of this patent or patent application publication with color drawing(s) will be provided by the office upon request and payment of the necessary fee.

FIG. 3 illustrates a method to perform an analytic rank-based enrichment analysis (aREA).

FIGS. 4A-4C illustrate the effect of network quality on VIPER accuracy when using a non-tissue-matched interactome.

FIG. 4D illustrates VIPER accuracy results for progressive signature degradation obtained by addition of Gaussian noise.

FIG. 4E illustrates VIPER accuracy results for reduced signature coverage obtained by randomly removing genes.

FIG. 4F illustrates average correlation results between VIPER-inferred protein activity signatures and the corresponding signatures determined from lower-depth RNA-sequencing.

FIGS. 10A-10D illustrate TF Mode of Regulation results for the B-cell U133-based interactome.

FIG. 15C illustrates statistical significance for protein activity decrease.

FIG. 15D illustrates accuracy data expressed as position percentage of the evaluated regulators. FIG. 15D illustrates specificity, expressed as proportion (%) of regulators inferred as differentially active.

FIGS. 22A-22I illustrate the impact of specific non-silent somatic mutation (NSSM) variants on protein activity.

FIG. 28 illustrates the correlation between VIPER-inferred protein activity and coding-gene mRNA level.

DETAILED DESCRIPTION

The methods and systems presented herein can be used to infer protein activity by systematically analyzing expression of the protein's regulon. The disclosed subject matter will be explained in connection with an example method referred to herein as virtual inference of protein activity by enriched regulon analysis (hereinafter "VIPER") to perform an accurate assessment of protein activity from gene expression data. The disclosed subject matter can use VIPER to evaluate the functional relevance of genetic alterations in regulatory proteins across different samples. A regulatory protein can be defined as a protein that directly controls either the expression of a multiplicity of genes (e.g., transcriptional regulator) or the state of the chromatin (e.g., epigenetic regulator) or the post-translational modification of a multiplicity of other proteins (e.g., signal transduction regulator).

VIPER can also be used to identify tumors with aberrant activity of druggable oncoproteins despite a lack of mutations, and vice versa. In vitro and in vivo assays can confirm that VIPER-inferred protein activity can outperform mutational analysis in predicting sensitivity to targeted inhibitors.

FIG. 1 illustrates, for the purpose of illustration and not limitation, a schematic of molecular layers profiled by the VIPER technique. In some embodiments, expression of transcriptional targets of a protein, collectively referred to as its regulon, can represent an optimal multiplexed reporter of the respective protein's activity.

While regulon analysis can help identify aberrantly activated and inactivated proteins in a tumor, regulon analysis can require multiple samples representing the same tumor phenotype and cannot be used to assess aberrant protein activity from individual samples. To address this challenge, VIPER has been developed to infer protein activity from single gene expression profiles. VIPER can be used to systematically assess aberrant activity of oncoproteins for which high-affinity inhibitors are available, independent of their mutational state, thus establishing them as valuable therapeutic targets on an individual patient basis. The VIPER based analysis can be fully general and can be trivially extended to study the role of germ-line variants in dysregulating protein activity.

Figure 1A:
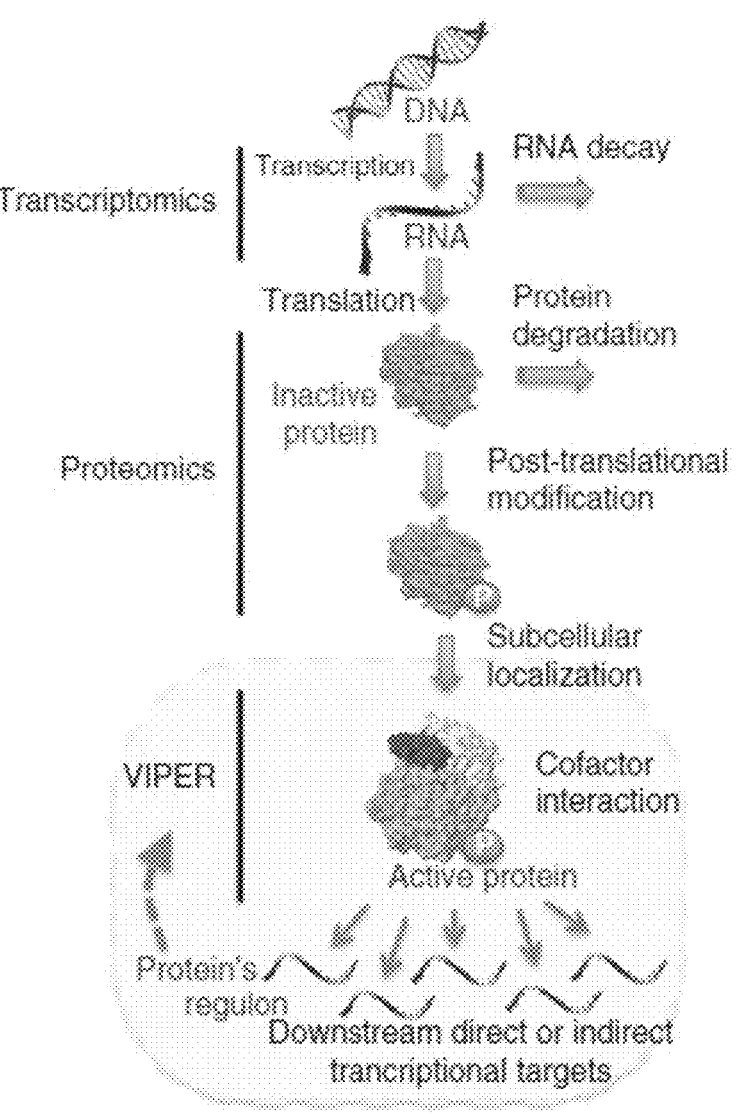
FIG. 1A illustrates a schematic of molecular layers profiled and an example method referred to as VIPER herein, in accordance with the disclosed subject matter, used to infer protein activity based on the protein's regulon.
Figure 1B:
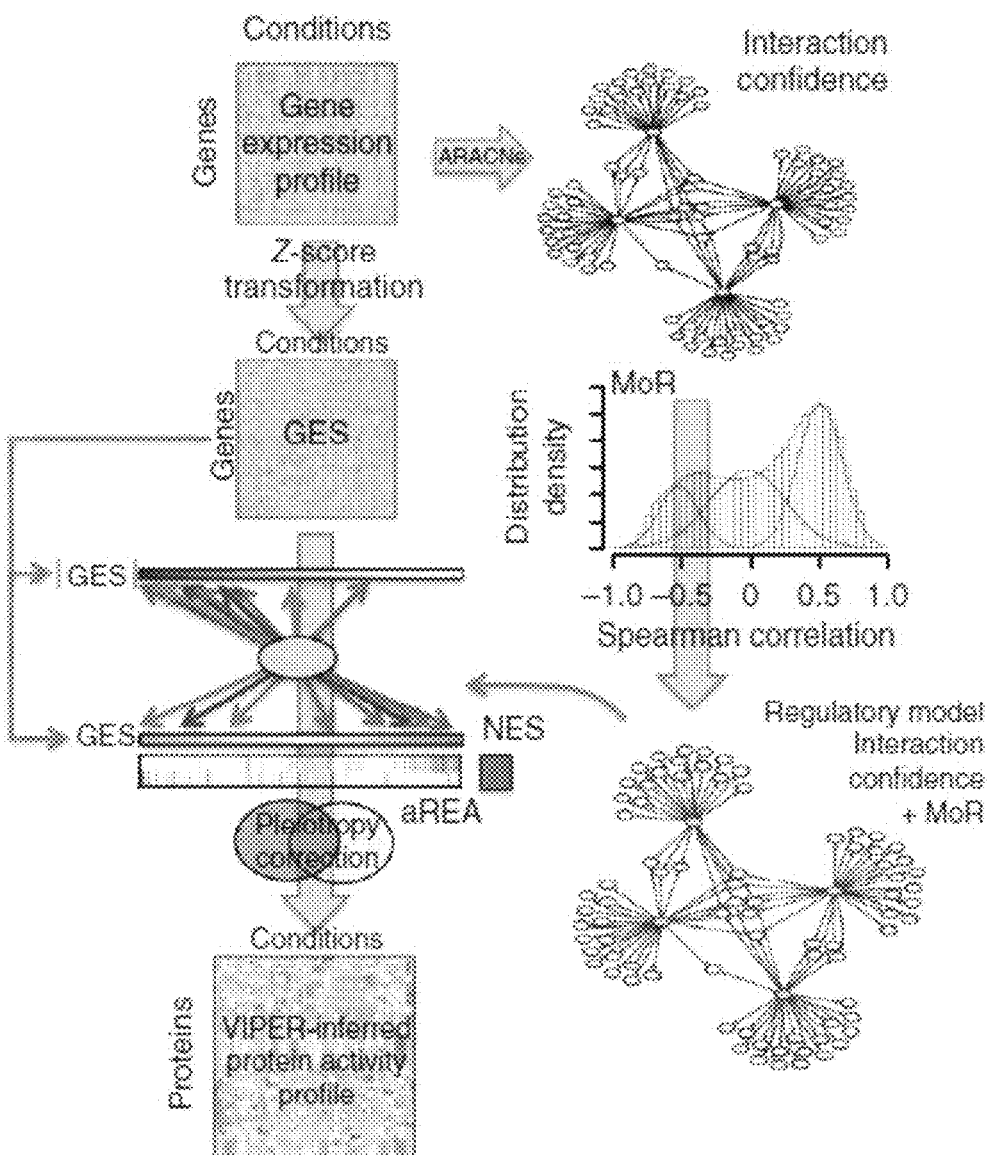
FIG. 1B illustrates a VIPER workflow in which a regulatory model is generated.
Figure 1C:
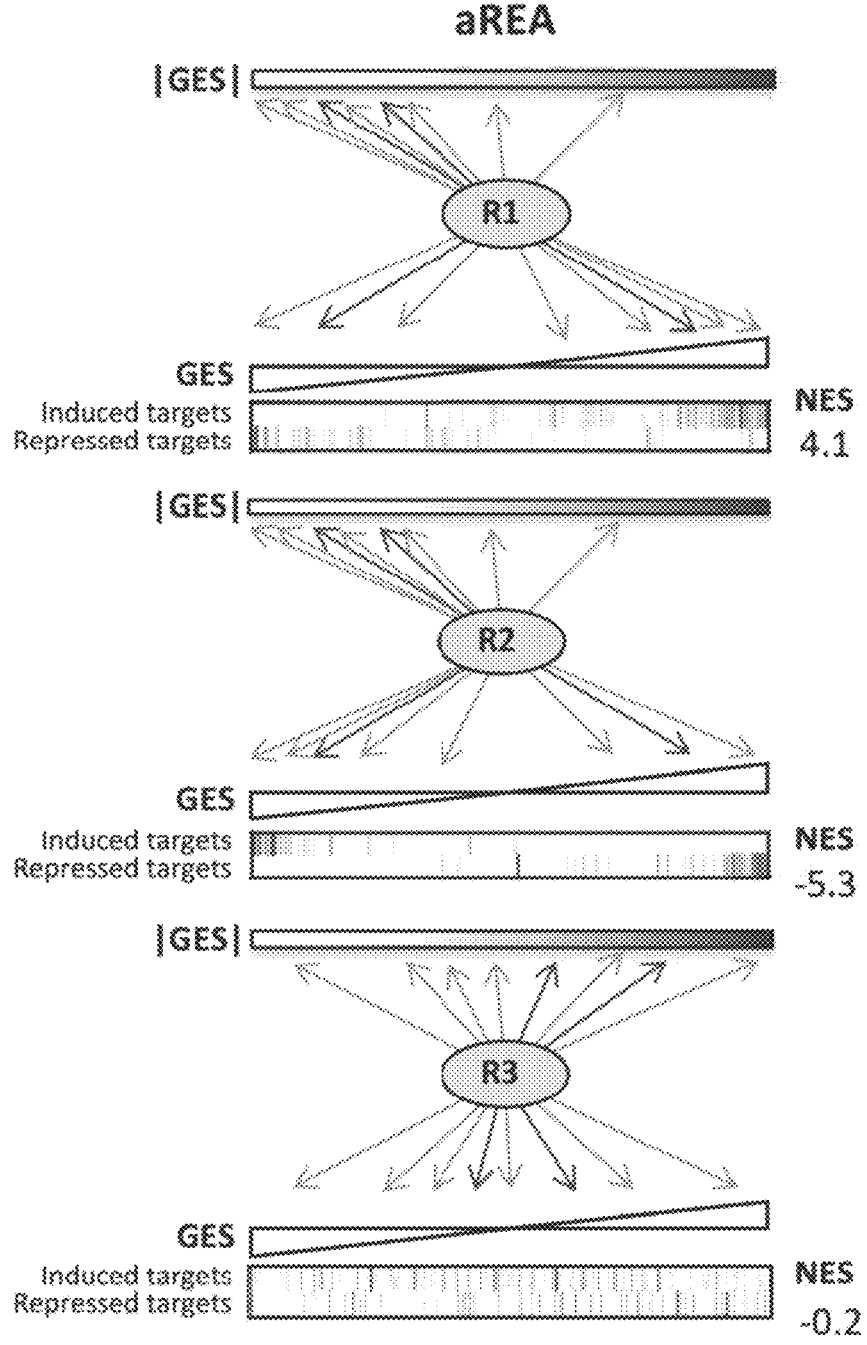
FIG. 1C illustrates three possible scenarios for the aREA analysis are increased, decreased or no change in activity for three regulatory proteins.
Figure 1D:
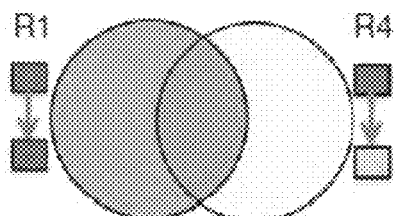
FIG. 1D illustrates pleiotropy correction being performed.
Figure 1E:
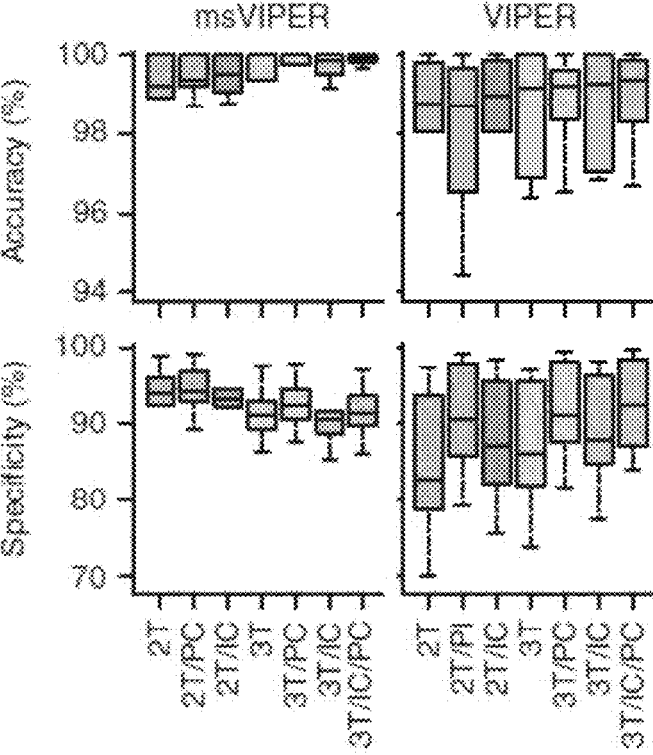
FIG. 1E illustrates accuracy and specificity data for benchmark experiments performed with VIPER.

FIG. 1A illustrates a schematic of molecular layers profiled: transcriptomics, used to measure steady-state mRNA levels and proteomics, used to quantify protein levels, including some defined post-translational isoforms. FIG. 1A also illustrates that VIPER can be used to infer protein activity based on the protein's regulon, reflecting the abundance of the active protein isoform, including post-translational modifications, proper subcellular localization and interaction with co-factors. FIG. 1B illustrates a VIPER workflow in which a regulatory model is generated from ARACNe-inferred context-specific interactome and mode of regulation (MoR) can be determined from the correlation between regulator and target genes. Single-sample gene expression signatures (GES) can be determined from genome-wide expression data, and transformed into regulatory protein activity profiles by the aREA algorithm. |GES| is the absolute value of GES and NES is the normalized enrichment score. FIG. 1C illustrates three possible scenarios for the aREA analysis (1) increased, (2) decreased or (3) no change in activity for three regulatory proteins (R1, R2, and R3). FIG. 1D illustrates pleiotropy correction, performed by evaluating whether the enrichment of a given regulon (R4) is driven by genes coregulated by a second regulator (R1). FIG. 1E illustrates the accuracy (e.g., relative rank for the silenced protein) and specificity (e.g., fraction of proteins inferred as differentially active at P<0.05) for the six benchmark experiments (shown in Table 2) with VIPER based on multiple-sample gene expression signatures (msVIPER) and single-sample gene expression signatures (VIPER). The colors indicate implementations of the aREA algorithm: two-tail (2T) and three-tail (3T), interaction confidence (IC) and pleiotropy correction (PC).

In some embodiments, VIPER can be used to infer protein activity by systematically analyzing expression of the protein's regulon, which is tumor-context-dependent (FIG. 1B). VIPER thus uses accurate cellular networks, which can be reconstructed using reverse engineering techniques such as the ARACNe technique to systematically use regulons inferred from tissue-specific gene expression data (FIG. 1B and Table 1). Table 1 illustrates the interactomes and the data sets that can be used to reverse engineer them.

TABLE 1

| Dataset | | | | Interactome | | |
|---|---|---|---|---|---|---|
| Tissue type | Samples | Platform | Reference | Regulator | Targets | Interactions |
| B-cell | 254 | HG-U95Av2 | 24 | 633(TFs) | 6,403 | 173,539 |
| B-cell | 264 | HG-U133plus2 | 34 | 1,223(TFs) | 13,007 | 327,837 |
| Glioblastoma | 176 | HG-U133A | 48 | 835(TFs) | 8,263 | 256,965 |
| Bladder carcinoma | 241 | RNAseq | TCGA | 1,813(TFs) | 20,006 | 245,871 |
| | | | | 666(coTFs) | 18,739 | 181,730 |
| | | | | 3,455(Sig) | 20,441 | 317,127 |
| Breast carcinoma | 1,037 | RNAseq | TCGA | 1,813(TFs) | 20,428 | 249,501 |
| | | | | 666(coTFs) | 20,220 | 217,916 |
| | | | | 3,455(Sig) | 20,515 | 366,924 |
| Colon adenocarcinoma | 434 | RNAseq | TCGA | 1,813(TFs) | 20,462 | 294,725 |
| | | | | 666(coTFs) | 19,742 | 204,682 |
| | | | | 3,456(Sig) | 20,492 | 369,870 |
| Head and neck squamous cell carcinoma | 424 | RNAseq | TCGA | 1,813(TFs) | 20,452 | 319,799 |
| | | | | 666(coTFs) | 19,874 | 212,214 |
| | | | | 3,456(Sig) | 20,520 | 395,966 |
| Kidney renal clear cellcarcinoma | 506 | RNAseq | TCGA | 1,813(TFs) | 20,474 | 355,932 |
| | | | | 666(coTFs) | 20,080 | 259,151 |
| | | | | 3,456(Sig) | 20,522 | 429,651 |
| Lung adenocarcinoma | 488 | RNAseq | TCGA | 1,813(TFs) | 20,405 | 341,285 |
| | | | | 666(coTFs) | 19,832 | 214,048 |
| | | | | 3,456(Sig) | 20,528 | 472,933 |
| Lung squamous cell carcinoma | 482 | RNAseq | TCGA | 1,813(TFs) | 20,426 | 342,737 |
| | | | | 666(coTFs) | 19,948 | 221,178 |
| | | | | 3,453(Sig) | 20,498 | 397,774 |
| Ovarian serous cystadenocarcinoma | 262 | RNAseq | TCGA | 1,813(TFs) | 20,261 | 247,063 |
| | | | | 666(coTFs) | 19,082 | 150,949 |
| | | | | 3,456(Sig) | 20,459 | 334,906 |
| Prostate aderiocarcinoma | 297 | RNAseq | TCGA | 1,813(TFs) | 20,215 | 228,977 |
| | | | | 666(coTFs) | 19,599 | 180,315 |
| | | | | 3,456(Sig) | 20,466 | 315,155 |
| Rectum adenocarcinoma | 163 | RNAseq | TCGA | 1,810(TFs) | 18,506 | 236,899 |
| | | | | 666(coTFs) | 16,939 | 173,579 |
| | | | | 3,455(Sig) | 19,773 | 332,088 |
| Stomach adenocarcinoma | 238 | RNAseq | TCGA | 1,808(TFs) | 22,017 | 267,138 |
| | | | | 661 (coTFs) | 20,984 | 194,782 |
| | | | | 3,442(Sig) | 22,458 | 438,054 |
| Thyroid carcinoma | 498 | RNAseq | TCCA | 1,813(TFs) | 20,478 | 333,725 |
| | | | | 666(coTFs) | 20,038 | 225,544 |
| | | | | 3,369(sig) | 20,511 | 408,356 |
| Uterine corpus endometrial carcinoma | 517 | RNAseq | TCGA | 1,813(TFs) | 20,471 | 150,994 |
| | | | | 666(coTFs) | 20,190 | 237,518 |
| | | | | 3,456(Sig) | 20,527 | 501,212 |
| Glioblastoma multiforme | 154 | RNAseq | TCGA | 1,811(TFs) | 18,354 | 259,025 |
| | | | | 660(coTFs) | 16,655 | 157,230 |
| | | | | 3,455(Sig) | 19,616 | 393,595 |
| Low grade glioma | 370 | RNAseq | TCGA | 1,813(TFs) | 20,357 | 328,373 |
| | | | | 666(coTFs) | 19,558 | 228,634 |
| | | | | 3,455(Sig) | 20,463 | 372,802 |
| Skin cutaneous melanoma | 374 | RNAseq | TCGA | 1,813(TFs) | 20,475 | 281,486 |
| | | | | 666(coTFs) | 19,656 | 177,388 |
| | | | | 3,453(Sig) | 20,501 | 418,136 |
| Sarcoma | 105 | RNAseq | TCGA | 1,715(TFs) | 14,262 | 142,041 |
| | | | | 620(coTFs) | 10,920 | 72,486 |
| | | | | 3,024(Sig) | 15,552 | 177,063 |

Although various techniques or experimental assay providing accurate, tissue-specific assessments of protein regulons can be effective, results indicate that ARACNe can outperform certain other techniques that derive regulons from genome-wide chromatin immunoprecipitation (ChIP) databases, including ChIP enrichment analysis (ChEA), Encyclopedia of DNA Elements (ENCODE), and literature curated Ingenuity networks. ARACNe can be used to detect maximum information path targets to allow identification of regulons that report on the activity of proteins representing indirect regulators of transcriptional target expression, such as signaling proteins.

In some embodiments, VIPER can be based on a probabilistic framework that directly integrates target 'mode of regulation,' (e.g., whether targets are activated or repressed) to compute the enrichment of a protein's regulon in differ-entially expressed genes (FIGS. 1B, 10, and 11). In some embodiments, VIPER can also be based on a probabilistic framework that directly integrates statistical confidence in regulator-target interactions to determine the enrichment of a protein's regulon in differentially expressed genes (FIG. 1B). In some embodiments, VIPER can also be based on a probabilistic framework that directly integrates target overlap between different regulators (e.g., pleiotropy) to determine the enrichment of a protein's regulon in differentially expressed genes (FIG. 1D). Several methods can be used to assess the enrichment of a plurality of genes (e.g., gene set) in genes that are differentially expressed in a specific gene expression signature. These methods can include the Fisher's exact test, T-profiler and gene set enrichment analysis (GSEA), hereinafter also referred to collectively as the gene enrichment analysis methods. In each of the gene enrichment analysis methods, the contribution of individual genes to signature enrichment can be binary (e.g., 0 or 1). In contrast, VIPER can use a fully probabilistic yet efficient enrichment analysis framework, supporting seamless integration of genes with different likelihoods of representing activated, repressed or undetermined targets, and probabilistic weighting of low vs. high-likelihood protein targets. To achieve this, an analytic rank-based enrichment analysis, hereinafter also referred to as "aREA," which is statistical analysis based on the mean of ranks (FIG. 1C) can be used and is described in greater detail below. A normalized enrichment score can be calculated using aREA to quantitatively infer differential protein activity.

Figure 2:
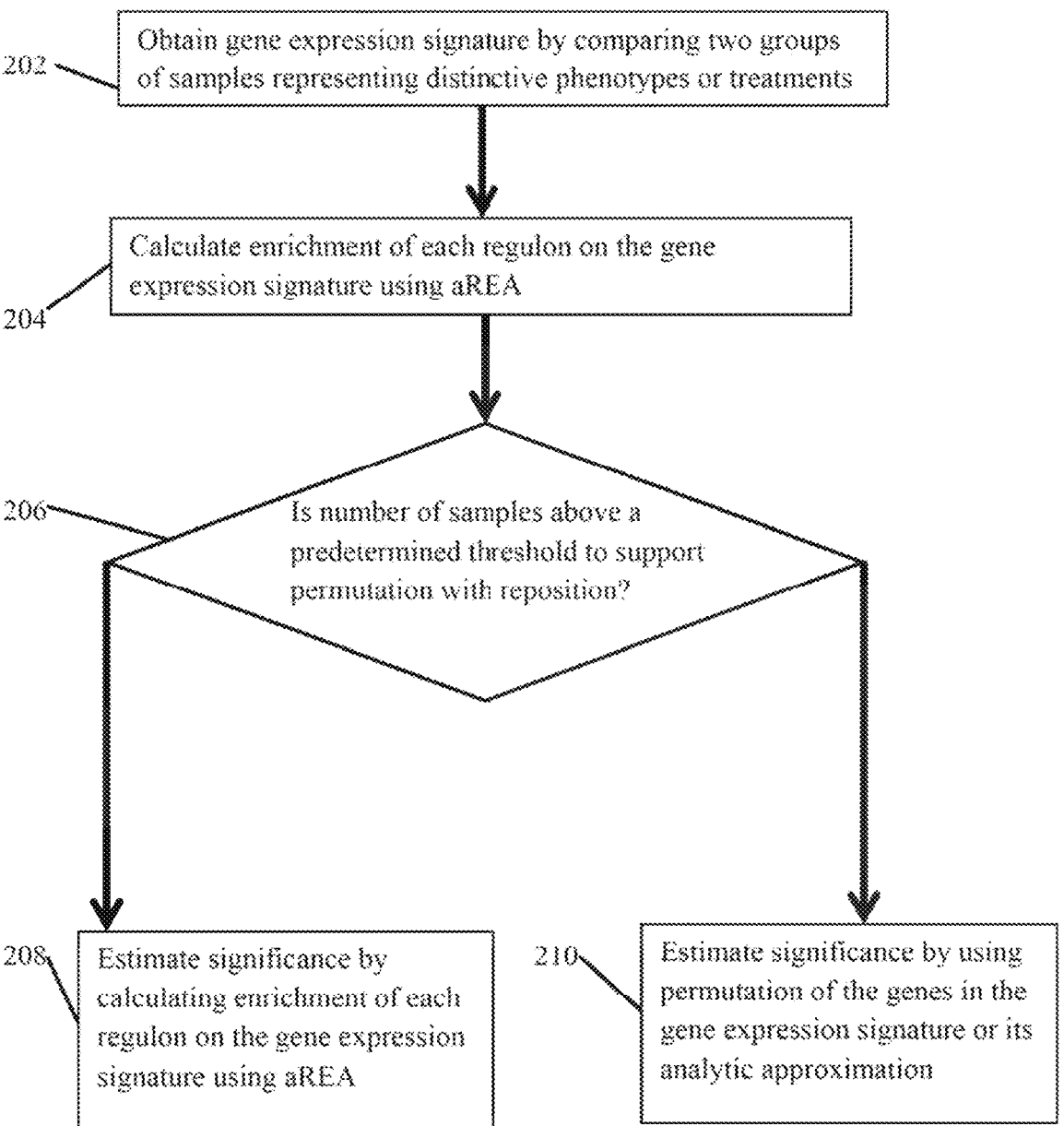
FIG. 2 illustrates the VIPER technique used to test for regulon enrichment on gene expression signatures.

FIG. 2 shows, for the purpose of illustration and not limitation, a method 200 to test for regulon enrichment on gene expression signatures, referred to herein as VIPER. At 202, the method can include obtaining gene expression signature by comparing two groups of samples representing distinctive phenotypes or treatments. Any suitable method that generates a quantitative measurement of difference between the groups can be used (e.g., fold change, Student's t-test, Mann-Whitney U test, etc.). Alternatively, single-sample-based gene expression signatures can be obtained by comparing the expression levels of each feature in each sample against a set of reference samples by any suitable method, including for example Student's t-test, Z-score transformation or fold change; or relative to the average expression level across all samples when clear reference samples are not available. At 204, the enrichment of each regulon on the gene expression signature can be calculated using different implementations of aREA as described in greater detail below with relation to FIG. 3. At 206, the method can include determining whether the number of samples is above a predetermined threshold to support permutation with reposition. For example, in an exemplary embodiment, the threshold can be set to be at least five samples per group. At 208, in response to determining that the number of samples is above a threshold to support permutation with reposition, the significance, including P value and normalized enrichment score, can be estimated by comparing each regulon enrichment score to a null model generated by randomly and uniformly permuting the samples 1,000 times. At 210, in response to determining that the number of samples is not enough to support permutation with reposition, permutation of the genes in the gene expression signature or its analytic approximation can be used to estimate significance.

FIG. 3 shows, for the purpose of illustration and not limitation, a method 300 to perform an analytic rank-based enrichment analysis (e.g., aREA). The aREA method can test for a global shift in the positions of each regulon gene when projected on the rank-sorted gene expression signature. The mean of the quartile-transformed rank positions can be used as a test statistic (e.g., enrichment score). The enrichment score can be determined twice. At, 302, a first enrichment score can be determined by using a one-tail approach, based on the absolute value of the gene expression signature (e.g., genes can be rank-sorted from the less invariant between groups to the most differentially expressed, regardless of the direction of change). At 304, a second enrichment score can be calculated by using a two-tail approach, in which the positions of the genes whose expression can be repressed by the regulator (R−) can be inverted in the gene expression signature before determining the enrichment score. At 306, the first and second enrichment scores can be integrated while weighting their contribution based on the estimated mode of regulation through a 'three-tail' approach technique. At 308, the contribution of each target gene from a given regulon to the enrichment score can be weighted based on the regulator-target gene interaction confidence. At 310, the statistical significance for the enrichment score can be calculated and/or estimated by comparison to a null model generated by permuting the samples uniformly at random or by an analytic approach equivalent to shuffle the genes in the signatures uniformly at random.

In some embodiments, the arithmetic mean-based enrichment score can have several desirable properties, both at the algebraic level, by making the weighted contribution of the targets to the enrichment score trivial to formulate, as well as at the computational level. Given the linear nature of the mean-based enrichment score, its computation across the elevated number of permutations required to generate the null model can be performed efficiently by matrix operations. Additionally, the use of the arithmetic mean as enrichment score can allow analytical approaches to estimate its statistical significance, which is equivalent to shuffle the genes in the signatures uniformly at random. In some embodiments, the null hypotheses tested by these two alternative approaches can be different and/or non-equivalent. For example, in the case of sample shuffling, it can be determined whether the calculated enrichment score for a given gene expression signature (e.g., for gene expression profiles associated with the phenotypes) is significantly higher than the enrichment score obtained when there is no association between the phenotype and the gene expression profile. Conversely, gene shuffling and/or its analytic approximation can be used to determine whether the enrichment score is higher than the enrichment score obtained when the set of genes to test is uniformly distributed in the gene expression signature. Gene shuffling can be approximated analytically as follows. According to the central limit theorem, the mean of a sufficiently large number of independent random variables can be approximately normally distributed. The enrichment score of the null hypothesis can fulfill this condition, and a mean of zero and variance equal to one for the enrichment score under the null hypothesis by applying a quartile transformation based on the normal distribution to the rank-transformed gene expression signature before determining the enrichment score. Under the null hypothesis, the enrichment score can be normally distributed with mean equals zero and variance of 1/n, where n is the regulon size. This definition can be generalized, when the weighted mean is used, by the following formula:

$$\sigma^2 = \sum_{i=1}^{n} w_i^2 \qquad (1)$$

where $w_i$ is the weight for target i.

Figures 11A, 11B:
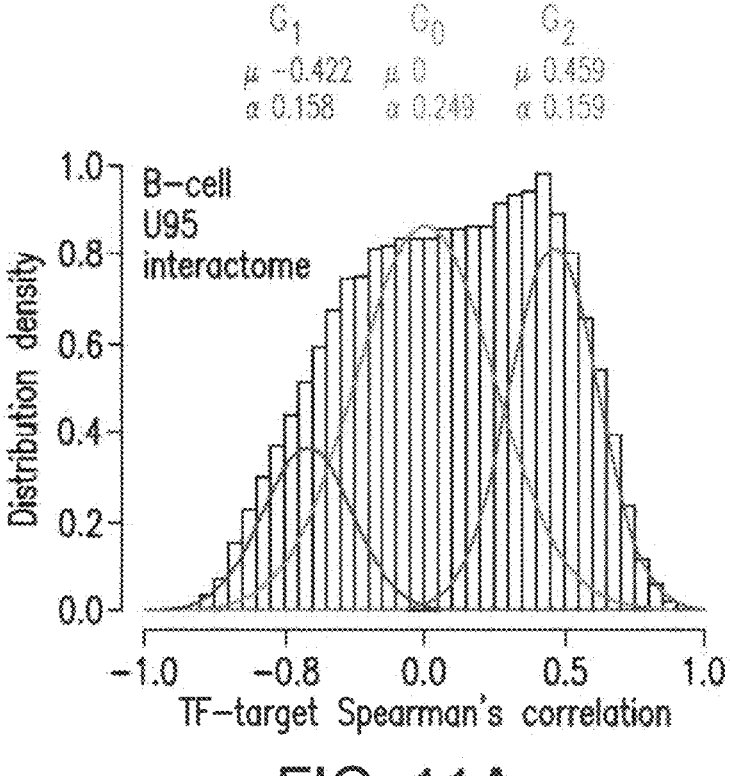
FIGS. 11A-11H illustrate results for inferring the mode of regulation.
Figure 11C:
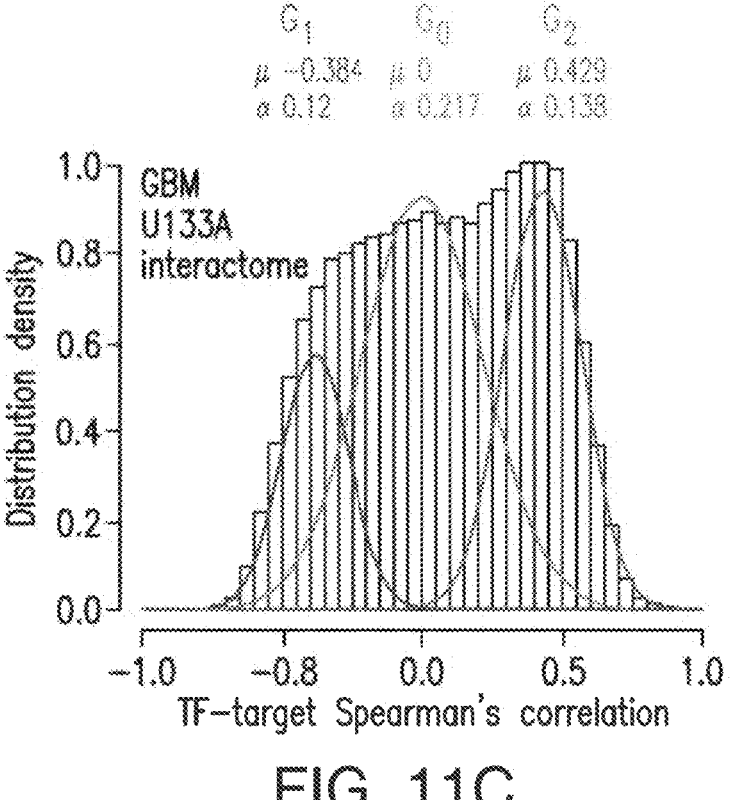
Figure 11D:
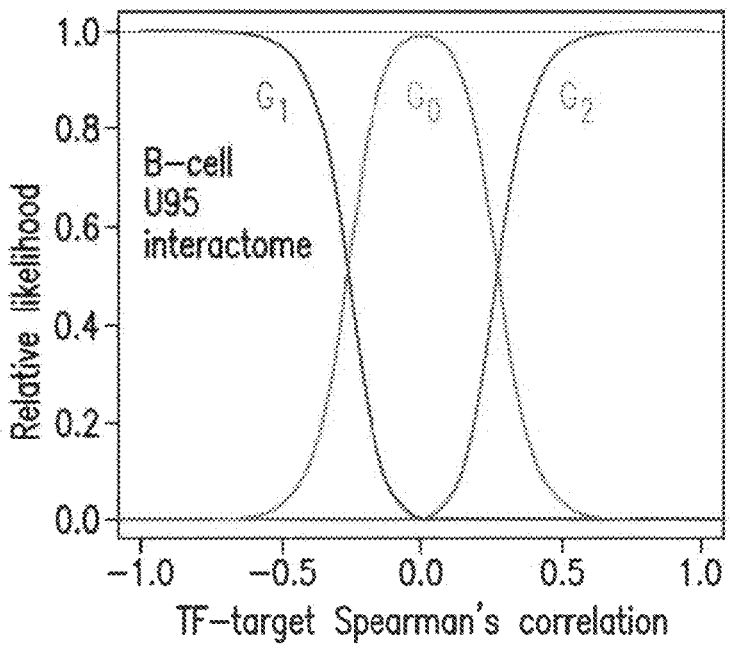
Figure 11E:
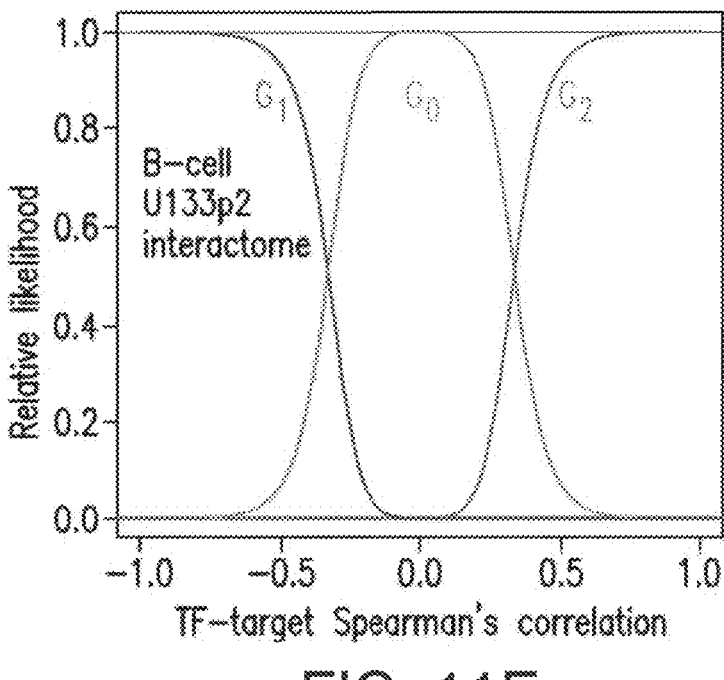
Figure 11F:
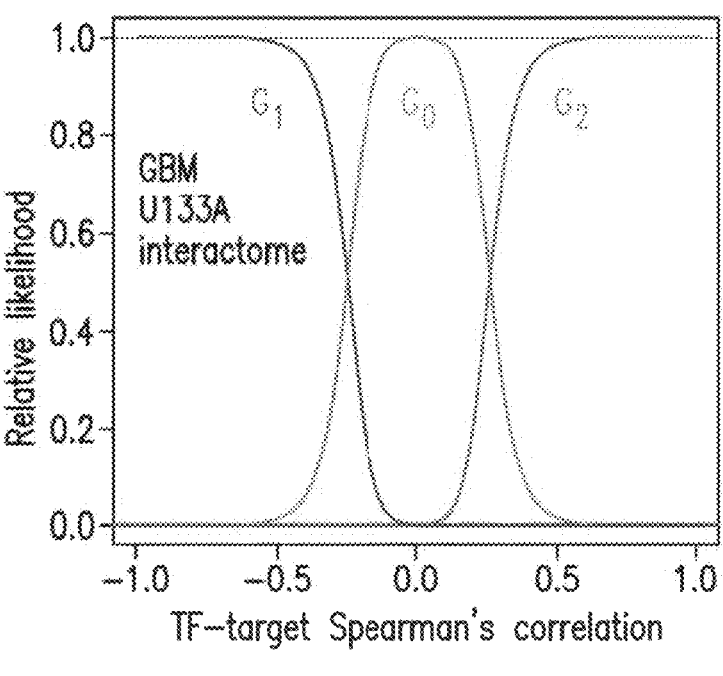
Figure 11G:
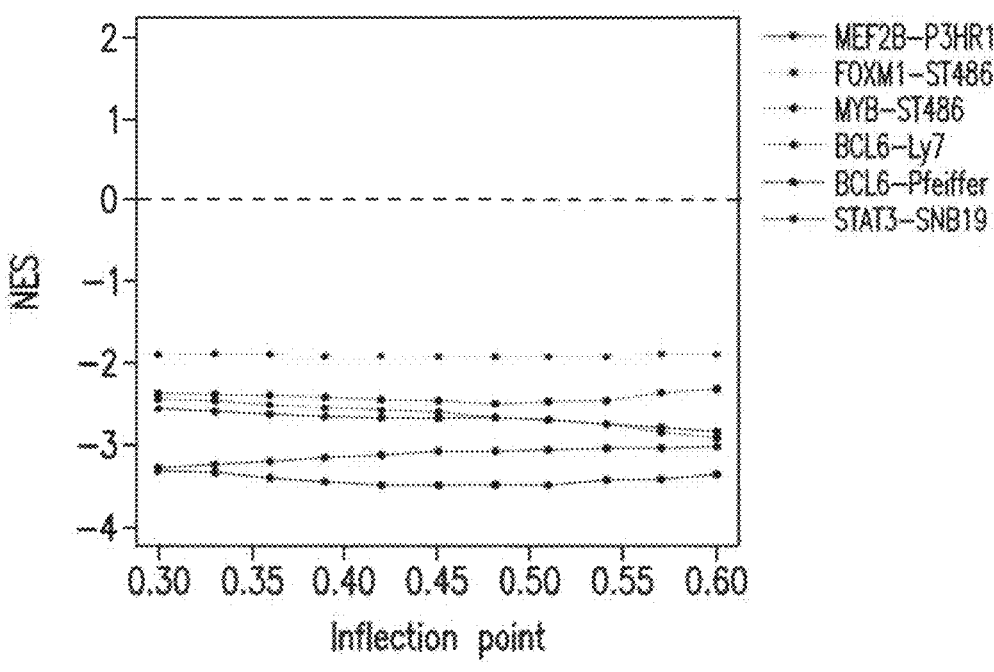
Figure 11H:
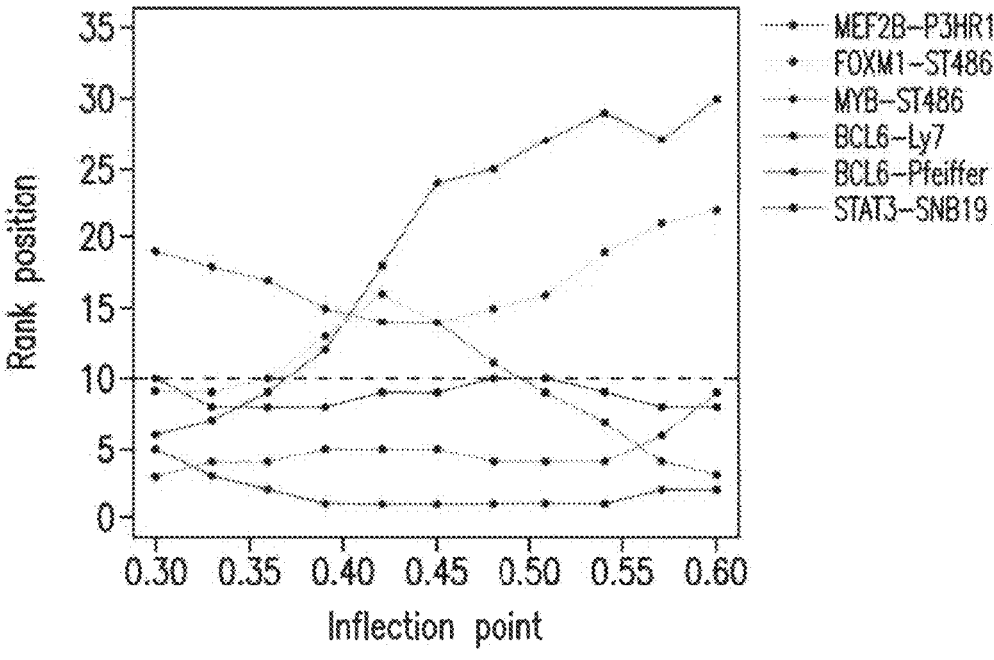

In some embodiments, the mode of regulation (MoR) can be determined based on the Spearman's correlation coefficient (SCC) between the regulator and the target expression, determined from the data set used to reverse engineer the network. However, for complex non-monotonic dependencies (e.g., for context-specific rewiring), assessing the MoR cannot be trivial. To address this issue, the SCC probability density can be modeled for all regulator-target interactions in the network using a three-Gaussian mixture (FIGS. 10A-10D), representing (i) clearly repressed targets (MoR−), (ii) clearly activated targets (MoR+), and (iii) non-monotonically regulated targets for which the MoR cannot be reliably estimated (MoRNM). For example, FIG. 10A illustrates the TF-target Spearman's correlation coefficient distribution fitted to 3-Gaussian models mixture and can illustrate is the estimated mean (m) and standard deviation (s) for each distribution and the final log-likelihood for the fit. FIGS. 10B-10D illustrate scatter-plots for TF (x-axis) and target genes (y-axis) showing the most negative (FIG. 10B), weakest (FIG. 10C), and most positive (FIG. 10D) Spearman's correlation coefficient. The parameters for the three-Gaussian mixture model can be estimated. Instead of defining MoR+ or MoR− targets based on the sign of the SCC, each target can be associated with three weights (e.g., pA, pR, pNM), representing the probability that, given its SCC, it can be activated, repressed, and/or non-monotonically regulated. These probabilities can be determined as the relative likelihood of a given regulator-target interaction to be described by any of these three models and determined as the difference between the cumulative distribution for activation (CDF(G2)) and the CDF for repression (CDF(G1)), divided by the total CDF: CDF(G1 upper-tail)+CDF(G2 lower-tail)+CDF(G0 lower-tail for Rho<0 or G0 upper-tail for Rho>0) (FIGS. 11A-11F). FIGS. 11A-11C illustrate histogram and distribution density (dotted line) of the TF-target Spearman's correlation coefficient for the B-cell U95, U133plus2 and GBM U133A interactomes, respectively. FIGS. 11A-11C also illustrate three Gaussians distributions that were fitted to the data (G1 for the repressed targets, G2 for the induced targets, and G0 for the targets for which MoR cannot be determined), whose parameters are shown in the figure. FIGS. 11D-11F illustrate the proportion of G1 (blue), G0 (green) and G2 (red) gaussian distributions relative to all three distributions for each interactome. FIGS. 11G-H illustrate the effect of the 'mean' parameter in G1 and G2 on the VIPER-inferred relative protein activity shown as NES (FIG. 11G) and the rank position of the silenced TF (FIG. 11H). Each line can represent the result from a different benchmarking experiment.

The aREA-3T approach can be implemented in VIPER can use MoR to weight the contribution of the one-tail- and two-tail-based enrichment scores as:

ES=|MoR|ES2+(1−|MoR|) ES1, where ES1 and ES2 are the one-tail aREA and two-tail aREA estimations of the enrichment score (FIG. 1C). Such probabilistic formulation can avoid selection of arbitrary thresholds for determining target MoR, reducing parameter choices and thus risk of data overfitting. The aREA-3T approach can demonstrate remarkable robustness to changes in the parameter estimates for the three-Gaussian mixed model. For example, upon scanning the 'mean' parameter space can be scanned on a wide range (e.g., from −0.3 to −0.6 for G1 and from 0.3 to 0.6 for G2), a uniform response of aREA on the estimated normalized enrichment score and P values across all benchmarking experiments can be found with only the rank positions being slightly affected (FIGS. 11G, 11H).

Regulator-Target Confidence

Figures 26A, 26B, 26C:
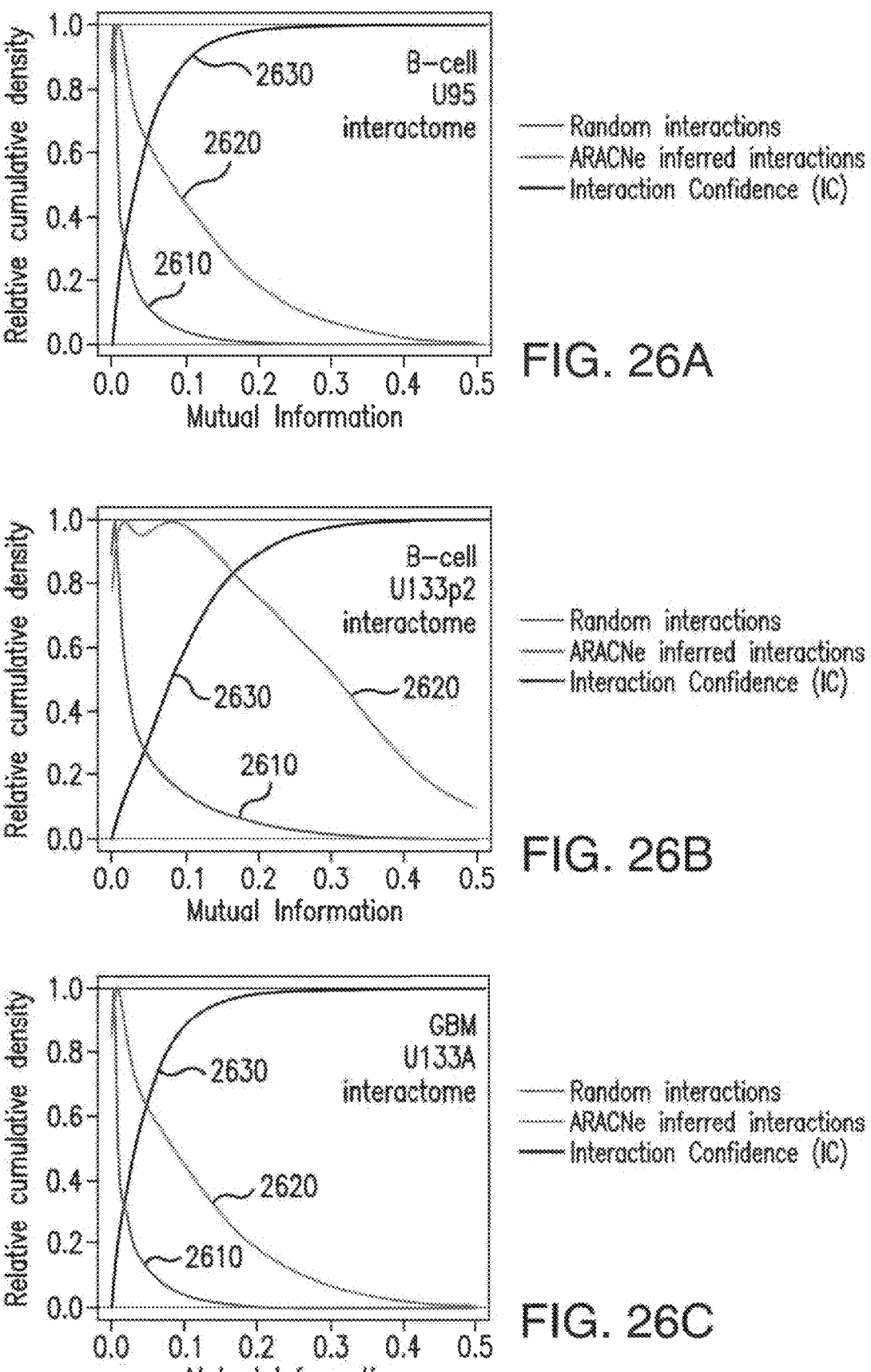
FIGS. 26A-26C illustrate Interaction Confidence (y-axis) as a function of the interaction mutual information (x-axis) for the B-cell U95 (FIG. 26A), B-cell U133plus2 (FIG. 26B), and GBM U133A (FIG. 26C) interactomes.

In some embodiments, the statistical significance of the mutual information (MI) or Spearman's correlation or other measures of statistical independence between a regulator and target gene mRNA levels can be used as a metric of the regulator-target interaction confidence. To compute a regulator-target interaction confidence score, a null set of interactions can be generated for each regulator by selecting target genes at random from all the profiled genes while excluding those in the actual regulon (e.g., ARACNe inferred). The number of target genes for the null regulon can be chosen to match those in the actual regulon. A CDF can be determined for the MI in the ARACNe regulons (CDF1) and null regulons (CDF2). The confidence score for a given regulator-target interaction (interaction confidence or IC) can be estimated as the ratio: IC=CDF1/(CDF1+CDF2). IC can be used to weight the contribution of each target gene to the enrichment score (FIGS. 26A-26C). FIGS. 26A-26C illustrate interaction confidence (y-axis) as a function of the interaction mutual information (x-axis) for the B-cell U95 (FIG. 26A), B-cell U133plus2 (FIG. 26B) and GBM U133A (FIG. 26C) interactomes. FIGS. 26A-C also illustrate kernel estimates for the distribution density of random interactions (2610), and interactions inferred by ARACNe (2620). Both curves can be scaled so their maximum value is one. Curve 2630 can illustrate the IC.

Pleiotropy

Figure 27A:
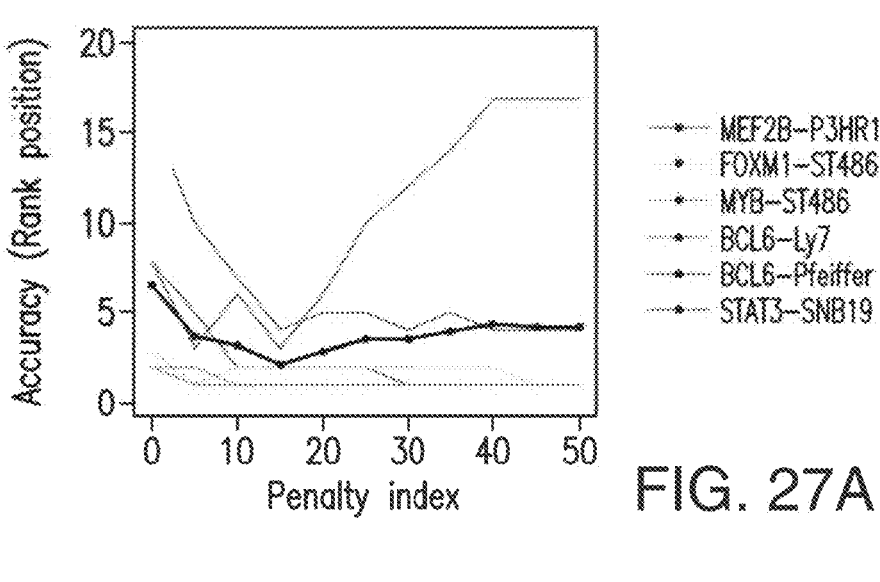
FIGS. 27A-27C illustrate the effect of the pleiotropy index parameter (PI) on VIPER results assessed with the benchmark data.
Figure 27B:
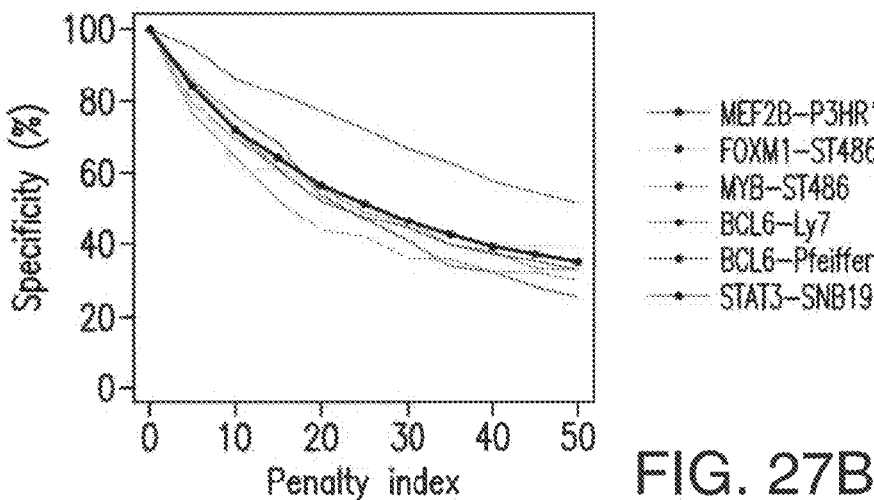
Figure 27C:
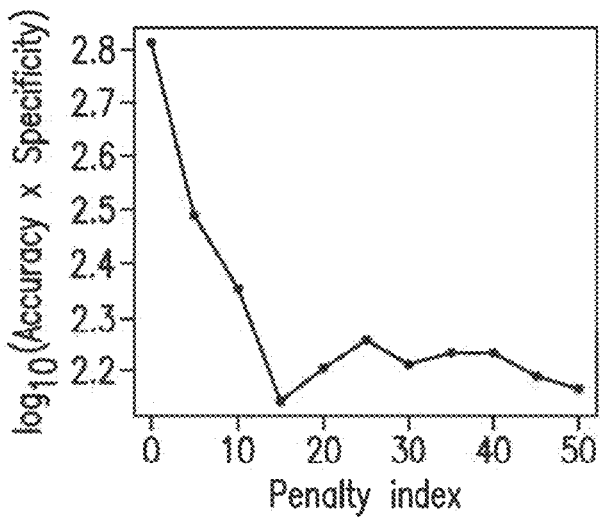

In some embodiments, the pleiotropic regulation of gene expression (e.g., genes regulated by several different transcription factors) can lead to false positive results if a non-active regulator shares a significant proportion of its regulon with a bona fide active regulator (FIG. 1D and Table 10). To account for this effect, a shadow analysis procedure can be used to take full advantage of the probabilistic framework used by VIPER. All possible pairs of regulators AB satisfying two conditions can be generated, the first condition being that both A and B regulons are significantly enriched in the gene expression signature (P<0.05), and the second condition being that they co-regulate (A∩B) at least ten genes. Whether the regulons in each pair are enriched can be determined in the gene expression signature a result of the co-regulated genes. Such a determination can be performed by determining the enrichment of the co-regulated genes (A∩B) on a subset of the gene expression signature representing only the genes in A (pA) and in B (pB), where pA and pB represent the estimated P values for the enrichment determined by aREA. The pleiotropy differential score can be determined as PDE=log 10(pB)−log 10(pA). If pA<pB, the co-regulated genes can be penalized for A by PDE PI/NT, where pleiotropy index (PI) is a constant and NT is the number of test pairs involving the regulon A. Conversely, if pA>pB, the co-regulated genes for B can be penalized by |PDE|PI/NT. VIPER results demonstrate robustness to different values for the pleiotropy index (FIGS. 27A-27C). PI can be set to a value of 20 based on the benchmark data (Table 2) to reach a compromise between accuracy and specificity (FIGS. 27A-27C). FIG. 27A illustrates the accuracy of VIPER predictions, expressed as the rank position for the protein coded by the silenced gene, for varying values of PI. FIGS. 27A-27C illustrate relative specificity expressed as the number of differentially active proteins inferred by VIPER for different values of PI, relative to the predictions obtained when no pleiotropy correction was applied (PI=0). The results for different silencing experiments are shown by the lines 2710, 2720, 2730, 2740, 2750, and 2760 as indicated in FIGS. 27A-27B. Line 2770 shows the average across all experiments. FIG. 27C illustrates the integration of accuracy and specificity across all benchmark experiments. Table 2 illustrates benchmark experiment data.

TABLE 2

| | Benchmark experiments | | | | |
|---|---|---|---|---|---|
| Cell line | Knockdown gene | Tech-nology | Repli-cates | Profile platform | DEG[a] at P < 0.01 |
| P3HR1 (lymphoma) | MEF2B | shRNA[b] | 5 | HG-U95Av2 | 960 |
| ST486 | FOXM1 | shRNA[b] | 3 | HG-U95Av2 | 276 |

TABLE 2-continued

| | | | | | DEG[a] |
|---|---|---|---|---|---|
| Cell line | Knockdown gene | Tech-nology | Repli-cates | Profile platform | at P < 0.01 |
| (lymphoma) | MYB | shRNA[b] | 3 | HG-U95Av2 | 469 |
| OCI-Ly7 (lymphoma) | BCL6 | siRNA[c] | 3 | HG-U133p2 | 646 |
| Pfeiffer (lymphoma) | BCL6 | siRNA[c] | 3 | HG-U133p2 | 1,311 |
| SNB19 (glioma) | STAT3 | siRNA[c] | 6 | Illumina HT12v3 | 501 |

[a]Differentially expressed genes.
[b]Short hairpin RNA.
[c]Small interfering RNA.

Fisher's Exact Test

Figures 25A, 25B:
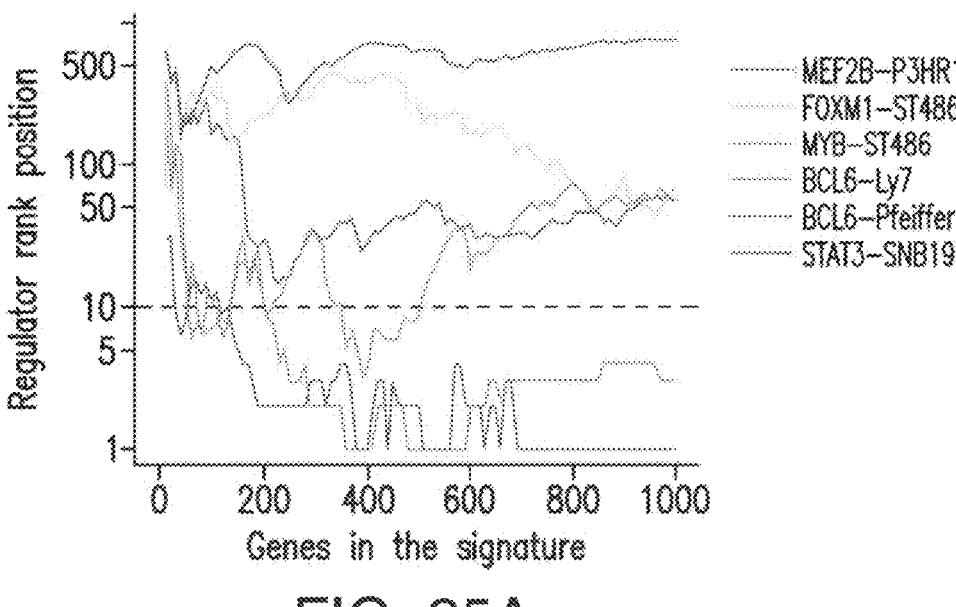
FIGS. 25A and 25B illustrate the rank position in the differential activity signature (y-axis) inferred by 1-tail (25A) and 2-tail FET (25B) as a function of the number of genes considered as differentially expressed (x-axis).

In some embodiments, it can be determined whether the overlap between the subset of genes that were differentially expressed following RNAi-mediated silencing of each gene (P<0.01) and the genes in its regulon is statistically significant by Fisher's exact test (FET). The conventional FET method can consider all differentially expressed genes equally, regardless of whether they are up- or downregulated and hence, FET cannot infer whether the regulator activity is increased or decreased by the perturbation. To address this issue, a modified FET approach is used to compute the enrichment of activated and repressed targets of a regulator (positive and negative parts of its regulon) independently on up- and downregulated genes, respectively. In particular, the genes in each regulon can be divided into two subsets: (i) transcriptionally activated ($R_+$) and (ii) transcriptionally repressed ($R_-$) targets. The sign of the Spearman's correlation can be used between the mRNA expression level for the regulator and each of the genes in its regulon to classify them as part of $R_+$ or $R_-$. This correlation analysis can be performed on the same data set used to infer the network by ARACNe. FET analysis can be performed independently for R. and R-on the two tails of each gene expression signature. Regulators with an increase in activity can show enrichment of $R_+$ targets in overexpressed genes and of R-targets in under expressed genes, respectively. Regulators with a decrease in activity can show an opposite effect. The use of discrete gene lists by FET can result in enrichments that are not robust with respect to threshold selection (FIGS. 25A and 25B). FIGS. 25A and 25B illustrate the rank position in the differential activity signature (y-axis) inferred by 1-tail (FIG. 25A) and 2-tail FET (FIG. 25B) as a function of the number of genes considered as differentially expressed (x-axis).

Gene set enrichment analysis (GSEA) In some embodiments, one-tail GSEA can be implemented. In some embodiments, two-tail GSEA can be used in which, the query regulon can be divided into two subsets: (1) a positive subset containing the genes predicted to be transcriptionally activated by the regulator ($R_+$), and (2) a negative subset encompassing the target genes predicted to be repressed by the regulator ($R_-$). The target genes can be classified as being part of the $R_+$ or $R_-$ subsets based on whether their mRNA levels are positively or negatively correlated with the regulator mRNA levels (e.g., Spearman's correlation). The gene expression signature can be sorted from the most upregulated to the most downregulated gene (e.g., signature A) and the rank positions for $R_+$ can be determined. The rank positions for $R_-$ can be determined from the gene expression signature that is sorted from the most downregulated to the most upregulated gene (e.g., signature B). The enrichment score can be determined, using the determined rank positions for the $R_+$ and $R_-$ subsets and taking the weighting score values only from signature A.

Figure 28:
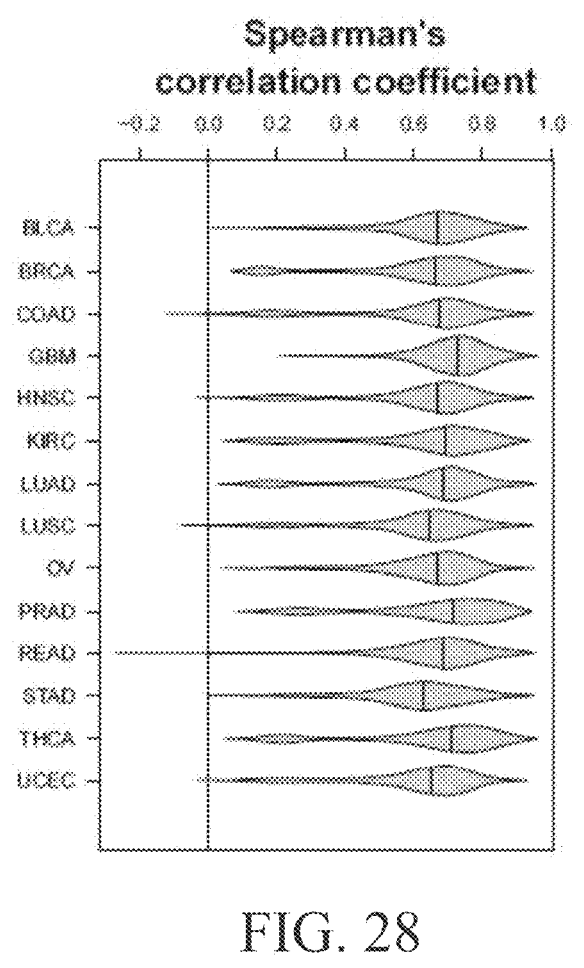

In some embodiments, the residual post-translational (RPT) activity can be determined. In some embodiments, a strong association between VIPER-inferred protein activity and the coding gene mRNA level can be found (FIG. 28). FIG. 28 illustrates a correlation between VIPER-inferred protein activity and coding-gene mRNA level. FIG. 28 illustrates a violin plot showing the density distribution of the Spearman's correlation coefficient for each tumor type.

In some embodiments, the variance in VIPER-inferred protein activity owing to the expression level of the coding gene can be calculated by fitting a lineal model to the rank transformed data. The residuals of such a fit can constitute the remaining variance in protein activity after removing the expression effect. This residual post-translational protein activity (RPT activity) and the expression level of the coding genes can be decoupled.

In some embodiments, the association between nonsilent somatic mutations and three quantitative traits can be estimated by determining the enrichment of the mutated samples on each of the traits using the aREA technique. The quantitative traits can be: (i) mutated gene mRNA levels, (ii) VIPER-inferred global protein activity (G activity), and (iii) VIPER-inferred residual post-translational RPT activity. An integrated association can be obtained by determining the maximum association (e.g., minimum P value) among these traits. The mutant phenotype score can be determined by integrating the relative likelihoods of mutation for a given G- and RPT-activity level. Distribution densities for the mutated and non-mutated (WT) samples, for genes mutated in at least ten samples, can be estimated by a Gaussian kernel. The probabilities, which can be determined by the derived cumulative distribution functions, can be used to compute the relative likelihood for each trait as follows:

$$RL(x) = \frac{p_M(x) - p_{wt}(x)}{p_M(x) + p_{wt}(x)} \qquad (2)$$

where pM and pwt are the estimated probabilities for mutant and WT phenotypes at a given value x of the evaluated trait, either G or RPT activity. The mutant phenotype score (MPS) can be defined as the maximum deviance from zero of the relative likelihood (RL) as defined in equation (2) among the two evaluated traits.

Regulatory Networks

In some embodiments, the regulatory networks can be reverse engineered by ARACNe from any of 20 different data sets (e.g., two B-cell context data sets profiled on Affymetrix HG-U95Av2 and HG-U133plus2 platforms, respectively; a high-grade glioma data set profiled on Affymetrix HG-U133A arrays; and 17 human cancer tissue data sets profiled by RNA-seq from TCGA (Table 1)). In an exemplary embodiment, the Affymetrix platform data sets can be summarized by using probe clusters generated by the 'Cleaner' technique[1]. The cleaner technique[1] can generate 'informative' probe-clusters by analyzing the correlation structure between probes mapping to the same gene and discarding noncorrelated probes, which can represent poorly hybridizing or cross-hybridizing probes. When RNA sequencing data is used, raw counts can be normalized to account for different library size, and the variance can be stabilized by fitting the dispersion to a negative-binomial distribution. The ARACNe network can be executed with 100 bootstrap iterations using all probe clusters mapping to a set of 1,813 transcription factors (e.g., genes annotated in Gene Ontology molecular function database (GO)55 as GO:0003700, 'transcription factor activity,' or as GO:0004677, 'DNA binding,' and GO:0030528, 'transcription regulator activity,' or as GO:0004677 and GO:0045449, 'regulation of transcription'), 969 transcriptional cofactors (a manually curated list, not overlapping with the transcription factor list, built upon genes annotated as GO:0003712, 'transcription cofactor activity,' or GO:0030528 or GO:0045449) or 3,370 signaling pathway related genes (annotated in GO Biological Process database as GO:0007165 'signal transduction' and in GO cellular component database as GO:0005622, 'intracellular,' or GO:0005886, 'plasma membrane') as candidate regulators. Parameters can be set to 0 DPI corresponding to a data processing inequality tolerance and mutual information (MI) P-value threshold of 10-8. The regulatory networks based on ChIP experimental evidence can be assembled from ChEA and ENCODE data. The mode of regulation can be determined based on the correlation between transcription factor and target gene expression as described below.

Benchmarking Experiments

Figure 24A:
FIGS. 24A and 24B illustrate differential expression of the silenced genes.

In some embodiments, benchmarking experiments can be performed. Gene expression profile data can be used after MEF2B32, FOXM1, MYB17 (GSE17172), and BCL6 (GSE45838) silencing in human B cells, and STAT3 silencing in the human glioma cell line SNB19 (GSE19114, Table 2). BCL6 knockdown experiments can be performed in OCI-Ly7 and Pfeiffer GCB-DLBCL cell lines. Both cell lines can be maintained in 10% FBS supplemented IMDM and transiently transfected with either a BCL6-specific or a nontarget control siRNA oligo in triplicate. Total RNA can be isolated 48 hours after transfection, the time at which knockdown of BCL6 protein can be observed as illustrated by FIG. 24A. Gene expression can be profiled on H-GU133plus2 Affymetrix gene chips following the manufacturer protocol (e.g., Affymetrix Inc.).

Figure 24B:
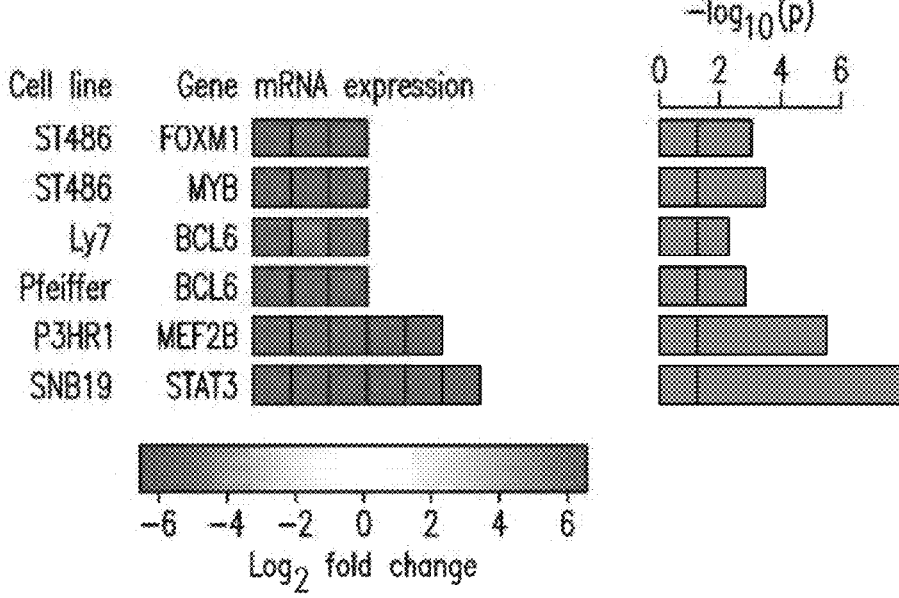

In an exemplary embodiments, all experiments can show a reduction at the mRNA level for the silenced gene as quantified by expression profile as illustrated by FIG. 24B. Gene expression signatures can be obtained by a t-test analysis of the gene expression profiles (Table 2).

Assessment of VIPER's Performance

In some embodiments, VIPER's ability to correctly infer loss of protein activity following RNA interference (RNAi)-mediated silencing of a gene can be determined. For example, MEF2B32, FOXM1, MYB17, and BCL6 genes can be silenced in lymphoma cells and STAT3 in glioblastoma cells can be silenced by RNAi-mediated silencing (Table 2). Multiple cell lines, distinct RNAi silencing protocols, and profiling platforms can be included to avoid bias associated with these variables. Such data can be used to benchmark different regulatory model attributes and enrichment methods.

Figure 12A:
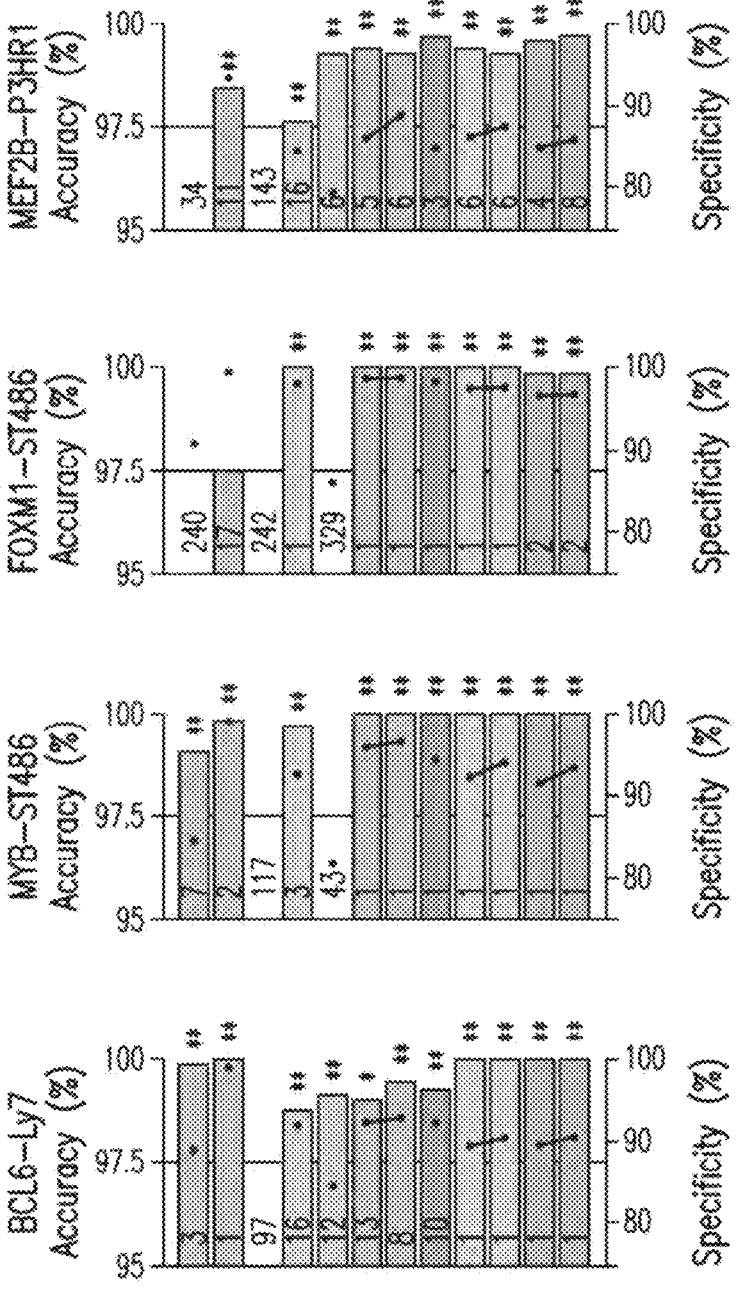
FIGS. 12A-12D illustrate accuracy and specificity results of VIPER for GES determined from multiple samples (FIG. 12A) and for single-samples (FIG. 12B).
Figure 12A:
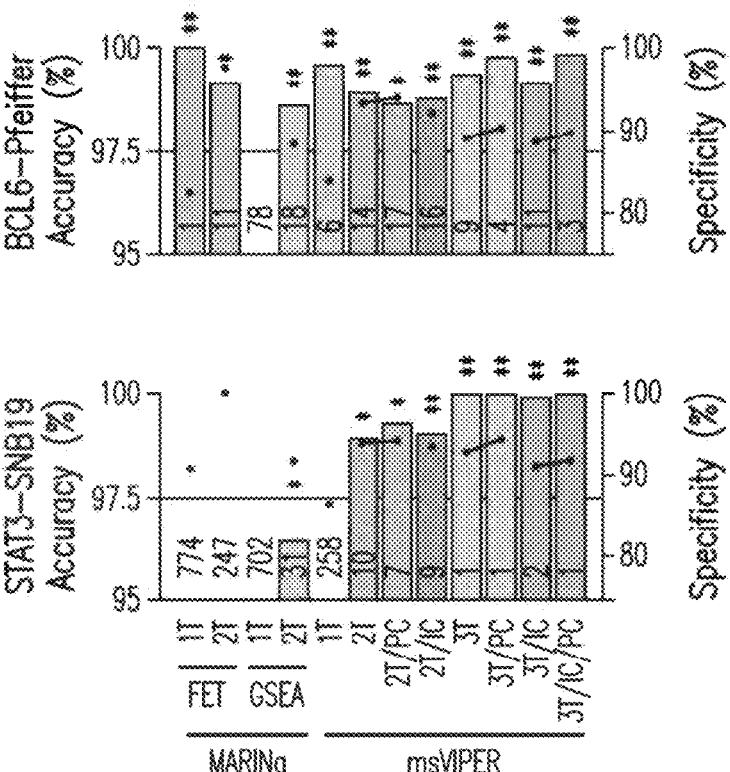
Figure 12B:
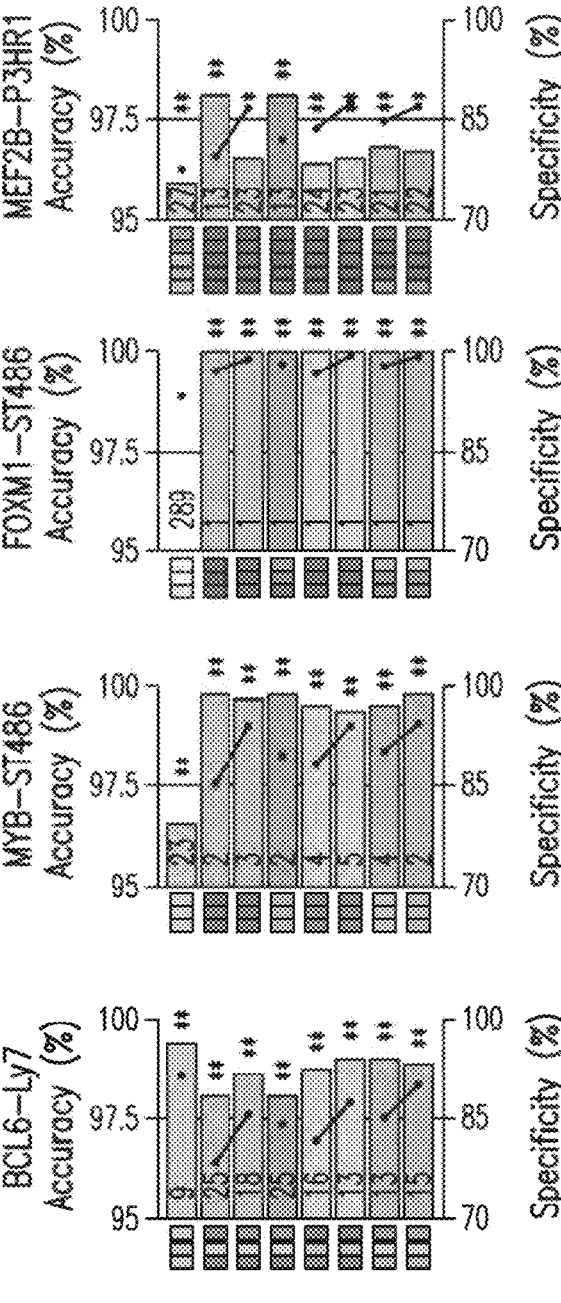
Figure 12B:
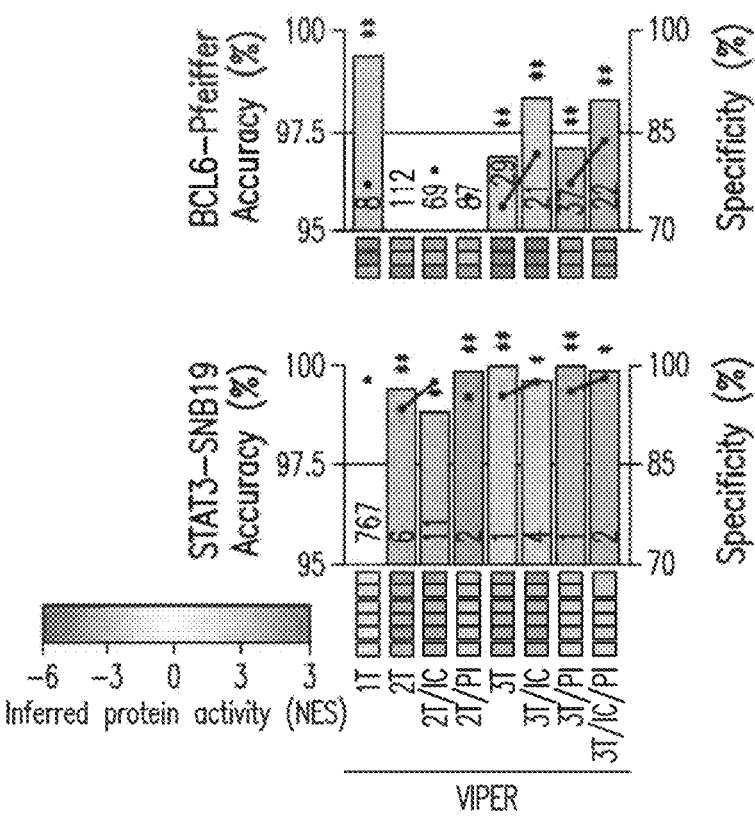
Figure 12C:
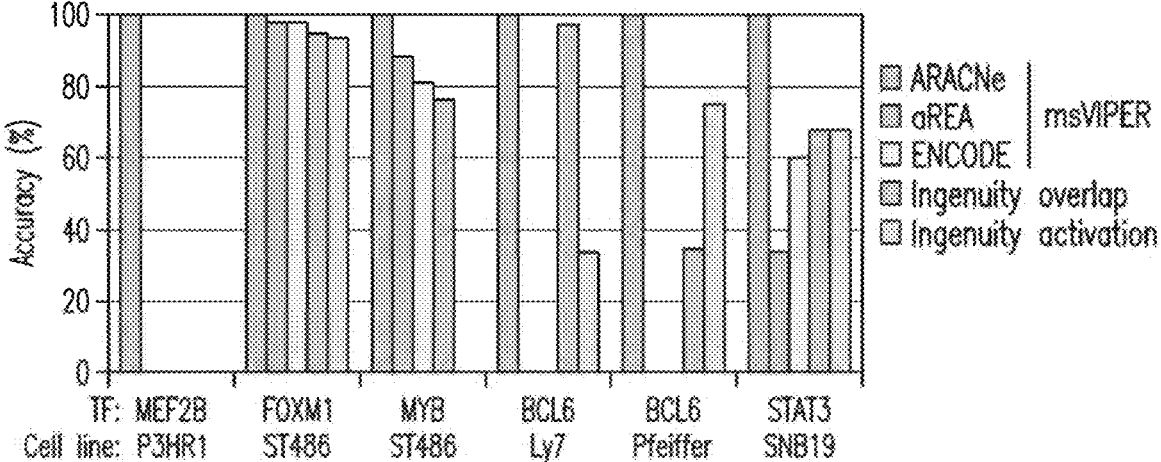
Figure 12D:
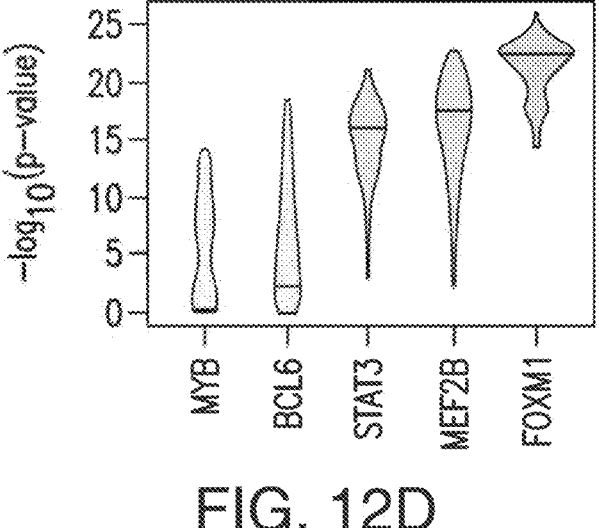
Figure 13:
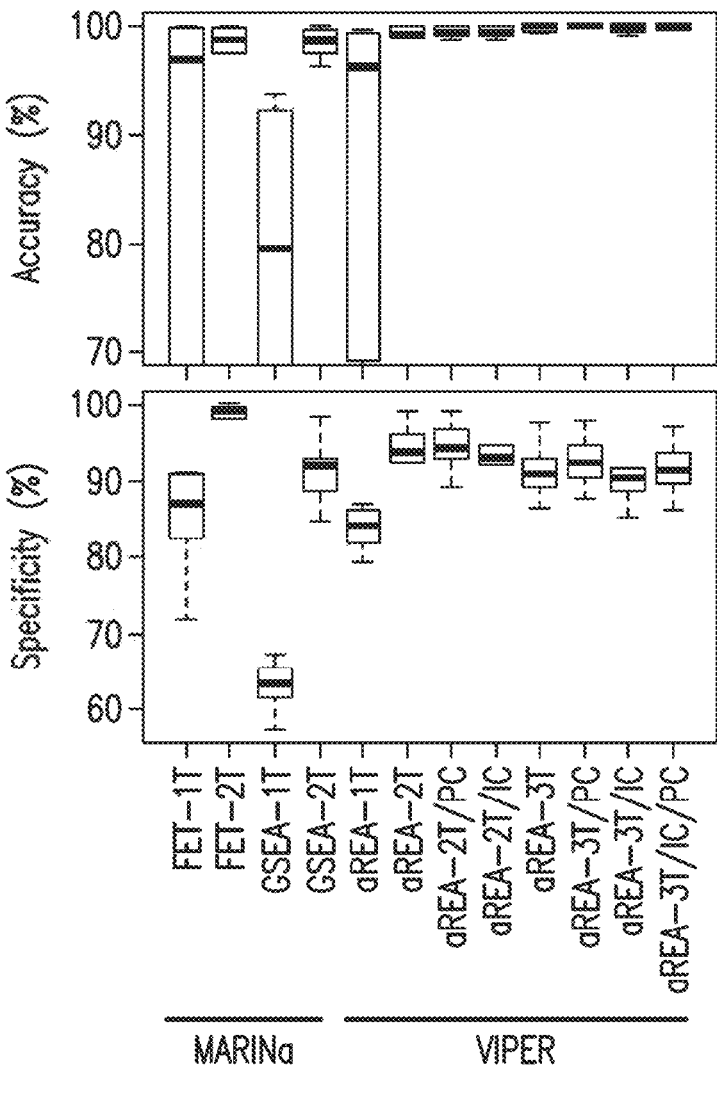
FIG. 13 illustrates accuracy and specificity of protein activity inferred by different algorithms.
Figure 14:
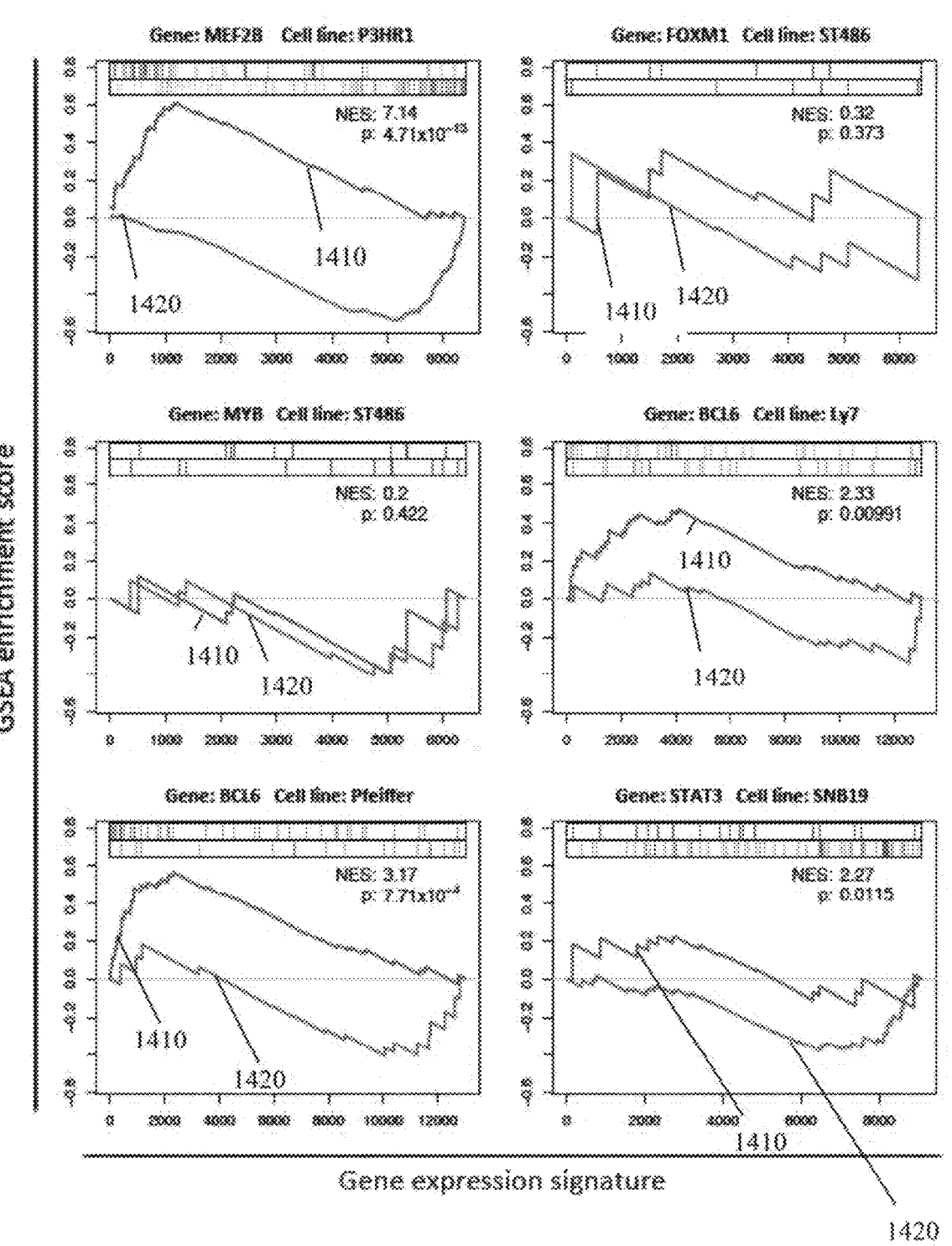
FIG. 14 illustrates Gene Set Enrichment Analysis results for the regulators identified by VIPER as differentially active.

In some embodiments, three metrics can be calculated to determine VIPER performance: (i) the P-value-based rank of the silenced gene (e.g., an accuracy metric), (ii) the total number of statistically significant regulators inferred by VIPER (e.g., a specificity metric), and (iii) the overall P value of the silenced gene. The enrichment analysis methods tested can include aREA, Fisher exact test (one-tail FET) and one-tail GSEA. In addition, extensions of FET and GSEA to account for the mode of regulation of a target gene (e.g., two-tail FET and two-tail GSEA), can also be tested. Use of a three-tail aREA (aREA-3T), accounting for target mode of regulation, confidence and pleiotropic regulation, can demonstrate that such techniques can systematically outperform all other known approaches (FIGS. 1E, 12A, 13, and Table 4). Accordingly, the aREA-3T method can be selected as the methodology of choice for the VIPER technique. The experimentally silenced proteins encoded by MYB, BCL6, STAT3, FOXM1, MEF2B, and BCL6 genes can be ranked as the 1st, 1st, 1st, 2nd, 3rd and 3rd most significantly inactivated proteins among all those tested, respectively (FIG. 12A and Table 4). The small number of additional transcription factors inferred by aREA can be enriched in differentially expressed genes and can accordingly represent downstream targets of the silenced regulators or RNAi off-target effects (FIG. 14). FIGS. 12A-12D illustrate accuracy and specificity of VIPER for GES computed from multiple samples (msVIPER, FIG. 12A) and for single-samples VIPER (FIG. 12B). The barplots of FIGS. 12A and 12B can show the accuracy (relative rank for the silenced gene) and dots showing the specificity (fraction of significant regulators at p<0.05) for six benchmark experiments. The numbers in the bars indicate the rank position for the protein coded by the silenced genes. FIG. 12A shows results obtained by 1-tail and 2-tail versions of FET and GSEA, as previously implemented in MARINa. VIPER results shown include the 1-tail (1T), 2-tail (2T) and 3-tail (3T) implementations of the aREA algorithm, including Interaction Confidence (IC) analysis and Pleiotropy Correction (PC). Different bar colors were used to highlight the use of different algorithms. Boxes under the bars in panel (FIG. 12B) show the single-sample estimation of relative protein activity. * p<0.05,  p<0.01, estimated by permutation analysis as described in methods. FIG. 12C illustrates the accuracy of msVIPER based on alternative regulatory models (ARACNe, ChEA, and ENCODE), and of Ingenuity upstream regulator analysis, for the six bench-mark experiments. FIG. 12**D illustrates the regulon functional conservation across 17 tissue con-text specific networks reverse-engineered by ARACNe from TCGA data (Table 2). Regulon conservation was computed as described in Aytes et. al[1] and expressed as –log 10(p-value).

FIG. 13 illustrates accuracy and specificity of protein activity inferred by different algorithms, including 1-tail (1T) and 2-tail (2T) Fisher's Exact Test (FET), 1-tail and 2-tail Gene Set Enrichment Analysis (GSEA), and the 1-tail, 2-tail, 3-tail implementations of aREA, with Interaction Confidence (IC) and Pleiotropy Correction (PC). Boxplots in FIG. 13 illustrate the accuracy (relative rank for the silenced gene) and specificity (fraction of significant regulators at p<0.05) for six benchmark experiments (see Table 2).

FIG. 14 illustrates Gene Set Enrichment Analysis for the regulators identified by VIPER as differentially active (p<0.05) in each benchmark experiment, on the corresponding experiment gene expression signature. The silenced gene and cell line is indicated on top of each plot. The horizontal axis represents the profiled genes sorted from the most downregulated (on the left) to the most up-regulated (on the right). Only genes represented in the regulatory network can be used for this analysis, including 6,403 genes for P3HR1 and ST486, 13,007 for Ly7 and Pfeiffer, and 8,263 genes for SNB19. The vertical axes indicate the GSEA enrichment score for the regulators showing a decreased (lines 1410) or increased (lines 1420) VIPER-inferred protein activity.

Table 4 shows accuracy and specificity of Fisher's Exact Test (FET), Gene Set Enrichment Analysis (GSEA) and msVIPER for the detection of a reduction in protein activity after coding gene silencing. Table 4 lists the accuracy (rank for the silenced gene), specificity (number of significant regulators at p<0.05) and silenced gene p-value inferred by 1-tail (1T) and 2-tail (2T) FET and GSEA, and by the 1-tail, 2-tail and 3-tail implementations of msVIPER, including Interaction Confidence (IC) analysis and Pleiotropy Correction (PC).

In some embodiments, to evaluate suitability of ARACNe-inferred regulons for use in VIPER, VIPER performance can be benchmarked with non-context-specific regulons, as assembled from ChIP-sequencing (ChIP-seq) data in ChEA and in ENCODE. VIPER can also be benchmarked against the upstream regulator module of Ingenuity Pathway Analysis. ARACNe-based VIPER can outperform these approaches (FIG. 12C). The alternative methods/models can correctly assess that protein activity decreases only for FOXM1 following its silencing. Among the five tested transcription factors, FOXM1 can be the only one representing a core cell cycle regulator, whose regulon is strongly conserved across multiple tissue contexts (FIG. 12D), thus not requiring use of context-specific regulatory models.

From each experiment, signatures can be generated using the control-sample-based Z transformation to allow analysis of individual samples (Table 2). Results from single-sample analyses can be virtually identical to those obtained with the multisample version of VIPER (FIGS. 1E, 12B, and Table 5), suggesting that single-sample analysis produces robust and highly reproducible results. Table 5 shows Accuracy and specificity of VIPER for the detection of a reduction in protein activity after coding gene silencing. The table lists the accuracy (rank for the silenced gene), specificity (number of significant regulators at p<0.05) and silenced gene p-value inferred by the 1-tail (1T), 2-tail (2T) and 3-tail (3T) implementations of VIPER, including Interaction Confidence (IC) analysis and Pleiotropy Correction (PC).

Additional benchmarks can be performed to assess the specific improvements owing to the aREA probabilistic analysis, compared to GSEA, and to assess the overall ability of the technique to correctly identify proteins whose activity was modulated by RNAi and small-molecule perturbations, or whose abundance was quantified by reverse-phase protein arrays (FIGS. 15-18 and Tables 6-8).

Table 6 shows the number of profiled samples, and profiled proteins and isoforms per sample in the RPPA dataset from TCGA. Table 7 shows the number of RPPA profiled proteins and significant associations at the transcripts (mRNA expression) and VIPER-inferred global protein activity (G-activity) levels (p<0.05, Spearman's correlation analysis). Table 8 shows the number of RPPA profiled protein isoforms and significant associations at the transcripts (mRNA expression), VIPER-inferred global protein activity (G-activity), residual post-translational VIPER-inferred activity (RPT-activity) and their integration (Integrated activity) with the protein isoform levels at p<0.05 by Spearman's correlation analysis.

Based on the benchmarking results, a comprehensive map of protein activity dysregulation can be generated in response to short-term pharmacologic perturbations. In some embodiments, 166 compounds can be selected in CMAP33 that induced reproducible perturbation profiles across replicates (FDR<0.05) and can affect the activity of 2,956 regulatory proteins.

Technique Robustness

Due to poor reproducibility across biological replicates, gene expression analysis has not been broadly adopted in clinical tests. In some embodiments, the reproducibility of the VIPER inferences can be rigorously assessed as a result of multiple sources of technical and biological noise (FIGS. 4A-4F).

Figure 4A:
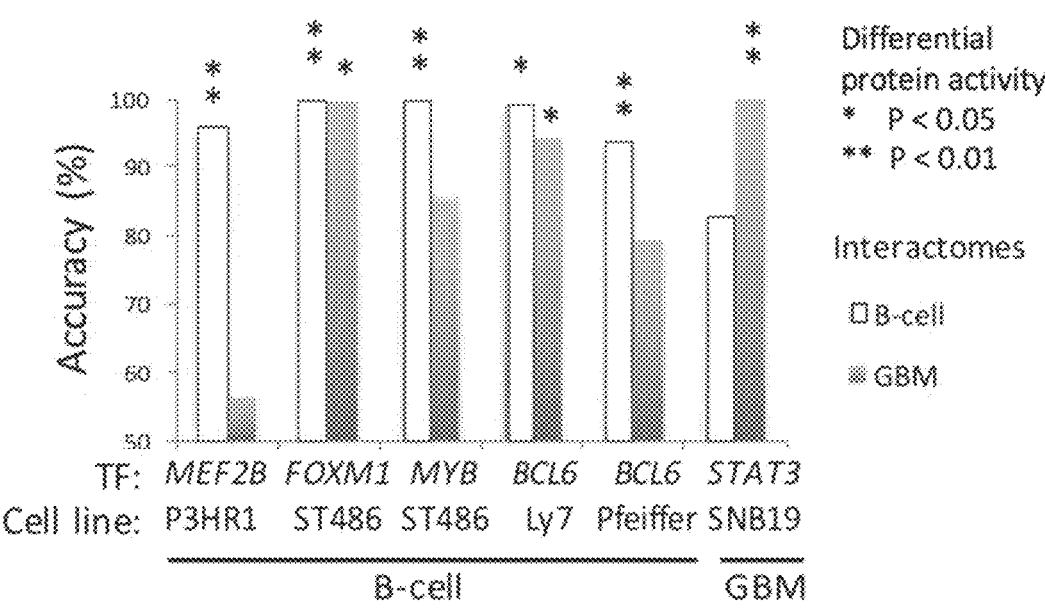
FIGS. 4A-4F illustrate the effects of network and signature quality on VIPER results.
Figure 4B:
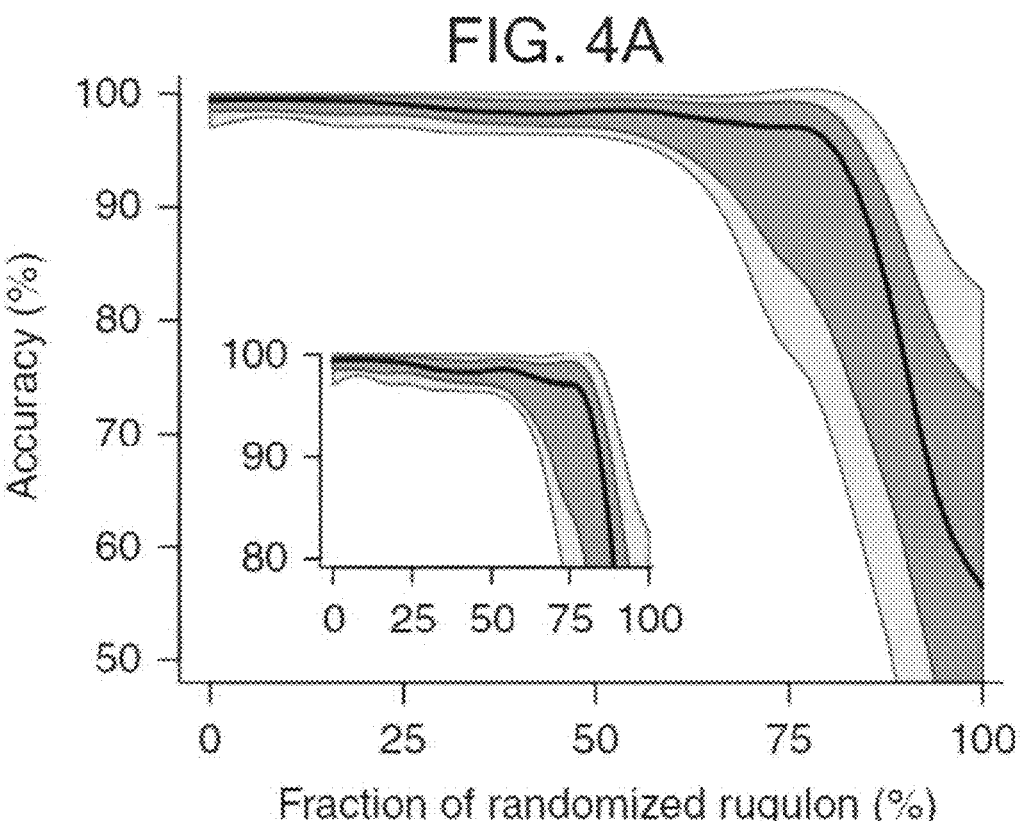
Figures 4C, 4D:
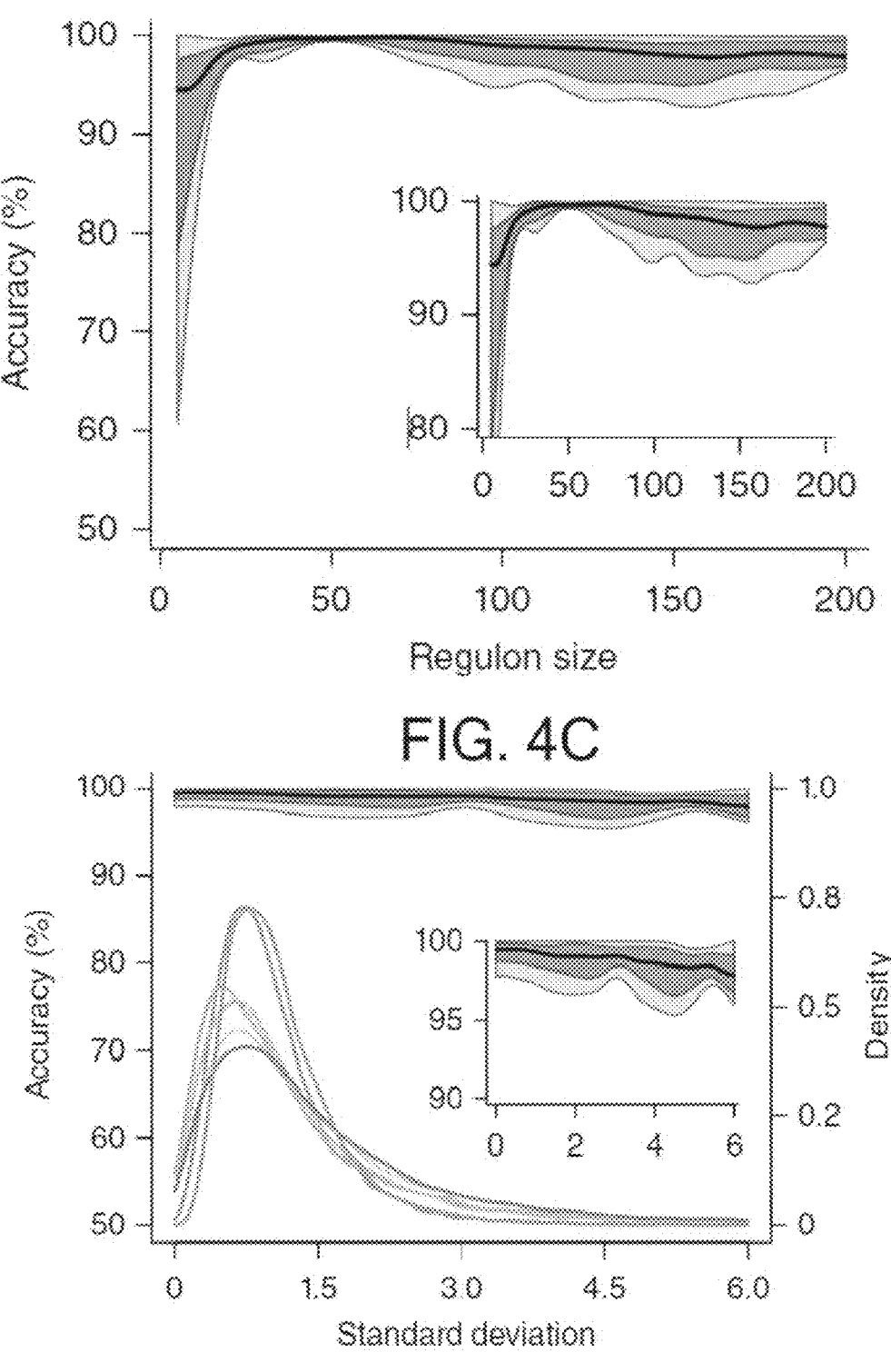
Figure 4E:
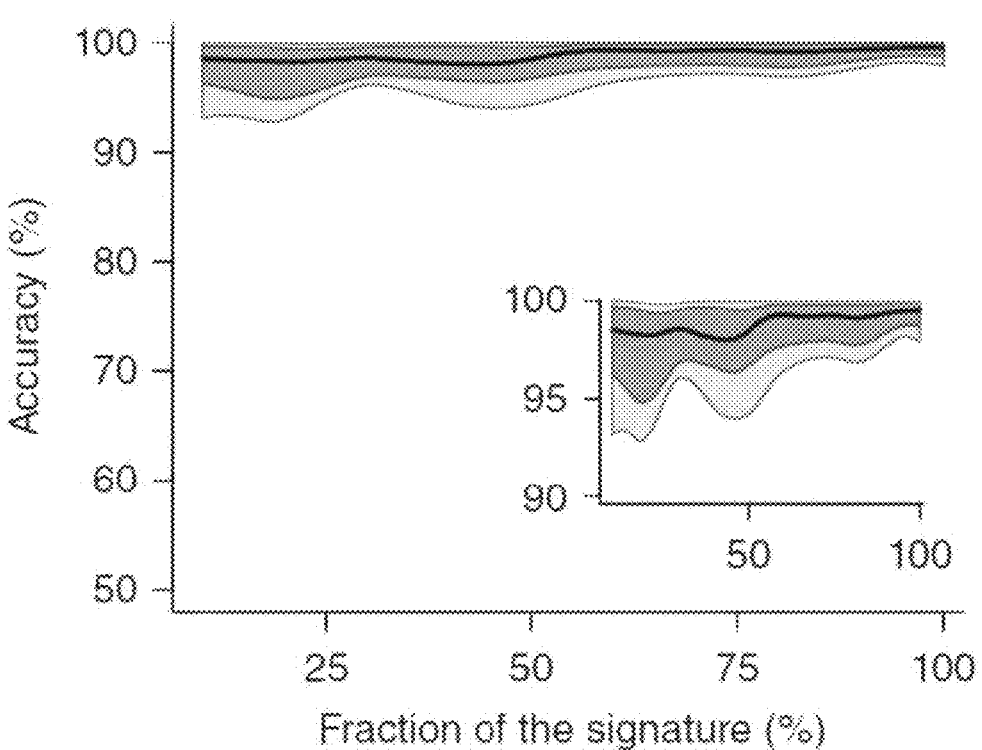
Figure 4F:
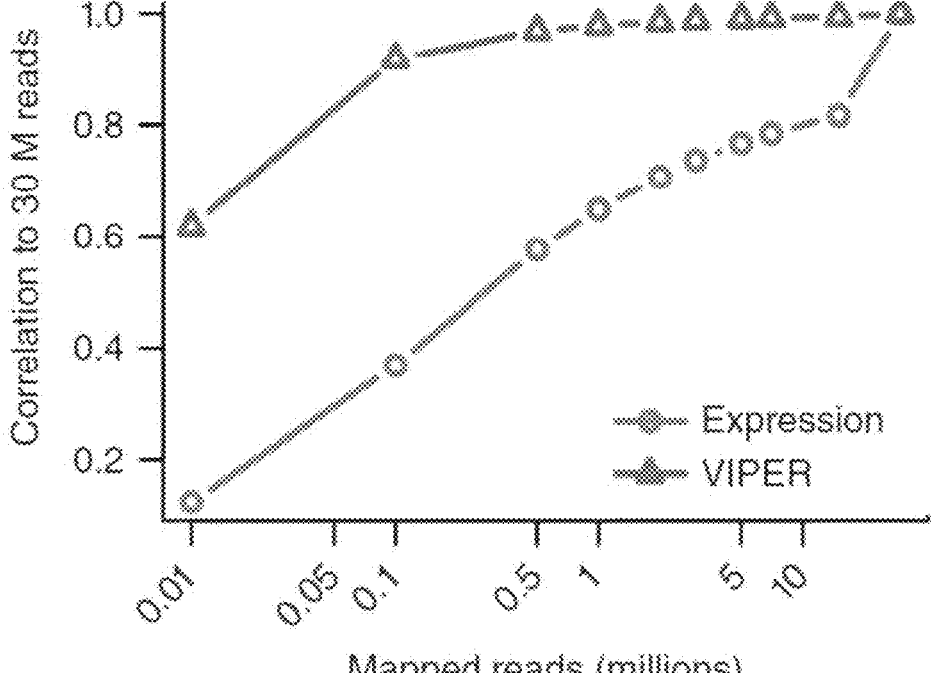

FIGS. 4A-4C illustrate the effect of network quality on VIPER accuracy (rank position of the silenced gene) when using a non-tissue-matched interactome, by computing protein activity with a B-cell interactome (B cell) or glioma interactome (GBM) (FIG. 4A); when the network was degraded by partially randomizing the regulons (FIG. 4B); or when the regulon size was progressively reduced (FIG. 4C). Accuracy is shown across the six benchmark experiments as a bar plot (FIG. 4A) or by the median (black line), IQR (blue) and the lowest and highest data points still inside 1.5 times the IQR away from the quartiles (light blue), resembling a box-and-whiskers plots (continuous boxplots; FIGS. 4A-C). (FIG. 4D) VIPER accuracy (continuous box-plot) for progressive signature degradation obtained by addition of Gaussian noise. Probability density plots show the distribution of gene expression variance for the six benchmark data sets (density). FIG. 4D illustrates VIPER accuracy (continuous boxplot) for reduced signature coverage obtained by randomly removing genes. FIG. 4F illustrates the average correlation between 30 M mapped-reads-based gene expression (expression) or VIPER-inferred protein activity signatures and the corresponding signatures computed from lower-depth RNA-seq. Signatures can be obtained from 100 breast carcinoma samples profiled by TCGA. The insets show magnification.

Regulons can be degraded by progressively randomizing regulatory interactions while maintaining network topology. Although VIPER's performance depends on availability of tissue-specific regulons (FIG. 4A), VIPER can tolerate a high fraction of false positive interactions, with noticeable performance degradation observed only when >60% of regulon interactions have been randomized (FIG. 4B). Assuming ~30% false positive rate by ARACNe, this suggests that as long as >28% of genes in a regulon can represent bona fide regulatory interactions, protein differential activity can be accurately inferred.

Figure 16A:
FIGS. 16A and 16B illustrate change detection results in protein activity after genetic perturbations.
Figure 16A:
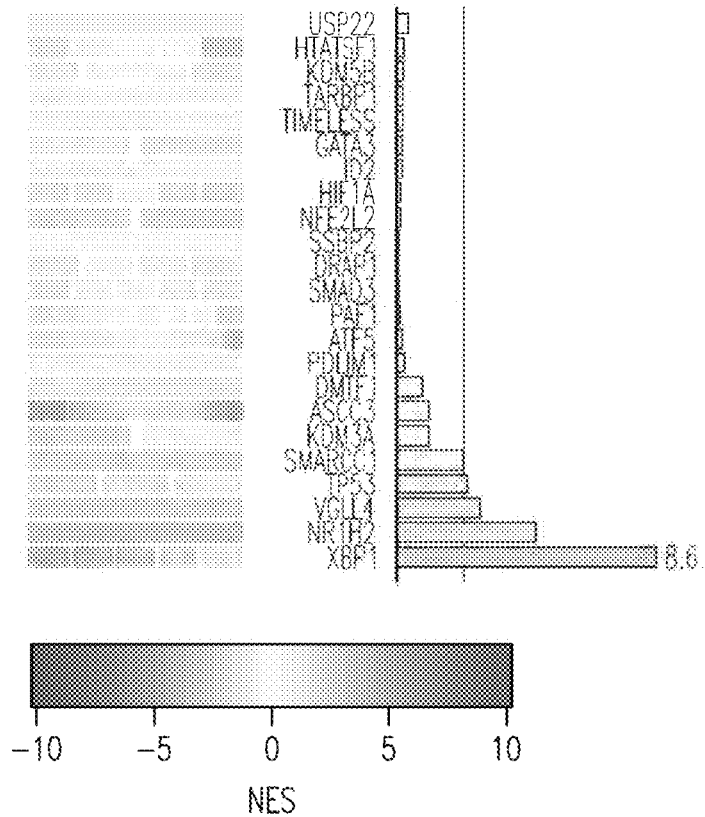
Figure 16B:
Figure 16B:
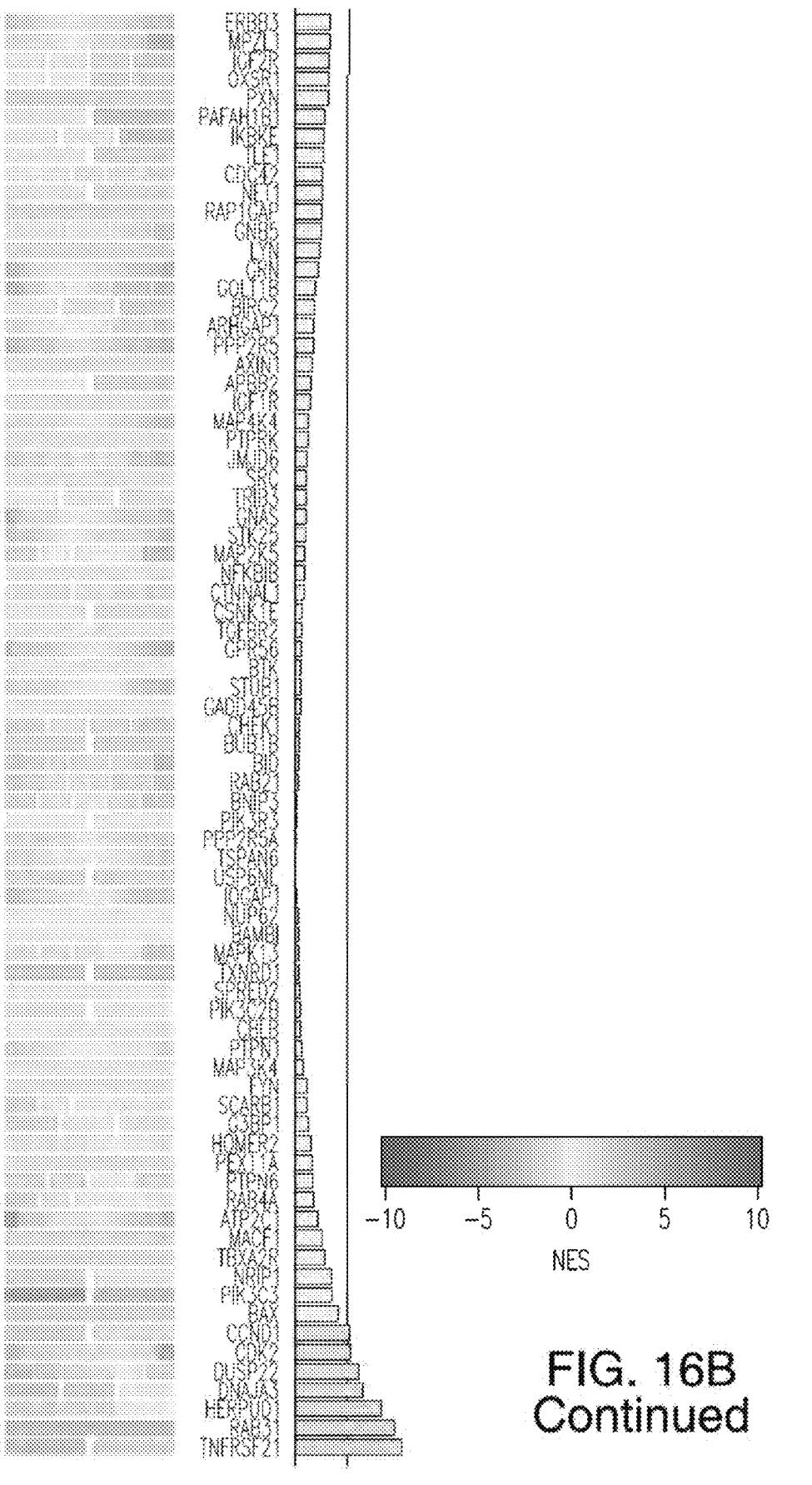

In an exemplary embodiment, VIPER assessment of protein activity can be determined to be robust to reduced regulon representation, as confirmed by the analysis of the library of integrated network-based cellular signatures (LINCS) data (FIGS. 16A and 16B). FIGS. 16A and 16B illustrate heatmaps showing the VIPER-inferred change in TF protein activity (FIG. 16A) and signaling protein activity (FIG. 16B) after coding gene expression knock-down. Displayed results correspond to silencing experiments in MCF7 breast carcinoma cells from LINCS showing a reduction in mRNA level of at least 2 standard deviations of the control samples. Statistical significance was estimated by Stouffers integration of the single-sample NES. The vertical black line crossing the bar-plot indicates the significance threshold of p=0.05. Bars showing a statistically significant change in protein activity at p<0.05 are highlighted in a lighter shade of grey (decreased protein activity, i.e., NES<0) and a darker shade of grey (increased protein activity, NES>0). Values higher than the axis scale are indicated to the right of each bar.

Progressive target removal can start with targets with lowest mutual information further increased accuracy, with optimal accuracy achieved at n=50 targets and only modest degradation down to n=25 targets (FIG. 4C). Regulons having fewer than 25 targets can showed a dramatic decrease in accuracy (FIG. 4C).

Figure 5A:
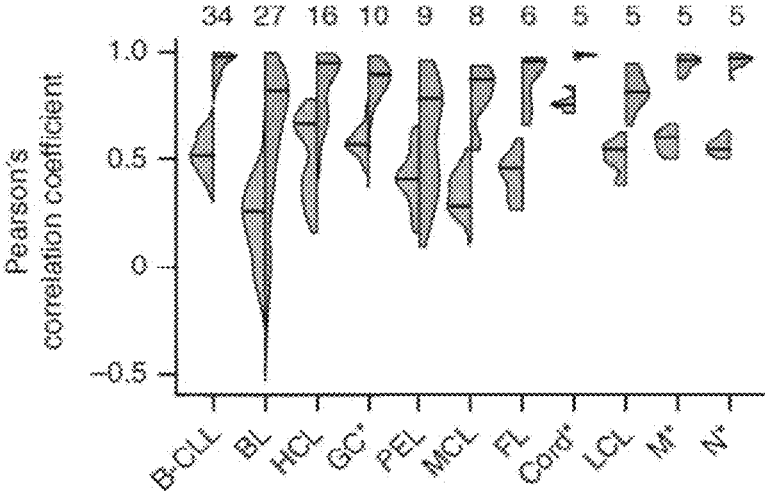
FIGS. 5A-5C illustrate data indicating reproducibility of VIPER results.
Figure 19A:
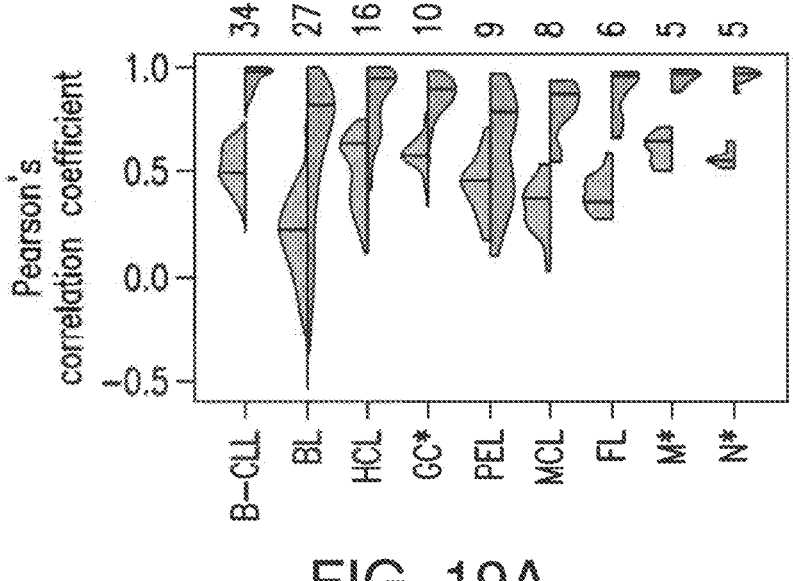
FIGS. 19A-19E illustrate reproducibility of single-sample gene expression, protein abundance and VIPER protein activity signatures.

In some embodiments, VIPER can be highly insensitive to gene expression signature degradation. Such results can be observed by adding zero-centered Gaussian noise with increasing variance (e.g., comparable to benchmark data sets variance) (FIG. 4D). Adding zero-centered Gaussian noise with increasing variance renders VIPER data well-suited for assessment of protein activity from noisy single-sample gene expression profiles, where the variance of VIPER-inferred activity is smaller than the variance of gene expression (FIGS. 5A, 5B, and 19A-19E). For example, considering a B cell phenotype, VIPER-based protein activity signatures can be significantly more correlated than gene expression signatures (e.g., P<10-15, Wilcoxon signed-rank test) (FIGS. 5A and 19A).

Figure 5B:
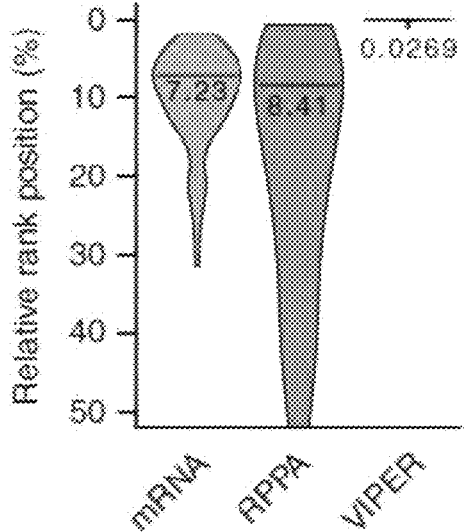
Figure 5C:
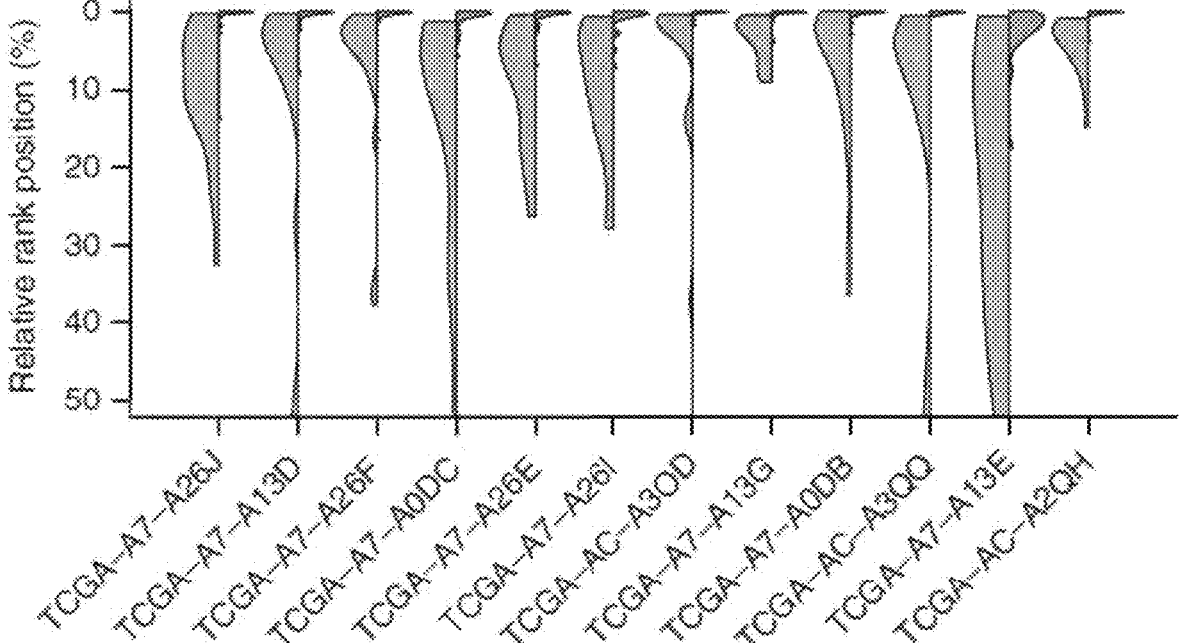

FIGS. 5A-5C illustrate reproducibility of VIPER results. FIG. 5A illustrates the distribution of correlation coefficients computed between all possible pairs of gene expression signatures (yellow) or VIPER protein activity signatures (cyan) for samples of the same B cell phenotype, including normal (indicated by asterisks: GC, germinal center reaction; M, memory and N, peripheral blood B cell) and pathologic (B-CLL, B cell chronic lymphocytic leukemia; BL, Burkitt lymphoma; HCL, hairy cell leukemia; PEL, primary effusion lymphoma; MCL, mantle cell lymphoma; FL, follicular lymphoma) phenotypes. The number of samples per phenotype is indicated on top. FIG. 5B illustrates the probability density for the relative rank position of the most upregulated gene (mRNA), relatively abundant protein (RPPA) or activated protein (VIPER), identified in each profiled basal breast carcinoma sample, across all the remaining profiled samples. The horizontal line and number under it indicates the distribution mode. FIG. 5C illustrates the probability density for the relative rank position of the top ten most upregulated genes (yellow) or VIPER-inferred activated proteins (cyan), identified from fresh-frozen samples on the corresponding FFPE samples.

Figure 19B:
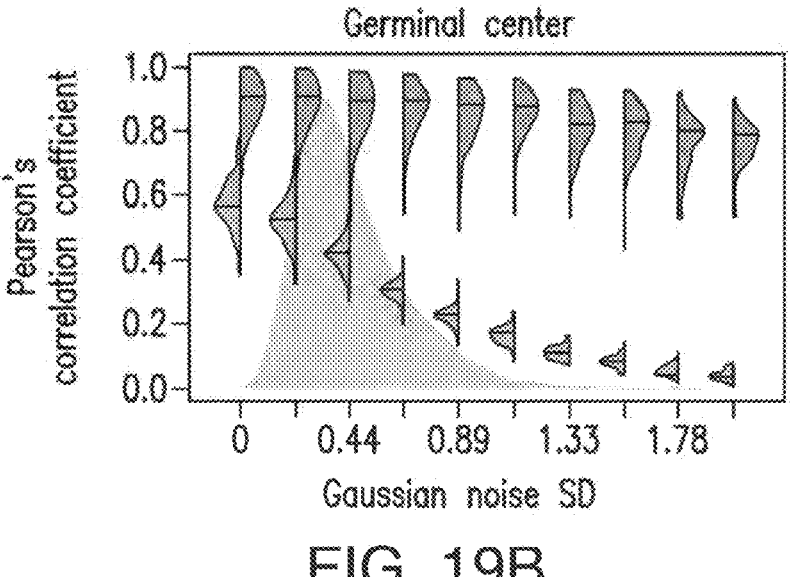
Figure 19C:
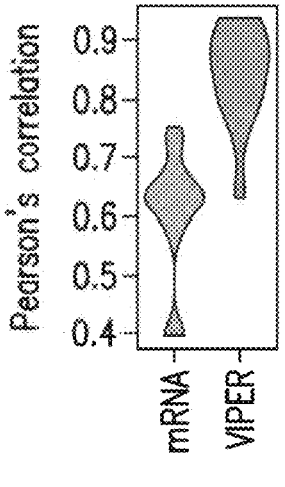
Figure 19D:
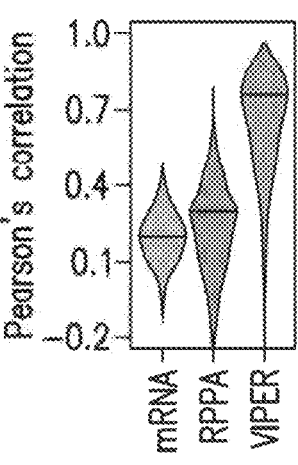
Figure 19E:
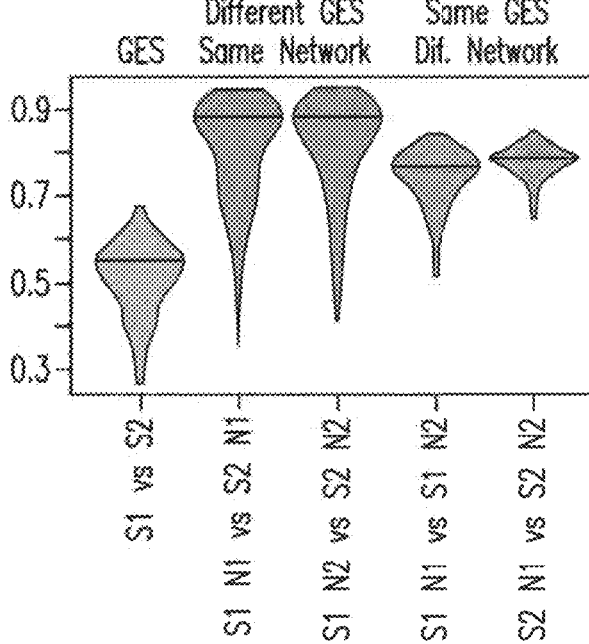

FIGS. 19A-19E illustrate reproducibility of single-sample gene expression, protein abundance and VIPER protein activity signatures. FIG. 19A illustrates a violin plot showing the distribution of correlation coefficients computed between gene expression signatures (yellow) or VIPER protein activity signatures (cyan) for samples of the same B cell phenotype, including normal (indicated by asterisks; GC, germinal center reaction; M, memory and N, peripheral blood B cell) and pathologic (B-CLL, B cell chronic lymphocytic leukemia: BL, Burkitt lymphoma; HCL, hairy cell leukemia; PEL, primary effusion lymphoma; MCL, mantle cell lymphoma; FL, follicular lymphoma) phenotypes. This analysis corresponds to the one shown in FIG. 3A but limiting the expression signatures to the regulators represented in the VIPER analysis. The number of samples per phenotype is indicated on top of the figure. FIG. 19B illustrates a violin plot for the correlation between all possible pairs of GC B cell single-sample gene expression (yellow) and VIPER protein activity (cyan) signatures, after adding different levels of Gaussian noise to the expression profiles (indicated in the x-axis in standard deviation (SD) units). The grey probability density plot shows the distribution for the variance across samples in the original data. FIG. 19C illustrates a probability density for the correlation coefficient computed between fresh frozen and FFPE derived expression (yellow) and VIPER-inferred protein activity (cyan) signatures. FIG. 19D illustrates a violin plot showing the probability density for the correlation coefficients computed between all possible pairs of gene expression (yellow), RPPA protein abundance (green) and VIPER-inferred protein activity (cyan) signatures, corresponding to basal-subtype breast carcinoma tumors profiled by TCGA. FIG. 19E illustrates a correlation of germinal center B cell gene expression signatures between two datasets (yellow), the corresponding VIPER-inferred protein activity signatures between two datasets (green), or between two different B cell context specific networks (cyan). The horizontal line in the violin plots indicates the major mode of the distribution. See Table 2 for information about the datasets and networks.

Addition of Gaussian noise can decrease expression-based sample-sample correlation with only a minimal effect on VIPER-inferred activity correlation (FIG. 19B). VIPER activity can be highly resilient to reduced transcriptome representation, showing minimal accuracy decrease when up to 90% of the genes in the signature were removed from the analysis (FIG. 4E) or when RNA-seq profiles have been subsampled from 30 million (M) reads to 0.5 M reads (FIG. 4F), rendering VIPER appropriate for the analysis of low-depth RNA-sequence profiles. This can be further evidenced when comparing protein activity profiles inferred from fresh-frozen against matched formalin-fixed paraffin-embedded (FFPE) samples (FIGS. 5C and 19C). The reproducibility of the results from FFPE samples can represent a critical prerequisite for precision medicine applications.

In some embodiments, to assess the effect of biological variability, VIPER activity signatures can be calculated for 173 TCGA basal breast carcinomas. VIPER-inferred activity signatures can be significantly more correlated across samples (P<10-15 by Wilcoxon signed-rank test for the correlation coefficients) (FIG. 19D) and top-ranking aberrantly activated proteins can be more conserved across samples based on differential activity than when based on differential expression of the associated gene (FIG. 5B). Overall, sample-to-sample variance can be reduced more than 250 times compared to gene expression (FIG. 5B). Accordingly, VIPER-inferred differentially activated proteins can be more conserved than differentially expressed genes or differentially abundant proteins (e.g., based on RPPA measurements) across different samples representing the same tumor subtype (FIG. 5B).

Functionalizing the Somatic Mutational Landscape of Cancer

In some embodiments, VIPER can be used to systematically test the effect of recurrent mutations on corresponding protein activity. A pan-cancer set of 3,912 TCGA samples, representing 14 tumor types can be used to test the effect of recurrent mutations on corresponding protein activity. The VIPER-inferred activity of each transcription factor and signaling protein in each of the analyzed samples can be calculated. It can be determined whether samples harboring recurrent mutations were enriched in those with high VIPER-inferred differential activity of the affected protein. Table 9 illustrates the number of samples harboring non-silent somatic mutations in COSMIC genes. From 150 recurrently mutated genes in COSMIC, 89 genes can be selected that were mutated in at least 10 samples in at least one tumor type and for which a matching regulatory model was available (Table 9), resulting in a total of 342 gene pairs (e.g., EGFR in glioblastoma multiforme, GBM) where a specific oncoprotein can be tested in a specific tumor cohort.

In some embodiments, as protein activity can vary based on either total protein abundance or on the abundance of specific, differentially active isoforms, global VIPER activity and the residual post-translational (RPT) VIPER activity (e.g., the component of activity that cannot be accounted for by differential expression) can be calculated by removing the transcriptional variance component. RPT activity can be statistically independent of gene expression and should account for the post-translational contribution to protein activity. Almost 30% of subtype-specific variation-harboring proteins (92/342) can be associated with statistically significant differential protein activity, as assessed by VIPER (P<0.05): 65/342 (19%) by global activity analysis and 51/342 (15%) by RPT activity analysis, respectively (FIGS. 20A-20C).

Figure 20A:
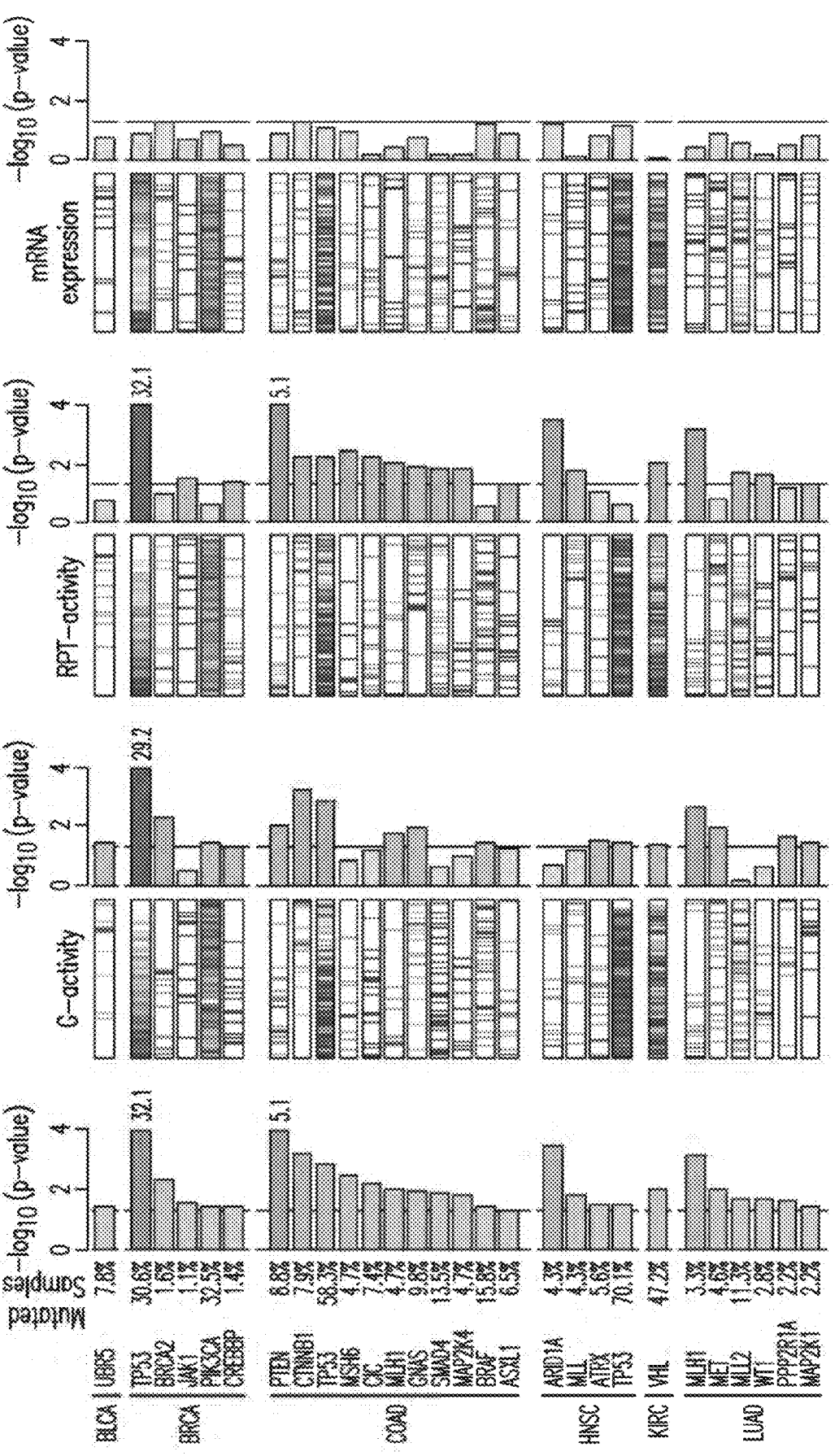
FIGS. 20A-20C illustrate change detection results in protein activity induced by non-silent somatic mutations.
Figure 20A:
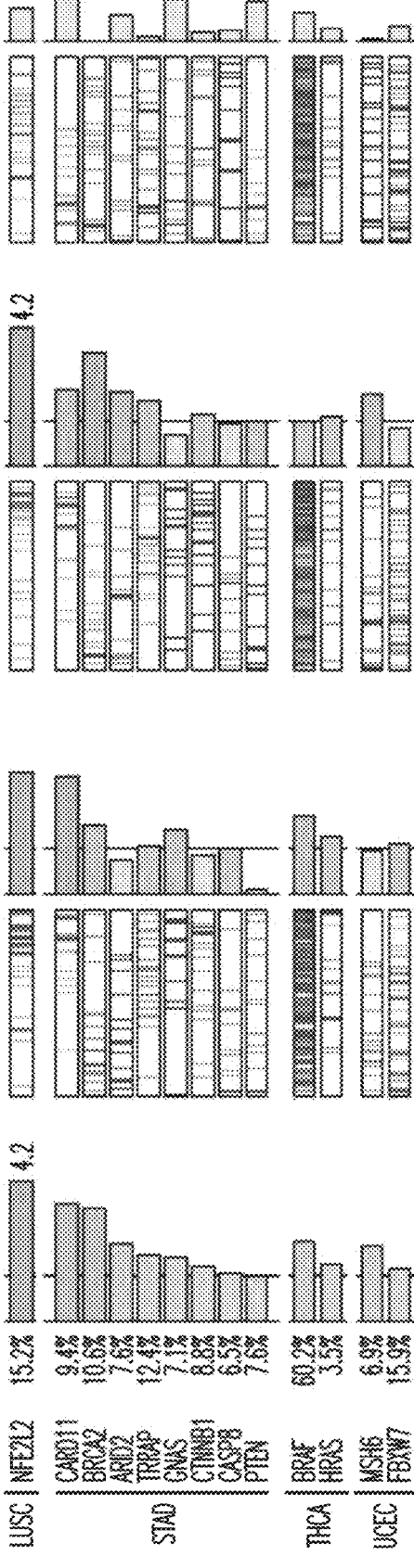
Figure 20B:
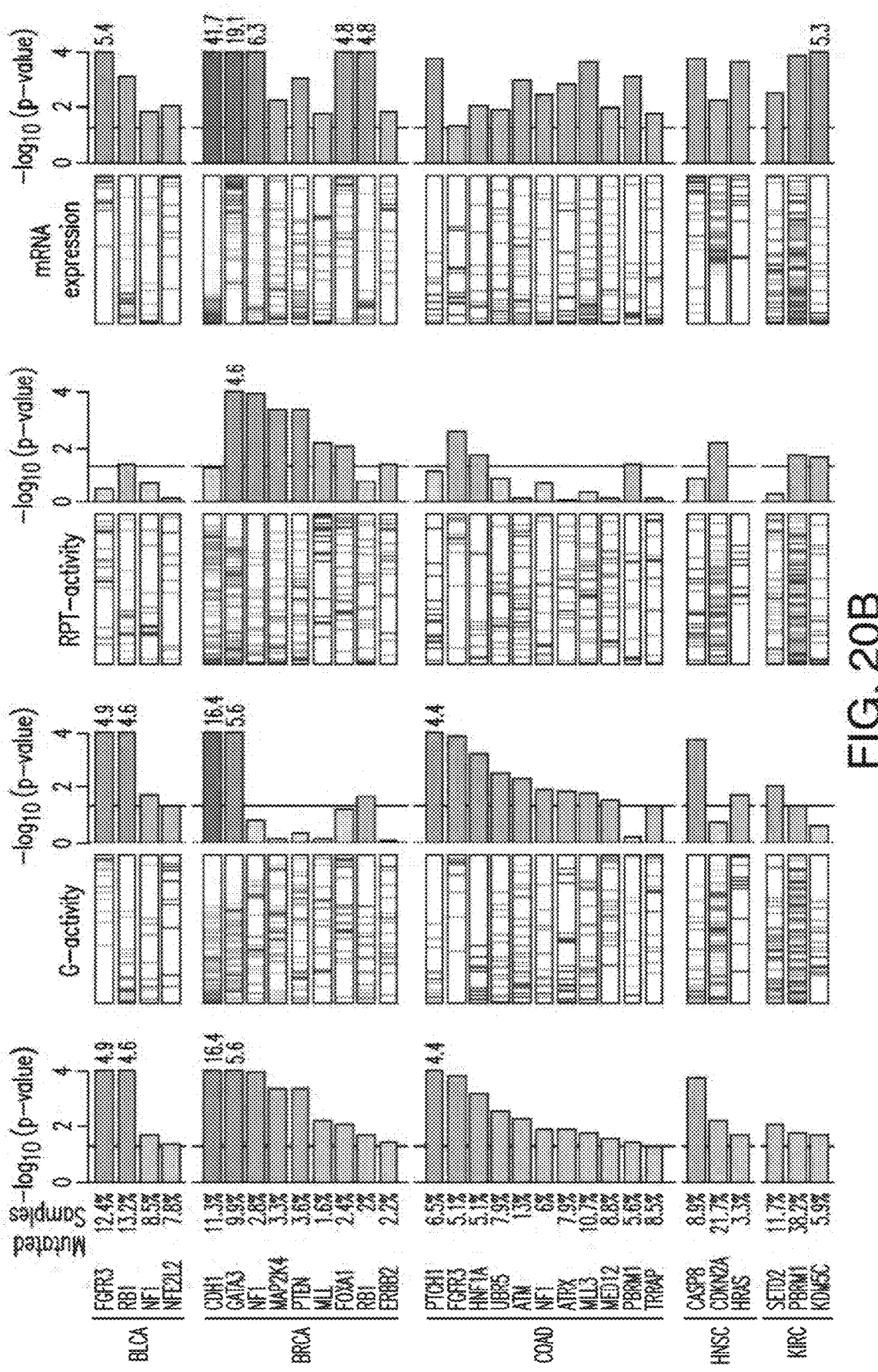
Figure 20B:
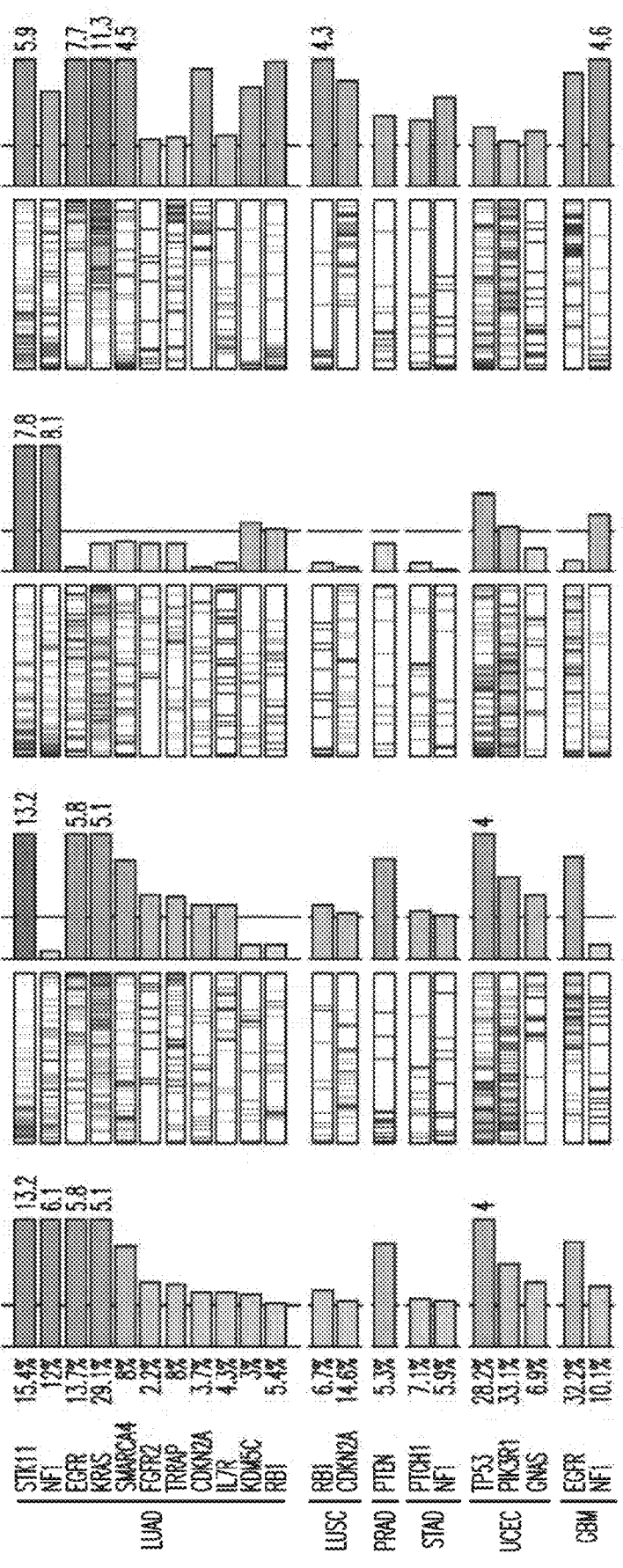
Figure 20C:
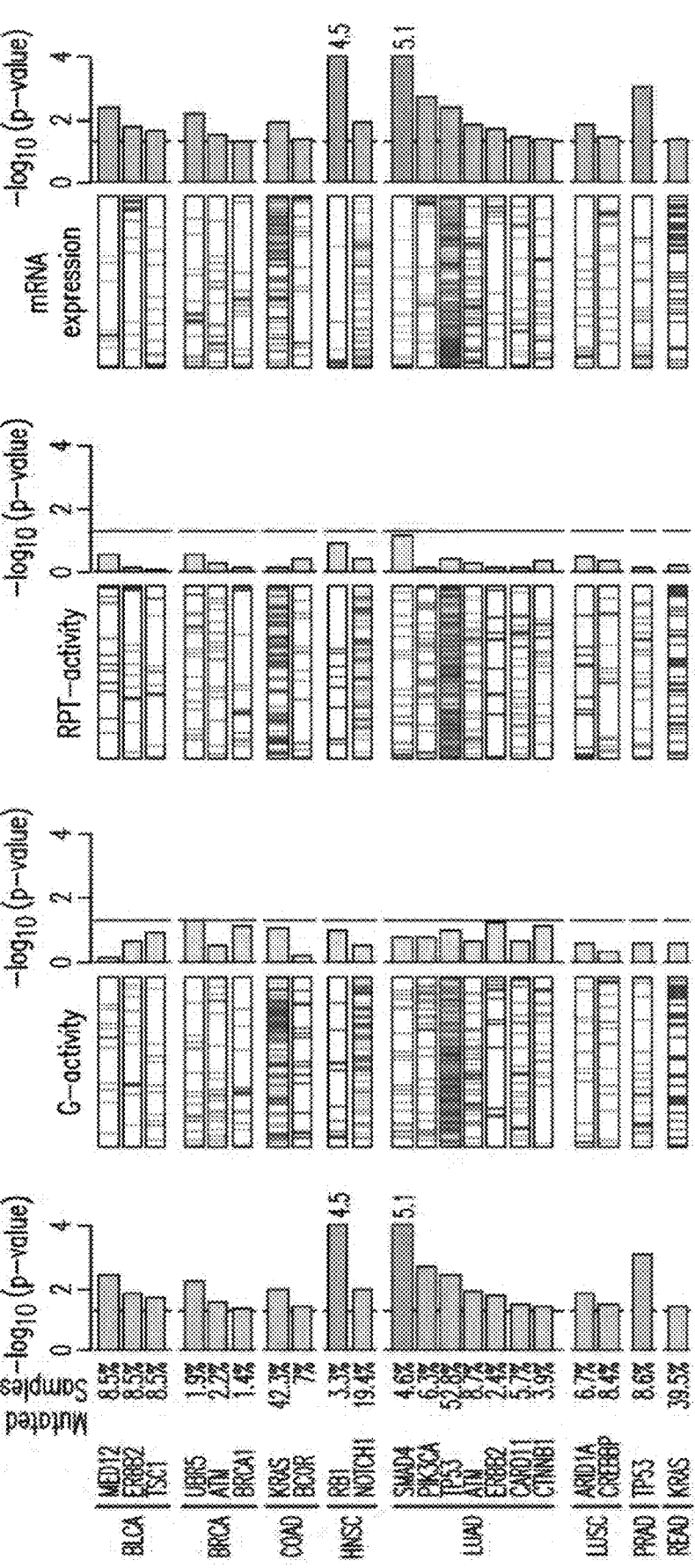
Figure 21A:
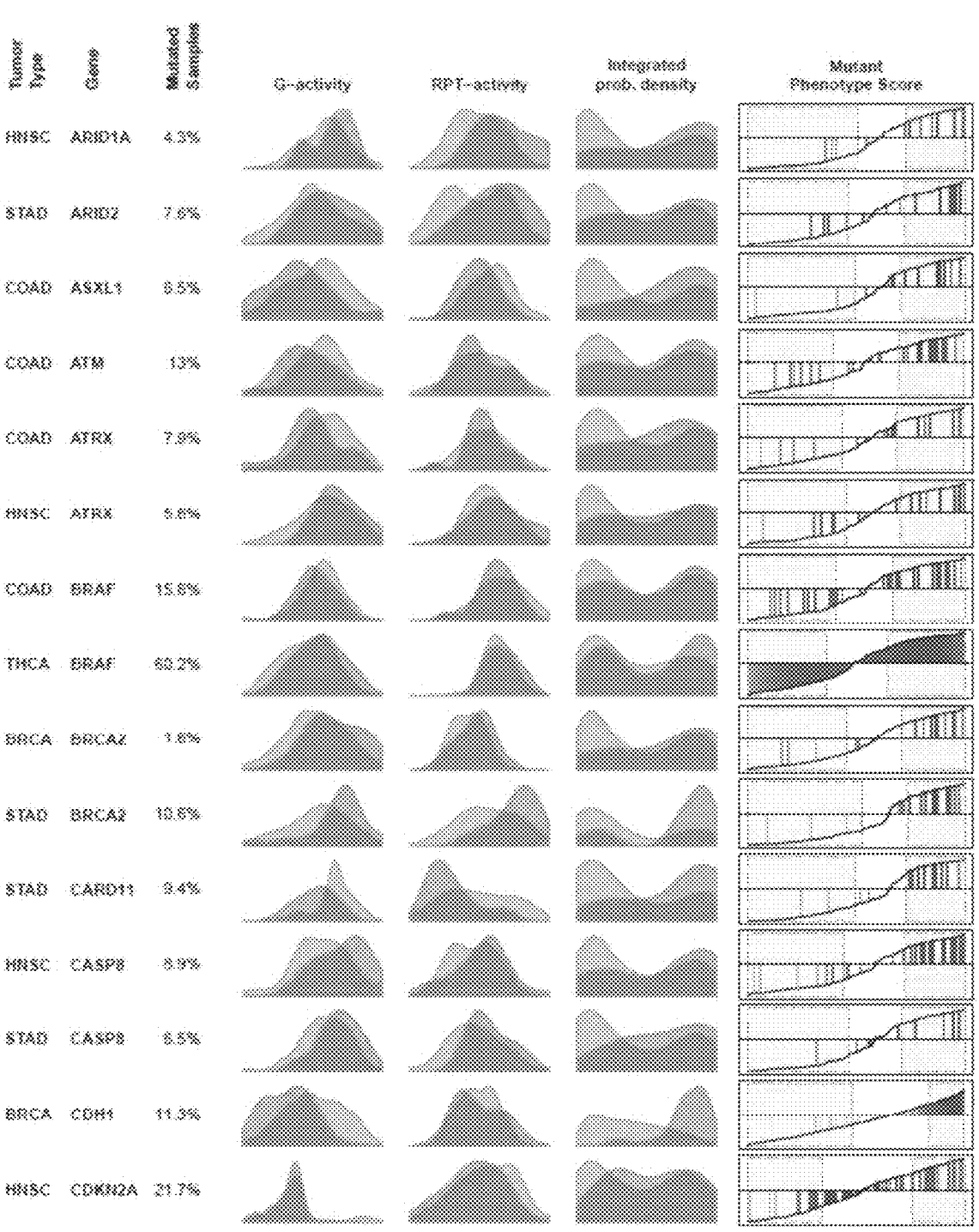
FIGS. 21A-21F illustrate MPS scores of all genes showing a significant association of mutations with either global activity (G-activity) or residual posttranslational activity.
Figure 21B:
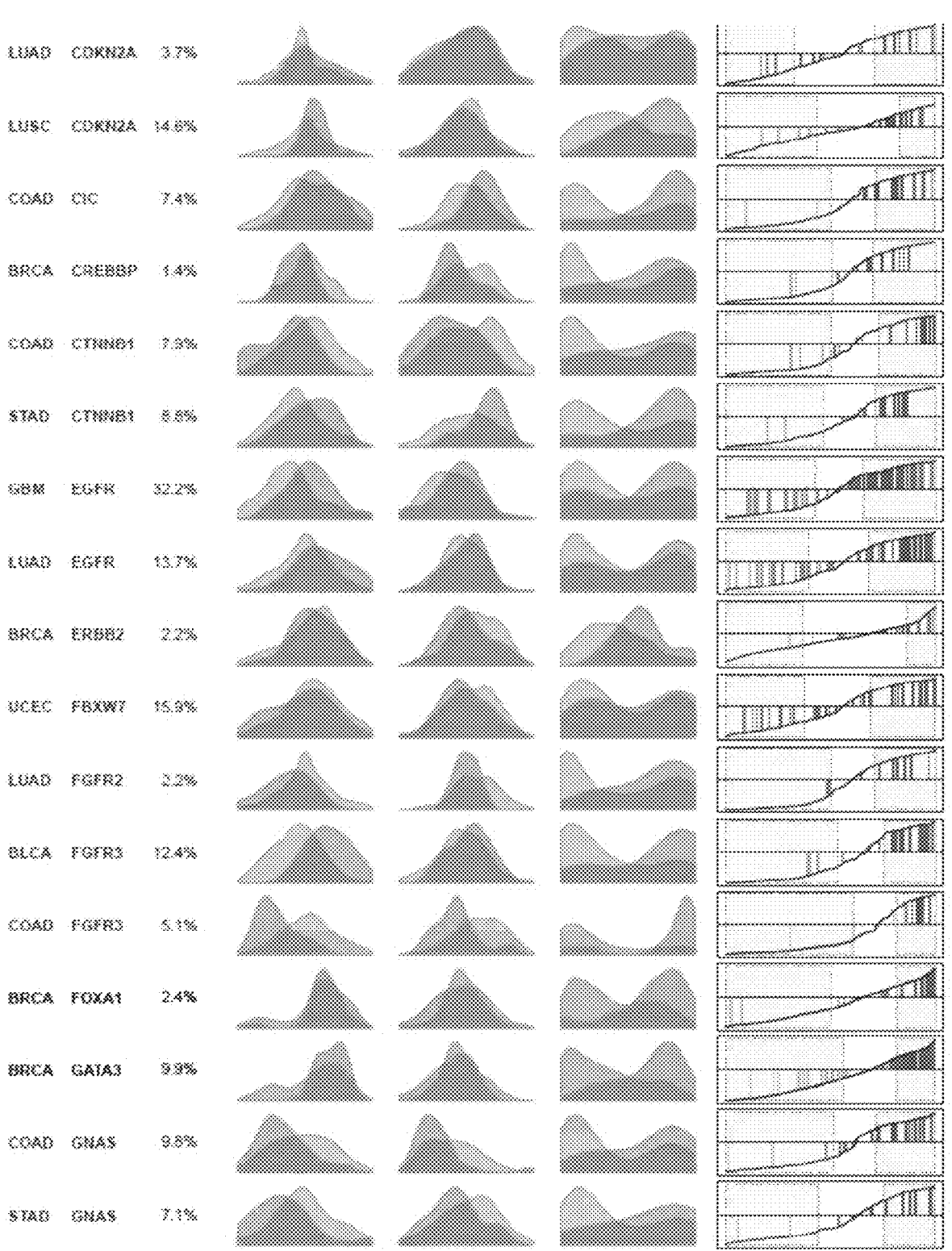
Figure 21C:
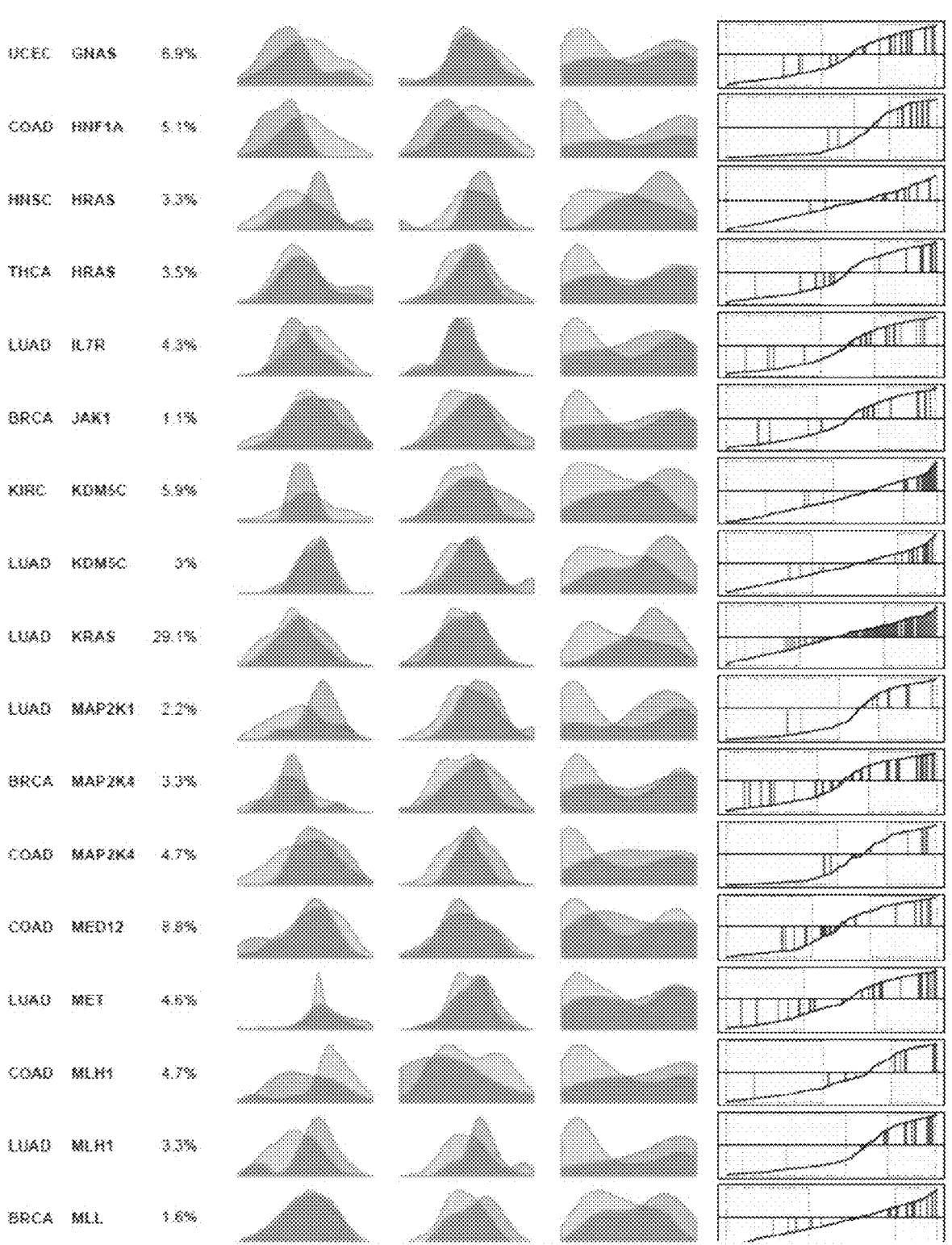
Figure 21D:
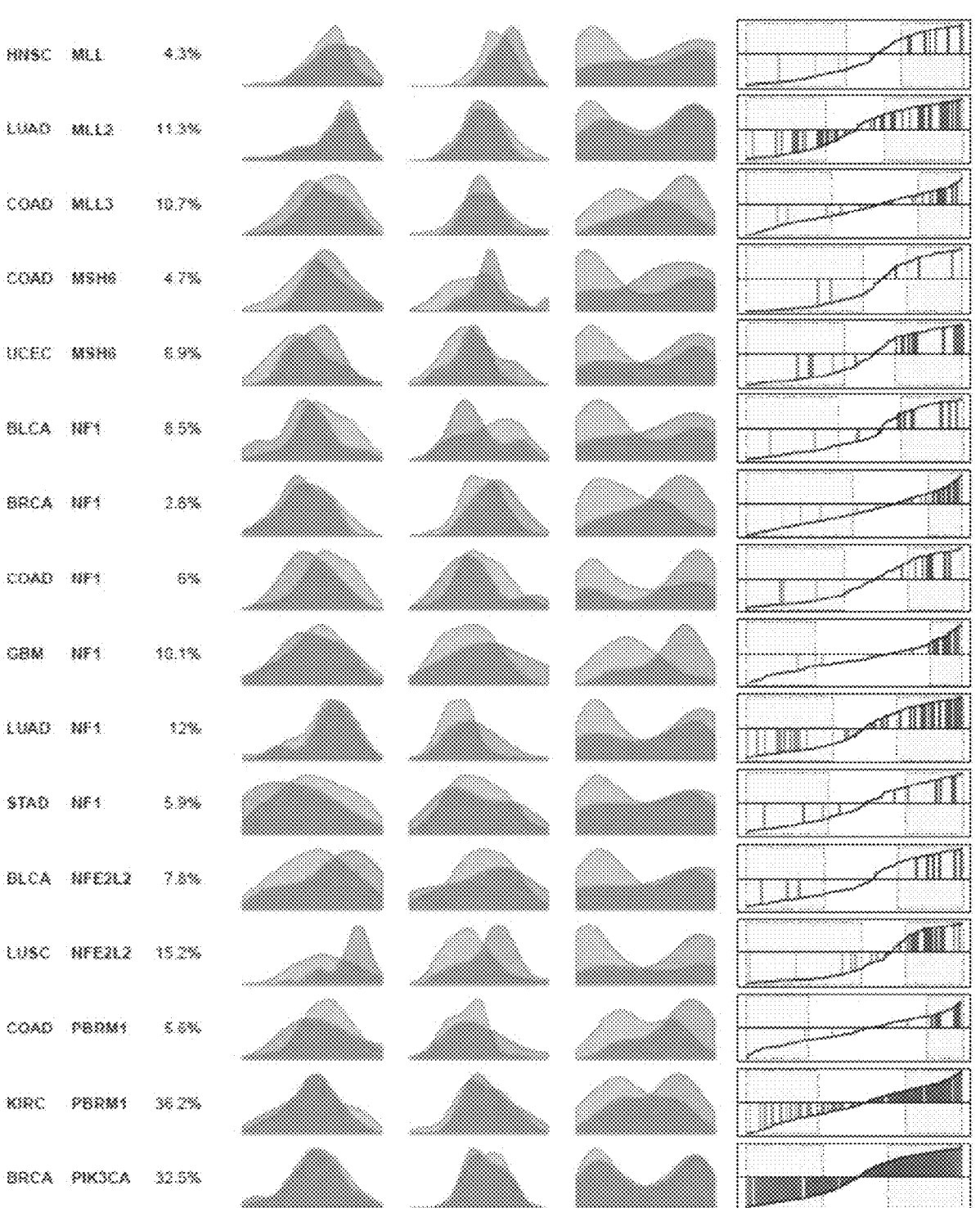
Figure 21E:
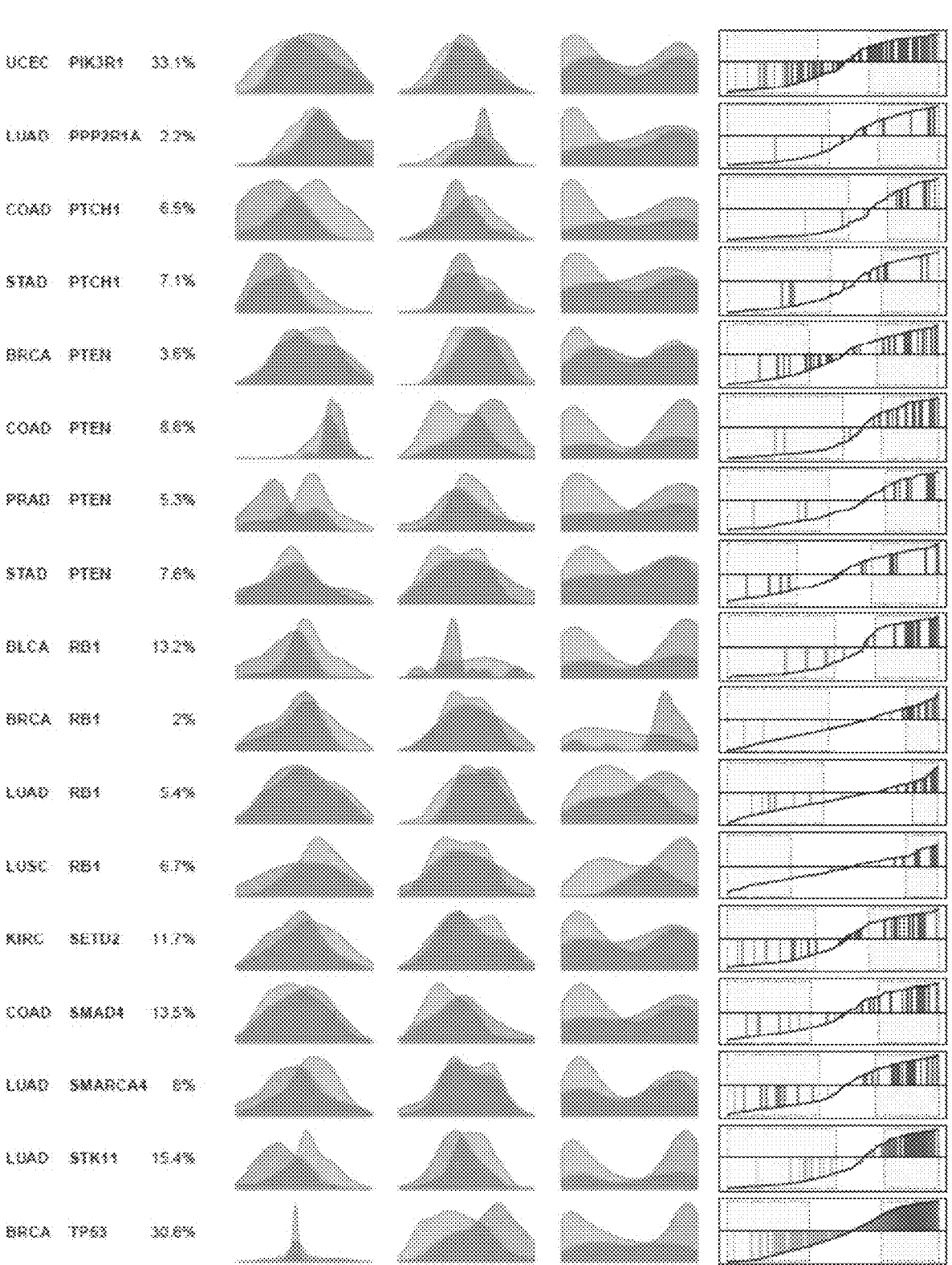
Figure 21F:
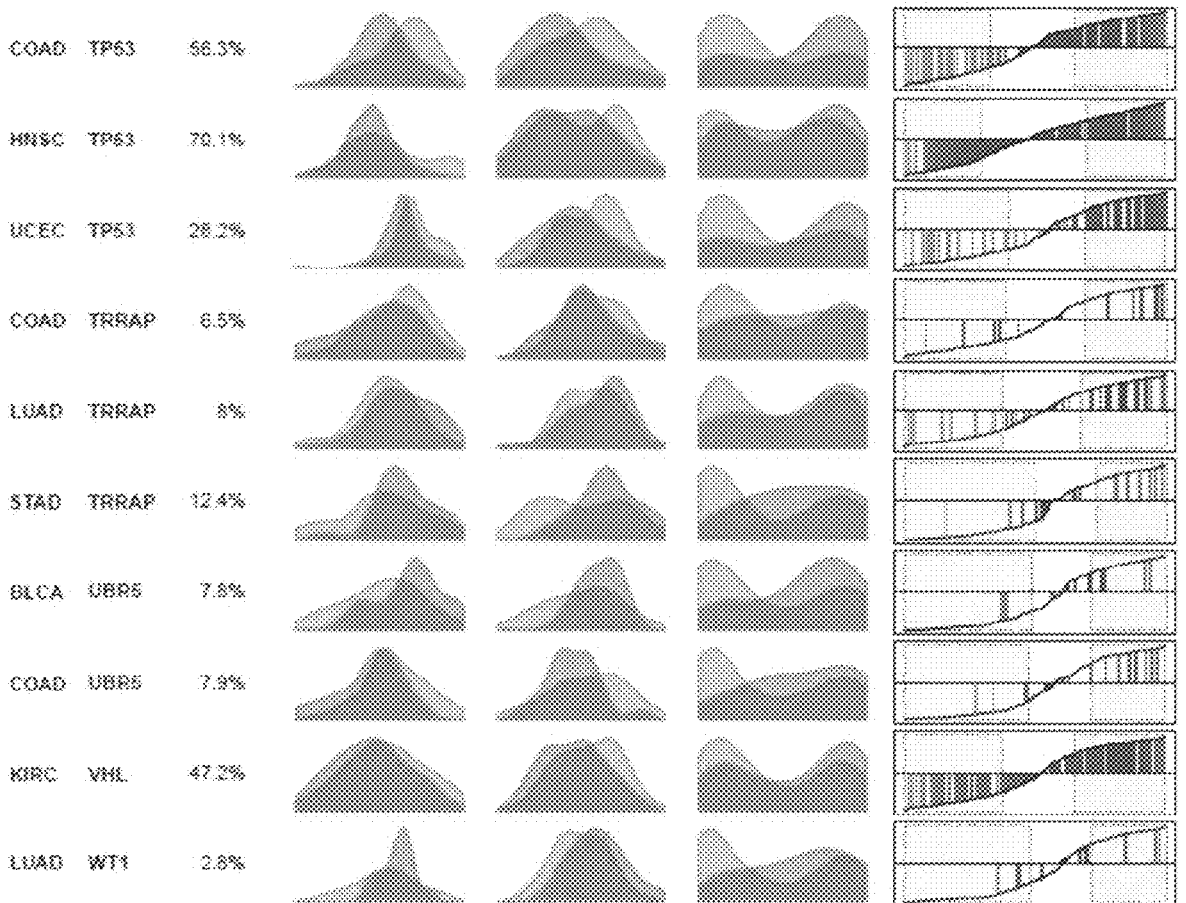

FIGS. 20A-20C illustrate detecting changes in protein activity induced by non-silent somatic mutations. Shown are all the genes listed in the Catalog Of Somatic Mutations in Cancer (COSMIC) where mutations are associated with: (FIG. 20A) protein activity but not mRNA expression, (FIG. 20B) inferred protein activity and mRNA expression, and (FIG. 20C) mRNA expression but not protein activity. The green bars indicate the integrated statistical significance for the effect of mutations on coding gene expression or protein activity. Each group of green enrichment plot and red/blue bar-plot indicates the enrichment of samples harboring non-silent somatic mutations (NSSM) on the VIPER-inferred global activity (G-activity) and residual post-translational activity (RPT-activity) for the coded protein, and differential gene expression, as indicated in the plot. The samples for each tumor type can be rank sorted according to G-activity (left enrichment plot), RPT-activity (center enrichment plot) and gene expression (right enrichment plot), and the samples harboring NSSM were indicated by the green vertical lines. The significance level for the association is shown as $+\log_{10}(p)$ (barplot), with significant associations (p<0.05), for mutations associated with high activity or expression, and blue bars for mutations associated with low activity or expression. The value for genes associated at $p<10^{-4}$ is shown beside the bars. Tumor type, gene name and proportion of mutated samples are indicated in the plot.

Such global activity analysis and RPT activity analysis can include the vast majority of established oncogenes and tumor suppressors (FIGS. 6A-6C, 20A, and 20B), suggesting that this integrative analysis provides an effective means to capture mutation-dependent dysregulation of oncogene and tumor suppressor activity (FIGS. 20A-20C).

Figure 6A:
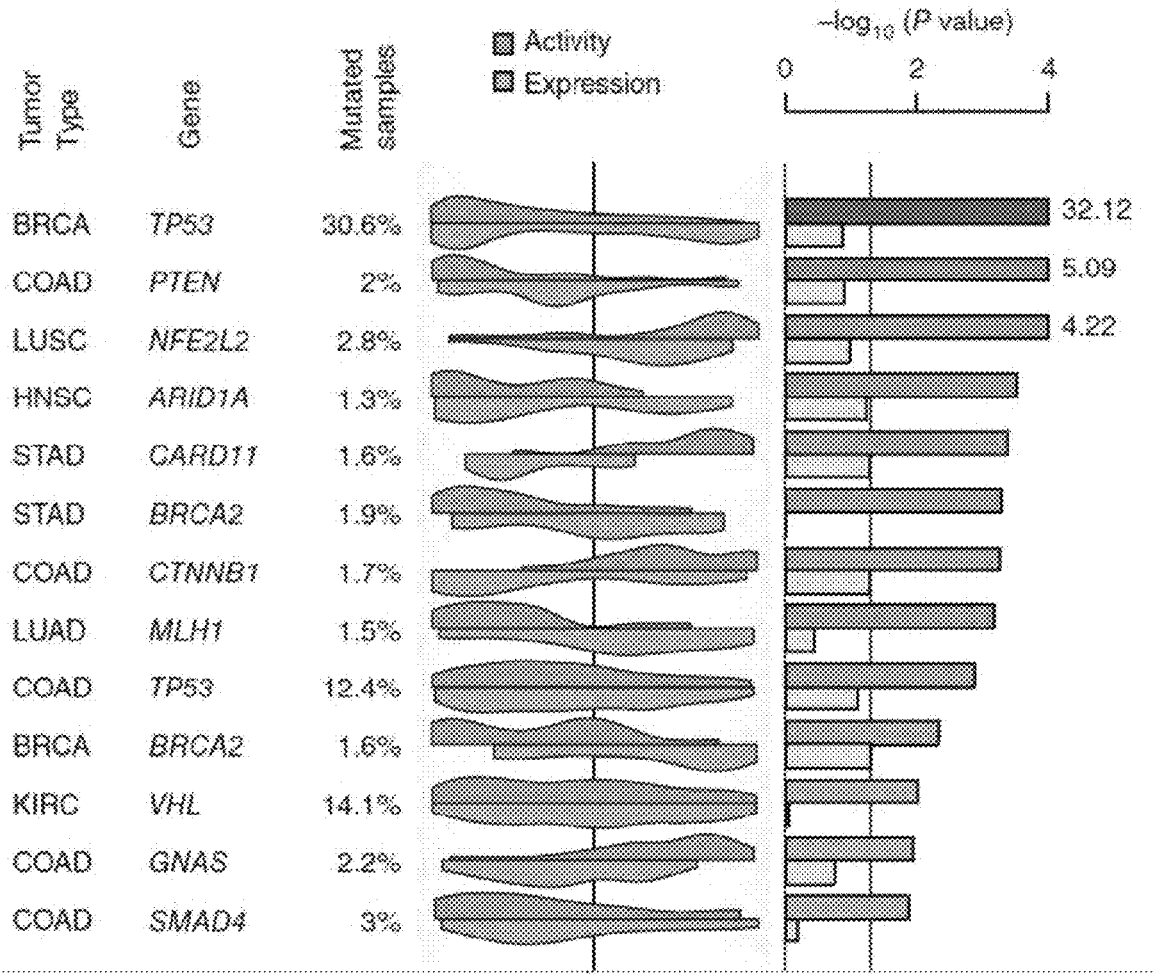
FIGS. 6A-6C illustrate data detecting changes in protein activity by non-silent somatic mutations.
Figure 6B:
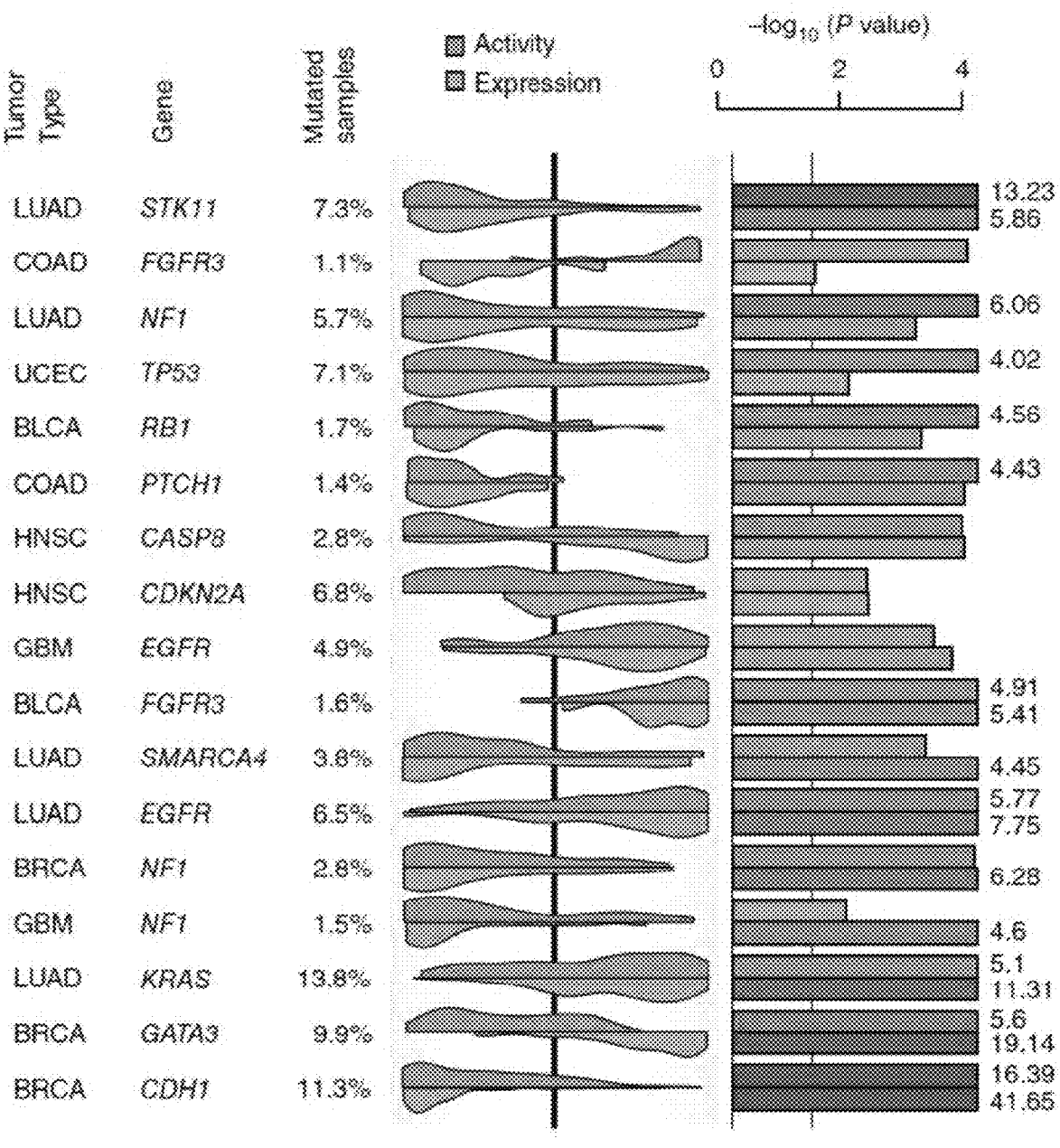
Figure 6C:
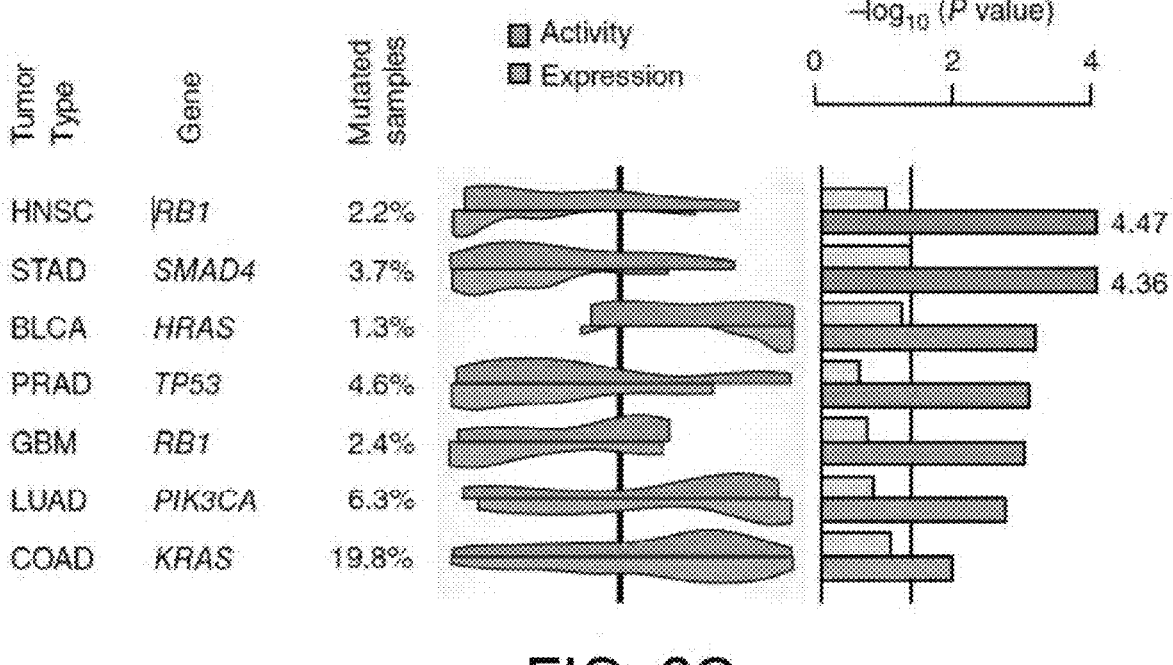

FIGS. 6A-6C illustrate Detecting changes in protein activity induced by nonsilent somatic mutations. FIGS. 6A-6C illustrate changes associated with protein activity only (FIG. 6A), protein activity and mRNA expression (FIG. 6B), and mRNA expression only (FIG. 6C) for GBM, COAD, breast carcinoma (BRCA), lung squamous carcinoma (LUSC), head and neck squamous carcinoma (HNSC), stomach adenocarcinoma (STAD), lung adenocarcinoma (LUAD), kidney renal clear cell carcinoma (KIRC), uterine corpus endometrial carcinoma (UCEC), bladder carcinoma (BLCA), and prostate adenocarcinoma (PRAD). The complete list of evaluated proteins is available in FIGS. 20A-20C. For each indicated gene harboring nonsilent somatic mutations, the proportion of mutated samples from that tumor type is indicated. Violin plots indicate the distribution density for the mutated samples on all samples rank-sorted by mRNA expression (yellow) and VIPER-inferred protein activity (cyan); background color gradient indicates both expression and VIPER-inferred protein activity signatures: downregulated genes and inactivated proteins (blue) and overexpressed genes and activated proteins (red). Bar plots show significance for the association computed by the aREA algorithm. Blue and red bars indicate enrichment of the mutated samples among low expression or protein activity, and among high levels of expression or protein activity, respectively.

VIPER-inferred RPT activity can effectively eliminate the effect of feedback loops on the corresponding gene's expression, thereby identifying mutations resulting only in post-translational effects (FIGS. 20A, 20B). It can be observed that 45% of mutations (e.g., 41/92 mutations) associated with VIPER-inferred differential activity induced no significant differential expression of the corresponding gene (FIGS. 6A and 20A), including mutations in established oncogenes and tumor suppressors, such as TP53, PTEN, NFE2L2, ARID1A, CARD11, BRCA2, CTNNB1, MLH1, VHL, and SMAD4, among others (FIGS. 6A and 20A).

In some embodiments, to assess whether a pharmacologically targetable protein can be aberrantly activated in a tumor sample, independent of the sample's mutational state, a sample's mutant phenotype score (MPS) can be generated. The MPS can indicate the probability of observing mutations in samples with equal or higher total VIPER activity (FIG. 21).

Figure 7A:
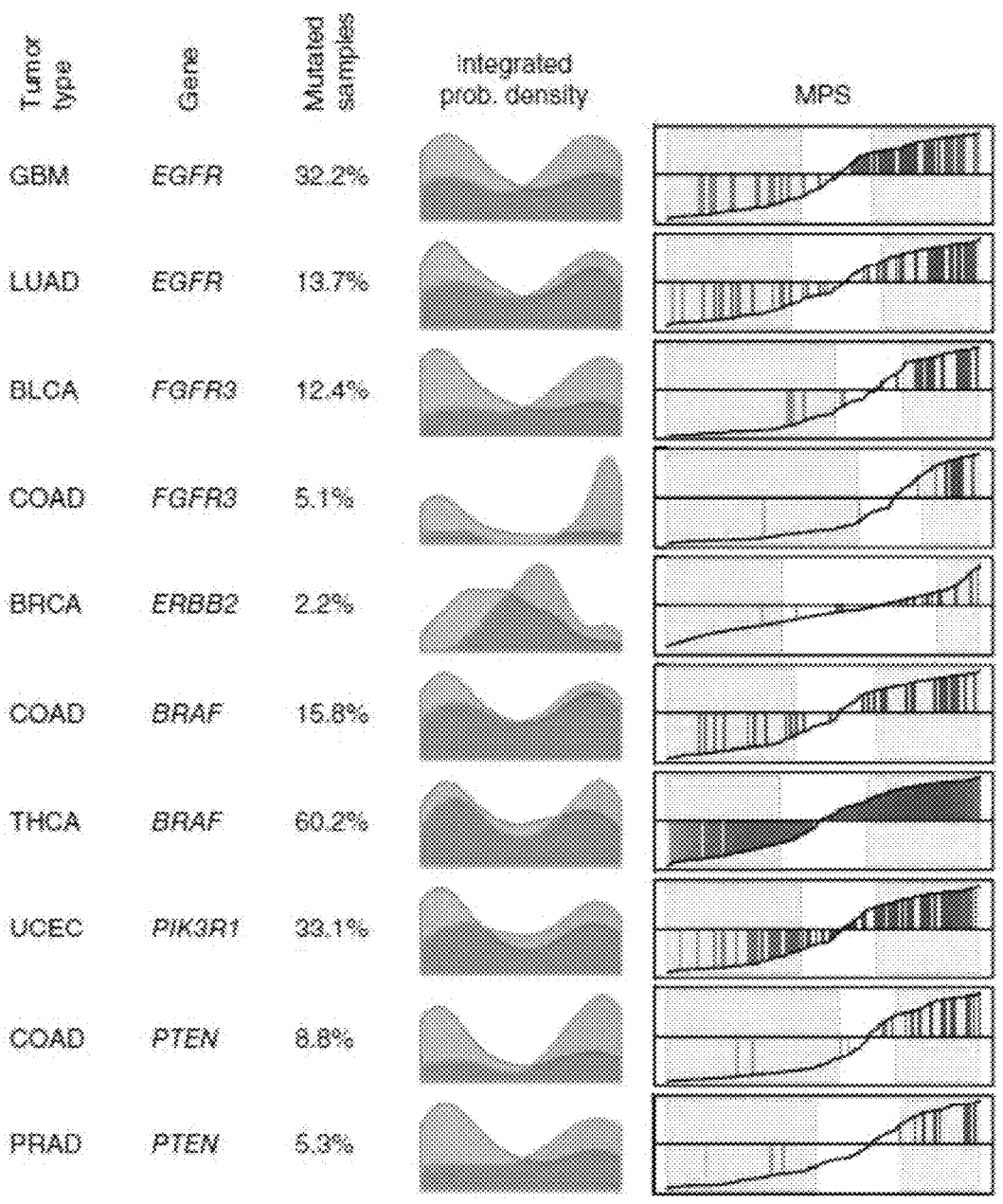
FIGS. 7A and 7B illustrate mutant phenotype scores and its association with drug sensitivity.
Figure 7B:
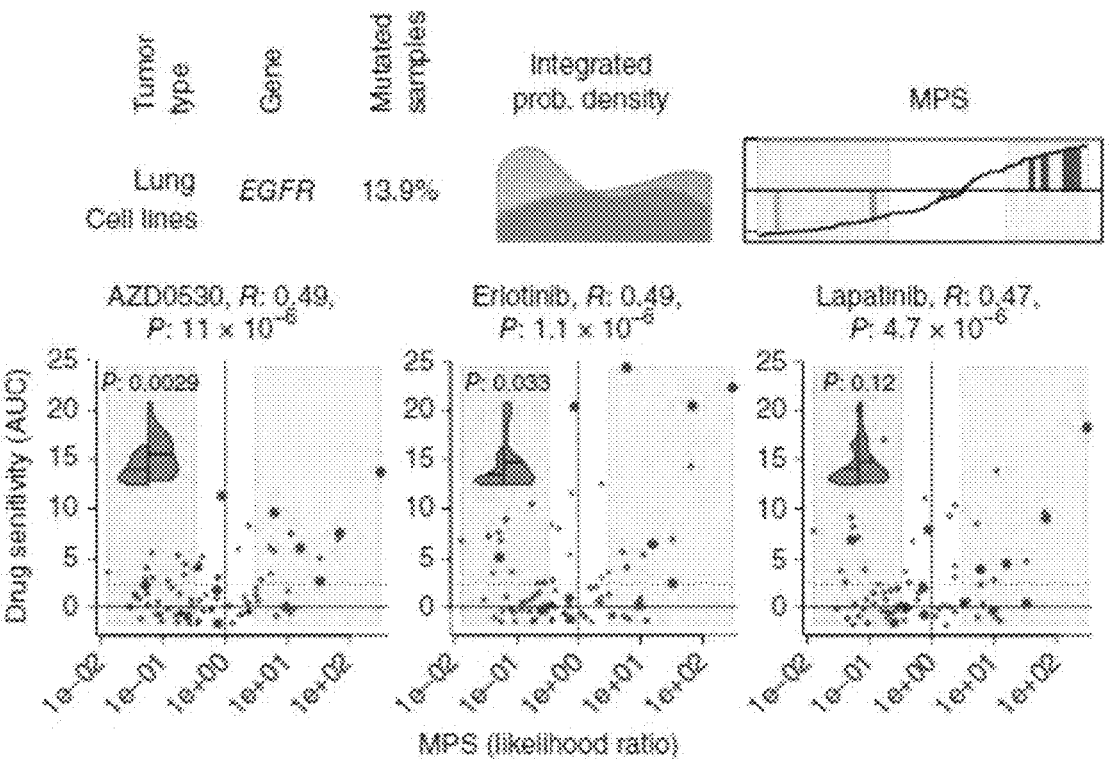

FIGS. 7A and 7B illustrate mutant phenotype score and its association with drug sensitivity. FIG. 7A illustrates the probability density for the nonmutated (salmon) and mutated (green) samples based on MPS for six actionable mutations (complete list in FIGS. 21A-21F). Right plots show MPS (v axis) for all samples rank-sorted by MPS; green vertical lines indicate the mutated samples. MPS-defined WT and mutant phenotypes (likelihood ratio >3) are highlighted in salmon and green. FIG. 7B shows the MPS analysis for EGFR on lung carcinoma cell lines. Scatter plots show drug sensitivity, quantified by the area under the titration curves (AUC), for EGFR-targeting drugs as a function of MPS (expressed as likelihood ratio). Cell lines resembling an EGFR mutated and WT phenotypes are highlighted in green (likelihood ratio >3) and salmon boxes, respectively. Green dots indicate cell lines harboring nonsilent mutations. Solid and doted horizontal lines indicate the mean and 2.33 standard deviation over the mean of the chemoresistant cell lines, respectively. The association between drug sensitivity and MPS is shown on top of each plot by the Pearson's correlation coefficient (R) and associated P value. Violin plots show the probability density for drug sensitivity (AUC) of the cell lines showing an EGFR WT (green) or mutant (brown) phenotype according to MPS; horizontal lines indicate distribution means, which were contrasted by Student t-test (P values in insets).

FIGS. 21A-21F illustrate a list of all genes showing a significant association of mutations with either global activity (G-activity) or residual postranslational activity (RPT-activity). Each row shows the tumor type, gene and proportion of mutated samples, histograms for the probability density estimation of wt (salmon) and mutated (green) samples for each of the traits: VIPER-inferred G-activity and VIPER-inferred RPT-activity. The Integrated probability density histograms show the distributions of wt and mutated samples for the computed MPS. The rightmost plots show the MPS values (y-axis) for the samples rank-sorted by MPS (x-axis), with the mutated samples indicated by green vertical lines. The light salmon and green boxes highlight the MPS range corresponding to a likelihood ratio >3 for wt and mutates phenotypes, respectively.

MPS can be calculated as the fraction of mutated vs. wild-type (WT) samples for the specific protein and tumor type. Samples can be ranked based on their MPS for each of the 92 protein/tumor-type pairs for which mutated samples were enriched in differentially activated proteins based on our previous analysis described above. Although the majority of mutated samples had a high MPS, a few had a low MPS, comparable to WT samples, suggesting nonfunctional mutations, or subclonal mutations or regulatory compensation of their effect (FIGS. 7A and 21A-21F), including samples harboring activating mutations in actionable proteins, such as those encoded by EGFR, ERBB2, BRAF, and PI3K, with MPSs≤−0.5 (e.g., three times more likely to have WT activity) (FIG. 7A), suggesting subpar response to targeted inhibitors. Many WT samples had MPSs≥0.5 (i.e., threefold more likely to have mutated activity) (FIG. 7A), suggesting they can respond to targeted inhibitors.

Validating Drug Sensitivity

In some embodiments, to assess whether MPS is a good predictor of drug sensitivity, EGFR-specific MPS analysis can be performed on 79 lung adenocarcinoma cell lines, for which gene expression profiles, EGFR status and chemo-sensitivity to EGFR inhibitors were available from the Cancer Cell Line Encyclopedia, including saracatinib (AZD0530), erlotinib and lapatinib. Of the cell lines with low EGFR MPS (e.g., <−0.5) that yet harbored EGFR mutations, 0/2, 1/2, and 1/2 cell lines can be observed to be sensitive to AZD0530, erlotinib and lapatinib, respectively. Conversely, 5/6, 5/6, and 4/6 cell lines of those with MPS>0.5, can be observed to be sensitive to those drugs, respectively (FIG. 7B), suggesting a strong association between MPS and chemosensitivity in EGFR-mutated cell lines. Additionally, considering only EGFR WT cell lines, the fraction responding to EGFR inhibitors can be higher among those with MPS>0.5 (50% vs. 33% for AZD0530, 43% vs. 33% for erlotinib and 36% vs. 27% for lapatinib, respectively) compared to those with MPS<−0.5 (FIG. 7B). MPS can be significantly associated with chemosensitivity, regardless of EGFR mutation status, by Pearson correlation analysis (e.g., P<10-5 for each of the three drugs) (FIG. 7B), and by comparing sensitivity of cells with MPS>0.5 and MPS<−0.5 by Student's t-test (e.g., P<0.01 and P<0.05 for AZD0530 and erlotinib, respectively) (FIG. 7B).

Assessing the Role of Site-Specific Mutations

Figure 22A:
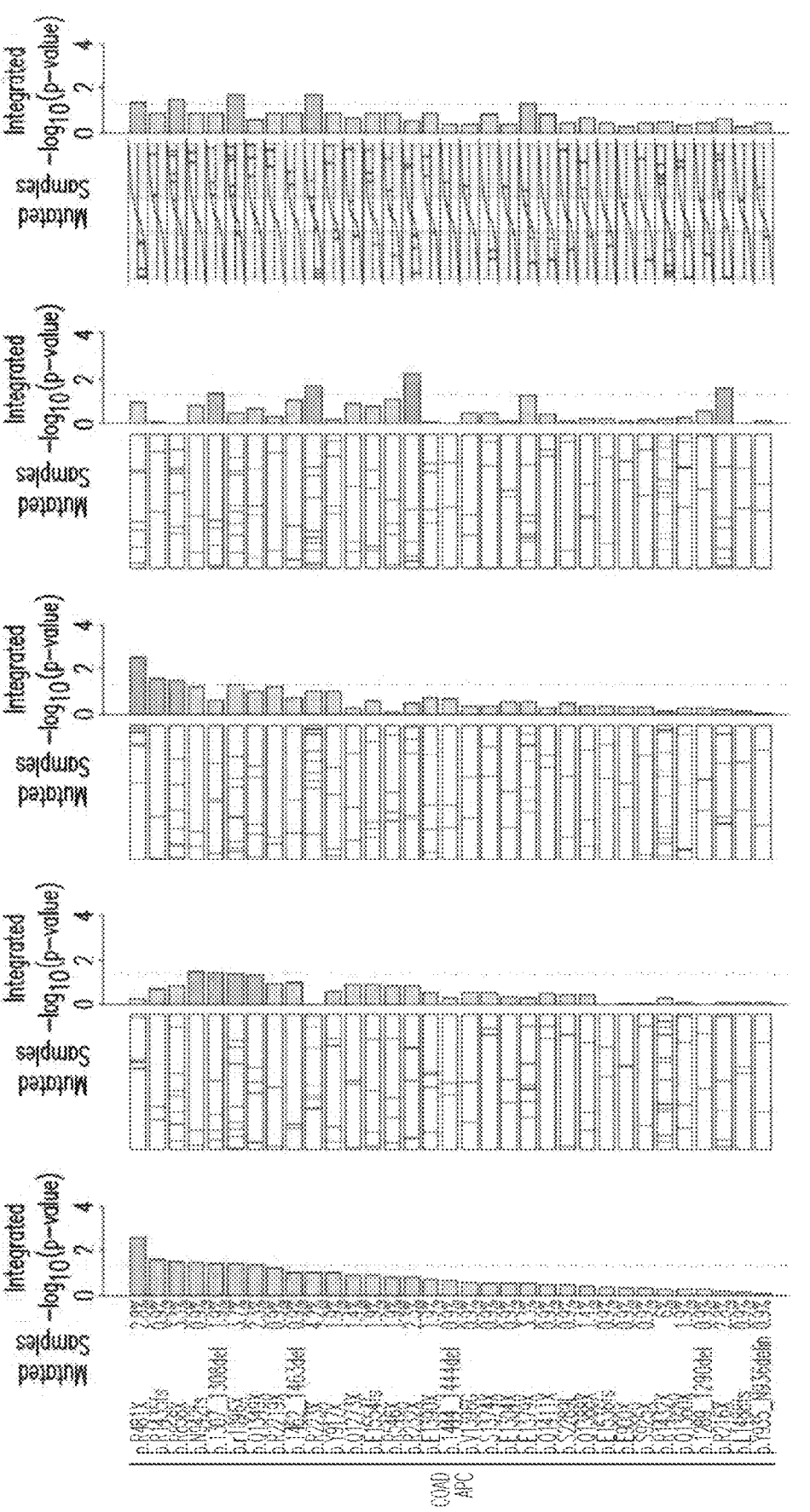
Figure 22A:
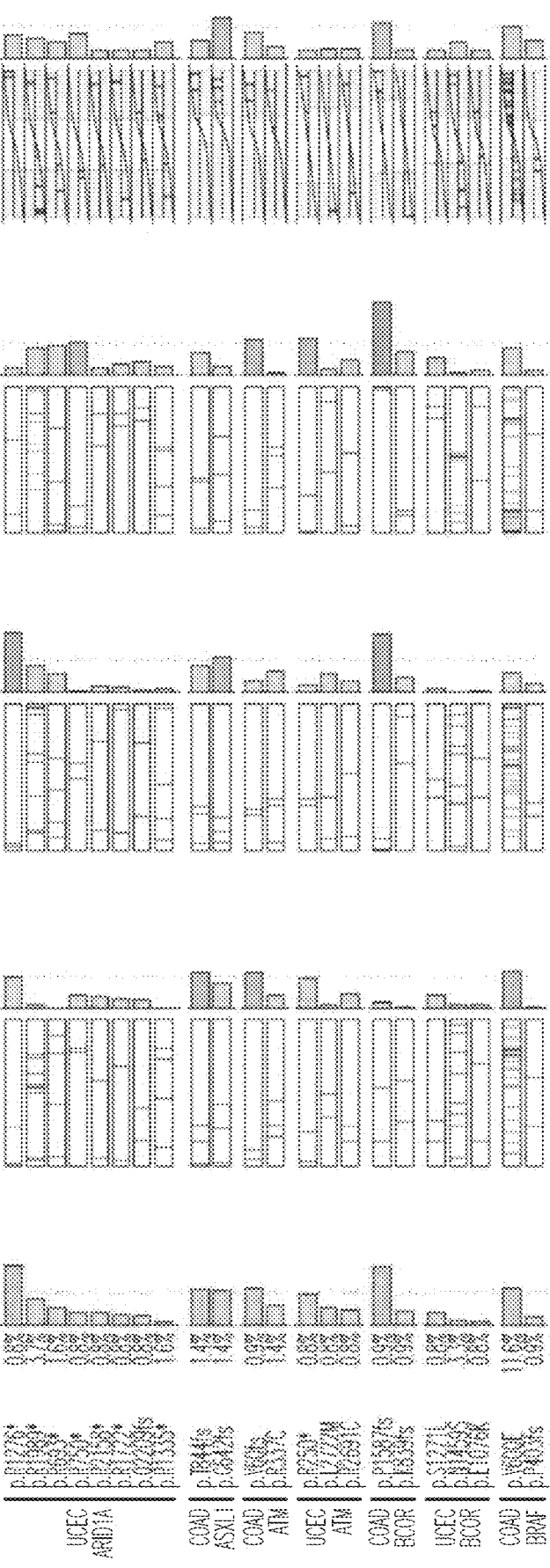
Figure 22B:
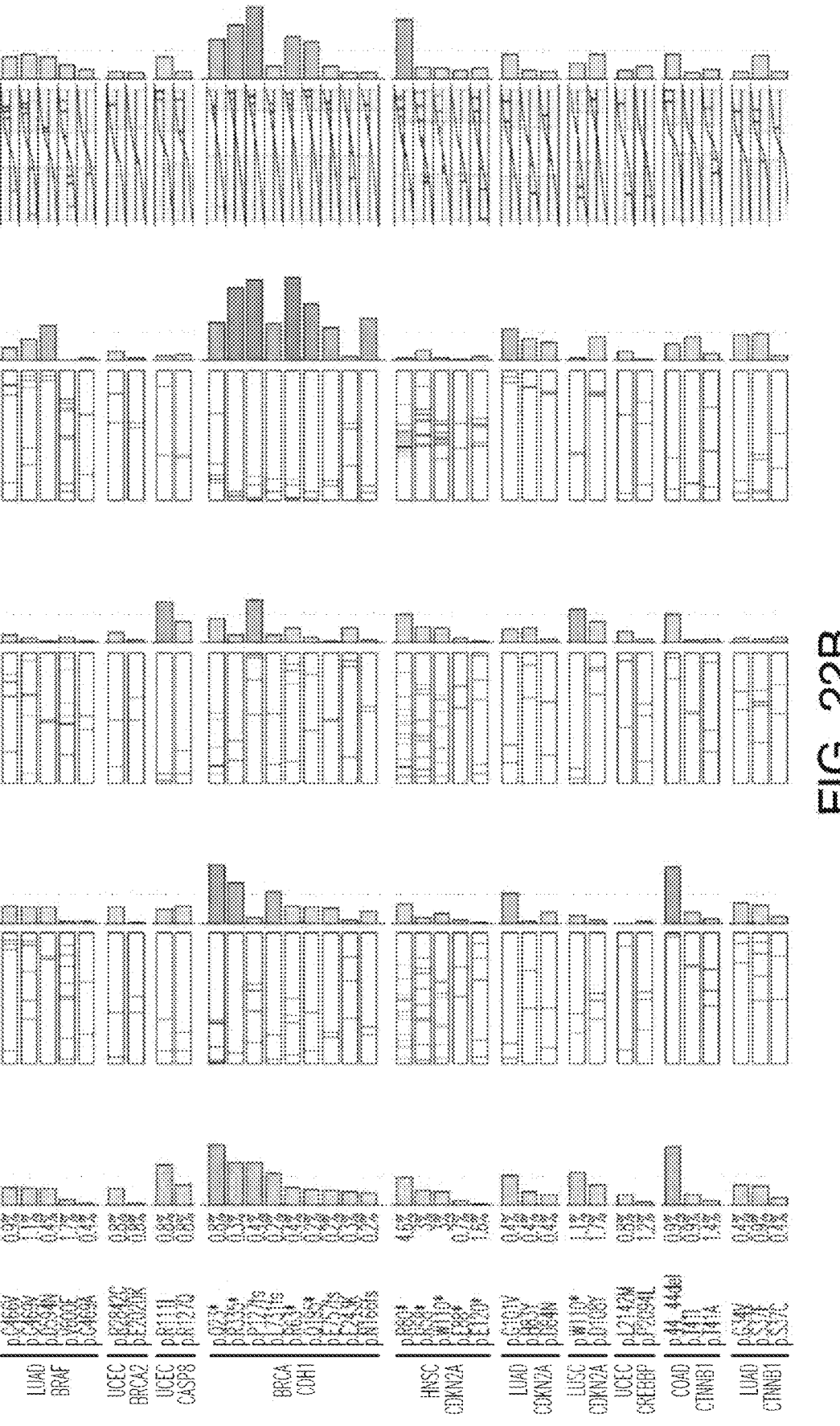
Figure 22B:
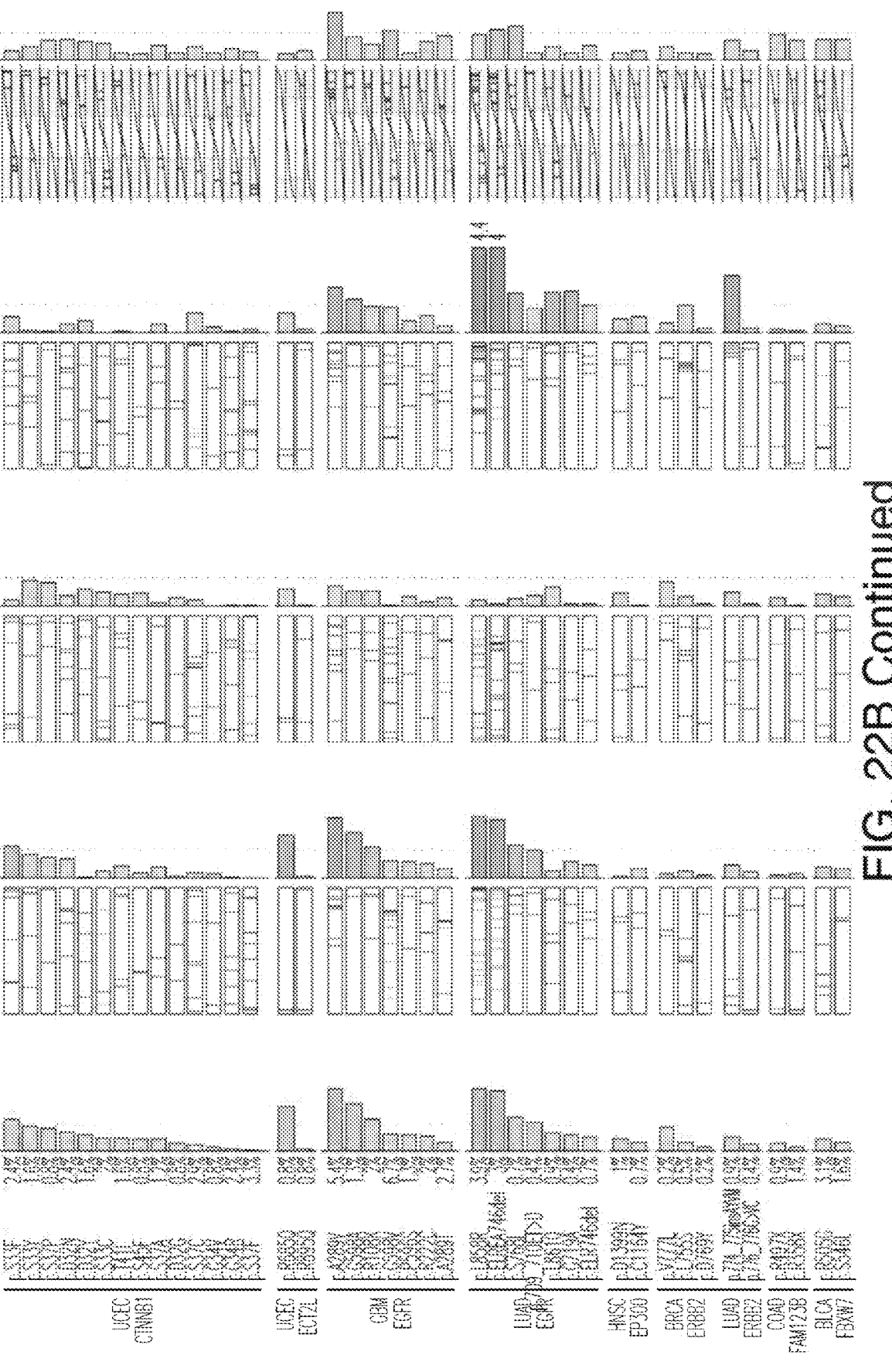
Figure 22C:
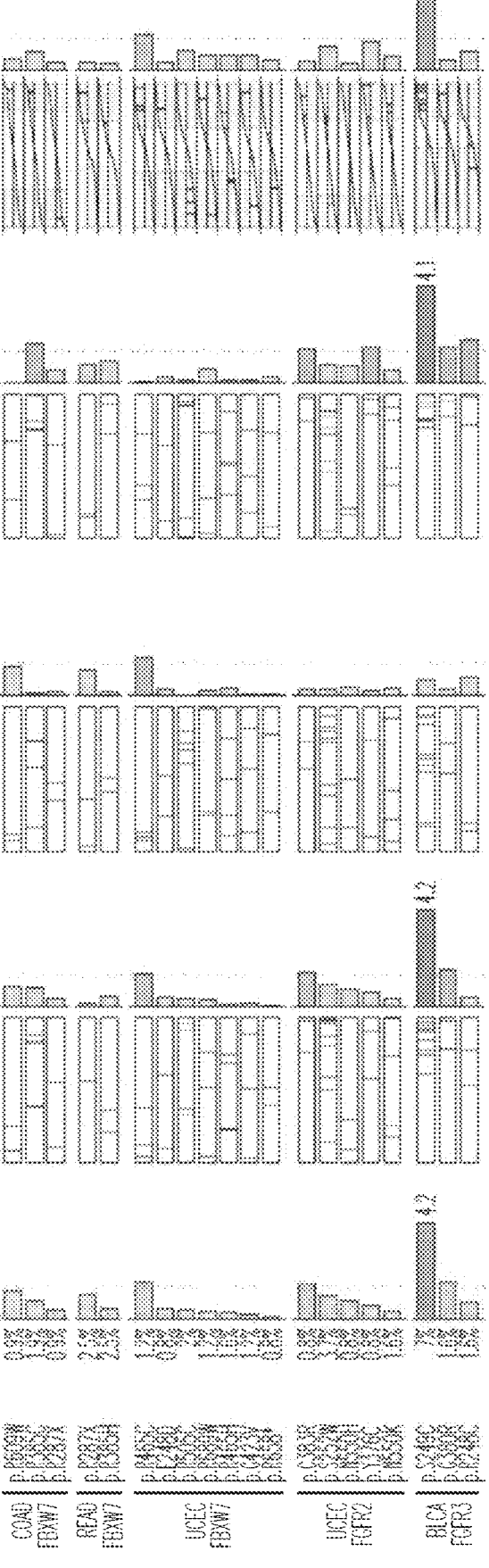
Figure 22C:
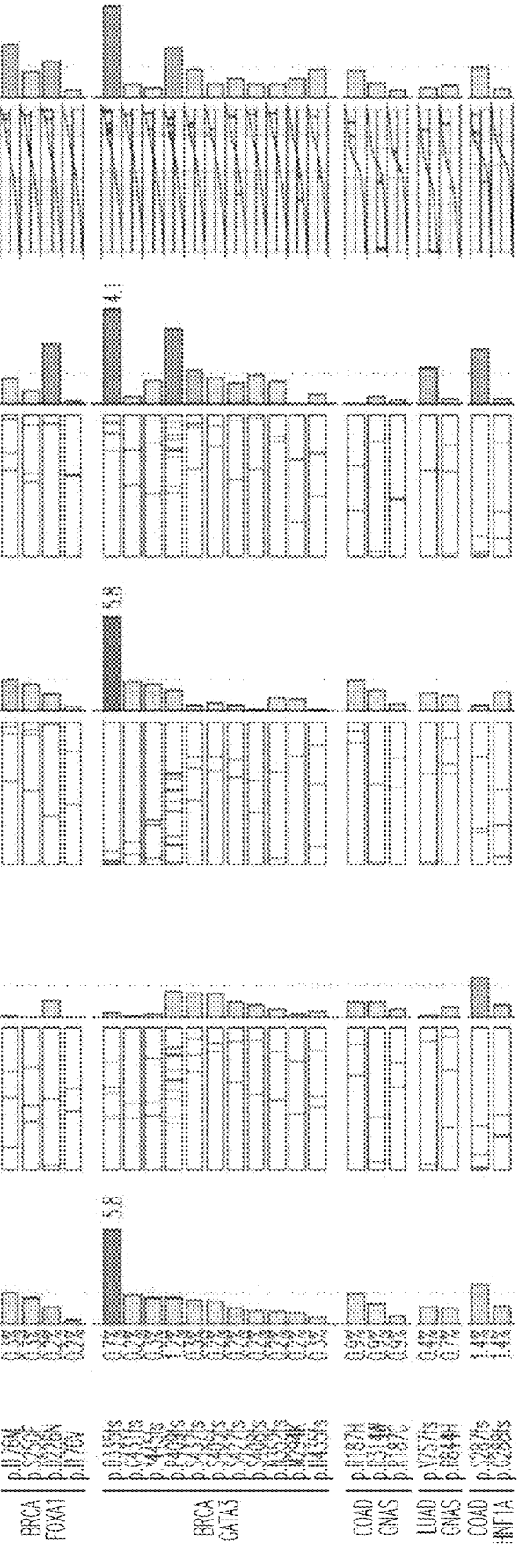
Figure 22C:
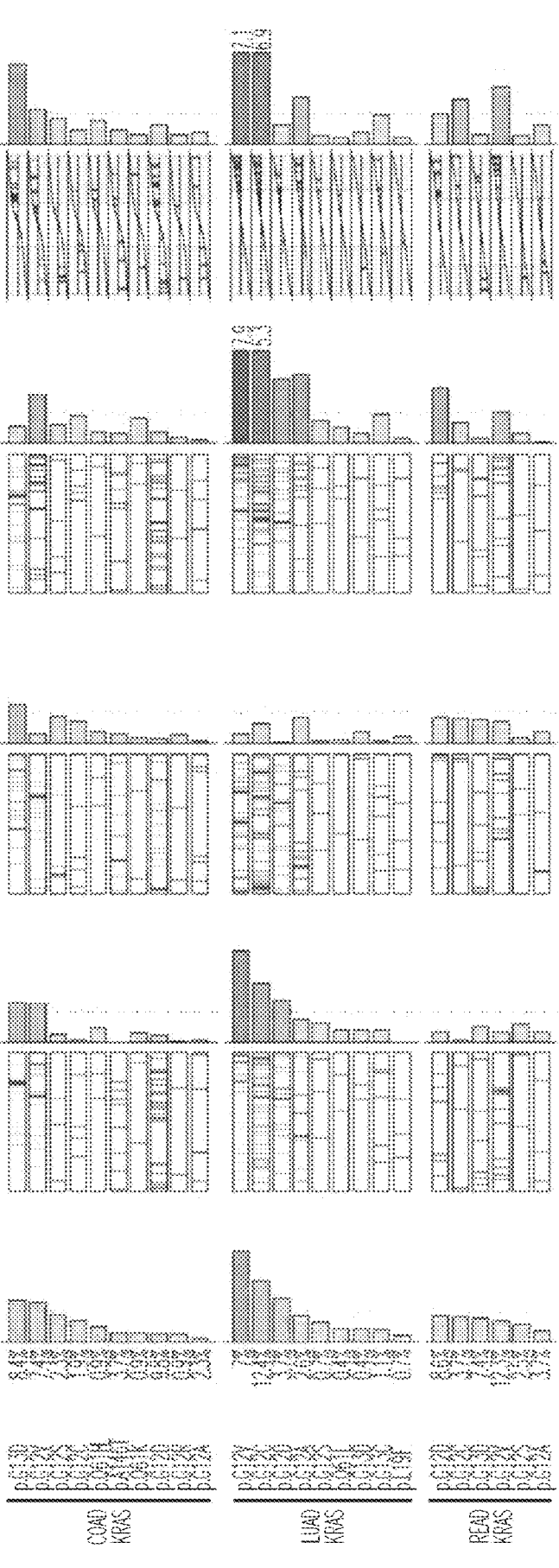
Figure 22D:
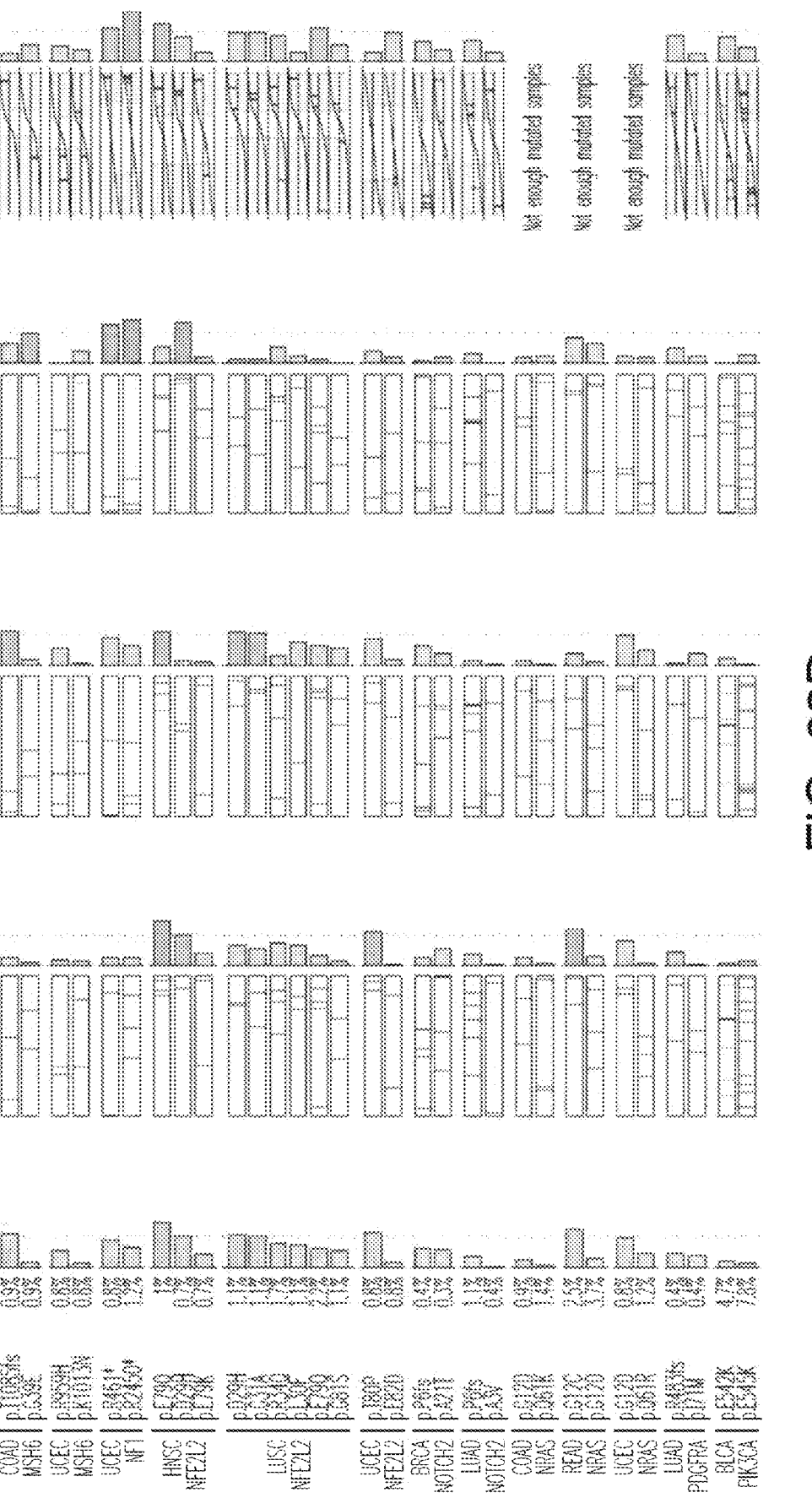
Figure 22F:
Figure 22F:
Figure 22G:
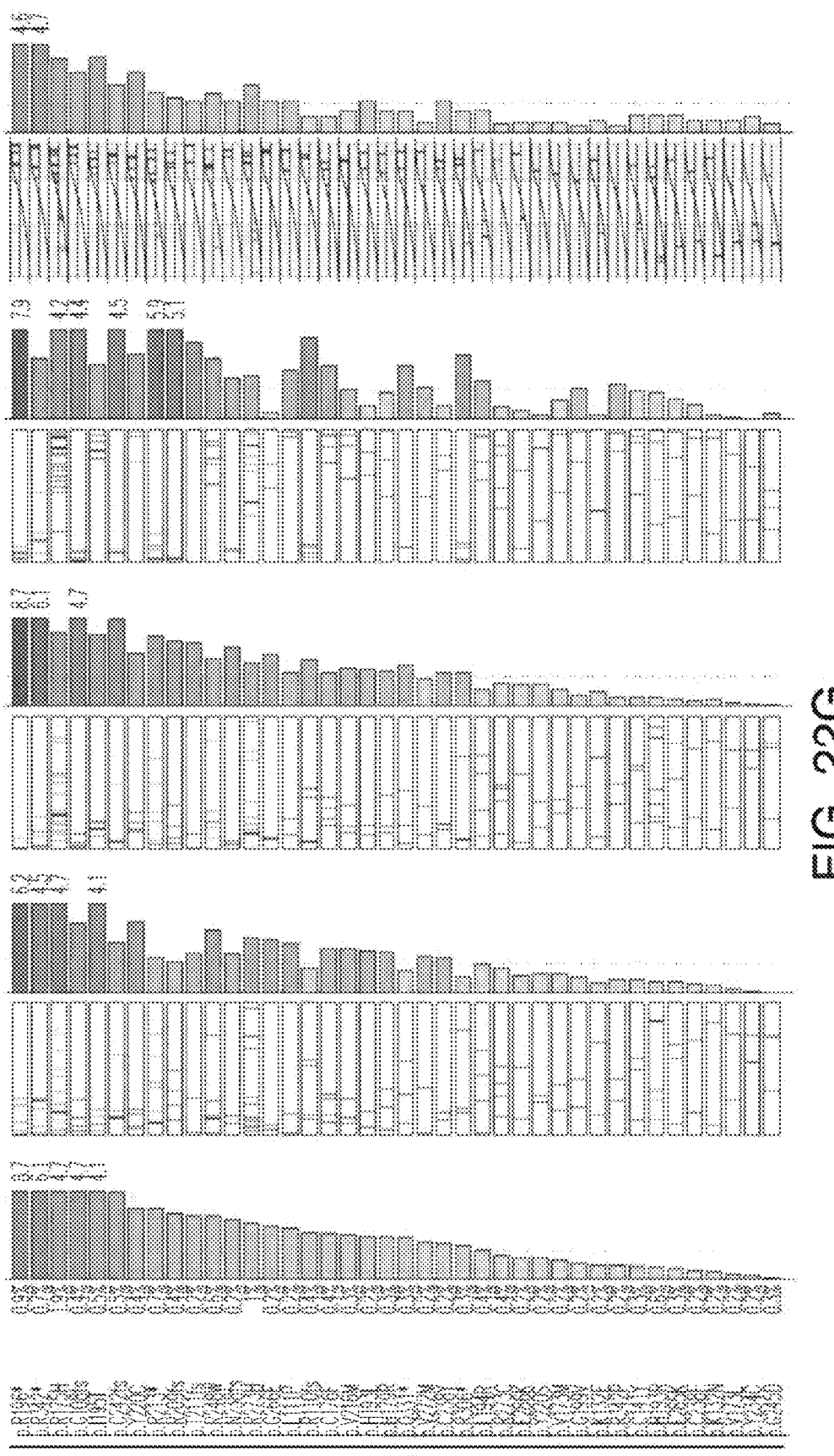
Figure 22G:
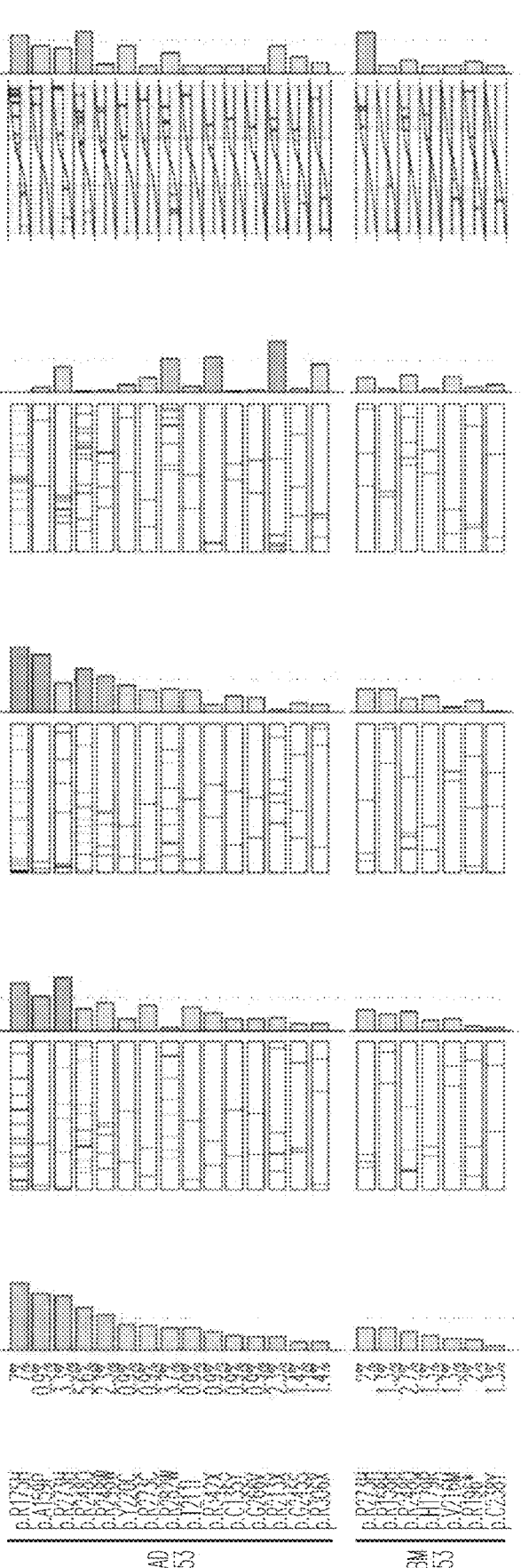
Figure 22H:
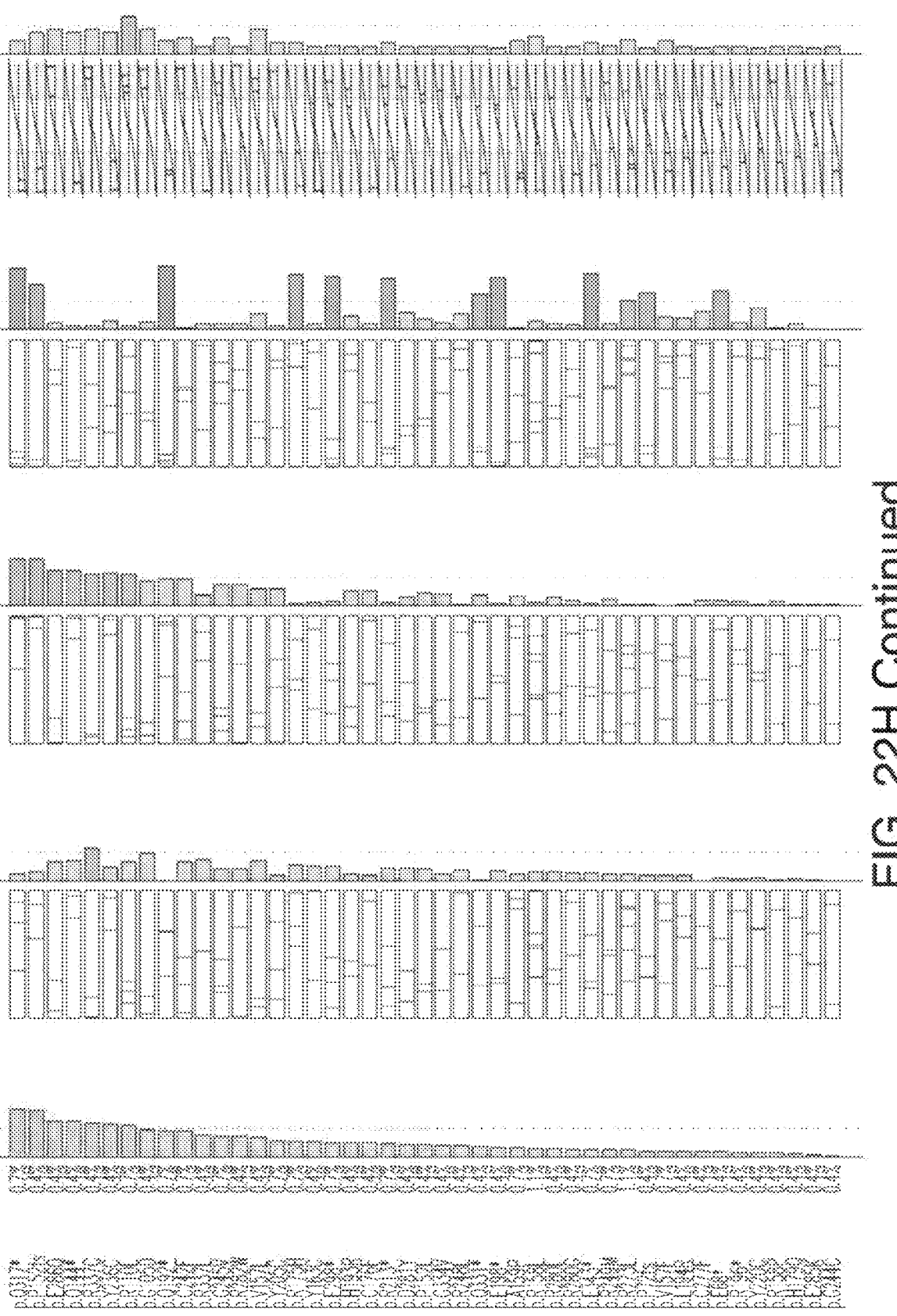
Figure 22I:
Figure 22I:
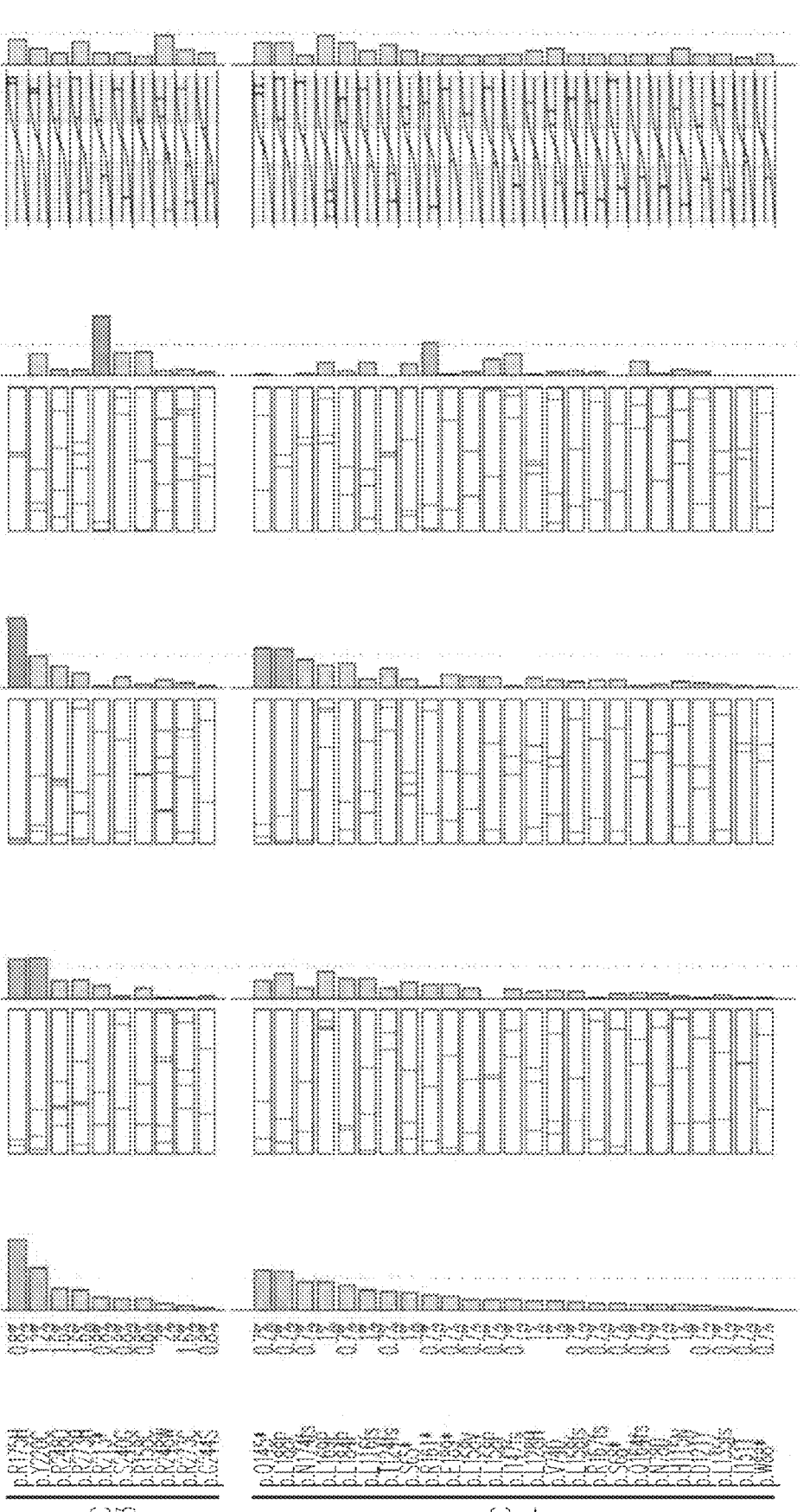
Figure 23A:
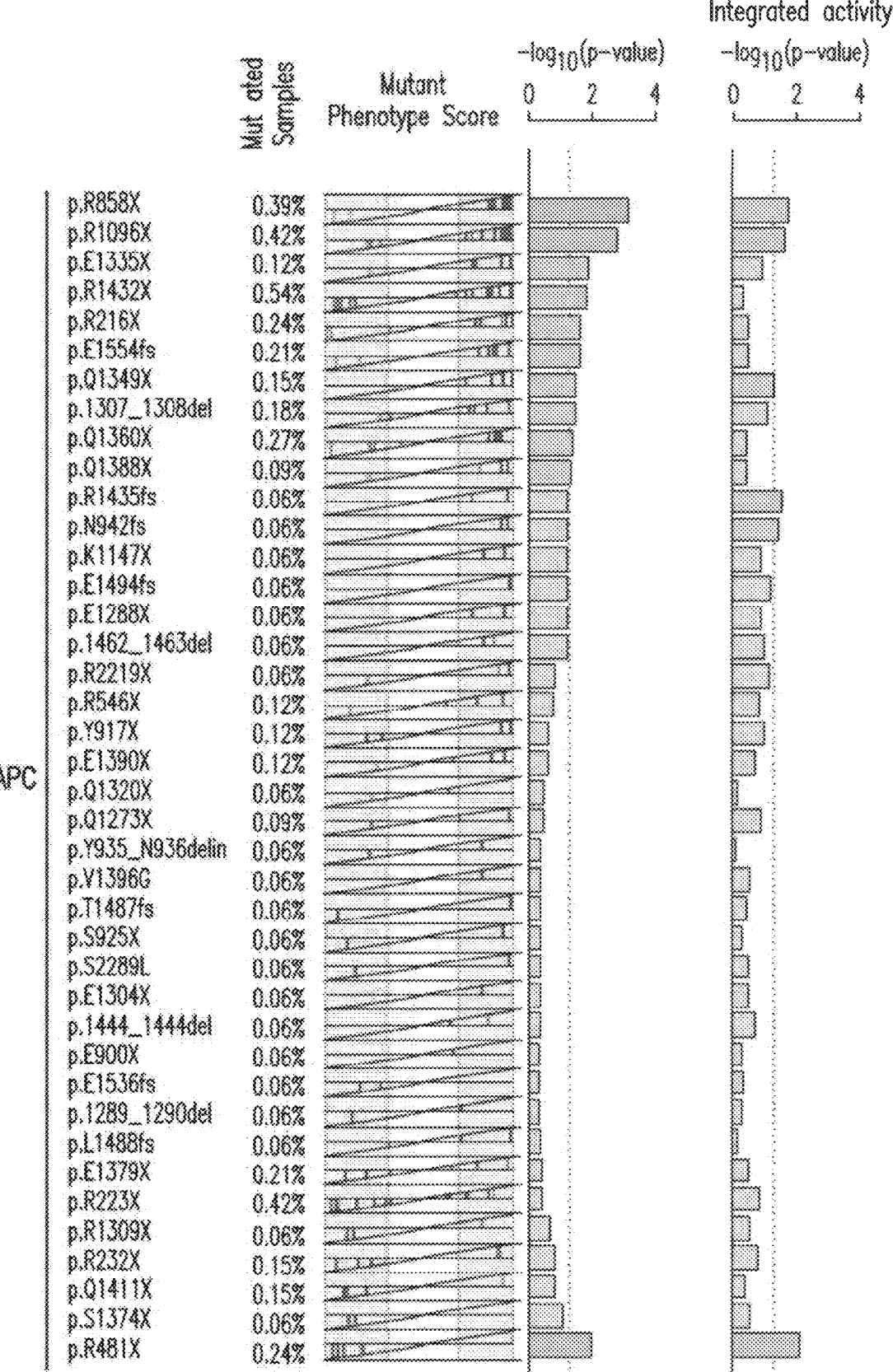
FIGS. 23A-23L illustrate a summary of the differential impact of non-silent somatic mutation (NSSM) variants on the coded protein activity.
Figure 23B:
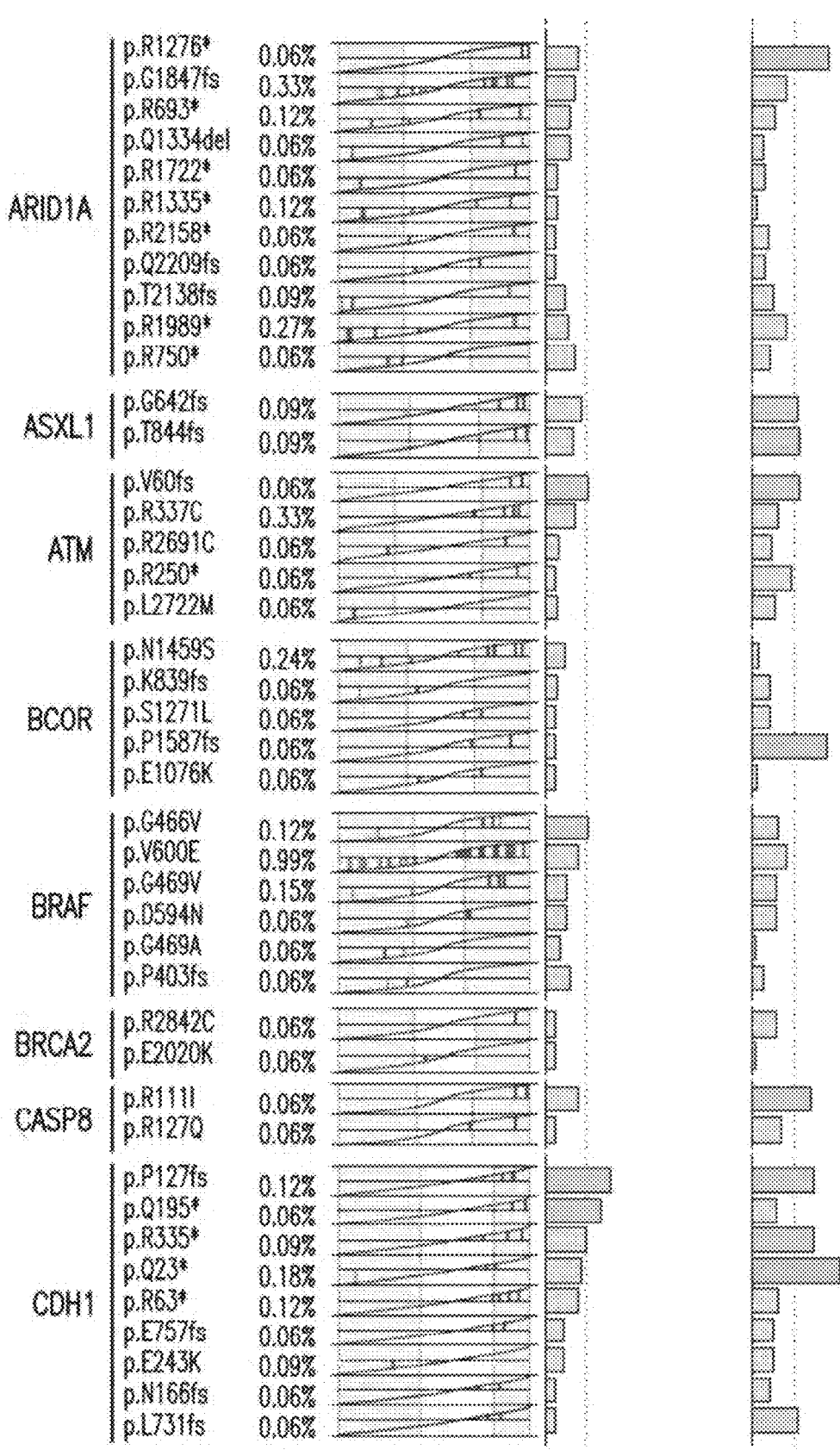
Figure 23C:
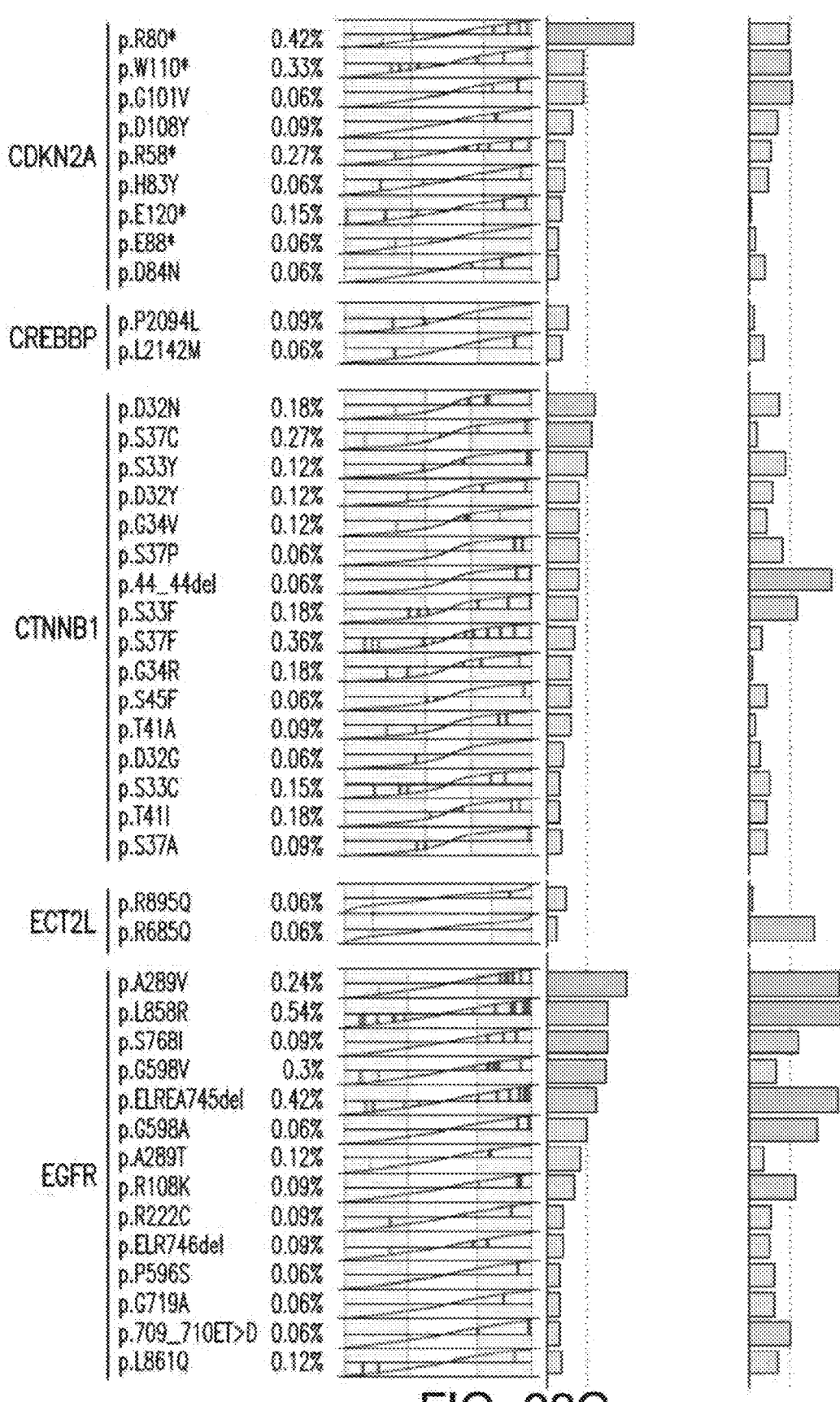
Figure 23D:
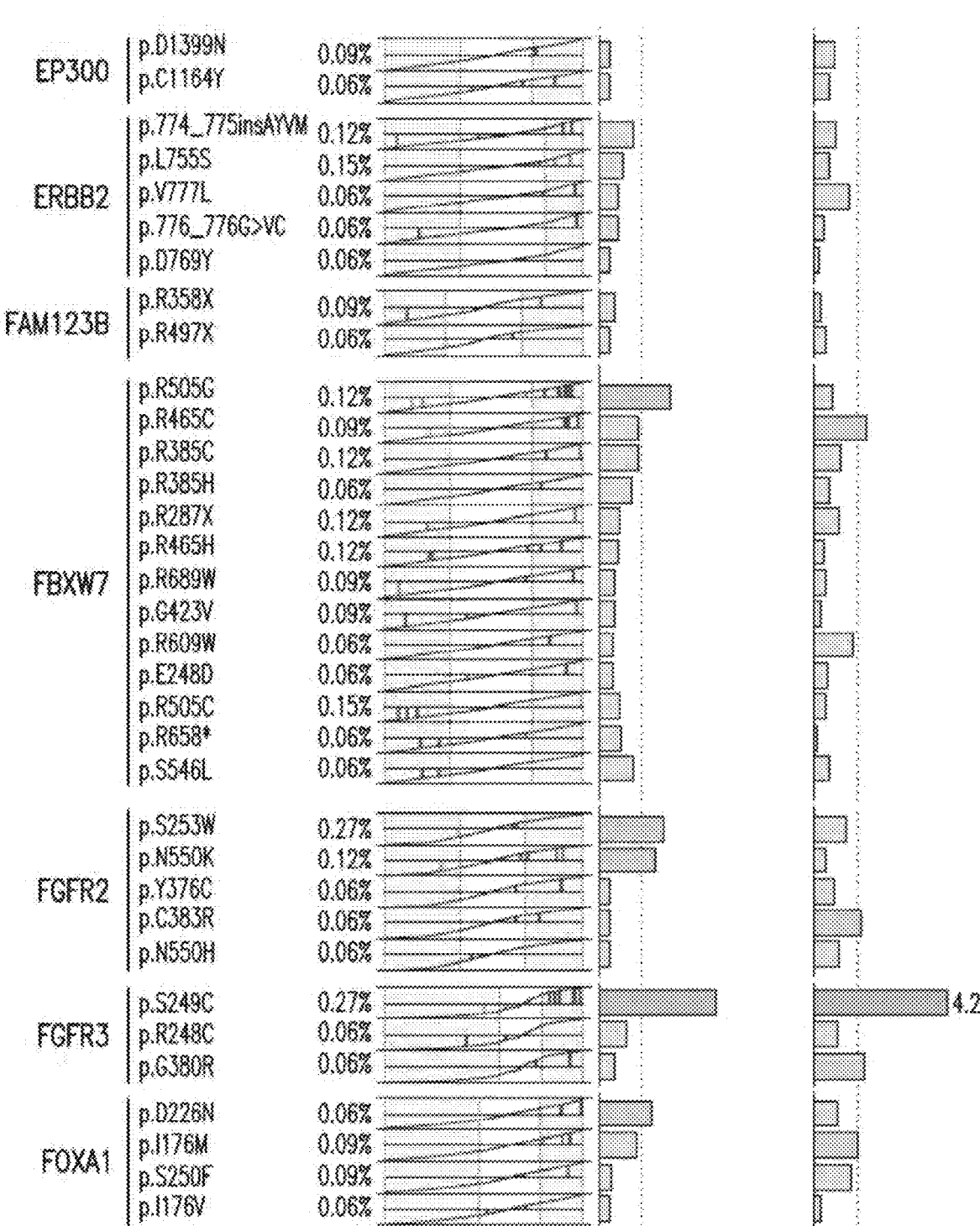
Figure 23E:
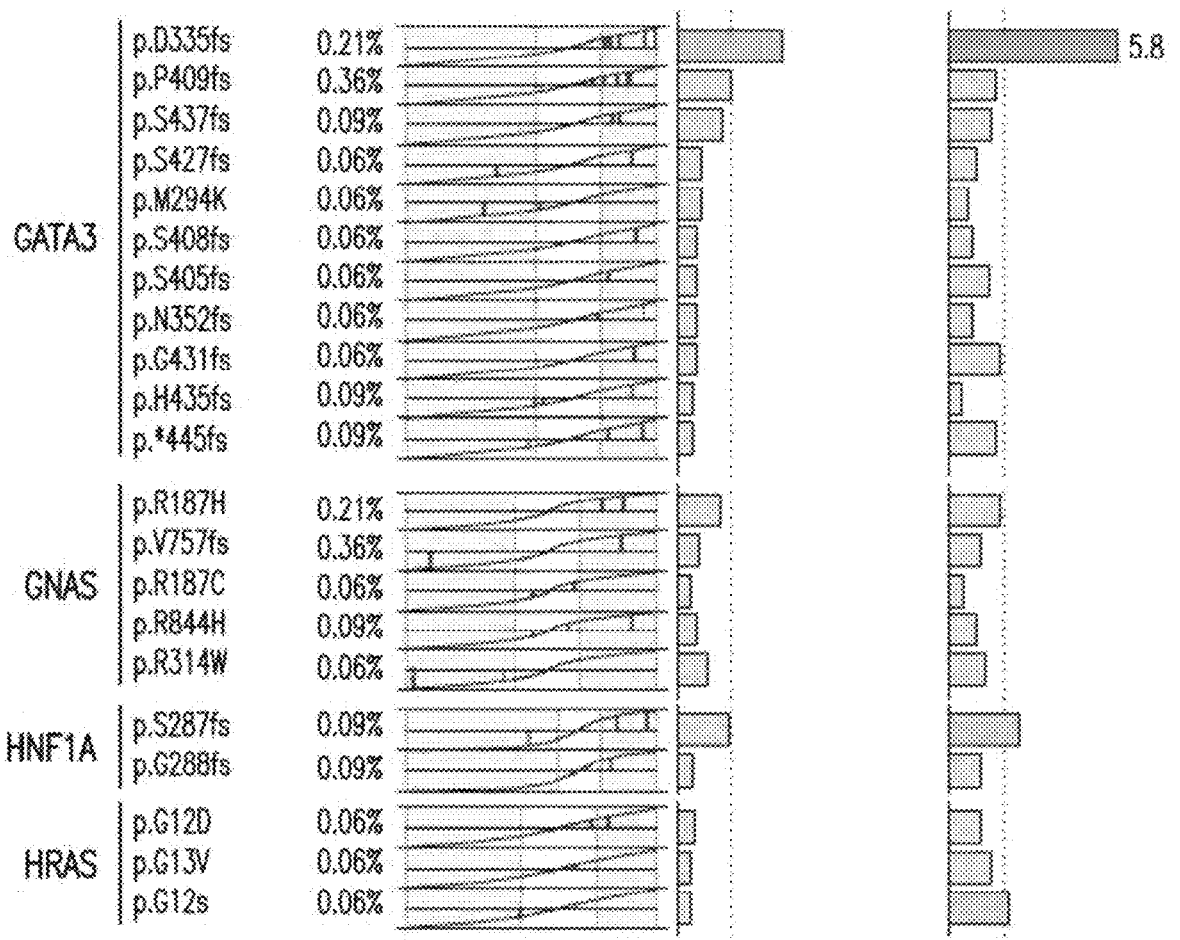
Figure 23E:
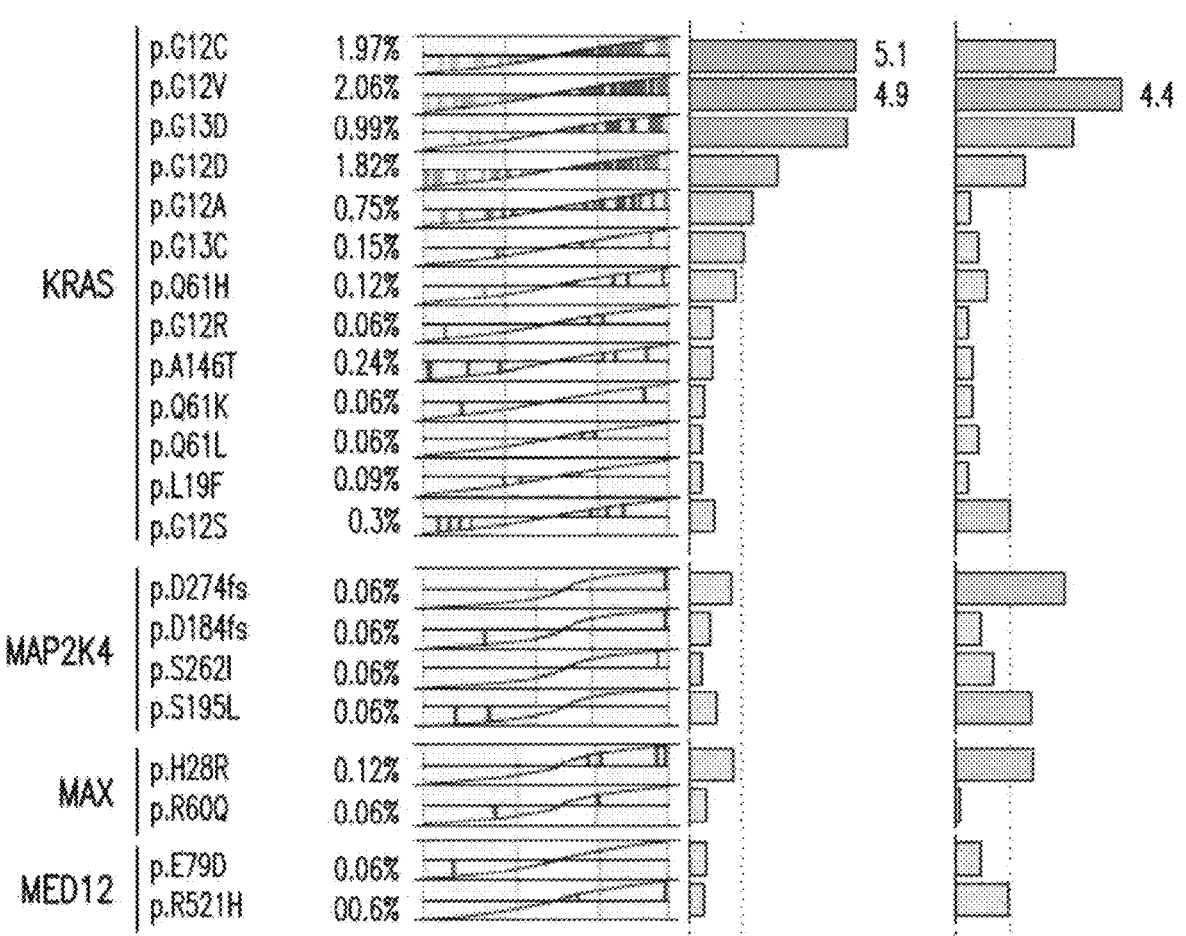
Figure 23F:
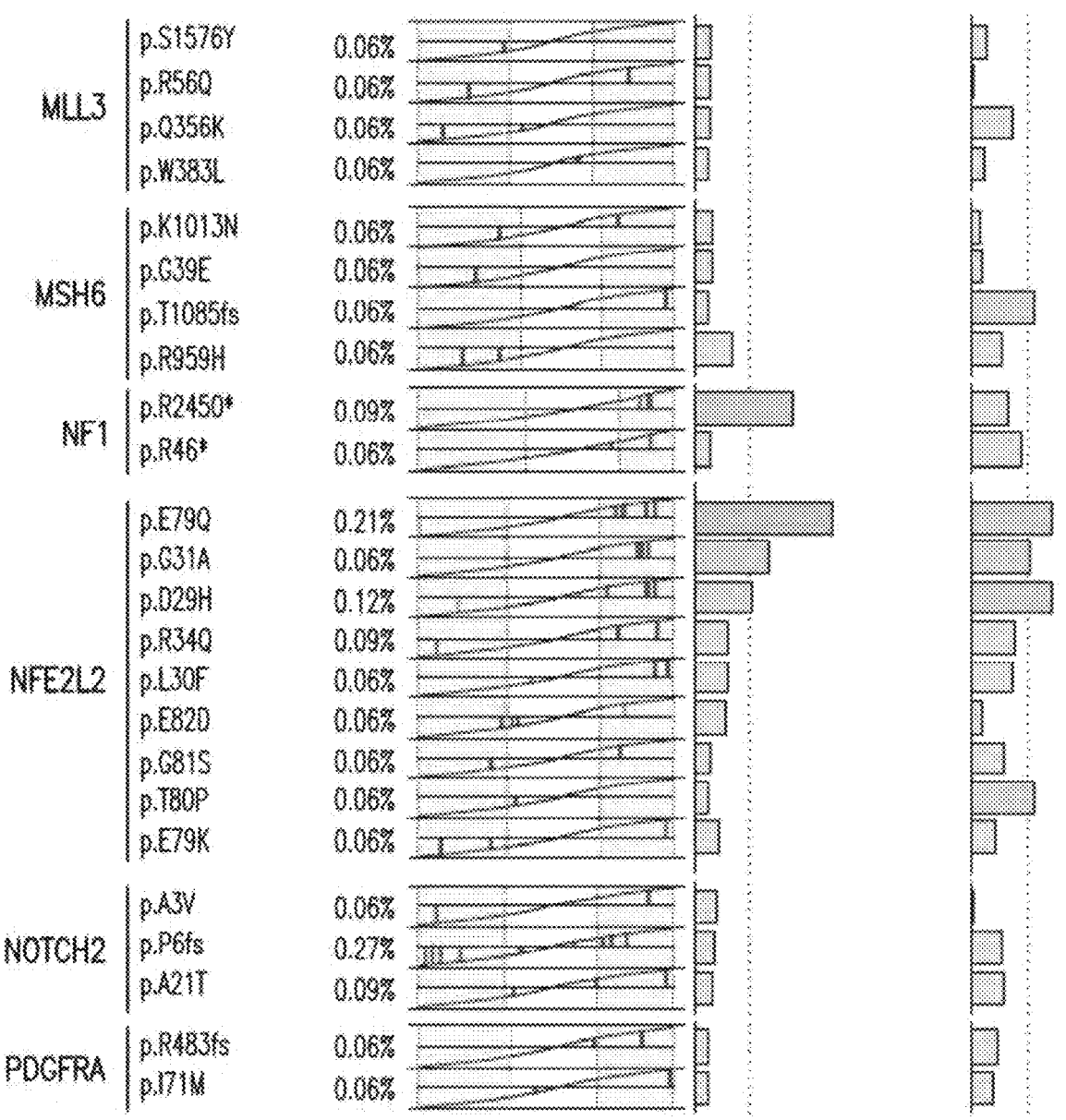
Figure 23G:
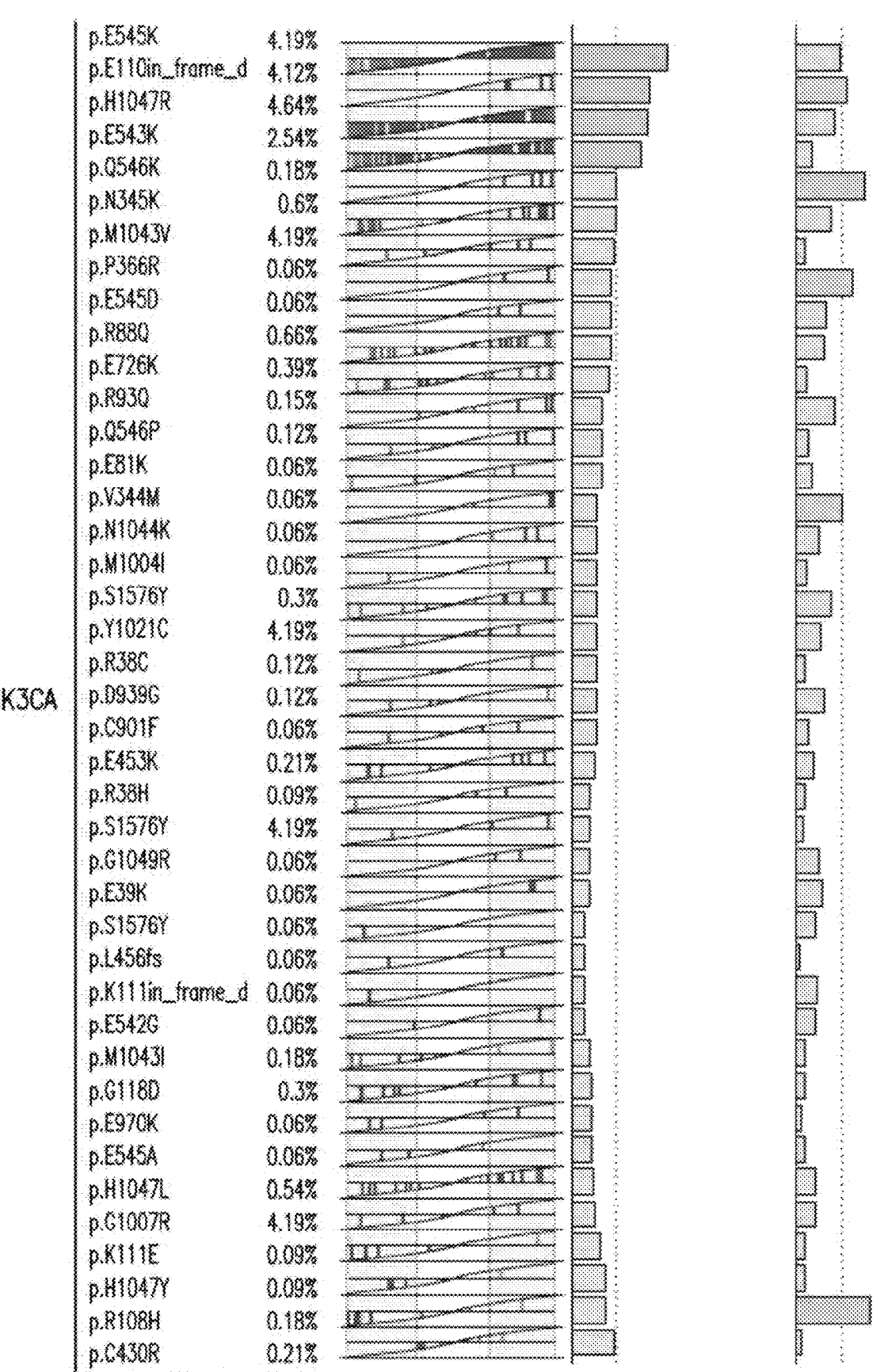
Figure 23H:
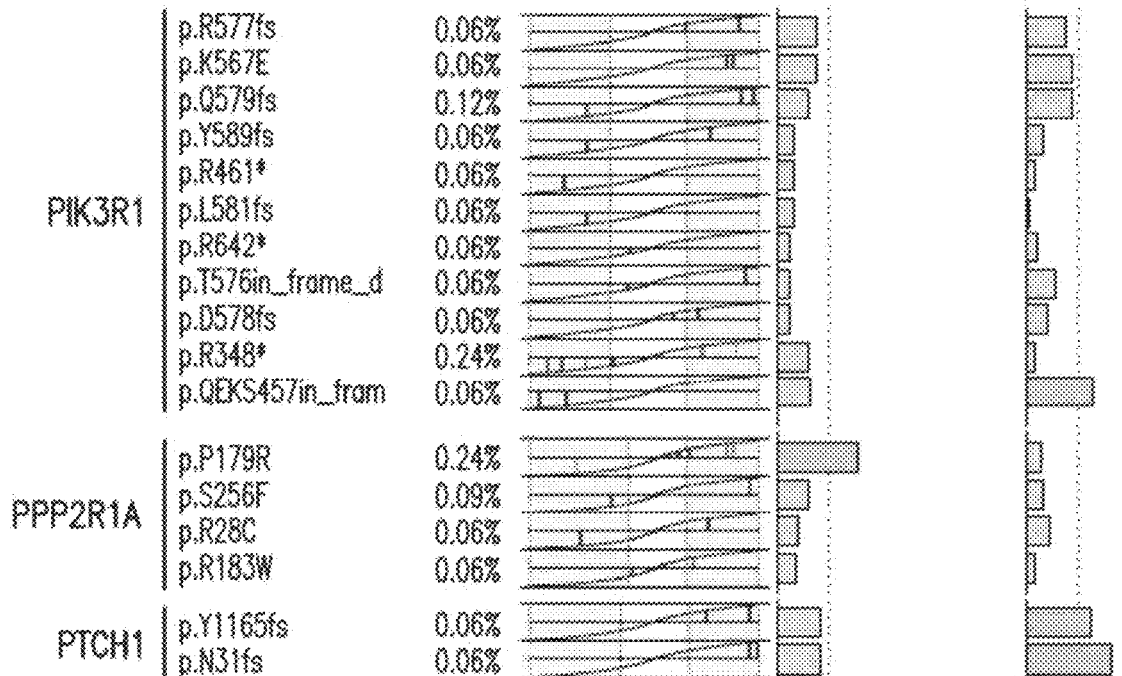
Figure 23H:
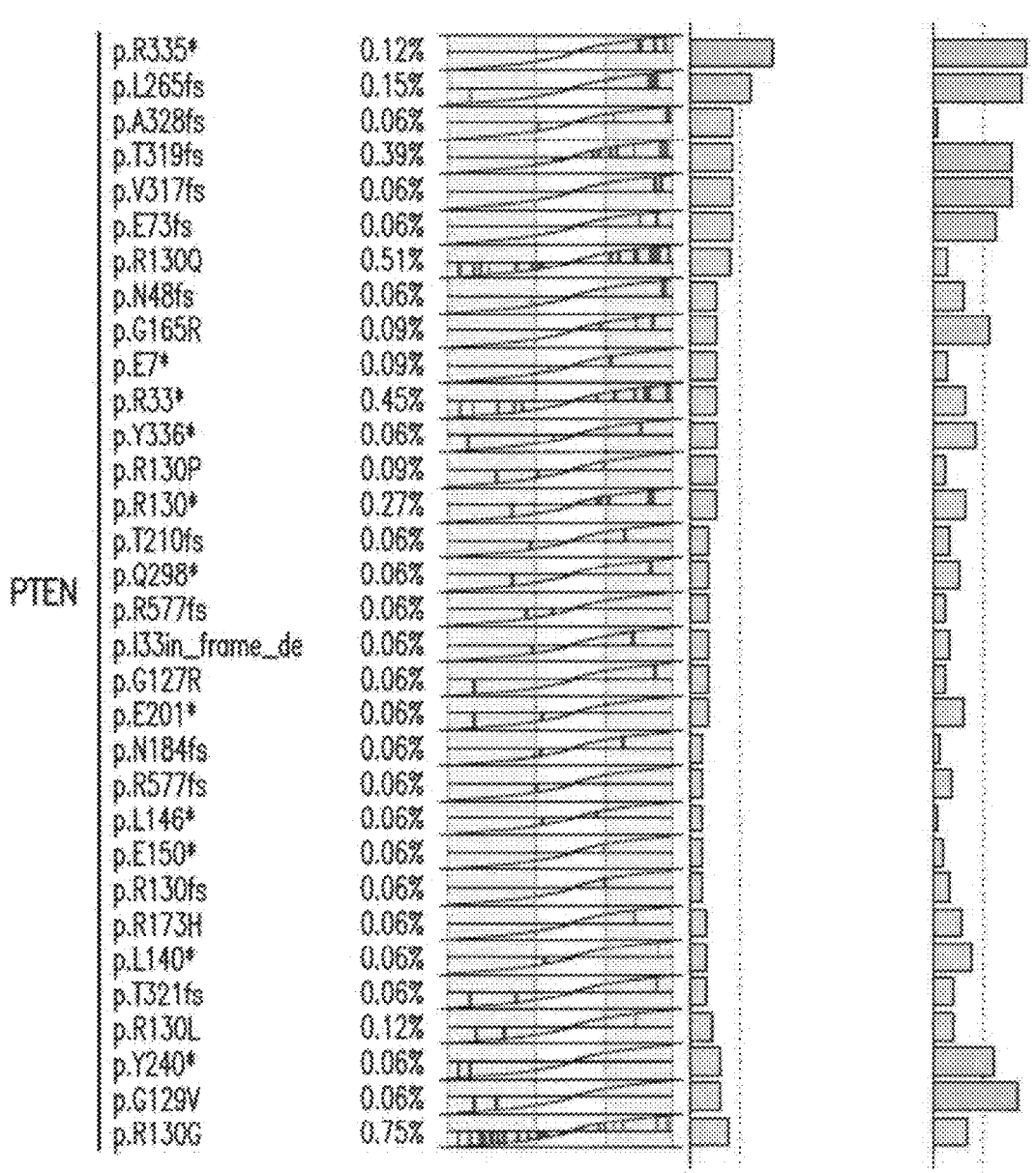
Figure 23I:
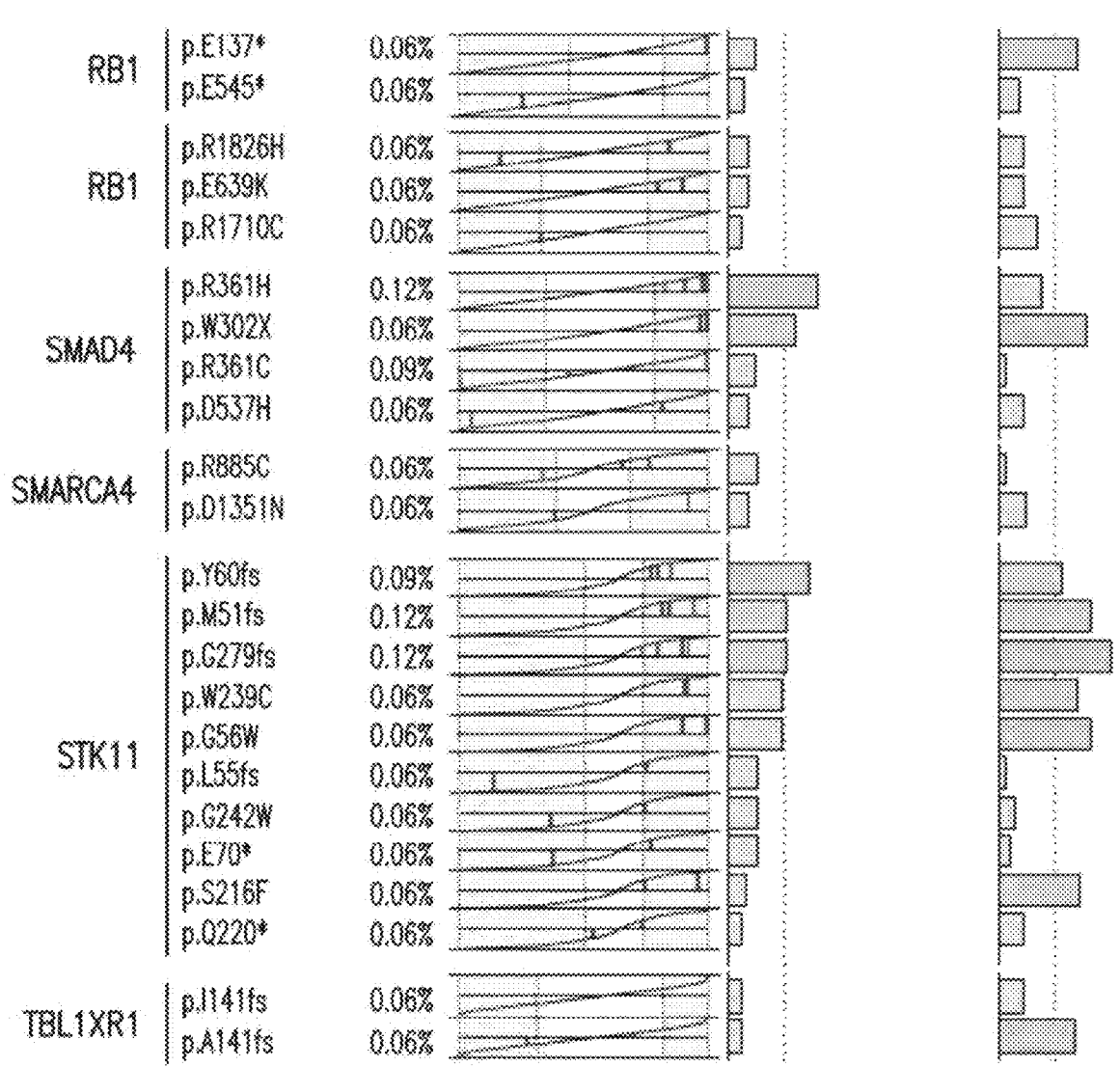
Figure 23J:
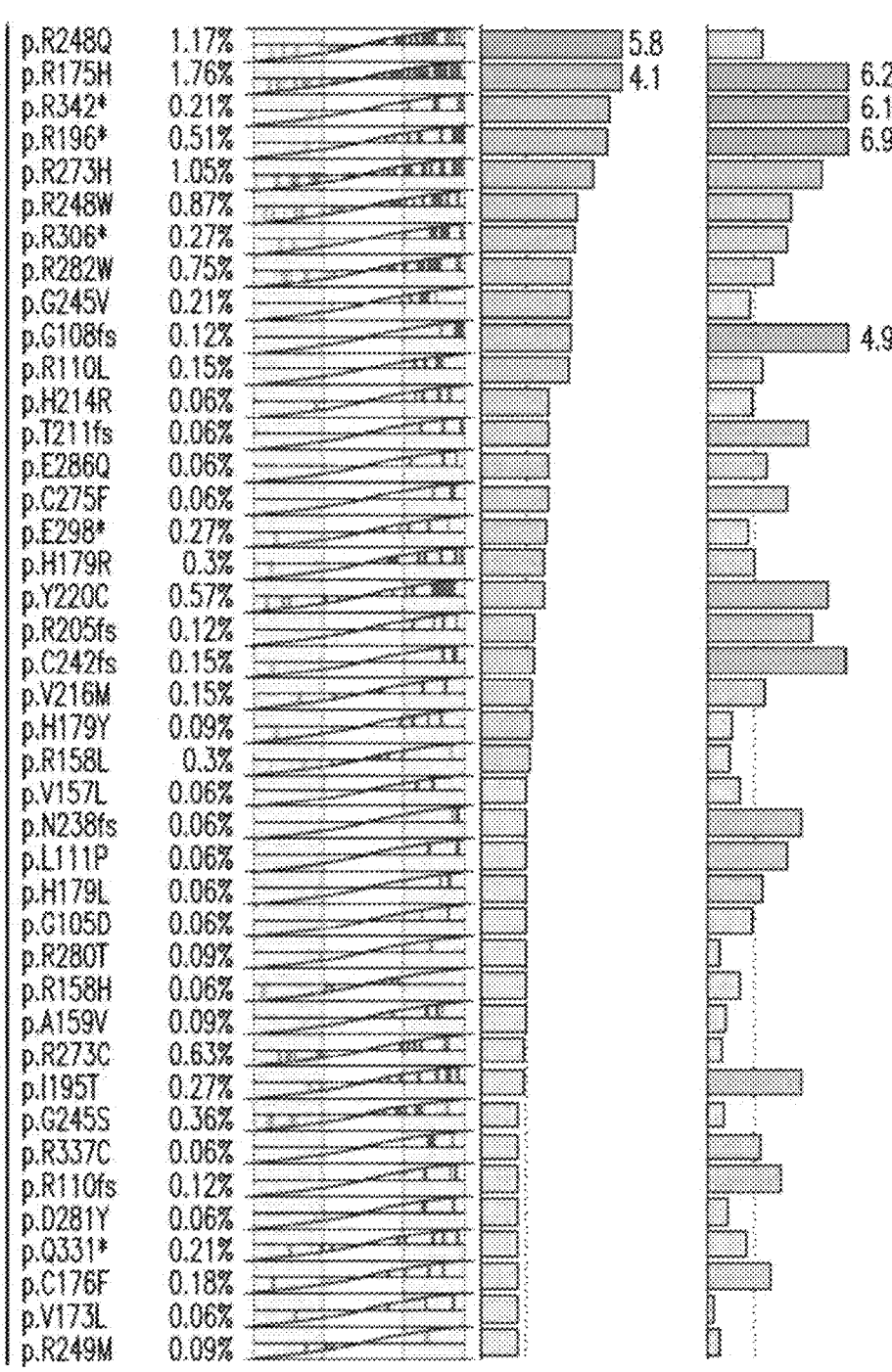
Figure 23J:
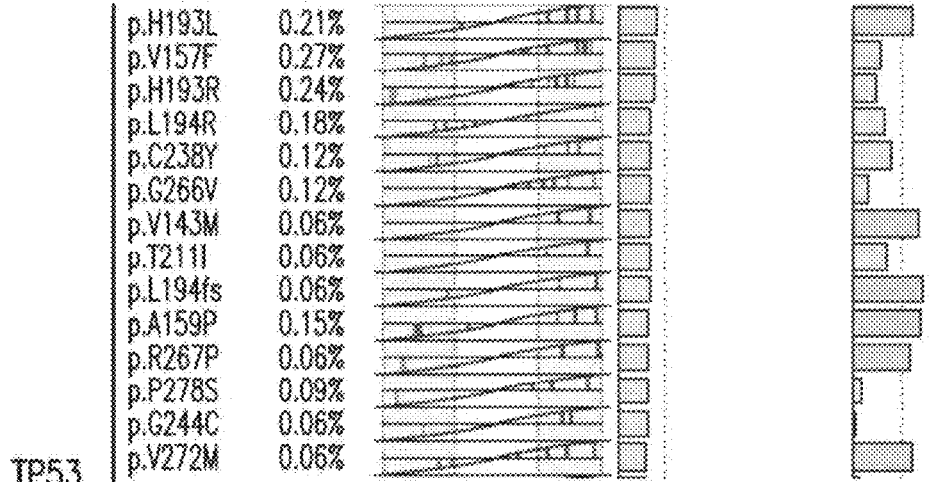
Figure 23K:
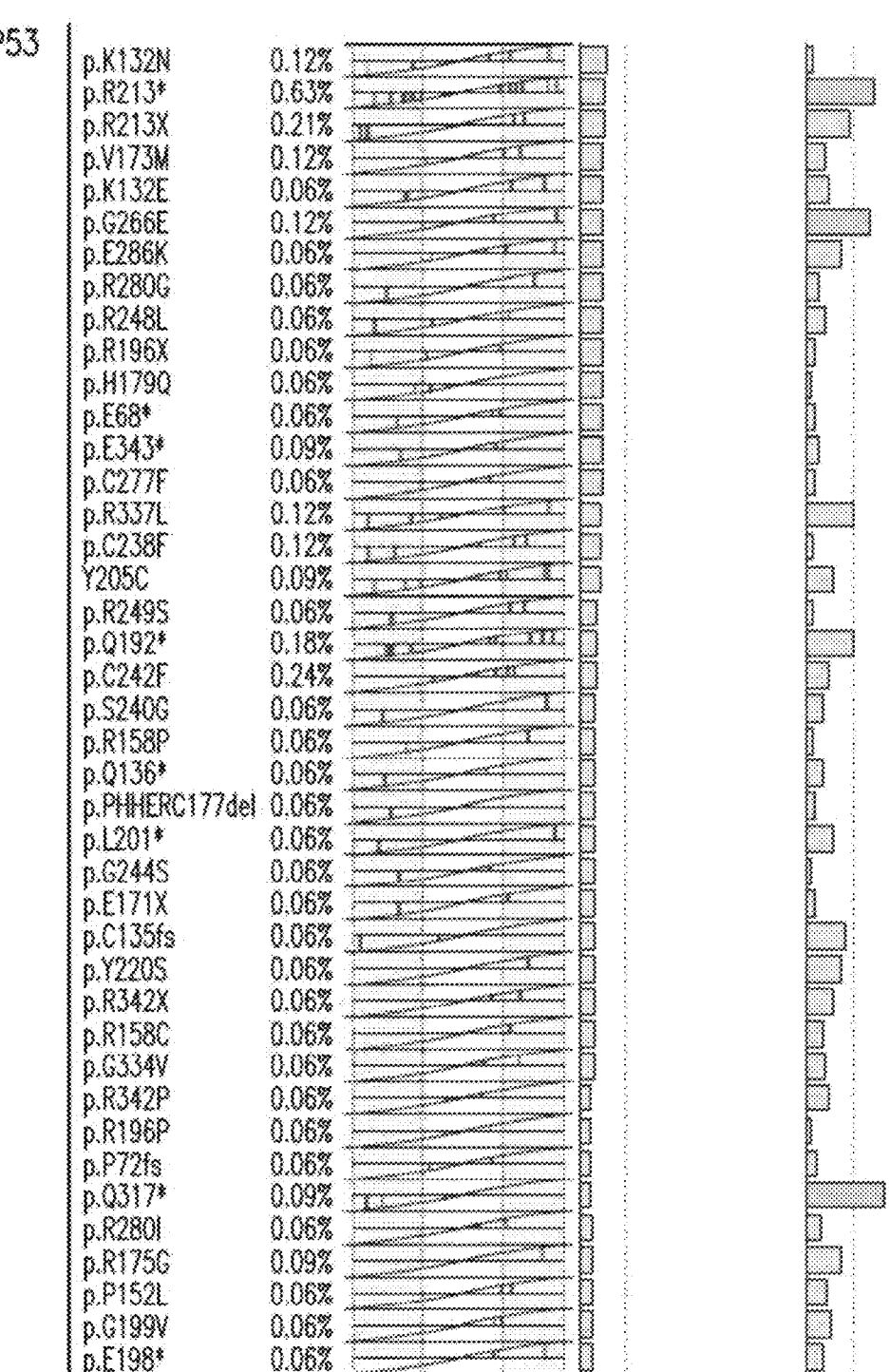
Figure 23K:
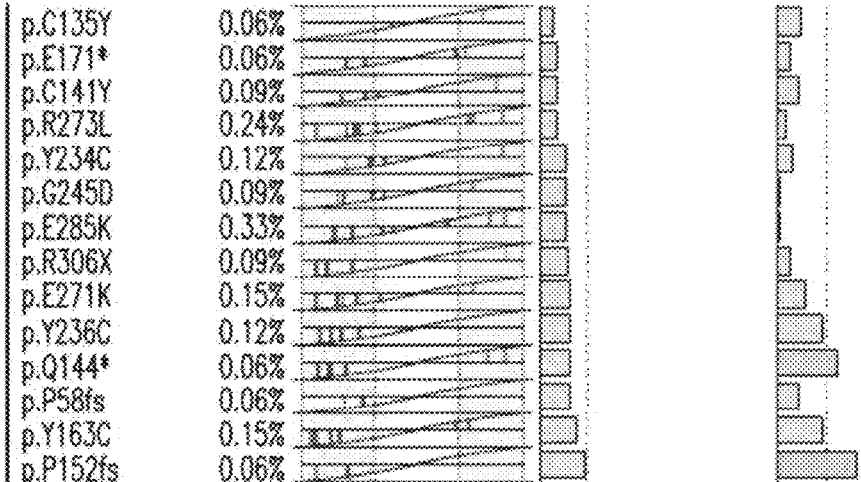
Figure 23L:
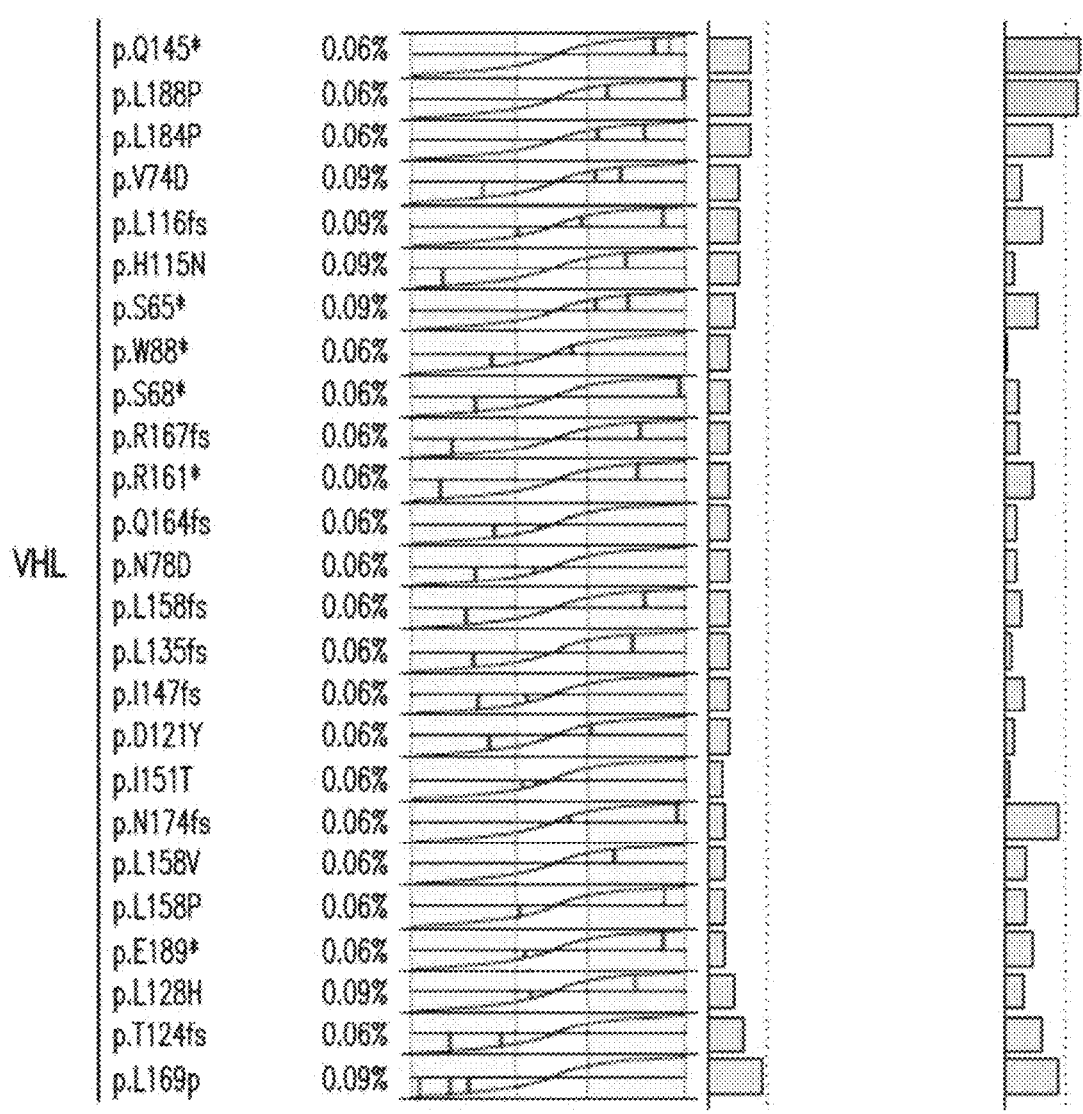

In some embodiments, it can be determined whether VIPER can also be used to assess differential activity associated with mutations at specific protein sites. Such differential activity assessment can be instrumental in elu-cidating the functional effect of rare or private mutations. In particular, it can be determined whether different mutations in the same gene (e.g., p.Gly12Val vs. p.Gly12Asp changes for the KRAS product) can produce quantitatively distinct effects on protein activity. Mutations affecting COSMIC genes that were detected in at least two samples of the same tumor type can be identified based on four quantitative measurements: (i) their VIPER-inferred global activity, (ii) their VIPER-inferred RPT activity, (iii) their differential gene expression, and (iv) their MPS (for mutations affecting at least 10 samples). In an exemplary embodiment, 648 locus-specific mutations were analyzed in 49 distinct genes, across 12 tumor types (FIGS. 22A-21I).

Figure 8A:
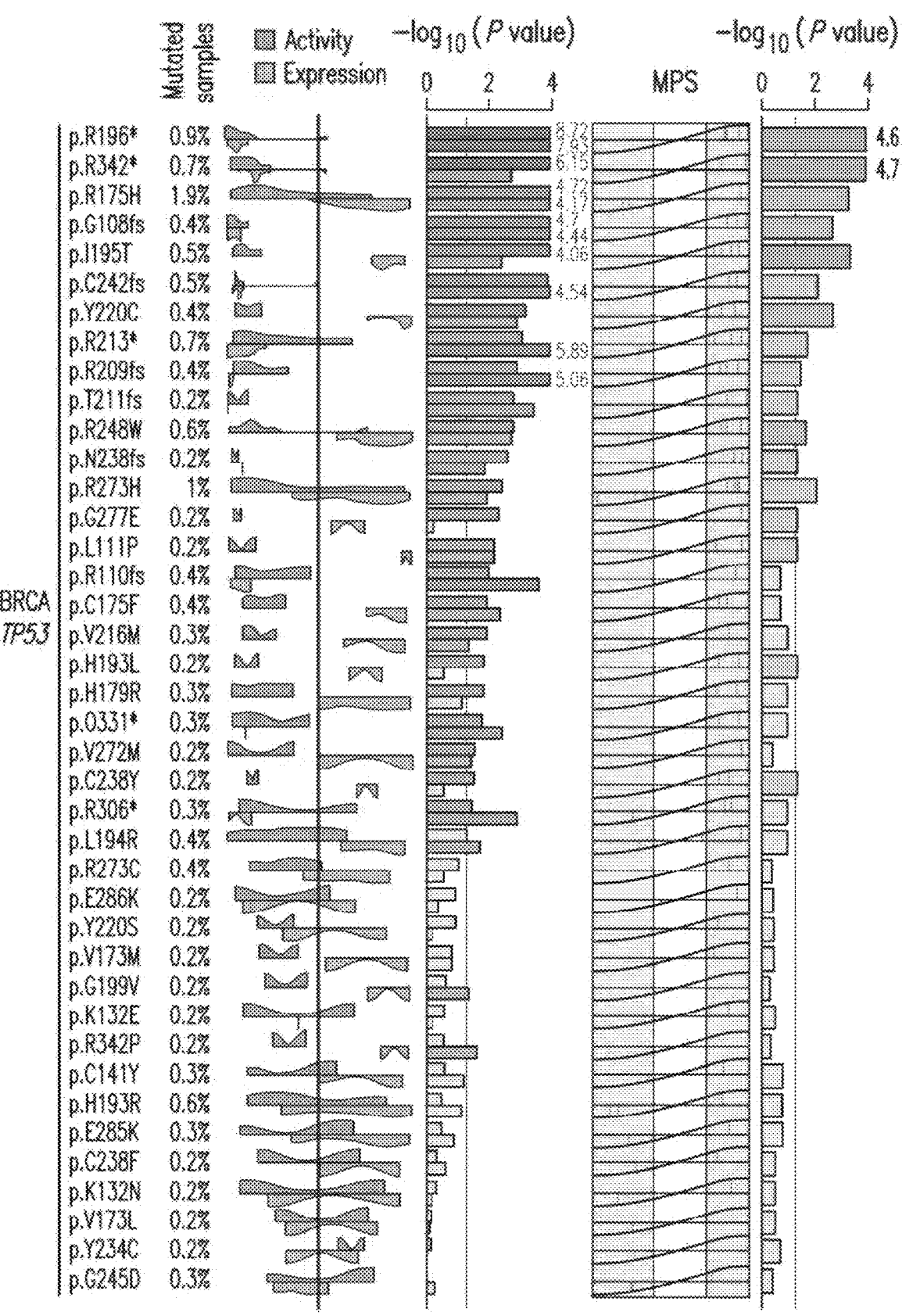
FIGS. 8A and 8B illustrate the effect of specific nonsilent somatic mutation variants on VIPER inferred protein activity.
Figure 8A:
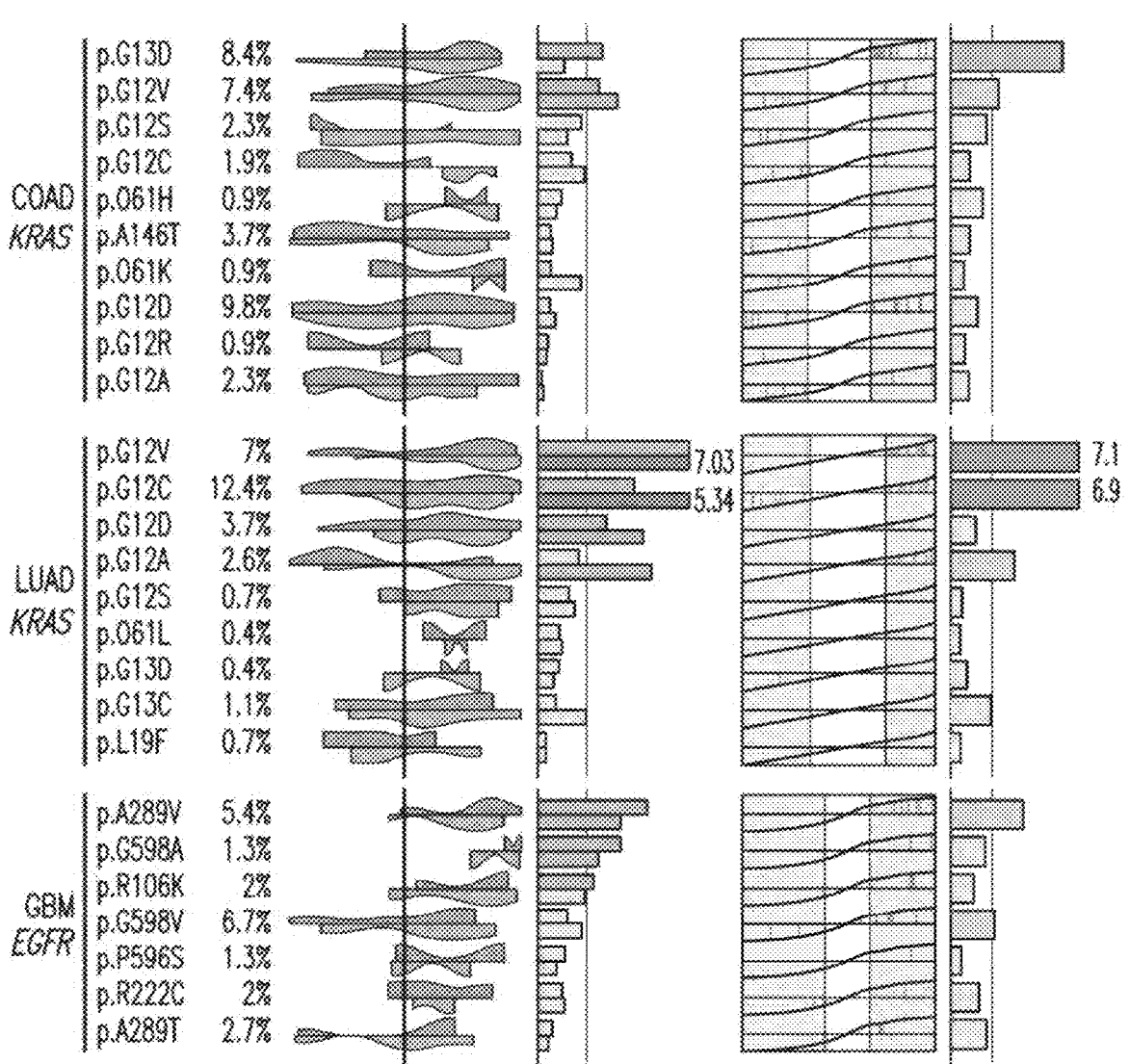
Figure 8B:
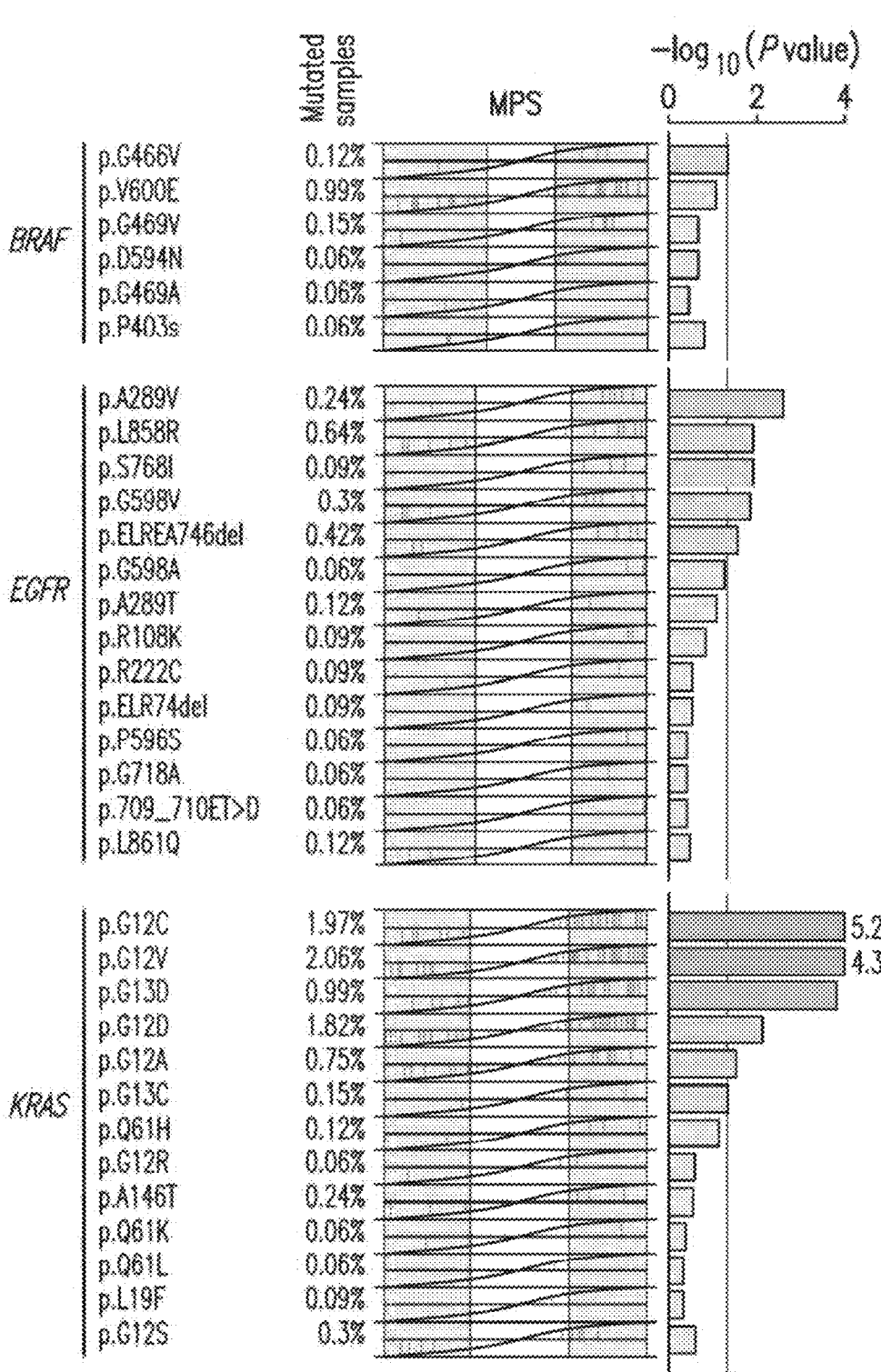
Figure 8B:
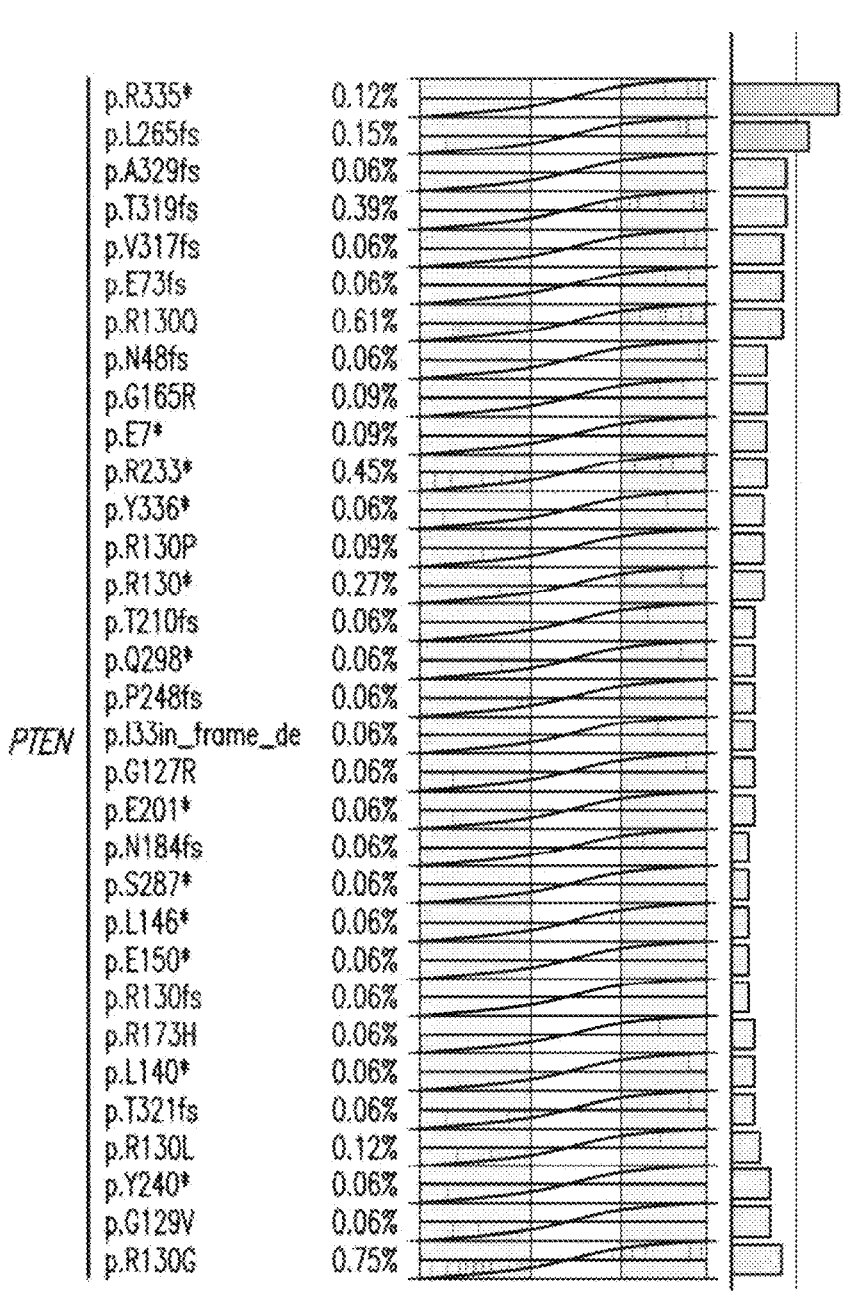

FIGS. 8A and 8B illustrate the effect of specific nonsilent somatic mutation variants on VIPER-inferred protein activity. FIG. 8A illustrates the association of nonsilent somatic mutation variants with VIPER-inferred protein activity and mRNA expression. Violin plots indicate the probability density for the mutated samples on all samples rank-sorted by coding gene mRNA levels (yellow) or VIPER-inferred protein activity (cyan). Background color gradient indicates both expression and VIPER-inferred protein activity signatures from decreased (blue) to increased (orange). Statistical level for the association, as estimated by aREA (bar plot), with color indicating association with increased (red) or decreased (blue) expression or protein activity. Rightmost bar plot shows the significance level for the association of mutation variants and the MPS-defined mutant phenotype (likelihood ratio >3, light-green box). The MPS-defined WT phenotype (likelihood ratio >3) is indicated by the light-salmon box. Missense mutations are indicated as p.XnY where X stands for 1-letter amino acid in position in that was mutated to Y. *, nonsense mutations; frameshift mutations are indicated as p.Xnfs. Vertical lines crossing the bars indicate the P-value threshold of 0.05. FIG. 8B illustrates the effect of nonsilent variants integrated across different tumor types. MPS can be integrated for all 12 tumor types (3,343 samples) and is shown as the x axis in the left side of the plot, while the enrichment of each variant among the samples with at least threefold likelihood of mutation vs. the WT samples (likelihood-ratio >3), is indicated as $-\log_{10}(P)$ by the bar plots. Dashed line indicates the P-value threshold of 0.05.

FIGS. 22A-22I illustrate the impact of specific non-silent somatic mutation (NSSM) variants on protein activity. FIGS. 22A-22I show all NSSM variants present in at least 2 samples in any of the 12 tumor types analyzed. The green barcode-like plots indicate the samples harboring each muta-tion when rank-sorted according to four quantitative traits: (1) VIPER-inferred G-activity (leftmost plot), (2) VIPER-inferred RPT-activity, (3) mutated gene mRNA expression levels, and (4) MPS (rightmost plot). The bars indicate the statistical significance, shown as $-\log 10(p)$, for the enrich-ment of the mutated samples on each of the four evaluated quantitative traits. The enrichment 'side' is indicated by the color of the bars, with over-expression or hyperactivity indicated by red bars, and under-expression or hypoactivity indicated by blue bars. The leftmost barplot, showing grey and green bars, indicates the statistical significance after integrating VIPER-inferred global activity (G-activity) and residual postranslational activity (RPT-activity). The right-most barplot, showing grey, green and salmon bars, indicates the statistical significance for the enrichment of the mutated samples among the MPS-defined mutant phenotype (likeli-hood-ratio 3, indicated by the light-green box), or wt phe-notype (likelihood-ratio 3, light-salmon box). The tumor type, gene name, mutation type and proportion of mutated samples are indicated in the plot. Missense mutations are indicated as p.XnY where X stands for the amino acid in position n that was substituted by Y. Nonsense mutations are indicated by '*' while frame shift mutations are indicated as p.Xnfs.

FIGS. 8A and 8B illustrate the cases with adequate statistical power. Careful examination can show that func-tional impact of these mutations was both variant-specific (e.g., KRAS: p.Gly12Val vs. p.Gly12Asp in colon adeno-carcinoma (COAD)) (FIG. 8A) and tumor specific (e.g., KRAS: p.Gly12Ala in COAD vs. lung adenocarcinoma (LUAD)) (FIG. 8A). In addition, although some mutations can induce effects equivalent to differential expression, others can produce exquisitely post-translational effects that can only be predicted by RTP activity (e.g., KRAS: p.Gly12Val in LUAD vs. p.Gly13Asp in COAD) (FIGS. 8A and 22A-22I).

In some embodiments, although different mutations can have similar impact on protein activity (e.g., all TP53 functional variants can be associated with reduction in inferred TP53 protein activity), their effects on gene expres-sion can be highly heterogeneous. For example, nonsense and frame-shift mutations in TP53 can invariably reduce mRNA levels (FIG. 8A), likely due to nonsense and non-stop-mediated mRNA decay. In contrast, missense muta-tions can be consistently associated with increased mRNA levels, likely due to feedback loops attempting to compen-sate for mutation-induced loss of TP53 protein activity (FIG. 8A). Such dichotomy in TP53 somatic variant effect can explain the lack of association between mutations and gene expression, when all variants are considered together.

In some embodiments, to compensate for the lack of statistical power due to the potentially small number of samples harboring locus-specific mutations (FIGS. 22A-22I), integrated analysis across all tumor types can be performed. Heterogeneity among tumor types can be accounted for by aggregating the samples at the protein activity level, originally inferred using tissue-matched inter-actomes. Such accounting can result in a pan-cancer reper-toire of functionally relevant somatic variants, based on the analysis of 3,343 samples across 12 tumor types, for which the statistical association between each locus-specific muta-tion and its MPS, as well as the pan-cancer VIPER P value are illustrated in FIGS. 8B and 23A-23L.

FIGS. 23A-23L illustrate a summary of the differential impact of non-silent somatic mutation (NSSM) variants on the coded protein activity. The leftmost plot shows the rank of mutated samples (vertical green lines) when all samples, across 12 tumor types, were rank sorted according to MPS. The center barplot shows the statistical significance, as $-\log_{10}(p)$, for the enrichment of the mutated samples among the MPS-defined mutant phenotype (likelihood-ratio >3, highlighted by a light-green box in the center plot), or wt phenotype (likelihood-ratio >3, light-salmon box). The rightmost barplot shows the association of each specific variant with either VIPER-inferred protein activity, condi-tional protein activity or mRNA levels, integrated across 12 tumor types. Bars indicate the statistical significance as $-\log_{10}(p)$ for each NSSM present in at least two samples. The gene name, mutation and proportion of samples har-boring the mutation are shown in the plot.

In some embodiments, conventional precision cancer medicine can rely on the identification of actionable muta-tions. Such actionable mutations can be reproducibly iden-tified from whole-genome and exome analysis of tumor tissue and can demonstrate clinical relevance. Approxi-mately, ~25% of adult cancer patients can be present with potentially actionable mutations. Since VIPER can be inde-pendent of mutational state, VIPER can complement and greatly extend the available genomic approaches. Genetic mutations can be neither necessary nor sufficient to induce aberrant activity and tumor essentiality of protein isoforms. An increasing catalog of non-oncogene dependencies whose aberrant activity depends on indirect genetic alterations, such as those in upstream pathways and cognate binding proteins, have emerged in recent years. Accordingly, several tumor cells can respond to inhibitors targeting established oncoproteins, such as EGFR, even in the absence of acti-vating mutations, as shown by large-scale dose-response studies in the cancer cell line encyclopedia and by recent analysis of pathways upstream of functional tumor drivers.

In some embodiments, VIPER can have three different roles. Firstly, VIPER can help elucidate aberrant protein activity resulting either from direct or pathway-mediated mutations. Secondly, VIPER can help prioritize the func-tional relevance of rare and private nonsynonymous muta-tions such as hypomorph, hypermorph, or neutral events. Systematic analysis of TCGA cohorts can show that 27% of nonsynonymous mutations can induce aberrant VIPER-inferred protein activity, which can be a substantial fraction considering that not all mutations substantially affect protein activity on canonical targets, including those resulting in entirely new protein functions (e.g., neomorphs), and not accounting for mutation clonality. Thirdly, VIPER can help distinguish between transcriptionally and post-translation-ally mediated mutational effects (FIGS. 4A-4C and 6A-6C).

In some embodiments, systematic VIPER-based analysis of TCGA samples (FIG. 7A) can illustrate that although genetic alterations can strongly co-segregate with aberrant VIPER-inferred oncoprotein activity, several WT samples can have VIPER-inferred activity comparable to and even greater than those harboring actionable mutations. Such results can be relevant for alterations in pharmacologically actionable oncogenes, such as BRAF, EGFR, ERBB2, and FGFR3, among others, and can indicate that VIPER can be used to identify additional patients who can benefit from targeted therapy. Similarly, VIPER can be used to identify samples with actionable mutations presenting no aberrant activity of the corresponding oncoprotein. Validation of the predictive value of VIPER-inferred activity to infer targeted inhibitor response, using the cancer cell line encyclopedia, can indicate that the VIPER technique can provide valuable insight in precision cancer medicine.

Several approaches have been proposed to estimate path-way activity, co-regulation of gene expression modules or activity of selected proteins from gene expression signa-tures. These approaches, however, cannot predict activity of arbitrary proteins, lack tumor specificity, and cannot be used to analyze individual samples. Other approaches developed for yeast and other model organisms have never been extended to mammalian cells. Earlier attempts based on transcription factor targets inferred from promoter sequence analysis or from proprietary, literature-based networks have not been systematically validated. VIPER is the first vali-dated method to systematically predict the activity of all signal transduction and transcription factors proteins in individual samples.

In some embodiments, VIPER can leverage protein regu-lons reverse-engineered from primary tumor sample data to quantitatively assess differential protein activity in indi-vidual samples, without any manual annotation or curated gene sets. Critically, VIPER's performance can be extremely robust and resilient to signature noise, regulon subsampling and sample quality. Indeed, VIPER can accurately infer protein activity for ~50% of all regulatory proteins using <1,000 genes from LINCS perturbational signatures (FIGS. 16A and 16B). Furthermore, inference of differentially active proteins from fresh-frozen or FFPE samples from the same tissue can be highly correlated, even though correla-tion of the corresponding gene expression data can be low. VIPER predictions can be remarkably reproducible across samples belonging to the same molecular tumor subtype, which can be useful for precision medicine applications.

In some embodiments, tissue specificity of protein-target can be an integral aspect of VIPER analysis. Genes with expression affected by changes in protein activity can be highly context-specific due to lineage-specific chromatin remodeling, combinatorial regulation by multiple transcrip-tion factors, and post-translational modification. Inference of protein activity using the incorrect regulatory model can produce substantially degraded results (FIG. 4A).

In some embodiments, VIPER can constitutes a contri-bution in accurately measuring protein activity in mamma-lian samples. Experimental results indicate that improve-ments in the accuracy and coverage of regulatory models can further increase the quality and breadth of these predic-tions, thereby helping determine which proteins drive key pathophysiological phenotypes. The disclosed subject mat-ter describes using VIPER to mine existing data sets, includ-ing expression profiles in TCGA and LINCS. VIPER can have the ability to infer relative protein activity as an extra layer of information, providing additional evidence over classical genetics and functional genomics data to assess the effect of nonsilent mutations.

Figure 9A:
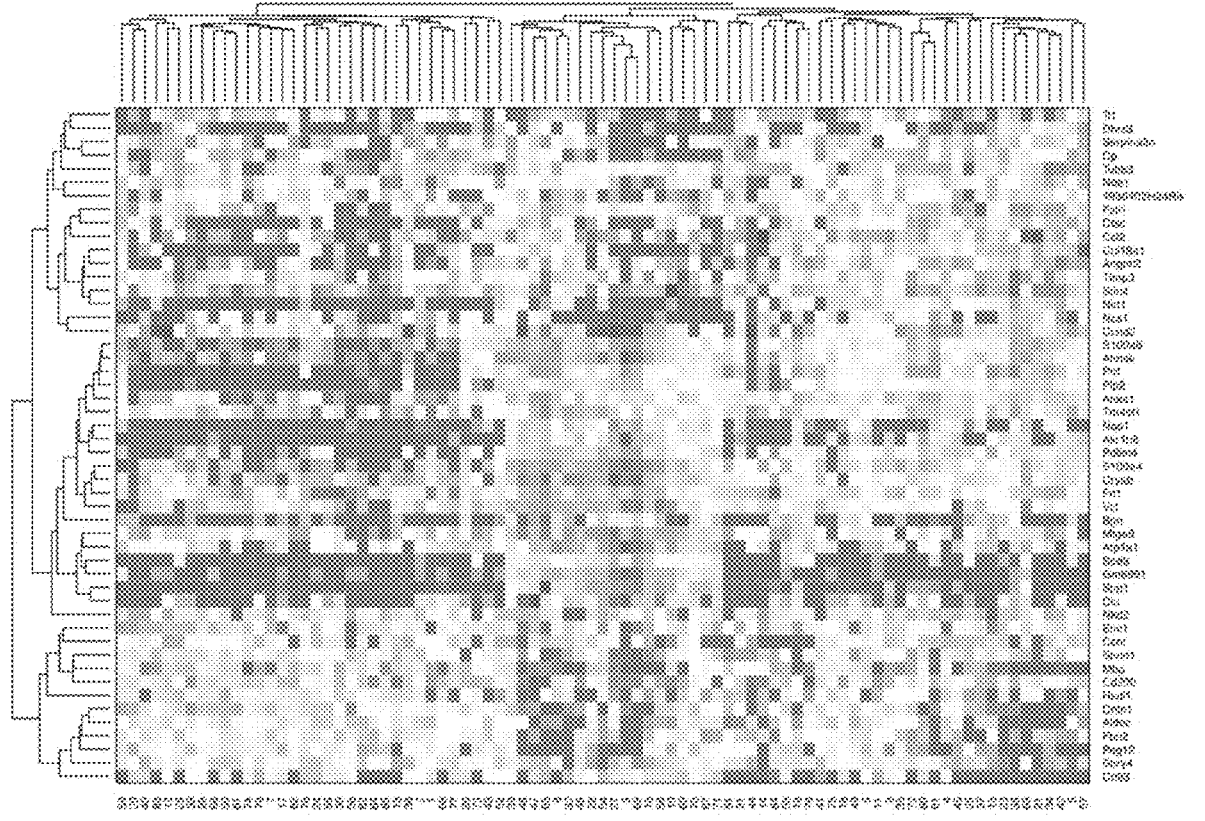
FIGS. 9A-9C illustrate heatmaps for gene expression (FIGS. 9A and 9C) and VIPER-inferred protein activity (FIG. 9B).
Figure 9B:
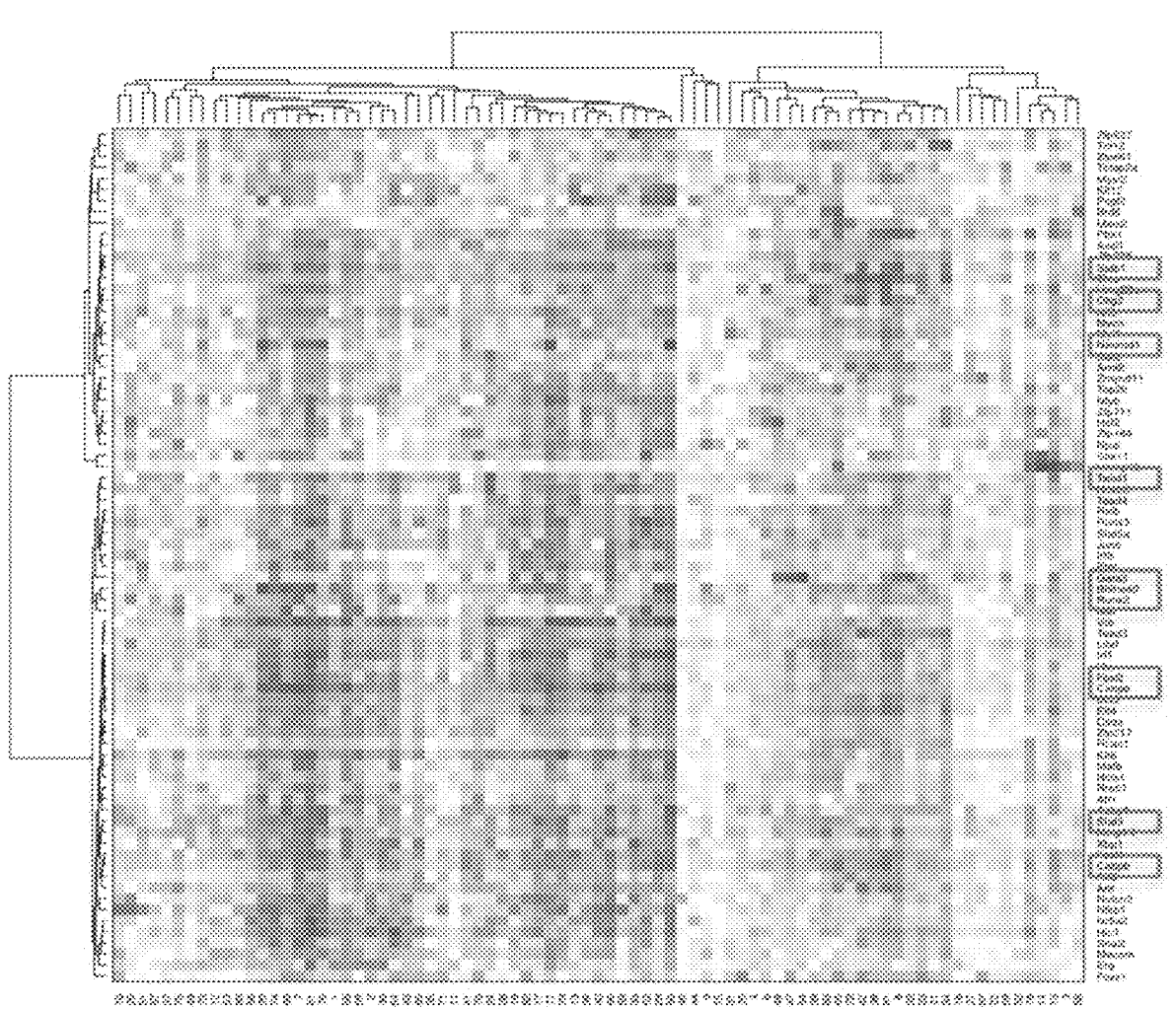
Figure 9C:
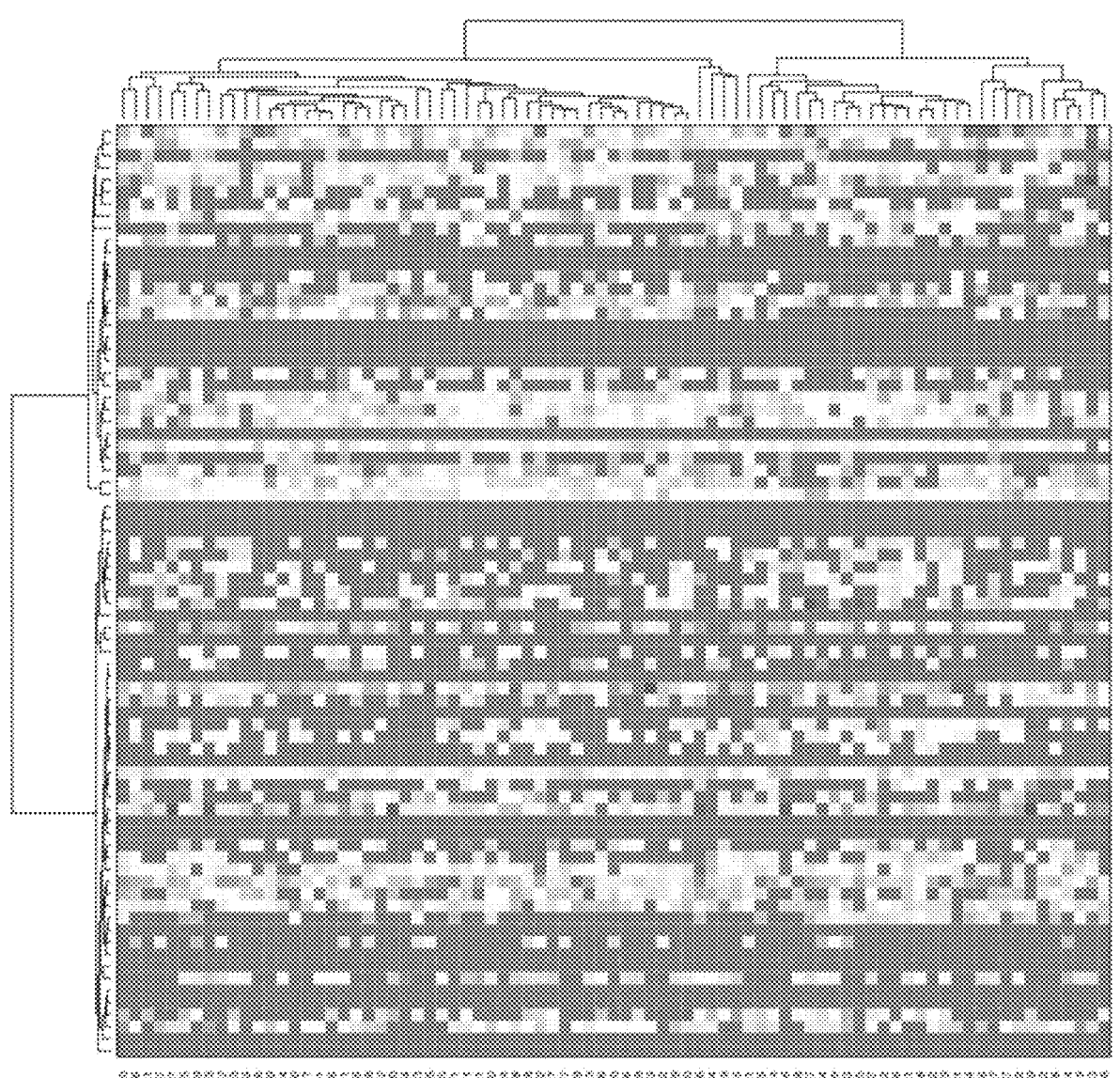

FIGS. 9A-9C illustrate heatmaps for single cell gene expression (FIGS. 9A and 9C) and VIPER-inferred protein activity (FIG. 9B). The red can indicate upregulated genes or activated proteins, the blue can indicate downregulated genes or inactivated proteins, and gray can indicate missing data. Unsupervised cluster analysis can be performed based on gene expression (FIG. 9A) or VIPER-inferred protein activity (FIGS. 9B and 9C). While no clear stratification can be detected based on gene expression (FIG. 9A), the analysis based on VIPER-inferred protein activity can show a strong separation of the cells in two sub-populations, which can be defined by the differential protein activity of previously characterized regulators of the proneural and mesenchymal subtypes (highlighted in panel of FIG. 9B). FIG. 9C shows the same arrangement of cells (columns) and genes (rows) as in FIG. 9B, indicating that the sub-populations and associated genes cannot be identified directly from the gene expression profile data.

Testing the Incremental Value of Different Techniques Implemented in VIPER

In some embodiments, to assess the incremental value of the additional refinements, a naive implementation of the technique can be used as a starting point that can assess enrichment of target genes against a gene expression signature (GES) ranked by absolute differential expression (e.g., 1-tail approach). This can only assess the absolute change in protein activity but not its sign (e.g., activity increase or reduction). Significant activity changes were assessed for 4 of the 6 silenced proteins, two of which (BCL6 and MEF2B) were inferred among the 10 most differentially active ones (FIG. 12A and Table 4).

In some embodiments, to differentiate between activity increase and decrease, the contribution of predicted positive (Spearman's correlation coefficient (SCC)≥0) and negative (SCC<0) targets (2-tail analysis) can be integrated. Such integration can correctly infer significantly decreased activity for all silenced proteins (p<0.05) and can show improved accuracy and sensitivity for most assays, compared to 1-tail analysis (FIGS. 12A, 13, and Table 4). However, the probabilistic mode of regulation model (e.g., 3-tail analysis) can outperform both the 1-tail and the 2-tail approaches across all assays (FIG. 1E, 12A, 13, and Table 4). All six silenced TFs can be inferred among the 10 most significant, with FOXM1, MYB, BCL6 (Ly7), STAT3, MEF2B, and BCL6 (Pfeiffer), ranking 1st, 1st, 1st, 1th, 5th, and 9th, respectively (FIG. 12A and Table 4).

In some exemplary embodiments, incorporation of the Interaction Confidence (IC) weight in the 3-tail analysis cannot further improve accuracy, as there was virtually no margin for improvement (FIGS. 1E and 12A). However, IC weight can improve the accuracy of most 2-tail analysis results (FIGS. 1E, 12A, and Table 4), suggesting that IC weight provides independent information and improves technique performance. Based on these results, the 3-tail approach can be selected with IC correction (3T/IC) as the best performing method.

In some embodiments, detailed analysis of these results can reveal that proteins whose regulon overlaps those of silenced TFs can have higher enrichment than expected by chance. For example, MYBL1, which had the most significant overlap with MEF2B (e.g., by Fisher's Exact Test) can be the second most significant TF following MEF2B silencing (see Table 10 for a list of TFs with overlapping programs). These observations can suggest that differential activity predictions can be the result of significant regulon overlap with the bona fide differentially-active protein. Indeed, the Pleiotropy Correction (PC) analysis can significantly improve specificity (p<0.02, by paired U-test, FIGS. 1E, 12A, and Table 4).

Comparison of VIPER with Other Methods

In some embodiments, the Fisher Exact Test (1-tail FET) and its extension can be tested to explicitly account for the Mode of Regulation of a target gene (2-tail FET), as originally implemented in a Master Regulator Analysis (MRA) technique. The latter can account independently for targets that are either activated (e.g., SCC≥0) or repressed (e.g., SCC<0) by the regulator. In an exemplary embodiment, the VIPER results can be compared to Master Regulator Inference technique (e.g., MARINa) results, which can compute enrichment based on 1-tail and 2-tail GSEA. Since MRA and MARINA can require multiple samples (N≥6), these comparisons can be limited to the multiple-sample version of VIPER (msVIPER).

In some embodiments, the FET methods can produce good accuracy for some of the experiments, but can fail to capture the change in FOXM1 and STAT3 protein activity after their coding genes have been silenced (FIG. 12A and Table 4). This lack of consistency across all experiments could be related to the use of small, discrete gene lists by FET, which produces enrichments that are often not robust with respect to threshold selection (FIGS. 25A-B). Despite the fact that GSEA eliminates the issue of threshold selection, it can partially improve the results previously obtained by FET (FIG. 12A and Table 4). Both FET and GSEA-based approaches illustrate a reduced accuracy, and in the case of GSEA also illustrate very poor specificity when compared to VIPER (FIG. 12A and Table 4).

In some embodiments, the performance of VIPER can be tested when using tissue context-independent regulons assembled from experimentally supported interactions. The ChIP-based ChEA and ENCODE databases can be used to infer the MoR from tissue-matched expression profile data. In agreement with the context-specificity of most of the TF regulatory programs (FIG. 4A), a weaker performance of this analysis can be found when compared against the ARACNe context-specific-based msVIPER analysis for all TFs but FOXM1, whose program seems to be more conserved across tissues (FIGS. 12C and 13). In an exemplary embodiment, MEF2B and BCL6 cannot be evaluated because their transcriptional program cannot be represented in the ChEA and ENCODE models, which included only 189 and 172 regulatory programs, respectively.

In some embodiments, msVIPER performance can be compared against the upstream regulator analysis module of Ingenuity Pathway Analysis (IPA). In an exemplary embodiment, msVIPER can outperform IPA for all the tested regulators in our benchmark experiment. IPA can infer correctly a decrease in the knocked-down TF protein activity only for FOXM1, and MEF2B cannot be evaluated since it was cannot represented in the IPA results (FIG. 12C).

Unbiased Validation of VIPER-Inferred Protein Activity Using Genetic Perturbations In some embodiments, to further benchmark the technique, the panel of gene knock-down data can be expanded to silence experiments performed in breast carcinoma cells, covering 19 genes and 12 different cell lines whose profiles are available from Gene Expression Omnibus. For this analysis, breast cancer specific regulons can be used to infer by ARACNe analysis of 1,037 TCGA breast carcinoma gene expression profiles (Table 1). VIPER analysis using the full probabilistic model can be implemented by the aREA technique and can be used to detect a significant protein activity dysregulation for 20 of the 23 silencing experiments (87%, p<0.05). The activity of 17 proteins can be inferred as a significant decrease in response to coding gene knock-down, while 3 can be inferred as significantly activated (FIG. 15A).

Figure 15B:
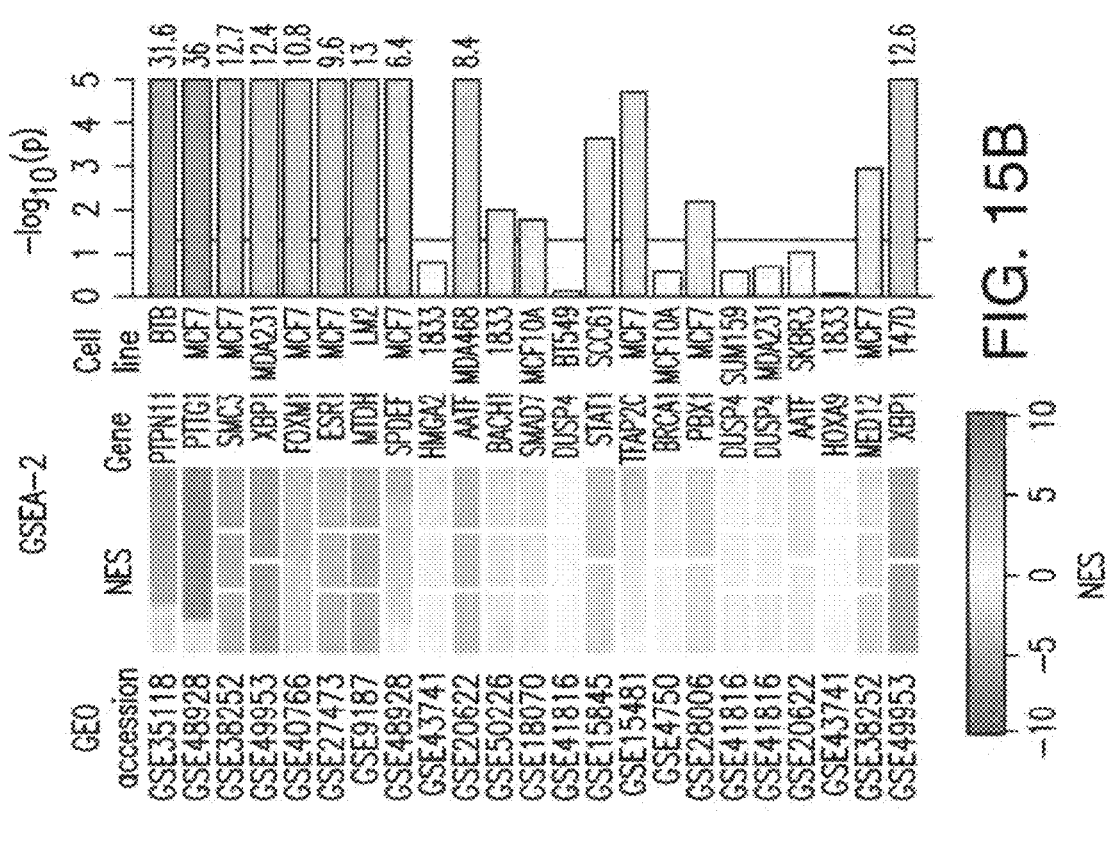
FIGS. 15A-15E illustrate detecting changes in protein activity after genetic perturbations.
Figure 15A:
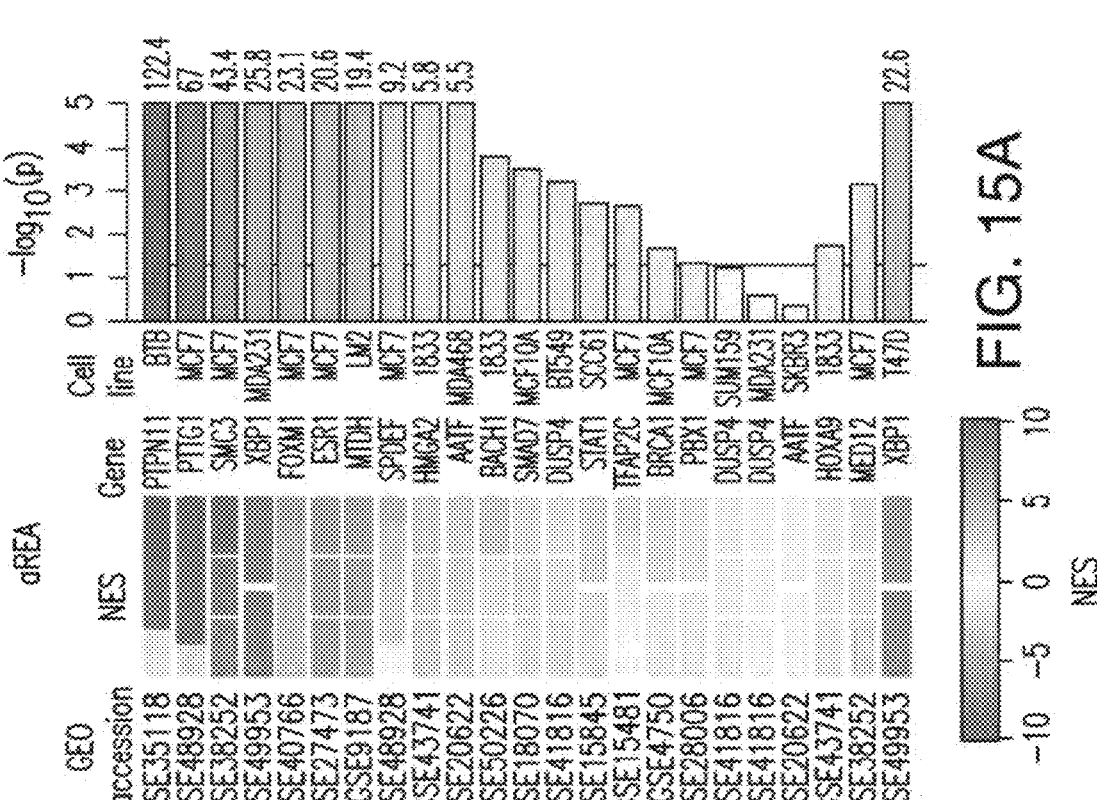
Figure 15C:
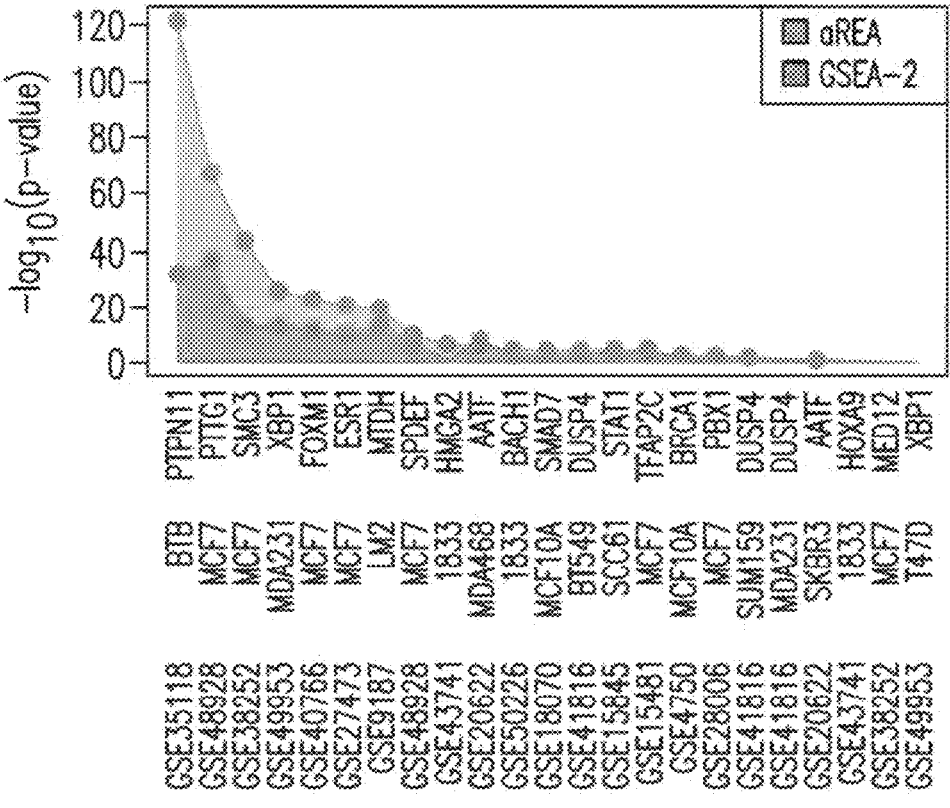
Figure 15D:
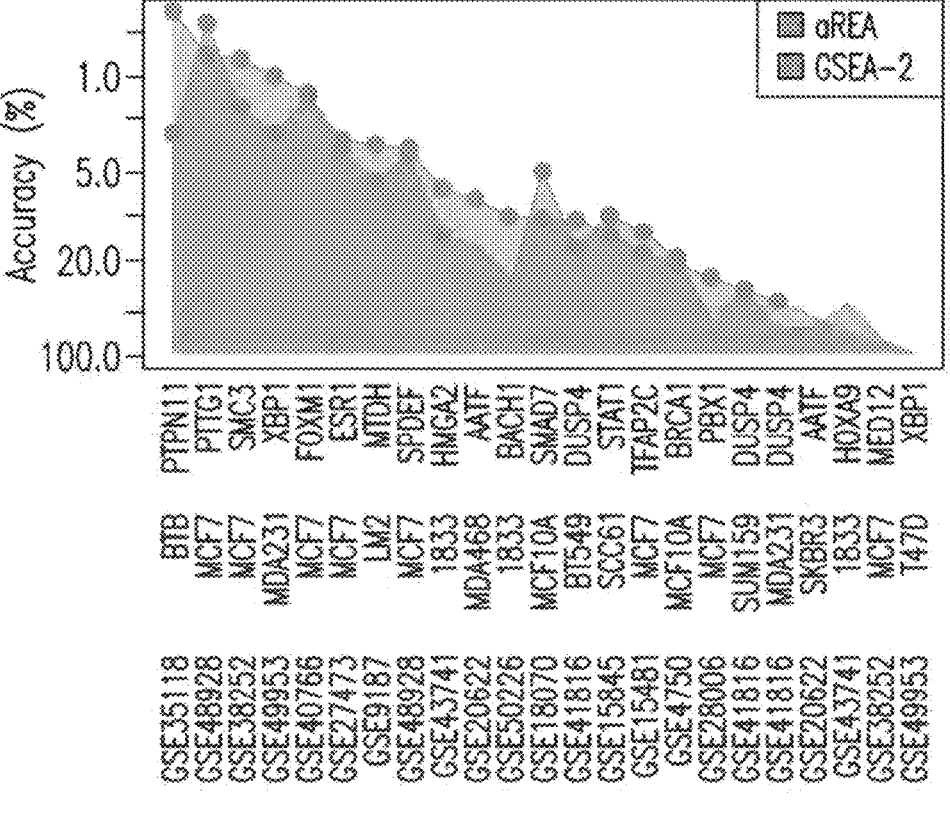
Figure 15E:
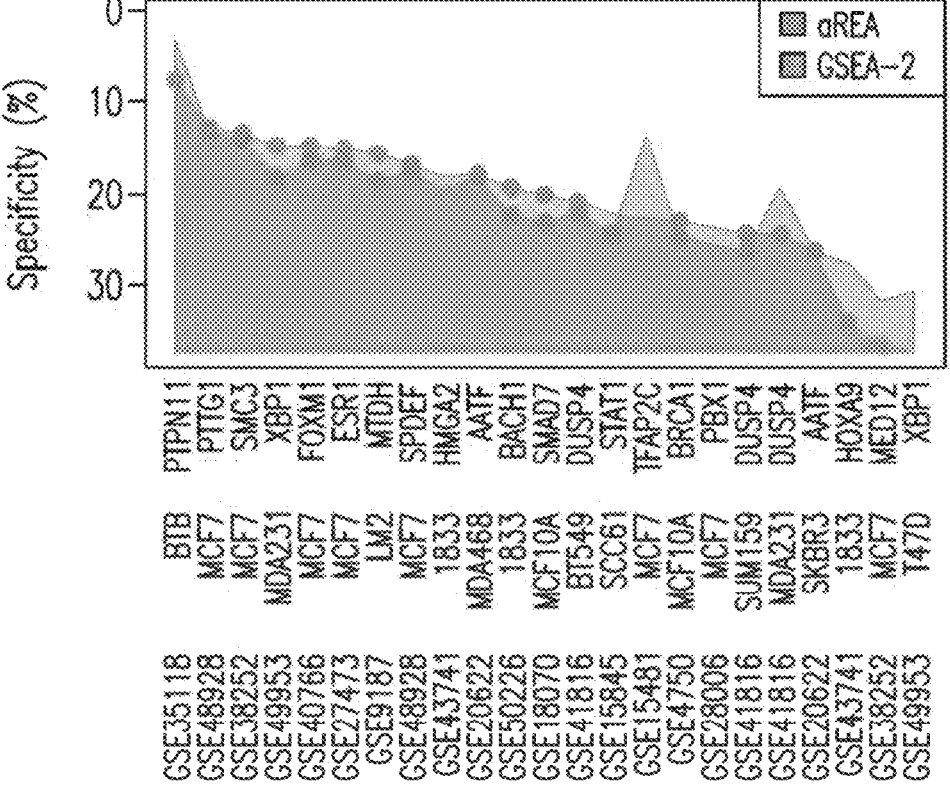

FIGS. 15A-15E illustrate detected changes in protein activity after genetic perturbations. FIGS. 15A and 15B illustrate heatmaps showing the VIPER-inferred change in TF protein activity based on aREA (FIG. 15A) and 2-tail GSEA (FIG. 15B) enrichment methods. Displayed results correspond to silencing experiments in breast carcinoma cells. Statistical significance can be estimated by Stouffer's integration of the single-sample NES. The vertical black line crossing the bar-plot indicates the significance threshold at p=0.05. Bars showing a statistically significant change in protein activity at p<0.05 are highlighted in blue (decreased protein activity, i.e., NES<0) and red (increased protein activity, NES>0). Values higher than the axis scale are indicated to the right of each bar. (c-e) VIPER analysis of 23 silencing experiments in breast carcinoma cells, using aREA (blue) or 2-tail GSEA (red) as gene enrichment methods. FIG. 15C illustrates the statistical significance for protein activity decrease expressed as $-\log_{10}$(p-value). FIG. 15D illustrates accuracy expressed as rank position percentage of the evaluated regulators. FIG. 15E illustrates specificity, expressed as proportion (%) of regulators inferred as differentially active.

In some embodiments, use of 2-tail GSEA for VIPER analysis can be consistently less sensitive and accurate than aREA, detecting 14 of the 23 assessed proteins (61%) as significantly dysregulated at p<0.05 (FIGS. 15A-15E). Additionally, GSEA can be dramatically more computationally demanding than aREA (e.g., 6.7 min of computer time for the aREA implementation vs. 23 days and 6 hours of computer time for 2-tail GSEA implementation, measured in an 8 Gb RAM×86 64 1.2 GHz computer node).

In some embodiments, this analysis can be expanded by leveraging gene expression profiles generated following shRNA-mediated silencing of 234 regulatory proteins in MCF7 cells, from the Library of Integrated Network-based Cellular Signatures (LINCS). LINCS can represent a large repertoire of expression profiles following shRNA silencing of 3,680 genes. However, to ensure proper knock-down of the silenced gene, experiments can be selected based on two criteria: (1) silenced genes have to be among the 978 experimentally assessed genes, such that their silencing could be assessed and (2) their expression can be reduced by at least 2 standard deviations (SD), compared to the average across controls. SD≥2 can emerge as a reasonable compromise between selecting assays with effective gene silencing and having enough samples for a representative analysis. Since LINCS expression profiles can be based on only 978 genes (i.e., <05% of a regulons genes, on average) by multiplexed Luminex technology (L1000), performance analysis on this dataset should be considered an extremely conservative lower bound. VIPER analysis can detect a statistically significant protein activity decrease for 44 (50%, p<0.05) of 87 silenced TFs (FIG. 16A), while only 4 TFs can be predicted as significantly activated following silencing (FIG. 16A). Similarly, VIPER can detect statistically significant protein activity decrease for 57 of the 147 silenced signaling proteins (39%, p<0.05), while only 7 can be predicted as significantly activated following silencing (FIG. 16B). Interestingly, MoR can be incorrectly inferred for some genes, due to regulatory feedback loops that induce inverse correlation between gene expression and protein activity for a small number of proteins, more frequently among signal transduction ones. Such observations can be consistent with ~10% of silenced proteins being inferred with significantly increased activity. MoR inversion can be experimentally evaluated within specific tissue contexts.

Protein Activity Changes Following Pharmacologic Perturbations

Short-term perturbation with targeted inhibitors can modulate protein activity, without affecting associated gene expression. The MCF7 connectivity map (CMAP) dataset, which contains 3,095 gene expression profiles of MCF7 cells, can be used following perturbation with 1,294 compounds. Among targeted TFs, the estrogen receptor (ESR1) can have the highest number of samples (n=27) and inhibitor diversity in this dataset, according to drugbank, including fulvestrant, tamoxifen, and clomifene. It can be determined whether ESR1 inhibition by these compounds can be effectively recapitulated by VIPER analysis, using a breast cancer specific ARACNe network (Table 1). VIPER-inferred ESR1 differential activity in samples treated with estrogen inhibitors can be determined from their differential gene expression signature against matched DMSO-treated controls. P-values from replicated samples can be integrated by the Stouffer's method. VIPER can infer statistically significant, dose-dependent decrease in estrogen receptor protein activity for all three targeted inhibitors (FIG. 17).

Figure 17:
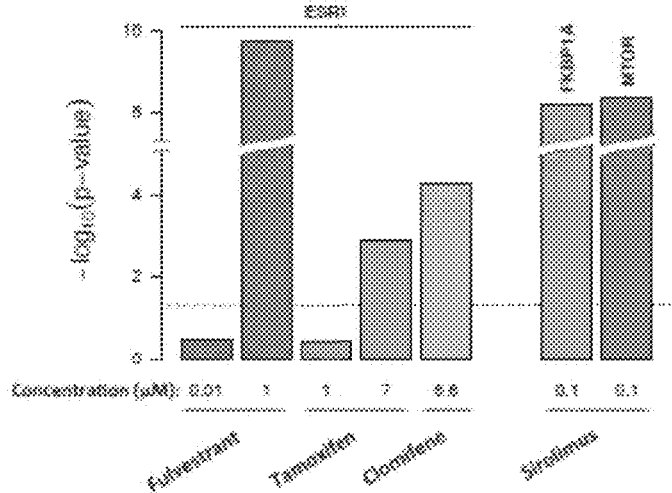
FIG. 17 illustrates change detection results in protein activity after pharmacologic perturbations.

FIG. 17 illustrates detecting changes in protein activity after pharmacologic perturbations. The barplot of FIG. 17 illustrates the statistical significance for the change in protein activity inferred by VIPER after pharmacological perturbation with fulvestrant, tamoxifen and clomifene (targeting ESR1), and sirolimus (targeting FKBP1A and MTOR). The horizontal dotted line indicated the threshold at p=0.05. A dose-dependent response can be observed for fulvestrant and clomifene (concentration indicated in μM units for each bar).

To extend the analysis to signaling proteins, the effect of sirolimus, an inhibitor of the FKBP1A and MTOR proteins, can be evaluated as the one with the highest number of treatment replicates (n=25). Consistently, VIPER can infer significant protein activity decrease for both FKBP1A and MTOR (FIG. 17). These results can show that VIPER can effectively detect protein activity dysregulation in response to short term pharmacologic perturbations, and can be used to extend this analysis to the remaining profiled compounds, complementing in this way the MCF7-CMAP dataset by adding the protein activity layer.

In some embodiments, to maximize the reliability of the results, only perturbations performed at least in duplicate were included and for which we could verify a significant correlation between the gene expression signatures (FDR<0.05, Spearman's correlation analysis). The mean correlation for each sample k∈P can be calculated, where P is a set of replicated perturbation conditions, as the mean Pearson's correlation coefficient between all sample pairs k×j|j∈P. The correlation can be determined between the rank-transformed signatures. Statistical significance can be estimated by comparison against the empirical distribution of correlation coefficients obtained between each rank-transformed signature and the remaining non-matching drug perturbation signatures, (e.g., k×j, ∀k, j|k∈P, j∉P).

In some embodiments, VIPER can be used together with a breast carcinoma context specific interactome (Table 1) to transform 573 gene expression signatures satisfying the reproducibility condition into inferred protein activity signatures. The mean and standard deviation across replicated samples is reported in Table 9 and can represent an unbiased portrait for the effect of 166 unique perturbation conditions, encompassing 156 distinct small molecule compounds, on the activity of 2,956 regulatory proteins.

Comparison of VIPER Results with Reverse Phase Protein Array Data

In some embodiments, to benchmark VIPER using a gold standard for which both gene expression and protein abundance were experimentally measured, sample-matched RNAseq and RPPA data can be leveraged for 4,417 tumor samples, across 17 tumor types. RPPA arrays monitor an average of 135 proteins and 60 phospho-specific isoforms per tumor type (Table 6). Protein regulons can be inferred by ARACNe analysis of the corresponding gene expression profile datasets (Table 1). VIPER-inferred activity can significantly correlate with RPPA-based protein abundance for 875 of the 1,359 tumor specific protein abundance profiles (64.4%, p<0.05, Table 7). While similar correlation between gene expression and protein abundance can also be observed (Table 7), the latter can have much larger variance at the individual sample level (FIG. 5B). Table 7 illustrates the number of RPPA profiled proteins and significant associations at the transcripts (mRNA expression) and VIPER-inferred global protein activity (G-activity) levels (p<0.05, Spearman's correlation analysis).

In some embodiments, to use the RPPA data to estimate changes in protein activity, associated with post-translational protein modifications, the ratio between the RPPA-measured abundance of 443 individual isoforms and their total protein abundance can be measured. Overall, protein activity can depend on either total protein abundance or on the abundance of specific, differentially active isoforms. To distinguish between these two contributions, both global VIPER activity can be calculated, as well as the residual post-translational VIPER activity (e.g., the component of activity that cannot be accounted for by differential expression), by removing the transcriptional variance component (RPT-activity). RPT-activity can be statistically independent of gene expression and can account for the purely post-translational contribution to protein activity. Remarkably, when taken together, global and RPT-activity can be predictive for the abundance of 105 protein isoforms (e.g., 24%, p<0.05, Spearmans correlation analysis), which can significantly outperform the 38 isoforms (8.6%) predicted by mRNA expression (p=8×10-10 by X2 test). Individually, RPT activity can be predictive for 77 isoforms (17.4%, p=7×10-5), of which only 19 can also be predicted by global activity, while global activity can be predictive for 47 isoforms (10.6%), suggesting that global and RPT-activity effectively can account for mostly complementary effects (Table 8). Table 8 illustrates the number of RPPA profiled protein isoforms and significant associations at the transcripts (mRNA expression), VIPER-inferred global protein activity (G-activity), residual post-translational VIPER-inferred activity (RPT-activity) and their integration (Integrated activity) with the protein isoform levels at p<0.05 by Spearman's correlation analysis.

Figure 18:
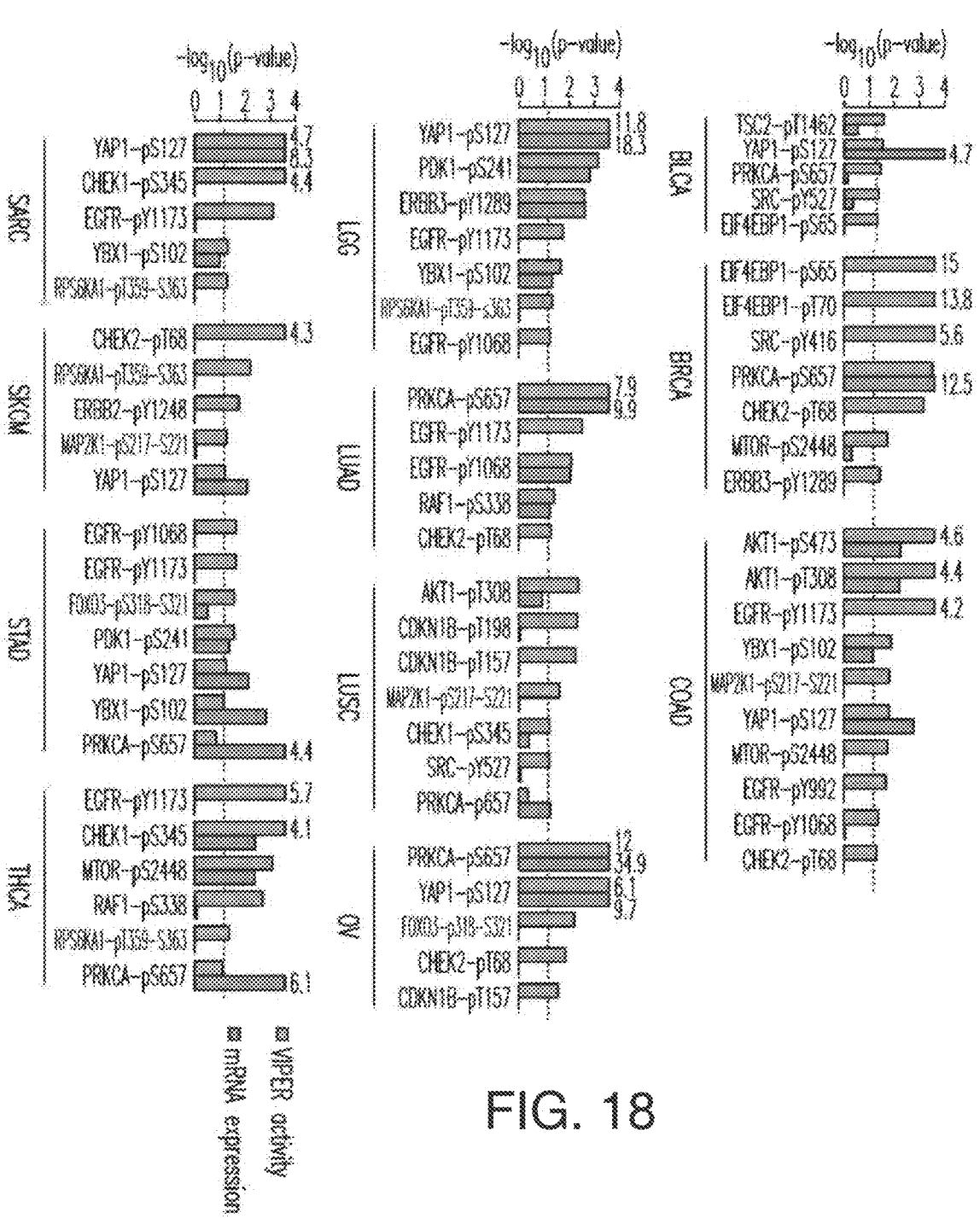
FIG. 18 illustrates association between VIPER-inferred protein activity and protein isoform abundance.
Figure 18:
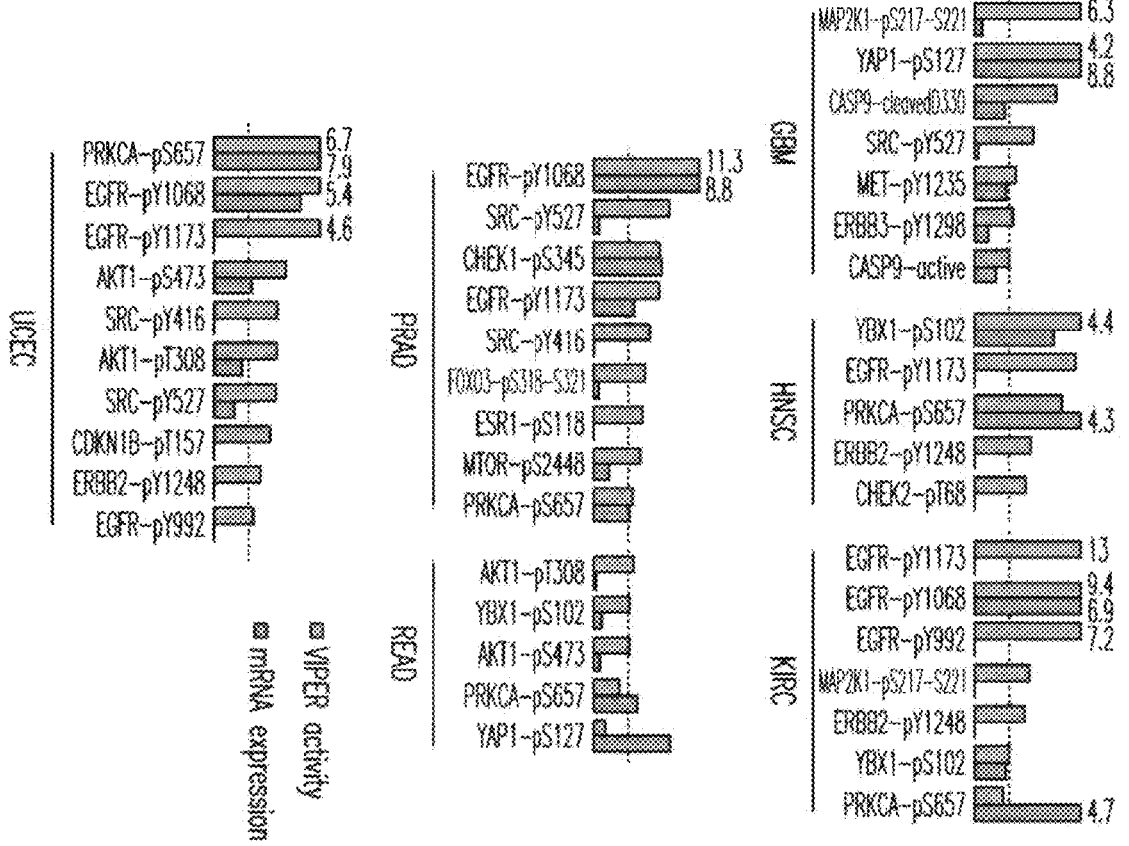

Since not all post-translational modified isoforms can have differential protein activity (FIG. 1A), not all isoform specific antibodies can provide accurate RPPA measurements, and most isoforms can present little abundance variability in TCGA cohorts, this represents a substantial fraction (>24%) of RPPA monitored proteins. Overall, of 105 VIPER correlated isoforms, 74 (70.5%) can be undetectable by differential expression, while only 7 of the isoforms captured by differential expression can be missed by VIPER (FIG. 18). FIG. 18 illustrates the association between VIPER-inferred protein activity and protein isoform abundance. Bars show the significance level as $-\log_{10}$ (p-value) for the Spearman's correlation between specific protein isoform abundance and either VIPER activity (green bars) or coding gene mRNA levels (red bars). VIPER activity shows the maximum association (correlation) between specific protein isoform abundance and either global (G-activity) or residual post-translational VIPER-inferred protein activity (RPT-activity).

Table 3 provides definitions for the acronyms used throughout this disclosure.

TABLE 3

| Acronym | Definition |
| --- | --- |
| aREA | analytic Rank-based Enrichment Analysis |
| aREA-3T | 3-tail aREA analysis |
| CDF | Cummulative Distribution Function |
| CMAP | Connectivity MAP |
| COSMIC | Catalogue Of Somatic Mutations In Cancer |
| ES | Enrichment Score |
| FET | Fisher's Exact Test |
| GES | Gene Expression Signature |
| GSEA | Gene Set Enrichment Analysis |
| IC | Interaction Confidence |
| LINCS | Library of Integrated Network-based Cellular Signatures |
| MARINa | Master Regulator Inference algorithm |
| MoR | Mode of Regulation |
| MPS | Mutant Phenotype Score |
| NES | Normalized Enrichment Score |
| NSSM | Non-Silent Somatic Mutations |
| PC | Pleiotropy Correction |
| PDE | Pleiotropy Differential Score |
| RPPA | Reverse Phase Protein Arrays |
| RPT | Residual Post-Translational |
| SCC | Spearman's Correlation Coeficient |
| TCGA | The Cancer Genome Atlas |
| TF | Transcription Factor |
| VIPER | Virtual Inference of Protein-activity by Enriched Regulon analysis |
| WT | Wild Type |

TABLE 4

| | | FET | | GSEA | | msVIPER | | |
| --- | --- | --- | --- | --- | --- | --- | --- | --- |
| | | 1T | 2T | 1T | 2T | 1T | 2T | 2T/IC |
| MEF2B | Accuracy | 34 | 11 | 143 | 16 | 6 | 6 | 3 |
| P3HR1 | Specificity | 179 | 43 | 271 | 98 | 132 | 132 | 95 |
| | p-value | 4.77E−07 | 1.24E−08 | 0.00147 | 0.00418 | 1.25E−12 | 1.25E−12 | 0.000127 |
| FOXM1 | Accuracy | 240 | 17 | 241.5 | 1 | 328.5 | 328.5 | 1 |
| ST486 | Specificity | 58 | 3 | 235 | 12 | 88 | 88 | 10 |
| | p-value | 0.346 | 0.145 | 0.0528 | 0.00584 | 0.434 | 0.434 | 0.0035 |
| MYB | Accuracy | 7 | 2 | 117 | 3 | 43 | 43 | 1 |
| ST486 | Specificity | 97 | 6 | 245 | 47 | 116 | 116 | 36 |
| | p-value | 0.000261 | 8.31E−05 | 0.00462 | 0.00429 | 0.000194 | 0.000194 | 0.00248 |

TABLE 4-continued

| | | | | | | | |
|---|---|---|---|---|---|---|---|
| BCL6 | Accuracy | 3 | 1 | 97 | 16 | 12 | 12 | 9.5 |
| Ly7 | Specificity | 133 | 13 | 403 | 98 | 191 | 191 | 95 |
| | p-value | 3.39E−07 | 0.00057 | 0.00244 | 0.00834 | 1.27E−07 | 1.27E−07 | 0.0075 |
| BCL6 | Accuracy | 1 | 11 | 78 | 18 | 6 | 6 | 16 |
| Pfeiffer | Specificity | 216 | 25 | 422 | 141 | 197 | 197 | 98 |
| | p-value | 4.52E−11 | 0.0123 | 0.00164 | 0.00751 | 8.90E−14 | 8.90E−14 | 0.0095 |
| STAT3 | Accuracy | 774 | 247 | 702 | 31 | 258 | 258 | 9 |
| SNB19 | Specificity | 76 | 0 | 304 | 68 | 111 | 111 | 54 |
| | p-value | 0.911 | 0.499 | 0.495 | 0.018 | 0.209 | 0.209 | 0.005 |

| | | msVIPER | | | | |
|---|---|---|---|---|---|---|
| | | 2T/PC | 3T | 3T/IC | 3T/PC | 3T/IC/PC |
| MEF2B | Accuracy | 6 | 5 | 4 | 6 | 3 |
| P3HR1 | Specificity | 70 | 87 | 95 | 79 | 89 |
| | p-value | 0.000624 | 0.000355 | 0.000157 | 7.00E−04 | 0.000164 |
| FOXM1 | Accuracy | 1 | 1 | 2 | 1 | 2 |
| ST486 | Specificity | 7 | 16 | 21 | 15 | 20 |
| | p-value | 0.0025 | 0.00116 | 0.00165 | 0.0055 | 0.004 |
| MYB | Accuracy | 1 | 1 | 1 | 1 | 1 |
| ST486 | Specificity | 22 | 49 | 54 | 38 | 42 |
| | p-value | 0.003 | 0.00029 | 0.00141 | 1.06E−06 | 0.000271 |
| BCL6 | Accuracy | 7.5 | 1 | 1 | 1 | 1 |
| Ly7 | Specificity | 88 | 130 | 128 | 116 | 114 |
| | p-value | 0.0085 | 0.000153 | 0.000185 | 0.000111 | 0.000358 |
| BCL6 | Accuracy | 17 | 9 | 11 | 4 | 3 |
| Pfeiffer | Specificity | 74 | 133 | 139 | 119 | 127 |
| | p-value | 0.022 | 0.00177 | 0.00202 | 0.00131 | 0.00209 |
| STAT3 | Accuracy | 7 | 1 | 2 | 1 | 1 |
| SNB19 | Specificity | 48 | 60 | 75 | 47 | 69 |
| | p-value | 0.0125 | 0.000661 | 0.00101 | 0.000463 | 0.000658 |

TABLE 5

| | | 1T | 2T | 2T/IC | 2T/PC | 3T | 3T/IC | 3T/PC | 3T/IC/PC |
|---|---|---|---|---|---|---|---|---|---|
| MEF2B | Accuracy | 27 | 13 | 13 | 23 | 24 | 21 | 23 | 22 |
| P3HR1 | Specificity | 142 | 130 | 114 | 84 | 104 | 97 | 80 | 83 |
| | p-value | 5.65E−05 | 8.35E−23 | 4.01E−21 | 2.88E−08 | 8.14E−15 | 3.03E−16 | 3.04E−07 | 1.14E−07 |
| FOXM1 | Accuracy | 289 | 1 | 1 | 1 | 1 | 1 | 1 | 1 |
| ST486 | Specificity | 41 | 18 | 12 | 7 | 20 | 13 | 5 | 4 |
| | p-value | 0.384 | 4.30E−10 | 2.28E−10 | 6.19E−06 | 1.50E−10 | 3.36E−11 | 7.63E−05 | 5.57E−05 |
| MYB | Accuracy | 23 | 2 | 2 | 3 | 4 | 4 | 5 | 2 |
| ST486 | Specificity | 69 | 92 | 65 | 37 | 74 | 62 | 37 | 35 |
| | p-value | 0.00968 | 1.72E−07 | 9.16E−07 | 0.000742 | 1.92E−05 | 7.46E−06 | 0.00515 | 0.00176 |
| BCL6 | Accuracy | 9 | 25 | 25 | 18 | 16 | 13 | 13 | 15 |
| Ly7 | Specificity | 106 | 262 | 193 | 176 | 222 | 181 | 151 | 122 |
| | p-value | 0.000584 | 0.000119 | 0.00036 | 0.00103 | 5.52E−05 | 5.79E−05 | 0.00157 | 0.00262 |
| BCL6 | Accuracy | 8 | 112 | 87 | 69 | 39 | 37 | 21 | 22 |
| Pfeiffer | Specificity | 280 | 368 | 301 | 255 | 321 | 277 | 225 | 198 |
| | p-value | 1.03E−06 | 0.000102 | 0.000285 | 0.00218 | 1.24E−06 | 4.21E−06 | 4.98E−05 | 0.000117 |
| STAT3 | Accuracy | 767 | 6 | 2 | 11 | 1 | 1 | 4 | 2 |
| SNB19 | Specificity | 17 | 56 | 40 | 19 | 38 | 33 | 18 | 14 |
| | p-value | 0.813 | 0.00136 | 0.000394 | 0.0307 | 6.91E−05 | 0.00022 | 0.0163 | 0.0122 |

TABLE 6

| | BLCA | SCA | COAD | GSM | HNSC | KIRC | LGG | LUAD | LUSC | OV | PRAD | READ | SARC |
|---|---|---|---|---|---|---|---|---|---|---|---|---|---|
| Samples | 127 | 410 | 331 | 214 | 212 | 454 | 260 | 181 | 195 | 412 | 164 | 130 | 227 |
| Proteins | 138 | 112 | 131 | 131 | 129 | 120 | 147 | 129 | 135 | 130 | 147 | 131 | 10 |
| Isoforms | 63 | 51 | 59 | 59 | 56 | 56 | 64 | 56 | 59 | 55 | 54 | 59 | 63 |

| | SKCM | STAD | THCA | UCEC |
|---|---|---|---|---|
| Samples | 206 | 2.64 | 430 | 200 |
| Proteins | 142 | 147 | 148 | 128 |
| Isoforms | 61 | 64 | 54 | 57 |

TABLE 7

|  | BLCA | SCA | COAD | GSM | HNSC | KIRC | LGG | LUAD | LUSC | OV | PRAD | READ | SARC |
|---|---|---|---|---|---|---|---|---|---|---|---|---|---|
| RPPA profiled | 81 | 66 | 85 | 84 | 76 | 74 | 88 | 75 | 83 | 81 | 85 | 84 | 58 |
| mRNA expression | 58 | 60 | 65 | 58 | 56 | 64 | 61 | 58 | 64 | 70 | 52 | 57 | 43 |
| G-activity | 52 | 52 | 55 | 49 | 47 | 58 | 57 | 51 | 62 | 68 | 37 | 39 | 38 |

|  | SKCM | STAD | THCA | UCEC | TOTAL |
|---|---|---|---|---|---|
| RPPA profiled | 84 | 87 | 85 | 82 | 1359 |
| mRNA expression | 65 | 67 | 57 | 54 | 1020 |
| G-activity | 62 | 54 | 46 | 48 | 875 |

TABLE 8

|  | BLCA | BRCA | COAD | GMB | HNSC | KIRC | LGG | LUAD | LUSC | OV | PRAD | READ | SARC |
|---|---|---|---|---|---|---|---|---|---|---|---|---|---|
| RPPA profiled | 30 | 23 | 28 | 28 | 21 | 22 | 29 | 21 | 28 | 25 | 29 | 28 | 19 |
| mRNA expression | 1 | 1 | 3 | 1 | 2 | 2 | 4 | 3 | 1 | 2 | 4 | 2 | 1 |
| G-activity | 1 | 1 | 4 | 5 | 2 | 3 | 4 | 3 | 2 | 2 | 6 | 0 | 2 |
| RPT-activity | 4 | 6 | 8 | 3 | 4 | 5 | 4 | 3 | 5 | 3 | 6 | 3 | 3 |
| Intergrated activity | 5 | 7 | 10 | 7 | 5 | 6 | 7 | 5 | 6 | 5 | 9 | 3 | 5 |

|  | SKCM | STAD | THCA | UCEC | TOTAL |
|---|---|---|---|---|---|
| RPPA profiled | 28 | 29 | 29 | 26 | 443 |
| mRNA expression | 1 | 4 | 3 | 3 | 38 |
| G-activity | 1 | 3 | 3 | 5 | 47 |
| RPT-activity | 4 | 3 | 4 | 9 | 77 |
| Intergrated activity | 5 | 5 | 5 | 10 | 105 |

TABLE 9

| Gene | BLCA | BRCA | COAD | GBM | HNSC | KIRC | LUAD | LUSC | OV | PRAD | READ | STAD | THCA | UCEC |
|---|---|---|---|---|---|---|---|---|---|---|---|---|---|---|
| ABL1 | 4 | 7 | 6 | 2 | 0 | 3 | 6 | 3 | 0 | 1 | 2 | 5 | 1 | 8 |
| AKT1 | 0 | 2 | 7 | 1 | 2 | 1 | 3 | 1 | 0 | 1 | 0 | 2 | 3 | 4 |
| AKT2 | 0 | 5 | 0 | 0 | 3 | 2 | 6 | 0 | 0 | 1 | 1 | 4 | 2 | 6 |
| ALK | 1 | 0 | 0 | 1 | 8 | 5 | 26 | 4 | 0 | 0 | 2 | 8 | 1 | 16 |
| APC | 7 | 16 | 157 | 1 | 13 | 3 | 20 | 8 | 2 | 2 | 69 | 22 | 2 | 29 |
| ARID1A | 34 | 28 | 28 | 1 | 13 | 6 | 39 | 12 | 0 | 4 | 4 | 49 | 0 | 82 |
| ARID2 | 12 | 10 | 13 | 1 | 10 | 1 | 24 | 9 | 1 | 5 | 2 | 13 | 1 | 14 |
| ASXL1 | 9 | 7 | 14 | 0 | 10 | 3 | 13 | 10 | 0 | 2 | 3 | 9 | 1 | 13 |
| ATM | 15 | 21 | 28 | 2 | 8 | 10 | 40 | 8 | 1 | 12 | 10 | 21 | 5 | 28 |
| ATRX | 7 | 17 | 17 | 9 | 17 | 9 | 32 | 11 | 0 | 3 | 4 | 15 | 1 | 24 |
| AXIN1 | 3 | 5 | 7 | 2 | 3 | 1 | 6 | 0 | 0 | 0 | 2 | 7 | 1 | 8 |
| BCL6 | 0 | 4 | 7 | 3 | 2 | 3 | 8 | 4 | 1 | 3 | 1 | 3 | 1 | 12 |
| BCOR | 3 | 13 | 15 | 2 | 6 | 0 | 15 | 8 | 1 | 1 | 1 | 10 | 2 | 30 |
| BIRC3 | 1 | 0 | 1 | 0 | 1 | 2 | 3 | 2 | 0 | 0 | 0 | 4 | 0 | 5 |
| BRAF | 1 | 5 | 34 | 3 | 4 | 2 | 38 | 8 | 0 | 5 | 3 | 9 | 240 | 7 |
| BRCA1 | 4 | 14 | 8 | 3 | 8 | 3 | 19 | 10 | 3 | 0 | 2 | 6 | 1 | 12 |
| BRCA2 | 11 | 16 | 18 | 1 | 11 | 9 | 25 | 11 | 0 | 5 | 5 | 18 | 3 | 24 |
| CALR | 0 | 1 | 1 | 0 | 2 | 1 | 2 | 1 | 0 | 0 | 0 | 2 | 0 | 3 |
| CARD11 | 4 | 8 | 11 | 4 | 0 | 3 | 26 | 5 | 1 | 1 | 5 | 16 | 0 | 16 |
| CASP8 | 4 | 12 | 9 | 0 | 27 | 0 | 4 | 2 | 0 | 0 | 2 | 11 | 0 | 17 |
| CBL | 3 | 4 | 3 | 1 | 2 | 1 | 8 | 3 | 0 | 1 | 2 | 1 | 0 | 11 |
| CBLB | 6 | 13 | 2 | 0 | 2 | 2 | 6 | 7 | 1 | 0 | 1 | 2 | 0 | 11 |
| CBLC | 0 | 7 | 4 | 0 | 0 | 1 | 2 | 0 | 0 | 0 | 0 | 1 | 0 | 5 |
| CCNE1 | 0 | 2 | 3 | 1 | 3 | 1 | 5 | 3 | 0 | 0 | 0 | 1 | 0 | 5 |
| CD79A | 1 | 0 | 2 | 0 | 0 | 0 | 2 | 1 | 1 | 0 | 0 | 4 | 0 | 1 |
| CD79B | 1 | 2 | 1 | 0 | 0 | 0 | 2 | 0 | 0 | 0 | 0 | 1 | 0 | 0 |
| CDH1 | 5 | 110 | 0 | 1 | 4 | 2 | 6 | 3 | 0 | 2 | 0 | 17 | 0 | 13 |
| CDK12 | 6 | 14 | 14 | 1 | 5 | 5 | 19 | 1 | 2 | 6 | 3 | 12 | 1 | 12 |
| CDKN2A | 7 | 2 | 3 | 2 | 66 | 1 | 17 | 26 | 0 | 2 | 1 | 5 | 0 | 2 |
| CEBPA | 0 | 0 | 1 | 0 | 0 | 0 | 0 | 1 | 0 | 0 | 0 | 0 | 0 | 0 |
| CIC | 2 | 6 | 16 | 1 | 4 | 2 | 8 | 4 | 1 | 0 | 1 | 13 | 0 | 17 |
| CNOT3 | 5 | 13 | 3 | 0 | 5 | 1 | 6 | 3 | 0 | 3 | 1 | 4 | 0 | 6 |
| KLF6 | 3 | 2 | 1 | 0 | 2 | 0 | 4 | 0 | 0 | 0 | 1 | 2 | 1 | 7 |
| CREBBP | 17 | 14 | 15 | 4 | 15 | 2 | 24 | 15 | 1 | 3 | 5 | 15 | 0 | 22 |
| CSF3R | 0 | 6 | 7 | 0 | 2 | 1 | 12 | 6 | 0 | 0 | 1 | 6 | 0 | 7 |
| CTNNB1 | 4 | 2 | 17 | 1 | 2 | 2 | 18 | 4 | 1 | 9 | 4 | 15 | 2 | 73 |
| DAXX | 1 | 2 | 4 | 1 | 0 | 3 | 6 | 3 | 0 | 1 | 1 | 6 | 0 | 8 |
| DNM2 | 3 | 7 | 7 | 1 | 6 | 1 | 2 | 3 | 0 | 1 | 3 | 9 | 0 | 6 |
| DNMT3A | 1 | 6 | 6 | 0 | 7 | 4 | 17 | 7 | 0 | 1 | 0 | 5 | 3 | 8 |

TABLE 9-continued

| Gene | BLCA | BRCA | COAD | GBM | HNSC | KIRC | LUAD | LUSC | OV | PRAD | READ | STAD | THCA | UCEC |
|---|---|---|---|---|---|---|---|---|---|---|---|---|---|---|
| ECT2L | 3 | 1 | 1 | 0 | 6 | 1 | 8 | 5 | 0 | 0 | 2 | 2 | 0 | 11 |
| EGFR | 3 | 5 | 4 | 48 | 14 | 2 | 63 | 6 | 0 | 3 | 1 | 10 | 0 | 8 |
| EP300 | 21 | 12 | 10 | 0 | 25 | 6 | 9 | 8 | 0 | 3 | 4 | 11 | 0 | 20 |
| ERBB2 | 11 | 21 | 7 | 0 | 6 | 3 | 11 | 2 | 0 | 1 | 3 | 7 | 1 | 8 |
| EZH2 | 3 | 3 | 7 | 1 | 1 | 3 | 8 | 4 | 0 | 1 | 0 | 3 | 0 | 12 |
| FBXW7 | 13 | 15 | 25 | 1 | 15 | 2 | 13 | 11 | 0 | 0 | 14 | 16 | 0 | 39 |
| FGFR2 | 3 | 11 | 8 | 0 | 2 | 2 | 10 | 4 | 0 | 3 | 1 | 7 | 1 | 30 |
| FGFR3 | 16 | 4 | 11 | 2 | 5 | 1 | 4 | 4 | 0 | 0 | 0 | 2 | 0 | 5 |
| FLT3 | 0 | 0 | 0 | 2 | 0 | 2 | 0 | 0 | 0 | 0 | 0 | 4 | 0 | 0 |
| FOXA1 | 7 | 23 | 2 | 2 | 2 | 0 | 2 | 1 | 0 | 11 | 0 | 0 | 0 | 5 |
| FOXL2 | 0 | 2 | 5 | 0 | 0 | 0 | 4 | 1 | 0 | 0 | 0 | 2 | 0 | 0 |
| FUBP1 | 3 | 3 | 6 | 0 | 5 | 1 | 9 | 4 | 0 | 0 | 2 | 5 | 0 | 7 |
| GATA1 | 1 | 2 | 3 | 0 | 1 | 0 | 3 | 3 | 0 | 0 | 0 | 2 | 0 | 8 |
| GATA2 | 0 | 1 | 5 | 0 | 2 | 4 | 4 | 1 | 0 | 0 | 2 | 1 | 0 | 2 |
| GATA3 | 1 | 96 | 6 | 0 | 6 | 0 | 11 | 6 | 1 | 0 | 2 | 8 | 0 | 3 |
| GNA11 | 0 | 4 | 2 | 0 | 0 | 1 | 3 | 1 | 0 | 0 | 0 | 2 | 0 | 2 |
| GNAQ | 0 | 1 | 5 | 0 | 0 | 0 | 5 | 0 | 0 | 0 | 0 | 3 | 0 | 3 |
| GNAS | 4 | 11 | 21 | 0 | 5 | 2 | 21 | 6 | 1 | 2 | 5 | 12 | 3 | 17 |
| ARHGAP26 | 3 | 8 | 2 | 1 | 4 | 2 | 8 | 0 | 0 | 1 | 1 | 3 | 2 | 7 |
| HEY1 | 0 | 1 | 0 | 0 | 1 | 1 | 1 | 1 | 0 | 0 | 0 | 1 | 0 | 0 |
| HRAS | 6 | 2 | 1 | 0 | 10 | 0 | 1 | 5 | 0 | 2 | 0 | 0 | 14 | 1 |
| IKZF1 | 0 | 3 | 6 | 1 | 2 | 2 | 12 | 2 | 0 | 0 | 0 | 3 | 0 | 9 |
| IL6ST | 3 | 7 | 5 | 0 | 2 | 3 | 3 | 1 | 0 | 2 | 1 | 5 | 0 | 11 |
| IL7R | 2 | 4 | 0 | 0 | 3 | 0 | 20 | 0 | 1 | 1 | 2 | 0 | 3 | 7 |
| JAK1 | 3 | 11 | 8 | 0 | 5 | 3 | 15 | 2 | 0 | 2 | 3 | 6 | 1 | 14 |
| JAK2 | 2 | 7 | 5 | 1 | 2 | 4 | 0 | 0 | 0 | 0 | 2 | 5 | 0 | 13 |
| JAK3 | 0 | 8 | 0 | 1 | 3 | 2 | 0 | 6 | 1 | 2 | 2 | 0 | 0 | 9 |
| JUN | 0 | 3 | 1 | 0 | 0 | 1 | 3 | 3 | 0 | 0 | 1 | 4 | 1 | 1 |
| KDM5A | 5 | 7 | 7 | 1 | 3 | 2 | 15 | 7 | 0 | 1 | 2 | 10 | 1 | 15 |
| KDM5C | 1 | 8 | 3 | 2 | 3 | 17 | 14 | 5 | 1 | 0 | 1 | 7 | 0 | 14 |
| KDR | 8 | 6 | 11 | 2 | 5 | 4 | 40 | 13 | 0 | 3 | 2 | 8 | 2 | 14 |
| KIT | 3 | 7 | 11 | 3 | 4 | 0 | 6 | 6 | 1 | 0 | 1 | 6 | 0 | 16 |
| KLF4 | 1 | 2 | 3 | 0 | 1 | 0 | 7 | 1 | 0 | 2 | 0 | 4 | 0 | 5 |
| KRAS | 0 | 6 | 91 | 1 | 1 | 3 | 134 | 2 | 1 | 0 | 32 | 18 | 4 | 52 |
| LMO1 | 0 | 0 | 1 | 0 | 1 | 0 | 1 | 0 | 0 | 1 | 0 | 2 | 0 | 2 |
| SMAD4 | 2 | 7 | 29 | 1 | 7 | 0 | 21 | 5 | 0 | 3 | 13 | 17 | 0 | 5 |
| MAP2K1 | 1 | 5 | 5 | 1 | 4 | 1 | 10 | 2 | 0 | 0 | 2 | 5 | 0 | 2 |
| MAP2K2 | 0 | 2 | 1 | 0 | 3 | 0 | 1 | 1 | 0 | 0 | 0 | 2 | 0 | 3 |
| MAP2K4 | 1 | 32 | 10 | 0 | 1 | 0 | 7 | 1 | 0 | 1 | 2 | 3 | 0 | 8 |
| MAX | 0 | 2 | 4 | 1 | 1 | 1 | 10 | 0 | 0 | 0 | 0 | 2 | 0 | 11 |
| MDM2 | 0 | 3 | 3 | 1 | 2 | 0 | 15 | 2 | 0 | 0 | 1 | 3 | 0 | 4 |
| MDM4 | 0 | 3 | 0 | 1 | 1 | 0 | 3 | 0 | 0 | 1 | 1 | 3 | 0 | 3 |
| MED12 | 11 | 22 | 19 | 2 | 14 | 4 | 33 | 6 | 0 | 6 | 6 | 7 | 0 | 25 |
| MEN1 | 1 | 4 | 4 | 2 | 2 | 1 | 4 | 3 | 0 | 1 | 0 | 4 | 1 | 7 |
| MET | 4 | 8 | 0 | 0 | 1 | 4 | 21 | 4 | 2 | 1 | 0 | 5 | 1 | 13 |
| MITF | 1 | 3 | 7 | 0 | 4 | 2 | 3 | 0 | 2 | 0 | 3 | 4 | 1 | 6 |
| MLH1 | 4 | 7 | 10 | 0 | 4 | 0 | 15 | 2 | 0 | 1 | 2 | 3 | 0 | 6 |
| MLL | 18 | 16 | 21 | 3 | 13 | 5 | 28 | 5 | 1 | 1 | 0 | 16 | 7 | 18 |
| MLL2 | 35 | 23 | 0 | 5 | 56 | 9 | 52 | 36 | 0 | 9 | 0 | 31 | 2 | 33 |
| MLL3 | 27 | 69 | 23 | 4 | 23 | 20 | 79 | 30 | 0 | 8 | 1 | 26 | 4 | 25 |
| MPL | 1 | 2 | 3 | 0 | 2 | 1 | 2 | 2 | 0 | 0 | 0 | 0 | 0 | 7 |
| MSH2 | 2 | 6 | 8 | 0 | 2 | 1 | 9 | 1 | 0 | 0 | 3 | 5 | 1 | 9 |
| MSH6 | 2 | 9 | 10 | 0 | 1 | 3 | 11 | 4 | 0 | 1 | 3 | 4 | 0 | 17 |
| MYC | 1 | 1 | 0 | 0 | 4 | 0 | 3 | 1 | 0 | 1 | 0 | 4 | 1 | 8 |
| MYCL1 | 0 | 2 | 3 | 0 | 2 | 2 | 2 | 1 | 0 | 0 | 0 | 3 | 0 | 2 |
| MYCN | 2 | 2 | 1 | 1 | 3 | 1 | 5 | 1 | 0 | 0 | 1 | 3 | 0 | 4 |
| MYD88 | 1 | 1 | 1 | 0 | 0 | 0 | 3 | 0 | 0 | 0 | 0 | 0 | 0 | 3 |
| NF1 | 11 | 27 | 13 | 15 | 9 | 6 | 55 | 21 | 2 | 0 | 3 | 10 | 2 | 20 |
| NF2 | 2 | 4 | 4 | 0 | 4 | 4 | 6 | 2 | 0 | 1 | 1 | 3 | 1 | 7 |
| NFE2L2 | 10 | 3 | 2 | 0 | 17 | 5 | 11 | 27 | 0 | 0 | 0 | 1 | 1 | 14 |
| NKX2-1 | 0 | 0 | 4 | 0 | 0 | 0 | 5 | 1 | 0 | 0 | 0 | 4 | 2 | 0 |
| NOTCH1 | 6 | 8 | 9 | 0 | 59 | 3 | 20 | 14 | 0 | 2 | 0 | 9 | 0 | 8 |
| NOTCH2 | 9 | 27 | 9 | 2 | 16 | 5 | 24 | 10 | 0 | 3 | 2 | 15 | 1 | 14 |
| NPM1 | 0 | 0 | 2 | 1 | 1 | 0 | 5 | 0 | 0 | 0 | 0 | 0 | 0 | 3 |
| NRAS | 2 | 2 | 9 | 0 | 1 | 1 | 3 | 1 | 1 | 0 | 8 | 1 | 34 | 9 |
| PAX5 | 0 | 6 | 7 | 0 | 7 | 0 | 7 | 3 | 0 | 1 | 2 | 0 | 0 | 6 |
| PBRM1 | 9 | 7 | 12 | 0 | 8 | 105 | 7 | 7 | 0 | 0 | 3 | 13 | 0 | 11 |
| PDGFRA | 7 | 6 | 10 | 6 | 6 | 5 | 42 | 10 | 1 | 5 | 1 | 7 | 0 | 12 |
| PHF6 | 3 | 3 | 0 | 1 | 1 | 2 | 2 | 2 | 1 | 0 | 0 | 2 | 1 | 8 |
| PHOX2B | 1 | 3 | 2 | 0 | 3 | 0 | 7 | 1 | 0 | 0 | 0 | 5 | 0 | 6 |
| PIK3CA | 26 | 316 | 60 | 13 | 64 | 10 | 29 | 27 | 0 | 7 | 9 | 39 | 2 | 130 |
| PIK3R1 | 2 | 15 | 11 | 13 | 6 | 1 | 4 | 2 | 0 | 0 | 3 | 7 | 0 | 81 |
| PPP2R1A | 1 | 2 | 5 | 0 | 3 | 0 | 10 | 8 | 1 | 0 | 1 | 4 | 2 | 27 |
| PRDM1 | 2 | 8 | 5 | 0 | 3 | 1 | 7 | 5 | 1 | 0 | 0 | 2 | 0 | 9 |
| PRKAR1A | 1 | 6 | 1 | 0 | 2 | 1 | 0 | 2 | 0 | 0 | 1 | 1 | 0 | 4 |
| PTCH1 | 7 | 0 | 14 | 1 | 11 | 2 | 14 | 4 | 1 | 2 | 1 | 12 | 2 | 19 |
| PTEN | 5 | 35 | 19 | 48 | 6 | 9 | 6 | 14 | 0 | 13 | 5 | 13 | 2 | 158 |
| PTPN11 | 0 | 1 | 4 | 3 | 1 | 1 | 4 | 3 | 0 | 0 | 2 | 3 | 0 | 7 |

TABLE 9-continued

| Gene | BLCA | BRCA | COAD | GBM | HNSC | KIRC | LUAD | LUSC | OV | PRAD | READ | STAD | THCA | UCEC |
|---|---|---|---|---|---|---|---|---|---|---|---|---|---|---|
| PTPRC | 5 | 7 | 9 | 1 | 12 | 4 | 29 | 7 | 0 | 3 | 5 | 9 | 0 | 13 |
| RAC1 | 1 | 0 | 2 | 0 | 9 | 0 | 0 | 1 | 0 | 1 | 0 | 0 | 0 | 1 |
| RB1 | 17 | 19 | 5 | 11 | 10 | 1 | 25 | 12 | 0 | 1 | 3 | 4 | 2 | 20 |
| REL | 2 | 4 | 3 | 0 | 1 | 0 | 4 | 1 | 0 | 0 | 1 | 3 | 0 | 7 |
| RET | 5 | 8 | 0 | 1 | 8 | 0 | 15 | 3 | 1 | 1 | 2 | 6 | 0 | 11 |
| SETD2 | 9 | 16 | 11 | 5 | 7 | 34 | 28 | 5 | 1 | 5 | 2 | 10 | 1 | 22 |
| SH2B3 | 0 | 3 | 3 | 0 | 2 | 0 | 0 | 0 | 0 | 1 | 0 | 0 | 0 | 2 |
| SMARCA4 | 11 | 8 | 13 | 1 | 13 | 7 | 37 | 8 | 0 | 0 | 3 | 6 | 1 | 15 |
| SMARCB1 | 3 | 2 | 4 | 0 | 2 | 3 | 2 | 1 | 0 | 3 | 1 | 5 | 0 | 6 |
| SMO | 2 | 5 | 0 | 1 | 1 | 3 | 15 | 1 | 0 | 0 | 0 | 6 | 0 | 5 |
| SOCS1 | 0 | 0 | 0 | 1 | 0 | 0 | 0 | 0 | 0 | 0 | 0 | 1 | 0 | 0 |
| SOX2 | 1 | 2 | 4 | 0 | 3 | 1 | 1 | 1 | 0 | 0 | 0 | 1 | 1 | 3 |
| SRSF2 | 3 | 3 | 0 | 0 | 2 | 1 | 3 | 2 | 0 | 2 | 0 | 3 | 1 | 0 |
| STAT3 | 0 | 5 | 5 | 1 | 3 | 1 | 6 | 2 | 0 | 4 | 0 | 4 | 0 | 9 |
| STAT5B | 2 | 5 | 6 | 0 | 4 | 0 | 7 | 0 | 3 | 1 | 1 | 6 | 1 | 5 |
| STK11 | 0 | 2 | 2 | 0 | 1 | 0 | 71 | 3 | 0 | 0 | 0 | 2 | 0 | 2 |
| SUFU | 0 | 3 | 1 | 0 | 1 | 0 | 2 | 2 | 0 | 1 | 0 | 4 | 1 | 3 |
| TBL1XR1 | 2 | 10 | 3 | 0 | 3 | 3 | 4 | 2 | 0 | 2 | 1 | 1 | 0 | 12 |
| HNF1A | 17 | 7 | 11 | 1 | 1 | 0 | 3 | 3 | 0 | 1 | 0 | 5 | 0 | 7 |
| TNFAIP3 | 2 | 3 | 7 | 0 | 3 | 0 | 7 | 5 | 1 | 1 | 2 | 0 | 0 | 2 |
| TNFRSF14 | 0 | 0 | 1 | 0 | 0 | 1 | 1 | 0 | 0 | 0 | 0 | 0 | 0 | 2 |
| FAS | 0 | 1 | 0 | 0 | 1 | 3 | 3 | 1 | 0 | 0 | 0 | 3 | 0 | 8 |
| TP53 | 64 | 297 | 121 | 49 | 1213 | 6 | 243 | 141 | 66 | 21 | 64 | 80 | 3 | 69 |
| TRAF7 | 0 | 6 | 2 | 0 | 2 | 2 | 4 | 0 | 1 | 0 | 0 | 5 | 0 | 5 |
| TRRAP | 9 | 15 | 14 | 4 | 10 | 5 | 37 | 12 | 0 | 2 | 2 | 21 | 2 | 26 |
| TSC1 | 11 | 5 | 8 | 0 | 2 | 4 | 10 | 5 | 0 | 0 | 1 | 2 | 0 | 9 |
| TSC2 | 3 | 8 | 6 | 1 | 3 | 2 | 10 | 5 | 0 | 2 | 1 | 5 | 0 | 13 |
| TSHR | 0 | 0 | 0 | 1 | 0 | 0 | 0 | 0 | 0 | 1 | 0 | 5 | 2 | 7 |
| UBR5 | 10 | 18 | 17 | 0 | 11 | 3 | 28 | 10 | 0 | 2 | 1 | 22 | 1 | 20 |
| VHL | 0 | 0 | 1 | 0 | 0 | 137 | 1 | 1 | 0 | 1 | 0 | 0 | 0 | 3 |
| WT1 | 2 | 4 | 4 | 0 | 0 | 2 | 13 | 4 | 0 | 0 | 0 | 2 | 1 | 3 |
| FAM123B | 3 | 12 | 22 | 1 | 12 | 2 | 30 | 8 | 0 | 0 | 5 | 11 | 0 | 17 |
| ZRSR2 | 3 | 1 | 0 | 1 | 1 | 0 | 2 | 0 | 0 | 1 | 0 | 1 | 0 | 5 |

TABLE 10

| MEF2B P3HR1 | FOXM1 ST486 | MYB ST486 | BCL6 Ly7 | BCL6 Pfeifer | STAT3 SNB19 |
|---|---|---|---|---|---|
| MYBL1 4.22 (9.66e−10) | ILF3 2.32 (5.11e−06) | FOXM1 2.31 (0.000785) | CUX1 11.63 (1.74e−39) | ZEB2 7.19 (1.32e−55) | IRF1 3.54 (8.49e−12) |
| BCL6 2.73 (1.99e−06) | BCL6 1.96 (0.000132) | PLAGL1 2.17 (0.00246) | ZFP64 5.71 (7.89e−32) | HHEX 5.49 (1.26e−46) | ZNF529 3.12 (8.59e−10) |
| CUX1 2.67 (1.88e−05) | STAT5A 1.95 (0.000267) | | IKZF2 4.14 (1.74e−30) | BACH2 6.55 (1.43e−45) | HLX 2.9 (1.15e−09) |
| BACH1 2.83 (2e−05) | KLF10 2.1 (0.000479) | | MYBL1 6.11 (1.05e−23) | ZNF828 6.65 (4.82e−45) | GATA DI 2.9 (5.23e−08) |
| ESR2 3.06 (4.42e−05) | | | MEF2B 5.35 (2.33e−20) | TGIF1 6.19 (7.38e−40) | ATF5 3.09 (1.73e−07) |
| KLF9 2.53 (5.97e−05) | | | ZBTB32 5.58 (2.31e−17) | CUX1 11.63 (1.74e−39) | MAZ 2.8 (2.3e−07) |
| MORC3 2.62 (6.35e−05) | | | LHX2 5.28 (1.4e−16) | IKZF1 7.18 (1.36e−33) | IRF7 2.75 (2.4e−07) |
| CLOCK 2.71 (7.25e−05) | | | SCML1 2.61 (3.03e−16) | IKZF2 4.14 (1.74e−30) | BCL3 2.26 (8.7e−06) |
| ZMNYD11 2.22 (0.000139) | | | HOXA5 4.65 (5.35e−16) | NOTCH2 4.6 (8.8e−30) | ZNF248 2.21 (1.13e−05) |
| E2F5 2.69 (0.000153) | | | MTA3 4.78 (5.64e−12) | ZNF74 7.17 (1.11e−28) | TEAD3 2.47 (1.37e−05) |
| CREB3L2 2.16 (0.000583) | | | DDIT3 5.08 (2.56e−11) | LYL1 5.4 (4.87e−24) | CAMTA1 2.04 (2.14e−05) |
| PTTG1 1.97 (0.000899) | | | ETV6 3.64 (1.45e−10) | MYBL1 6.11 (1.05e−23) | ZNF142 2.23 (2.14e−05) |
| ZEB2 2.2 (0.0013) | | | SMAD2 4.49 (3.3e−10) | ZBTB32 5.58 (2.31e−17) | TAF5L 2.47 (9.13e−05) |
| ZNF248 2.25 (0.0021) | | | SCMH1 3.85 (1.44e−09) | TFEC 4.53 (9.76e−17) | ZNF3 2.33 (0.000129) |
| ETV6 2.33 (0.00238) | | | HOXA1 3.98 (3.99e−09) | E2F7 4.4 (5.1e−16) | ZNF365 1.9 (0.000252) |
| IRF5 2.43 (0.00384) | | | ZNF318 3.73 (4.96e−09) | BCL11A 3.8 (2.23e−15) | ZNF638 2.26 (0.000266) |
| MYBL2 2.14 (0.0053) | | | ZNF354A 3.65 (3.67e−08) | IRF8 4.31 (2.27e−14) | JUNB 2.39 (0.000343) |
| TADA3 | | | BATF3 | SP140 | CEBPD |

TABLE 10-continued

| MEF2B | FOXM1 | MYB | BCL6 | BCL6 | STAT3 |
|-------|-------|-----|------|------|-------|
| P3HR1 | ST486 | ST486 | Ly7 | Pfeifer | SNB19 |
| 2.03 (0.00693) | | | 2.86 (5.86e−08) | 3.36 (6.51e−14) | 2.15 (0.000423) |
| SRF | | | HDAC1 | IRF4 | MSRB2 |
| 1.99 (0.00835) | | | 2.8 (7.64e−07) | 3.53 (2.43e−13) | 1.75 (0.000501) |
| CSDA | | | POU2F2 | MTA8 | LASS2 |
| 1.91 (0.00837) | | | 2.79 (9.92e−06) | 4.78 (5.64e−12) | 1.97 (0.0014) |
| | | | WHSC1 | CREB3L2 | NFYA |
| | | | 2.4 (1.57e−05) | 3.32 (1.15€-11) | 1.88 (0.00305) |

OncoTarget

In some embodiments, VIPER can be extended to an application that does not require a drug perturbation database, which is hereinafter referred to as "OncoTarget." OncoTarget can identify all druggable proteins that are aberrantly activated in a tumor regardless of whether they harbor activating mutations or not. This can include key druggable proteins, such as, topoisomerases and HDACs, that are rarely if ever mutated in cancer and yet represent eminently druggable targets of proven utility in cancer treatment.

In some embodiments, OncoTarget can be based on an extension of the concept of Oncogene addiction, which can represent the foundation for targeted therapy. According to Oncogene addiction, tumors become addicted to the activity of oncogenes that are mutated. Targeting these mutated genes with a specific inhibitor can induce tumor cell death. Examples of such phenomena can include chronic myelogenous leukemia (CML) where the drug imatinib targets a mutated protein originating from the fusion of two proteins (BCR and ABL), breast cancer with amplification or mutation of the HER2 (ErbB2) receptor targeted with the drug trastuzumab, lung cancer with mutations in the EGFR or ALK kinases, targeted with drugs such as erlotiniv/afatinib, and crizotinib, and several other examples.

OncoTarget can extend oncogene addiction by hypothesizing that tumor addiction is not manifested for oncogenes that harbor activating mutations but also to any oncoprotein(s) that is aberrantly activated as a result of the full mutational burden of the tumor cell. Oncogene mutations can thus be one of many possible ways to induce aberrant activity of the corresponding proteins.

In some embodiments, OncoTarget can proceed as follows. First, VIPER can be used to assess the differential activity of all "druggable proteins" (e.g., proteins that can be effectively inhibited using an FDA approved drug and/or an investigational compound) in a tumor sample compared to a multiplicity of "control samples," from which an average gene expression profile (control profile) is generated. Depending on specific application, control profiles can be generated by averaging the gene expression of many types of samples including, but not limited to, (a) all tumors in a specific tumor subtype (e.g. luminal A breast cancers), (b) all tumors across all subtypes, (c) samples representing the normal counterpart of a tumor (e.g., normal breast ductal epithelium), (d) samples representing primary tumors for the study of metastatic progression, and (e) samples representing drug-sensitive tumors for the study of drug-resistance. For example, to identify the proteins that control resistance to a drug in a specific triple negative breast cancer, the differential activity of proteins can be inferred in that sample compared to all triple negative breast cancer samples that are sensitive to the drug. A useful dataset to generate these reference gene expression profiles is The Cancer Genome Atlas (TCGA), which can contain >12,000 tumor samples from >25 human malignancies.

Next, a statistical significance can be attributed to the differential activity of each tested protein by comparing the specific sample against the distribution of all available control samples. In the preferred implementation, a statistical significance (p-value) can be determined using both control samples representing the average of the tumor specific subtype (e.g. breast adenocarcinoma) as well as the average of all tumor subtypes (e.g., pancancer). Each sample gene expression signature can be determined by comparing the expression level of each gene against the distribution of expression across all profiled samples from the same malignancy, or across all tumors (pan-cancer). Statistical significance for the enrichment of each regulon genes on the individual sample gene expression signature can be determined as the probability of finding an equal or higher enrichment when the genes in the regulon are selected uniformly at random from all the profiled genes.

Third, druggable proteins with a statistically significant aberrant expression can be prioritized on an individual patient basis using a predefined significance threshold (e.g., p=0.001) as potentially relevant pharmacological targets for that specific patient. Various criteria can be used to prioritize the specific drugs and targets including but not restricted to: (a) the affinity and IC50 of the specific compound for the specific target oncoprotein (b) the p-value of the aberrant oncoprotein differential activity against all tumors in the subtype (c) the p-value of the aberrant oncoprotein differential activity against all tumors across all subtypes (d) the toxicity of the compound (e) whether the compound is FDA approved or investigational (f) whether the drug is approved for the specific tumor subtype of the patient (g) whether there is any literature or clinical trial results suggesting some activity for the specific drug in the specific tumor subtype.

The foregoing merely illustrates the principles of the disclosed subject matter. Various modification and alterations to the described embodiments will be apparent to those skilled in the art in view of the teachings herein. It will thus be appreciated that those skilled in the art will be able to devise numerous techniques which, although not explicitly described herein, embody the principles of the disclosed subject matter and are thus within the spirit and scope.

LIST OF REFERENCES

1. Alvarez, M. J., et al., "Correlating Measurements Across Samples Improves Accuracy of Large-Scale Expression Profile Experiments," *Genome Biol.* 10(12):R143 (2009).

The invention claimed is:

1. A method for determining targeted therapy using a cell or tissue sample from an individual subject having a disease or disorder, comprising:

identifying the cell or tissue sample from the individual subject having the disease or disorder;

quantifying a protein activity of each of a plurality of regulator proteins (RP) in the individual subject's sample to provide a subject sample-specific RP activity signature comprising a plurality of activated and/or deactivated RPs characteristic of the disease or disorder, wherein quantifying the protein activity of each RP comprises computationally inferring each RP activity of the individual subject's sample based, at least in part, on measured expression levels of a plurality of transcriptional targets of the respective RP's (regulon) not including the expression level of the RP, for the individual subject's sample and for a plurality of samples representing a control phenotype, in the context of a tissue-specific regulatory model; and determining a targeted therapy for the subject, based on a ranking of the activated and/or deactivated RPs of the sample specific RP activity signature of the individual subject's sample, wherein at least one of the ranked RPs is not differentially expressed relative to the control phenotype.

2. The method of claim 1, wherein computationally inferring each RP activity of the individual subject's sample based, at least in part, on the measured expression levels of the plurality of transcriptional targets (regulon) comprises using a comparison method that generates a quantitative measurement of difference between the test sample and the control samples.

3. The method of claim 2, wherein the comparison method can include one or more of a fold change, a Student's t-test, and a Mann-Whitney U test analysis.

4. The method of claim 1, wherein quantifying the protein activity of each RP comprises:

calculating a regulon enrichment score for each regulon in the subject sample-specific RP activity signature;

determining whether the number of control samples in the control phenotype is above a predetermined threshold to support evaluation of statistical significance using permutation analysis; and in response to determining that the number of control samples is above the predetermined threshold, calculating a significance value by comparing each regulon enrichment score to a null model.

5. The method of claim 4, wherein the significance value includes one or more of a P value and a normalized enrichment score.

6. The method of claim 4, wherein the null model is generated by randomly permuting the control samples for a preset number of iterations.

7. The method of claim 4, wherein in response to determining that the number of control samples is below the predetermined threshold, calculating the significance value by performing permutation of the genes in at least one or more control gene expression signatures and providing an analytic approximation of the gene expression signatures.

8. The method of claim 4, wherein the subject sample-specific RP activity signature is obtained by comparing the expression levels of each regulon in the individual subject's test sample against the control samples.

9. The method of claim 4, wherein the enrichment value of each regulon in the subject sample-specific RP activity signature is calculated using an analytic rank-based enrichment analysis configured to determine whether a shift in the positions of each regulon gene occurs when each regulon gene is projected on a corresponding rank-sorted gene expression signature.

10. The method of claim 9, wherein the analytic rank-based enrichment analysis further comprises:

(a) calculating a first regulon enrichment score by using a one-tail approach based on an absolute value of the gene expression signature;

(b) calculating a second regulon enrichment score by using a two-tail approach;

(c) generating the regulon enrichment score by combining the first and the second regulon enrichment scores;

(d) determining a weighting of the first and the second regulon enrichment scores in the regulon enrichment score based on an estimated mode of regulation using a three-tail approach; and (e) calculating a statistical significance for the regulon enrichment score by comparison to the null model.

11. The method of claim 10, further comprising determining a contribution of each target gene from a given regulon to the regulon enrichment score based on at least one or more of a regulator-target gene interaction confidence, direction of regulation, and pleotropic correction.

12. The method of claim 10, wherein the first and the second regulon enrichment scores are calculated for the given regulon.

13. The method of claim 10, wherein the two-tail approach further comprises inverting positions of genes whose expression can be repressed by a regulator in the gene expression signature before determining the second regulon enrichment score.

14. A method for determining a targeted therapy using a tissue sample from an individual subject, comprising:

identifying a cell or tissue sample from an individual subject having a disease or disorder;

obtaining a gene expression signature by comparing the test sample to a plurality of samples representing a distinctive or control phenotype;

calculating, in the context of a tissue-specific regulatory model, a regulon enrichment score of each regulon in the gene expression signature by combining a first regulon enrichment score calculated using a one-tail approach and a second regulon enrichment score calculated using a two-tail approach;

calculating a significance value by comparing each regulon enrichment score to a null model to provide a subject sample-specific regulatory protein (RP) activity signature; and determining a targeted therapy for the subject, based on a ranking of the activated and/or deactivated RPs of the sample specific RP activity signature of the individual subject's sample, wherein at least one of the ranked RPs is not differentially expressed relative to the control phenotype.

15. The method of claim 14, wherein the first regulon enrichment score is calculated based on an absolute value of the gene expression signature.

16. The method of claim 14, wherein the significance value is used to perform an assessment of regulatory protein (RP) activity from the gene expression data.

17. The method of claim 14, wherein the significance value is used to identify a mechanism of action of at least one of a small molecule, an antibody, and a perturbagen.

18. The method of claim 14, wherein the significance value is used to evaluate the functional relevance of genetic alterations in regulatory proteins across different samples.

19. The method of claim 14, wherein the subject's sample comprises a tumor, and wherein the significance value is used to identify tumors with aberrant activity of druggable oncoproteins having a lack of mutations.

20. The method of claim 19, comprising:

determining a differential activity for the druggable onco-proteins;

assigning a statistical significance value to the differential activity by comparing a specific sample against a distribution of all available samples; and identifying druggable proteins that are aberrantly activated in the tumor by prioritizing each druggable protein of the plurality of druggable proteins with a statistically significant aberrant expression on an individual patient basis using a predefined significance threshold as potentially relevant pharmacological targets for that specific patient.

21. The method of claim 20, wherein assigning the statistical significance value comprises calculating a sample gene expression signature by comparing an expression level of each gene against the distribution of expression across all profiled samples with a same malignancy.

22. The method of claim 20, wherein assigning the statistical significance value comprises determining a statistical significance for an enrichment score of each regulon on an individual sample gene expression signature by calculating a probability of finding an equal or higher enrichment when the genes in the regulon are selected uniformly at random from all profiled genes.

23. The method of claim 20, wherein the prioritizing each druggable protein of the plurality of druggable proteins comprises using one or more of the following criteria: an affinity of a specific compound for a specific target onco-protein, a p-value of an aberrant oncoprotein differential activity against all tumors in the subtype, a p-value of the aberrant oncoprotein differential activity against all tumors across all subtypes, a toxicity of the druggable protein, whether the druggable protein is FDA approved, whether the druggable protein is approved for a specific tumor subtype, and whether literature or clinical trial results exist indicating activity for the specific drug in the specific tumor subtype.

24. A system for determining targeted therapy using a cell or tissue sample from an individual subject having a disease or disorder, comprising:

one or more processors; and memory, including computer-executable instructions that, if executed by the one or more processors, cause the system to:

(a) identify the cell or tissue sample from the individual subject having the disease or disorder;

(b) quantify a protein activity of each of a plurality of regulator proteins (RP) in the individual subject's sample to provide a subject sample-specific RP activity signature comprising a plurality of activated and/or deactivated RPs characteristic of the disease or disorder, wherein quantifying the protein activity of each RP comprises computationally inferring each RP activity of the individual subject's sample based, at least in part, on measured expression levels of a plurality of transcriptional targets of the respective RP's regulon not including the expression level of the RP, for the individual subject's sample and for a plurality of samples representing a control phenotype, in the context of a tissue-specific regulatory model; and (c) determine a targeted therapy for the subject, based on a ranking of the activated and/or deactivated RPs of the sample specific RP activity signature of the individual subject's sample, wherein at least one of the ranked RPs is not differentially expressed relative to the control phenotype.

25. The system of claim 24, wherein computationally inferring each RP activity comprises use of virtual inference of protein activity by enriched regulon analysis (VIPER) algorithm.

\* \* \* \* \*